(12) United States Patent
Sintim et al.

(10) Patent No.: US 10,130,625 B2
(45) Date of Patent: Nov. 20, 2018

(54) LINKED DIARYL COMPOUNDS WITH ANTICANCER PROPERTIES AND METHODS OF USING THE SAME

(71) Applicants: University of Maryland, College Park, College Park, MD (US); University of Maryland, Baltimore, Baltimore, MD (US)

(72) Inventors: Herman O. Sintim, West Lafayette, IN (US); Jie Zhou, Adelphi, MD (US); Changhao Wang, College Park, MD (US); Rena Lapidus, Baltimore, MD (US)

(73) Assignees: University of Maryland, College Park, College Park, MD (US); University of Maryland, Baltimore, Baltimore, MD (US)

(*) Notice: Subject to any disclaimer, the term of this patent is extended or adjusted under 35 U.S.C. 154(b) by 0 days.

(21) Appl. No.: 15/327,485

(22) PCT Filed: Jul. 22, 2015

(86) PCT No.: PCT/US2015/041551
§ 371 (c)(1),
(2) Date: Jan. 19, 2017

(87) PCT Pub. No.: WO2016/014674
PCT Pub. Date: Jan. 28, 2016

(65) Prior Publication Data
US 2017/0174620 A1    Jun. 22, 2017

Related U.S. Application Data

(60) Provisional application No. 62/027,718, filed on Jul. 22, 2014, provisional application No. 62/027,715, filed on Jul. 22, 2014.

(51) Int. Cl.
| | | |
|---|---|---|
| A61K 31/472 | (2006.01) |
| A61K 31/4725 | (2006.01) |
| C07C 257/18 | (2006.01) |
| C07C 245/24 | (2006.01) |
| C07D 217/22 | (2006.01) |
| C07D 401/12 | (2006.01) |
| C07D 413/12 | (2006.01) |
| C07D 401/04 | (2006.01) |
| C07D 471/04 | (2006.01) |

(52) U.S. Cl.
CPC ........ *A61K 31/472* (2013.01); *A61K 31/4725* (2013.01); *C07C 245/24* (2013.01); *C07C 257/18* (2013.01); *C07D 217/22* (2013.01); *C07D 401/04* (2013.01); *C07D 401/12* (2013.01); *C07D 413/12* (2013.01); *C07D 471/04* (2013.01)

(58) Field of Classification Search
CPC .......................... A61K 31/472; A61K 31/4725
USPC .......................................................... 514/299
See application file for complete search history.

(56) References Cited

U.S. PATENT DOCUMENTS

| | | | |
|---|---|---|---|
| 6,486,158 B1 | 11/2002 | Wang et al. | |
| 2005/0054708 A1* | 3/2005 | Nichols | A61K 31/155 514/408 |
| 2007/0072901 A1* | 3/2007 | Washio | C04B 35/632 514/307 |
| 2010/0298562 A1 | 11/2010 | Dubreuil et al. | |

OTHER PUBLICATIONS

Messner et al, Tetrahedron (1986), vol. 42(19), pp. 5415-5426.*
Messner et al, Tetrahedron (1986), vol. 42(19), pp. 5415-5426. (Year: 1986).*

* cited by examiner

*Primary Examiner* — Craig D Ricci
*Assistant Examiner* — Janet L. Coppins
(74) *Attorney, Agent, or Firm* — Hodgson Russ LLP

(57) ABSTRACT

Provided are compositions comprising linked diaryl compounds that possess anticancer properties. Methods of use are also disclosed herein. The method comprises administering an effective amount of a compound described herein to an individual in need thereof.

11 Claims, 40 Drawing Sheets

Specification includes a Sequence Listing.

A

B

C

SEQUENCE LISTING

```
<160> NUMBER OF SEQ ID NOS: 19

<210> SEQ ID NO 1
<211> LENGTH: 18
<212> TYPE: DNA
<213> ORGANISM: Homo sapien

<400> SEQUENCE: 1
gcagtcctct cggactgc                                                      18

<210> SEQ ID NO 2
<211> LENGTH: 18
<212> TYPE: DNA
<213> ORGANISM: Homo sapien

<400> SEQUENCE: 2
gcaattctct cgaattgc                                                      18

<210> SEQ ID NO 3
<211> LENGTH: 20
<212> TYPE: DNA
<213> ORGANISM: Homo sapien

<400> SEQUENCE: 3
cgaatttcaa aagaaattcg                                                    20

<210> SEQ ID NO 4
<211> LENGTH: 15
<212> TYPE: DNA
<213> ORGANISM: Homo sapien

<400> SEQUENCE: 4
ggttggtgtg gttgg                                                         15

<210> SEQ ID NO 5
<211> LENGTH: 18
<212> TYPE: DNA
<213> ORGANISM: Homo sapien
```

-continued

```
<400> SEQUENCE: 5
gggcgggccg ggggcggg                                                 18

<210> SEQ ID NO 6
<211> LENGTH: 22
<212> TYPE: DNA
<213> ORGANISM: Homo sapien

<400> SEQUENCE: 6
agggttaggg ttagggttag gg                                            22

<210> SEQ ID NO 7
<211> LENGTH: 22
<212> TYPE: DNA
<213> ORGANISM: Homo sapien

<400> SEQUENCE: 7
agggagggcg ctgggaggag gg                                            22

<210> SEQ ID NO 8
<211> LENGTH: 24
<212> TYPE: DNA
<213> ORGANISM: Homo sapien

<400> SEQUENCE: 8
tggggagggt ggggagggtg ggga                                          24

<210> SEQ ID NO 9
<211> LENGTH: 23
<212> TYPE: DNA
<213> ORGANISM: Homo sapien

<400> SEQUENCE: 9
gggcgcggga ggaattgggc ggg                                           23

<210> SEQ ID NO 10
<211> LENGTH: 27
<212> TYPE: DNA
<213> ORGANISM: Homo sapien

<400> SEQUENCE: 10
cgggcgcggg aggaaggggg cgggagc                                       27

<210> SEQ ID NO 11
<211> LENGTH: 21
<212> TYPE: DNA
<213> ORGANISM: Homo sapien

<400> SEQUENCE: 11
gggttagggt tagggttagg g                                             21

<210> SEQ ID NO 12
<211> LENGTH: 26
<212> TYPE: DNA
<213> ORGANISM: Homo sapien

<400> SEQUENCE: 12
cccgggcggg cgcgagggag gggagg                                        26

<210> SEQ ID NO 13
<211> LENGTH: 21
<212> TYPE: DNA
```

```
<213> ORGANISM: Homo sapien

<400> SEQUENCE: 13
agggcggtgt gggaagaggg a                                              21

<210> SEQ ID NO 14
<211> LENGTH: 22
<212> TYPE: DNA
<213> ORGANISM: Homo sapien

<400> SEQUENCE: 14
tgagggtggg tagggtgggt aa                                             22

<210> SEQ ID NO 15
<211> LENGTH: 26
<212> TYPE: DNA
<213> ORGANISM: Homo sapien

<400> SEQUENCE: 15
tatagctata tttttttata gctata                                         26

<210> SEQ ID NO 16
<211> LENGTH: 26
<212> TYPE: DNA
<213> ORGANISM: Homo sapien

<400> SEQUENCE: 16
caatcggatc gaattcgatc cgattg                                         26

<210> SEQ ID NO 17
<211> LENGTH: 27
<212> TYPE: DNA
<213> ORGANISM: Homo sapien

<400> SEQUENCE: 17
tggggagggt ggggagggtg gggaagg                                        27

<210> SEQ ID NO 18
<211> LENGTH: 27
<212> TYPE: DNA
<213> ORGANISM: Homo sapien

<400> SEQUENCE: 18
tggggagggt ggaaagggtg gggaagg                                        27

<210> SEQ ID NO 19
<211> LENGTH: 25
<212> TYPE: DNA
<213> ORGANISM: Homo sapien

<400> SEQUENCE: 19
atcgatcgct tctcgtcctt cccca                                          25
```

LINKED DIARYL COMPOUNDS WITH ANTICANCER PROPERTIES AND METHODS OF USING THE SAME

CROSS-REFERENCE TO RELATED APPLICATIONS

This application claims priority to U.S. Provisional Patent Application No. 62/027,718, filed on Jul. 22, 2014, and U.S. Provisional Patent Application No. 62/027,715, filed on Jul. 22, 2014, the disclosures of each of which are incorporated herein by reference in their entirety.

BACKGROUND OF THE DISCLOSURE

Cancer is the number two killer disease in the US, second to heart disease. In particular, cancers of the human reproductive organs, such as ovarian, prostate and breast, kill millions of people annually worldwide. Although there are several therapeutics against these cancers, aggressive forms remain problematic to treat. For example, although there are myriad hormone-based therapeutics against breast cancer, hormone insensitive breast cancer such as triple negative breast cancer remains difficult to treat.

G-quadruplexes have shown great promise as chemotherapeutic targets, likely by inhibiting telomere elongation or downregulating oncogene expression. There have been many G-quadruplex ligands developed over the years but only a few have drug-like properties. Consequently only a few G-quadruplex ligands have entered clinical trials as cancer chemotherapeutic agents. In this regard, there are ~376,000 guanine-rich regions in the human genome, which have the potential to form G-quadruplexes, including those at the telomere end and promoter regions of some cancer-related genes. Guanine tracts in RNA are known to form G-quadruplexes in vivo but the formation of G-quadruplexes in chromosomal DNA has been a matter of debate due to the fact that the guanine tracts in chromosomal DNA can also form duplexes with complementary tracts of cytosines. After many years of fierce debate regarding a biological role for DNA G-quadruplexes in vivo, acceptance is now growing that DNA G-quadruplexes might indeed form in vivo and that there could be biological consequences of G-quadruplex formation in chromosomal DNA. Firstly, it has been demonstrated that fluorogenic G-quadruplex-specific ligands could become fluorescent inside cells, especially during cell division, when single stranded regions of chromosomal DNA are created during DNA replication. Secondly, G-quadruplex-specific antibodies have been used to provide compelling evidence that G-quadruplexes form in vivo. Additionally, biophysical approaches have demonstrated that synthetic G-rich oligonucleotides could form G-quadruplex structures in vivo.

If G-quadruplex formation in vivo has a biological consequence, then small molecules that target and stabilize these structures could have therapeutic value. In animal chromosomes, the telomerase enzyme (which is up-regulated in certain cancers) is responsible for maintaining the telomere length thereby rendering cancer cells immortal. The telomere is G-rich and has been shown via many biophysical experiments to be capable of forming G-quadruplexes. Many compounds that bind to G-quadruplexes have been shown to inhibit the activity of telomerase and some have even shown interesting anti-proliferative properties when added to cancer cells. In addition to telomeres, G-quadruplexes are present in the promoter regions a number of cancer-related genes such as c-myc, BCL-2, KRAS, c-kit and VEGF, where they are involved in the regulation of transcription of these genes by disrupting binding of transcription factors.

In light of these potential important biological roles of G-quadruplexes, there is a need for developing G-quadruplex-selective ligands for both fundamental studies (for example, fluorescent ligands that will allow for studying G-quadruplexes in vivo) and also drug-like molecules that will have suitable binding properties that will allow for selective targeting of G-quadruplexes related to cancer and other diseases. The present disclosure meets these and other needs.

Notwithstanding the need for improved agents for binding G-quadruplexes, other targets involved in a variety of conditions also need improved targeting agents. For example, the poly-(ADP)-ribose polymerases (PARP) enzymes belong to a family of proteins that are mainly involved in DNA repair and programmed cell death. Initiation of DNA damage is vital in many cancer therapies, especially chemo- and radiotherapy, and other biological processes. Because PARP enzymes have an important role in the repair of DNA damage, they are considered to be a promising target for drug development, and multiple PARP inhibitors are under development and various stages of preclinical testing. However, there remains an ongoing need for improved PARP inhibitors. Likewise, a wide variety of kinases are involved in the development, progression and recurrence of a variety of cancers, and many other disorders, such as diabetes, Alzheimer's disease, neurological pain, inflammation, pulmonary fibrosis, rheumatoid arthritis, diseases which require anticoagulants, polycystic kidney disease, and conditions that wold benefit from improved immune modulators. There remains an ongoing need for improved kinase inhibitors. Moreover, there are few if any compounds that have multi-pronged yet specific against disparate targets, such as kinases, PARP enzymes, and G-quadraplexes. Thus, compounds that can affect all three of these very distinct cancer related targets would be highly desirable. The present disclosure meets this need.

SUMMARY OF THE DISCLOSURE

The present disclosure is related to our discovery that DMZ or berenil, a compound used to treat African sleeping sickness for decades, potently binds to several DNA G-quadruplexes, and the development of two novel classes of molecules that we demonstrate stabilize G-quadruplexes and possess anticancer properties. Accordingly, the present disclosure provides compositions comprising linked diaryl compounds, pharmaceutical compositions comprising the compounds, and methods of using the compounds and compositions comprising them to treat individuals in need thereof, and particularly individuals in need of prophylaxis and/or therapy for cancer.

Methods of using the linked diaryl compounds are also disclosed. The method comprises administering an effective amount of a compound described herein to an individual in need thereof. In embodiments, the individual in need is an individual who has been diagnosed with, is suspected of having, or is at risk for developing a cancer. In embodiments, the individual has a condition that is positively correlated with the presence of polynucleotides comprising a G-quadruplex.

BRIEF DESCRIPTION OF THE FIGURES

FIG. 16. $^1$H-NMR spectra of DNA incubated with ligands. [DMZ] or [Triazene-1]=150 µM, [DNA]=300 µM (ratio Ligand:DNA=0.5:1), D$_2$O=10%, Buffer=10 mM K-phosphate Buffer (pH 7.5), [NaCl]=137 mM, [EDTA]=1 mM. The ligand was incubated with DNA for 2 hr at 4° C. before measurement. (A) DNA=c-kit1. (B) DNA=8 bp AT.

DESCRIPTION OF THE DISCLOSURE

Figure 1:
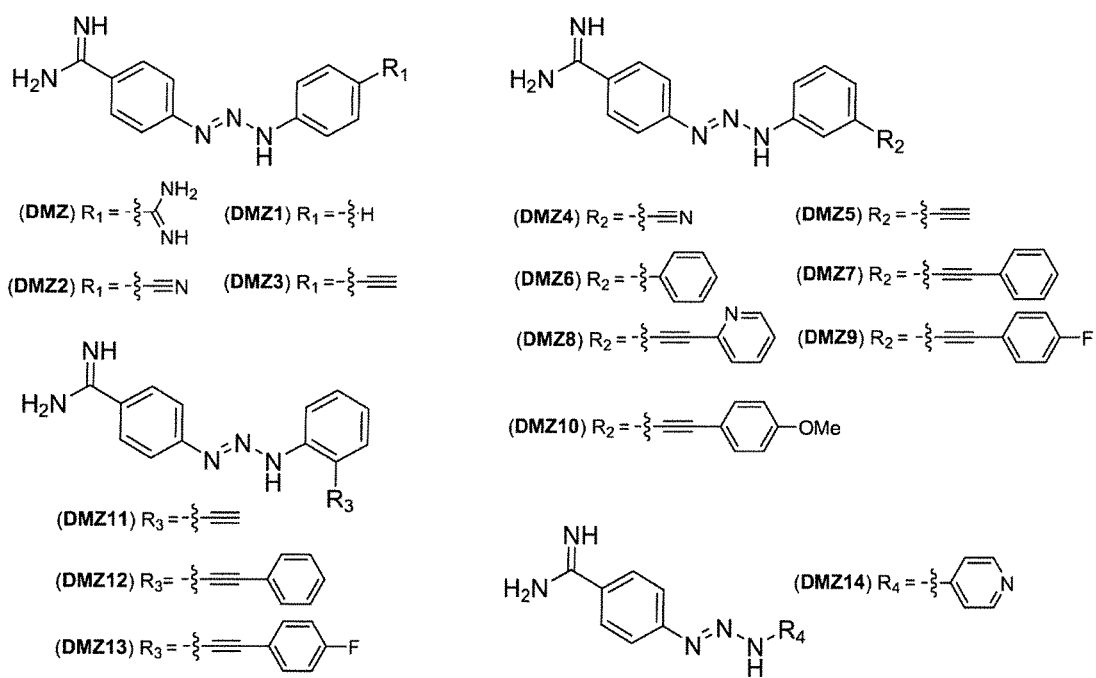
FIG. 1. The structures of diminazene (DMZ) analogues.
Figure 2:
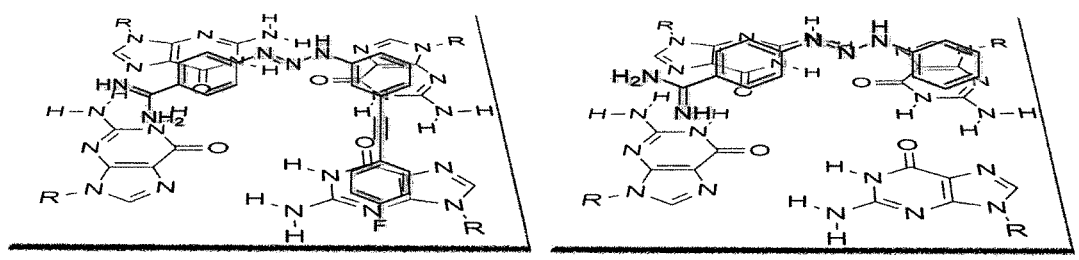
FIG. 2. Chemical structures of DMZ1 and DMZ9 in comparison to a chemical representation of a G-quartet.

The present disclosure provides linked diaryl compounds, and compositions comprising the compounds. The present disclosure also provides methods of using the compounds.

As used herein, the term "alkyl group," unless otherwise stated, refers to branched or unbranched hydrocarbons. Examples of such alkyl groups include methyl groups, ethyl groups, propyl groups, butyl groups, isopropyl groups, tert-butyl groups, and the like. For example, the alkyl group can be a $C_1$-$C_{14}$ alkyl group including all integer numbers of carbons and ranges of numbers of carbons there between. The alkyl group can be unsubstituted or substituted with various substituents (e.g., as described herein).

As used herein, the term "alkylene," or "alkenyl," unless otherwise stated refers to an alkyl group, as defined, containing one or more double bonds.

As used herein, the term "alkylyne," or "alkynyl," unless otherwise stated refers to an alkyl group, as defined, containing one or more triple bonds.

As used herein, the term "aryl group," unless otherwise stated refers to a $C_5$-$C_{14}$ aromatic carbocyclic group. The aryl group can be monocyclic, bicyclic or tricyclic. The aryl group can be unsubstituted or substituted with various substituents (e.g., as described herein) which may be the same or different. Non-limiting examples of suitable aryl groups include phenyl and napthyl.

As used herein, the term "cycloalkyl group," unless otherwise stated, refers to a to a saturated or partially unsaturated carbocyclic group (not aromatic) of from 3 carbons to 8 carbons having a single cyclic ring or multiple condensed rings. For example, the cycloalkyl groups can be cyclopropane, cyclobutane, cyclopentane, cyclohexane, cyclohexene, cycloheptane, cycloheptene, bicyclo[2.1.1]hexane, bicyclo[2.2.1]heptane, bicyclo[2.2.2]octane, bicyclo[3.3.0]octane, bicyclo[4.4.0]octane, and the like. Cycloalkyl also includes carbocyclic groups to which is fused an aryl or heteroaryl ring, for example indane and tetrahydronaphthalene. The cycloalkyl group can be unsubstituted or substituted with various substituents (e.g., as described herein).

As used herein, unless otherwise indicated, halogen means fluorine, chlorine, bromine, and iodine, and halo means fluoro, chloro, bromo and iodo.

As used herein, the term "heteroalkyl," unless otherwise stated, refers to a linear or branched-chain $C_1$-$C_{14}$ alkyl group, of which one or more carbons have been replaced by a heteroatom selected from the group consisting of S, O, P, B, and N. The heteroalkyl group can be unsubstituted or substituted with various substituents (e.g., as described herein) which may be the same or different. Examples of heteroalkyl groups include, but are not limited to, alkyl amines, alkyl ethers, amides, and alkyl sulfides.

As used herein, the term "heteroalkenyl," or "heteroalkylene," unless otherwise stated, refers to a linear or branched-chain $C_1$-$C_{14}$ alkyl group, containing one or more double bonds, of which one or more carbons have been replaced by a heteroatom selected from the group consisting of S, O, P, B, and N. The heteroalkenyl group can be unsubstituted or substituted with various substituents (e.g., as described herein) which may be the same or different. Examples of heteroalkyl groups include, but are not limited to, alkyl amines, alkyl ethers, amides, and alkyl sulfides.

As used herein, the term "heteroalkynyl," unless otherwise stated, refers to a linear or branched-chain $C_1$-$C_{14}$ alkyl group, containing one or more triple bonds, of which one or more carbons have been replaced by a heteroatom selected from the group consisting of S, O, P, B, and N. The heteroalkynyl group can be unsubstituted or substituted with various substituents (e.g., as described herein) which may be the same or different. Examples of heteroalkyl groups include, but are not limited to, alkyl amines, alkyl ethers, amides, and alkyl sulfides.

As used herein, the term "heteroaryl," unless otherwise stated, refers to a $C_5$-$C_{14}$ monocyclic, bicyclic, or tricyclic, ring system wherein 1-8 of the ring atoms are selected from the group consisting of S, O, P, B, and N. The heteroalkenyl group can be unsubstituted or substituted with various substituents (e.g., as described herein) which may be the same or different. Examples of heteroaryl groups include, benzofuranyl, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl groups.

As used herein, the term "substituents," unless otherwise stated refer to one or more of the following groups: alkyl groups, amines, alcohol groups, alkoxy groups, acyl groups, amidine groups, guanidine groups, halogen atoms, alkylhalides, alkylheteroaryl groups, alkoxy groups, hydroxyl groups, alkylalcohols, alkyl ethers, alkylamides, alkylamines, benzyl groups, ketones, carbamates, PEG (polyethylene glycol) groups, cycloalkyl groups, alkyl esters, heteroaryl groups, heteroalkyl groups, heteroalkylene groups, heteroalkynyl groups, aryl groups, nitriles, azido groups, amides, alkenyl groups, alkynyl groups, thiol groups, heterocyclyl groups, alkyleneheteroaryl groups, alkylaryl groups, alkylenearyl groups, alkylhetrocyclyl groups, alkylenehetrocyclyl groups, alkylcycloalkyl groups, and alkylenecycloalkyl groups.

In an aspect, the present disclosure provides compounds having the general formula: Q-Ar$^1$-L-Ar$^2$. Ar$^1$ is selected from the group consisting of

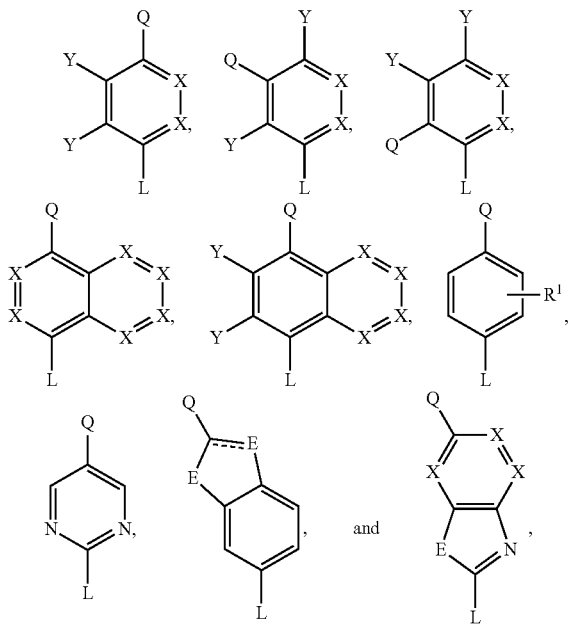

where E is selected from the group consisting of oxygen atom, sulfur atom, —N(R$^1$)—, and —N(OR$^1$)—. X is —N—, or —C(R$^1$)—. Y is selected from the group consisting of —R$^1$, -ER$^1$, —X(R$^1$)$_2$, and -halogen. R$^1$ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

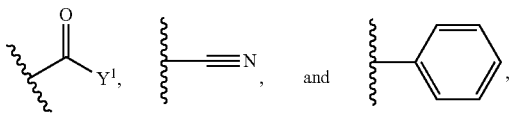

where Y$^1$ is selected from the group consisting of —OR$^1$, —NR$^1$, —SR$^1$, and —R$^1$. Ar$^2$ is selected from the group consisting of

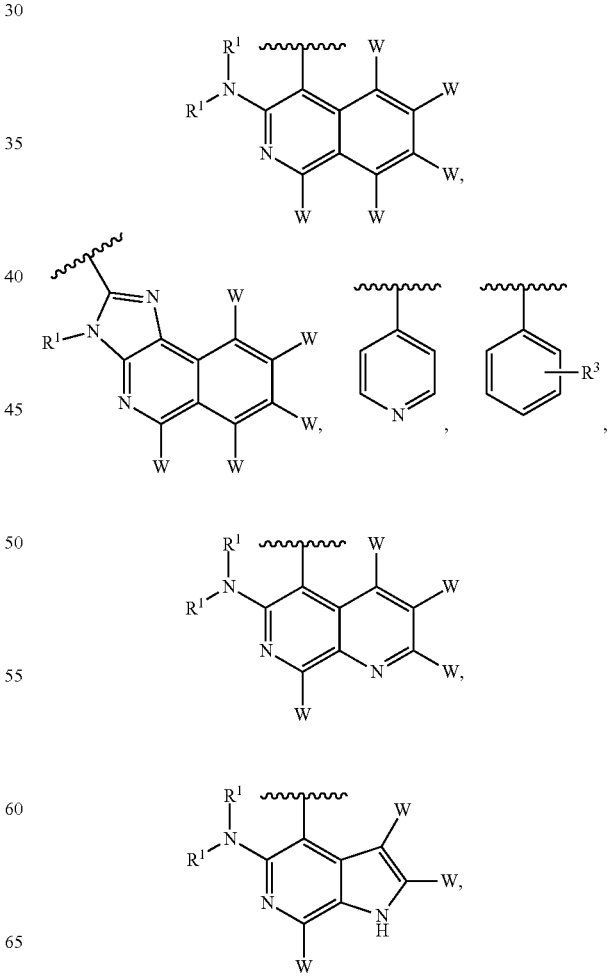

-continued

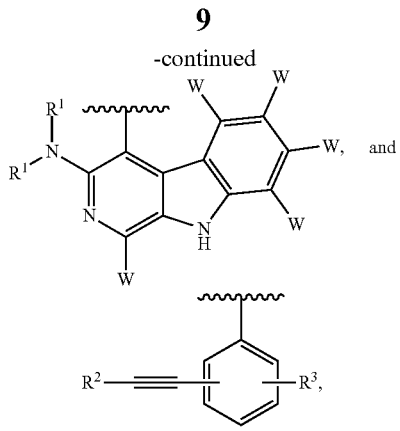

where $R^2$ is selected from the group consisting of H, $R^1$

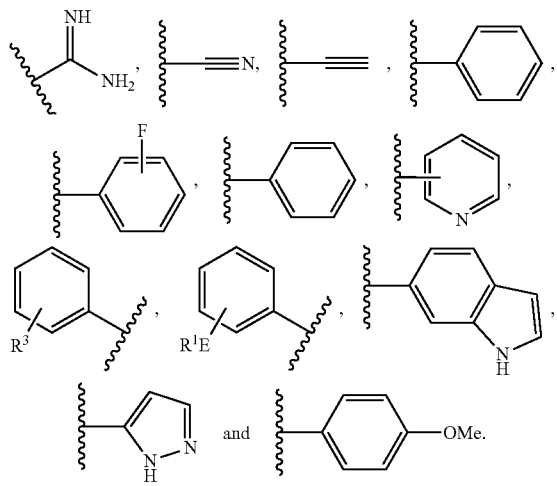

$R^3$ is selected from the group consisting —$R^1$, -halogen, -$ER^1$,

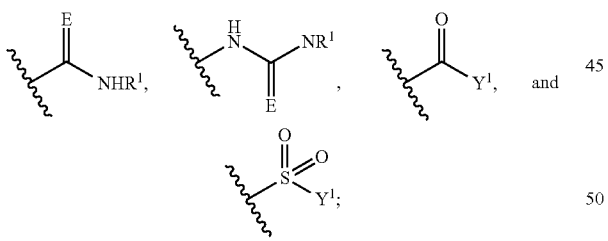

and W is selected from the group consisting of —$R^1$, —$OR^1$, —$N(R^1)_2$, —$NO_2$, -halogen,

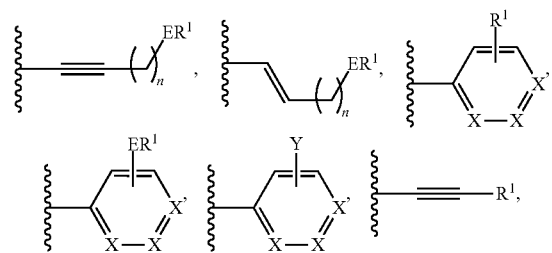

-continued

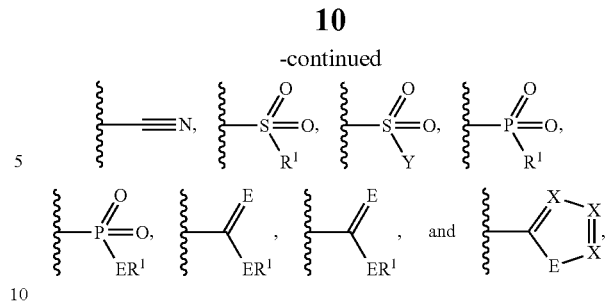

where n is 0-6. L is selected from the group consisting of direct covalent bond, —O—, —NH—, —O—$(CH_2)_m$—O—, —NH—$(CH_2)_m$—NH—,

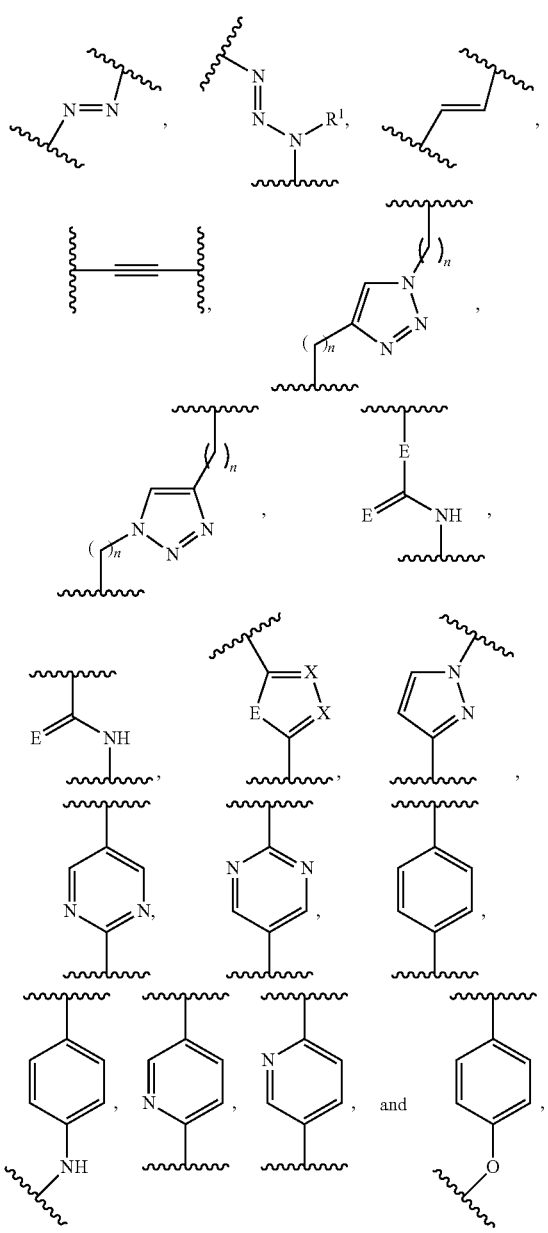

where m is 2-6. Q is selected from the group consisting of —OH, —SH, —$NR^1$,

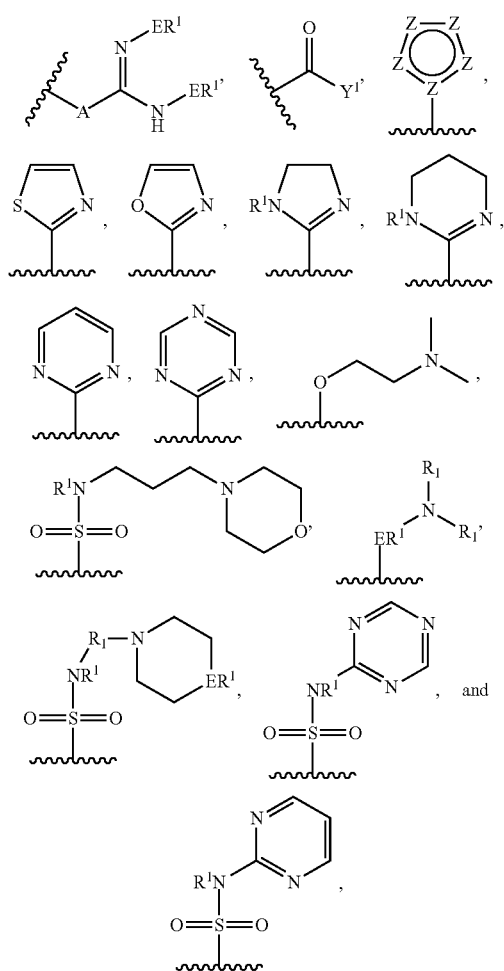
where A is selected from the group consisting of direct covalent bond, —SO$_2$—NH—, —NH—. Z is selected from the group consisting of —S—, —O—, -ER$^1$—, —CH, —N—, —NH—, —N$^+$(R$^1$)—, and —N(R$^1$)—. If L is
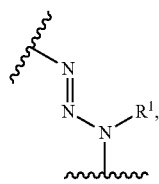
then Ar$^1$ is
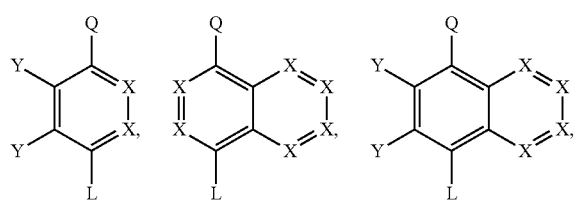
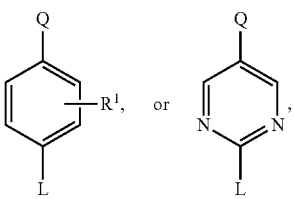
Ar$^2$ is
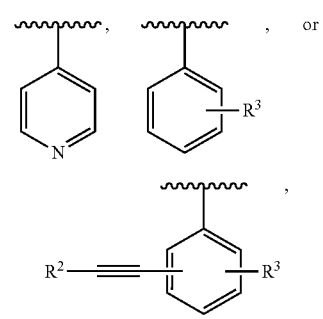
and Q is
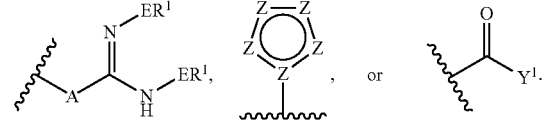
In an embodiment, the compound is not
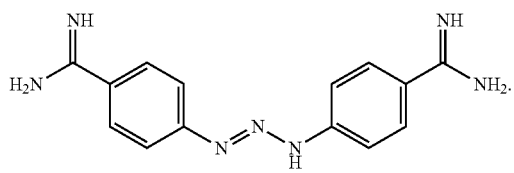 [SMILES: N=C(N)c1ccc(/N=N/Nc2ccc(C(=N)N)cc2)cc1]
In an embodiment, Ar$^1$ is selected from the group consisting of
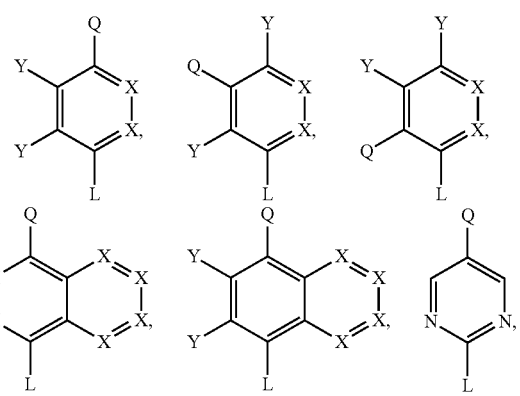

-continued

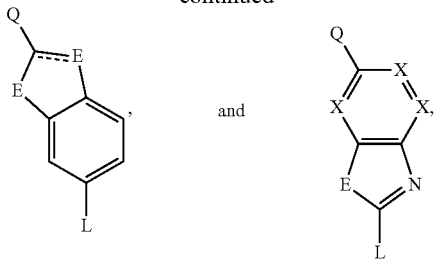

and

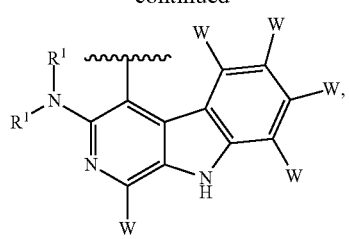

where E is selected from the group consisting of oxygen atom, sulfur atom, —N(R¹)—, and —N(OR¹)—. X is —N—, or —C(R¹)—. Y is selected from the group consisting of —R¹, -ER¹, —X(R¹)$_2$, and -halogen, where R¹ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

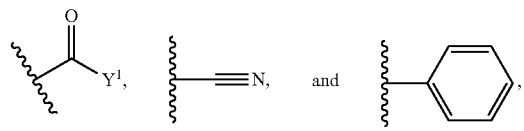

where Y¹ is selected from the group consisting of —OR¹, —NR¹, —SR¹, and —R¹. Ar² is selected from the group consisting of

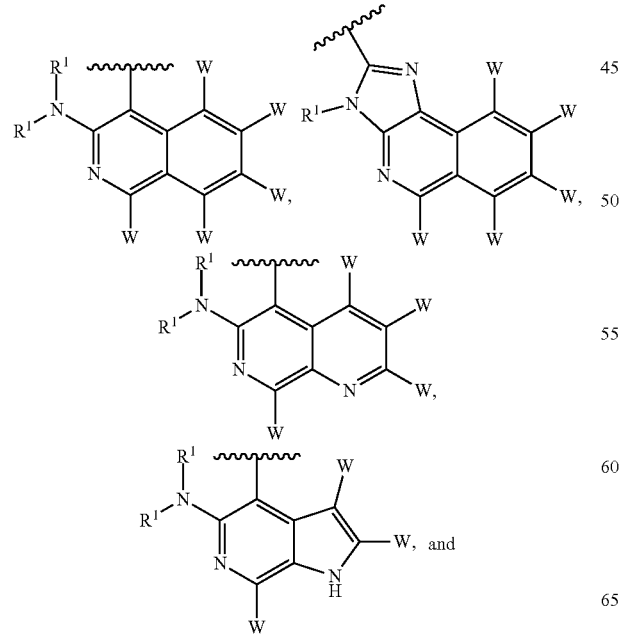

where W is selected from the group consisting of —R¹, —OR¹, —N(R¹)$_2$, —NO$_2$, -halogen,

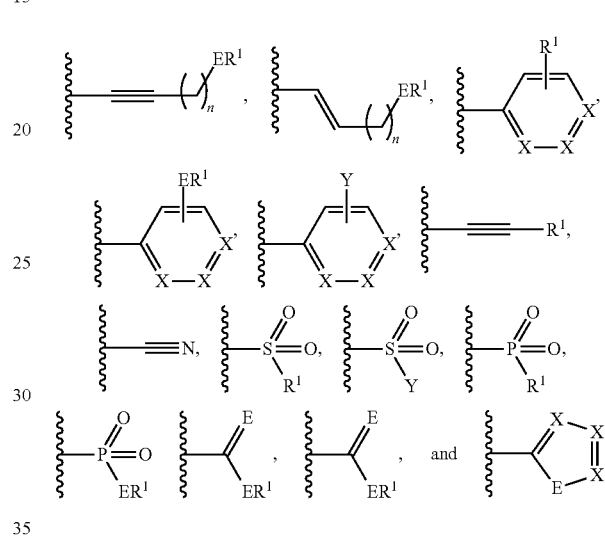

where n is 0-6. L is selected from the group consisting of direct bond, —O—, —NH—, —O—(CH$_2$)$_m$—O—, —NH—(CH$_2$)$_m$—NH—,

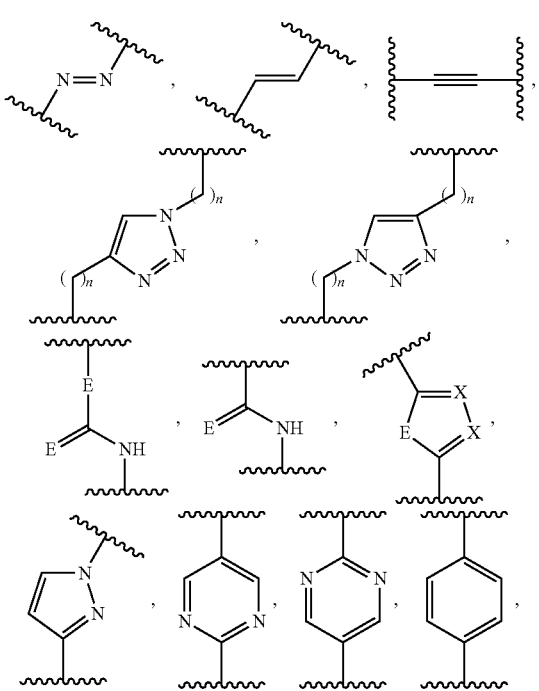

-continued

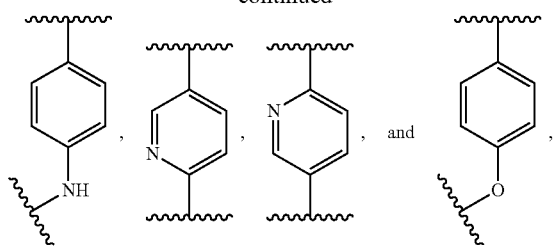

where m is 2-6. Q is selected from the group consisting of —OH, —SH, —NR$^1$,

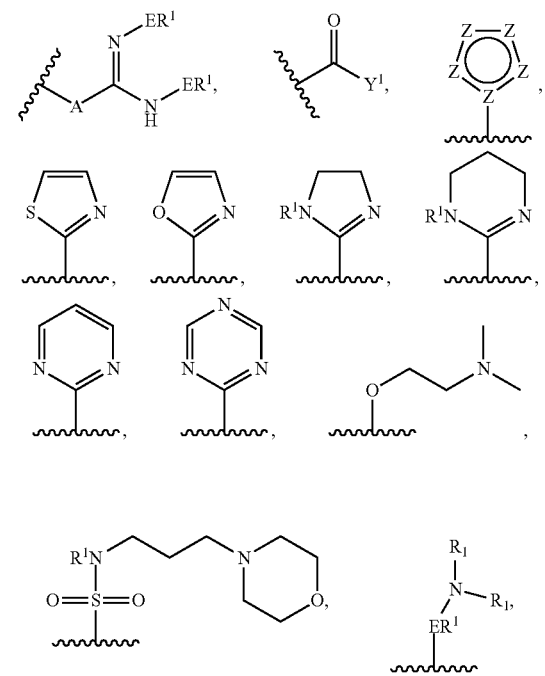

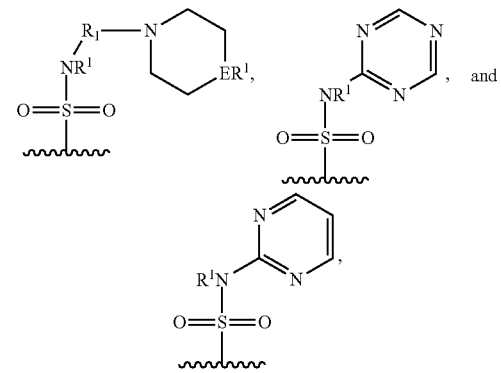

where A is selected from the group consisting of direct covalent bond, —SO$_2$—NH—, and —NH—. Z is selected from the group consisting of —S—, —O—, -ER$^1$—, —CH, —N—, —NH—, —N$^+$(R$^1$)—, and —N(R$^1$)—.

In an embodiment, the compound has the following general formula:

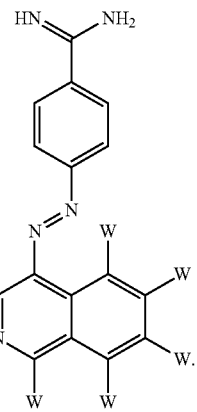

W is selected from the group consisting of —R$^1$, —OR$^1$, —N(R$^1$)$_2$, —NO$_2$, -halogen,

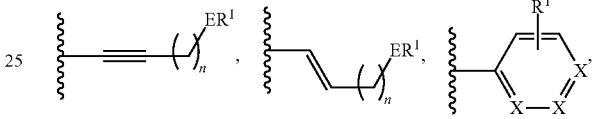

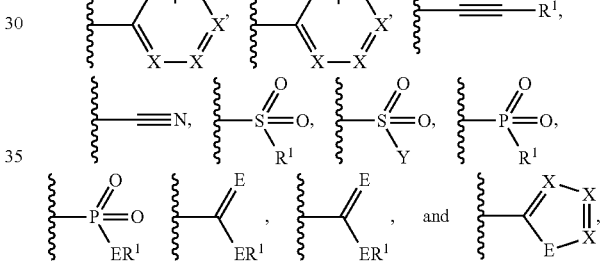

where E is selected from the group consisting of oxygen atom, sulfur atom, —N(R$^1$)—, and —N(OR$^1$)—. X is —N—, or —C(R$^1$)—. Y is selected from the group consisting of —R$^1$, -ER$^1$, —X(R$^1$)$_2$, and -halogen. R$^1$ is selected from the group consisting of H, substituted or unsubstituted C$_1$-C$_{14}$ alkyl, substituted or unsubstituted C$_1$-C$_{14}$ heteroalkyl, where 1-7 of the chain atoms are independently O, N, S, P, or B, substituted or unsubstituted C$_1$-C$_{14}$ alkenyl, substituted or unsubstituted C$_1$-C$_{14}$ heteroalkenyl, where 1-7 of the chain atoms are independently O, N, S, P, or B, substituted or unsubstituted C$_1$-C$_{14}$ alkynyl, substituted or unsubstituted C$_1$-C$_{14}$ heteroalkynyl, where 1-7 of the chain atoms are independently O, N, S, P, or B, substituted or unsubstituted C$_5$-C$_{14}$ aryl, halo, heteroaryl having 5-14 ring atoms, where 1-8 of the ring atoms are independently O, N, S, P, or B,

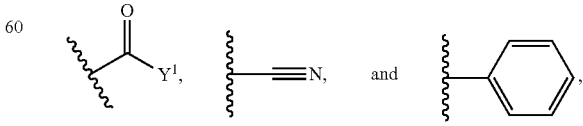

where n is 0-6. Y$^1$ is selected from the group consisting of —OR$^1$, —NR$^1$, —SR$^1$, and —R$^1$.

In an embodiment, the compound has the following general formula:

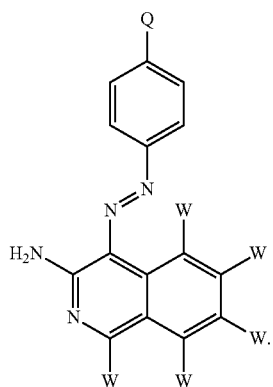

Q is selected from the group consisting of —OH, —SH, —NR$^1$,

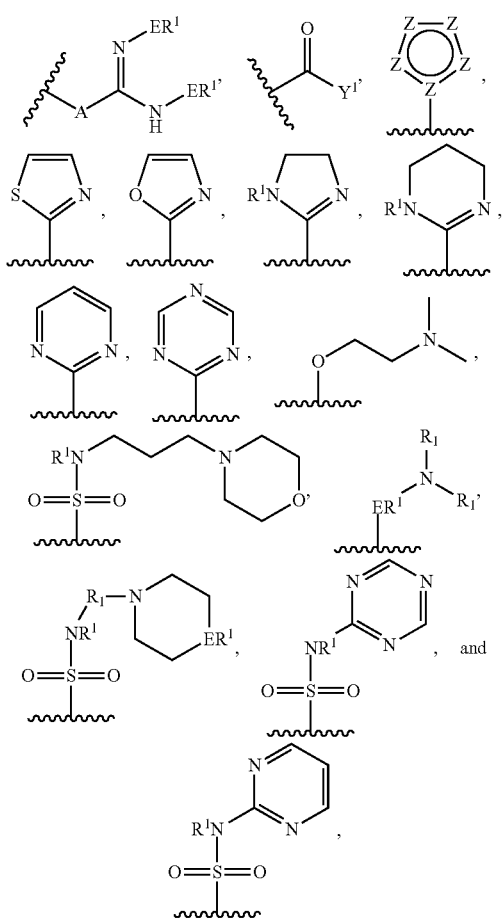

where E is selected from the group consisting of oxygen atom, sulfur atom, —N(R$^1$)—, and —N(OR$^1$)—. R$^1$ is selected from the group consisting of H, substituted or unsubstituted C$_1$-C$_{14}$ alkyl, substituted or unsubstituted C$_1$-C$_{14}$ heteroalkyl, where 1-7 of the chain atoms are independently O, N, S, P, or B, substituted or unsubstituted C$_1$-C$_{14}$ alkenyl, substituted or unsubstituted C$_1$-C$_{14}$ heteroalkenyl, where 1-7 of the chain atoms are independently O, N, S, P, or B, substituted or unsubstituted C$_1$-C$_{14}$ alkynyl, substituted or unsubstituted C$_1$-C$_{14}$ heteroalkynyl, where 1-7 of the chain atoms are independently O, N, S, P, or B, substituted or unsubstituted C$_5$-C$_{14}$ aryl, halo, heteroaryl having 5-14 ring atoms, where 1-8 of the ring atoms are independently O, N, S, P, or B,

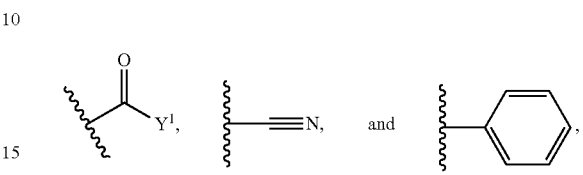

where Y$^1$ is selected from the group consisting of —OR$^1$, —NR$^1$, —SR$^1$, and —R$^1$. A is selected from the group consisting of direct covalent bond, —SO$_2$—NH—, —NH—. Z is selected from the group consisting of —S—, —O—, -ER$^1$—, —CH, —N—, —NH—, —N$^+$(R$^1$)—, and —N(R$^1$)—. W is selected from the group consisting of —R$^1$, —OR$^1$, —N(R$^1$)$_2$, —NO$_2$, -halogen,

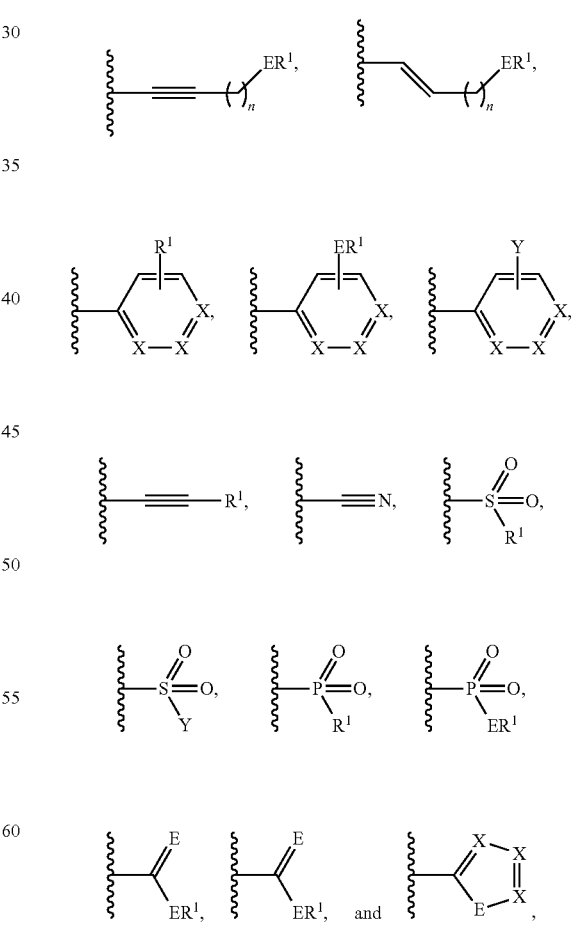

where X is —N—, or —C(R$^1$)—. Y is selected from the group consisting of —R$^1$, -ER$^1$, —X(R$^1$)$_2$, and -halogen.

In an embodiment, the compound has following general formula:

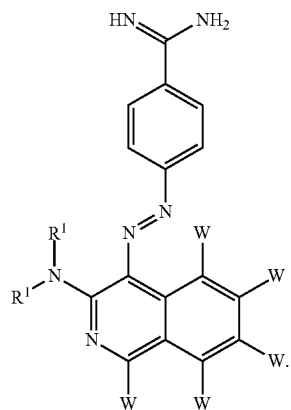

R¹ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

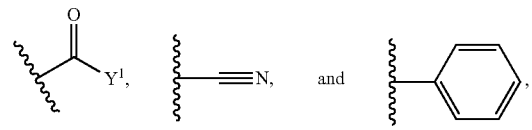

where $Y^1$ is selected from the group consisting of —OR¹, —NR¹, —SR¹, and —R¹. W is selected from the group consisting of —R¹, —OR¹, —N(R¹)₂, —NO₂, -halogen,

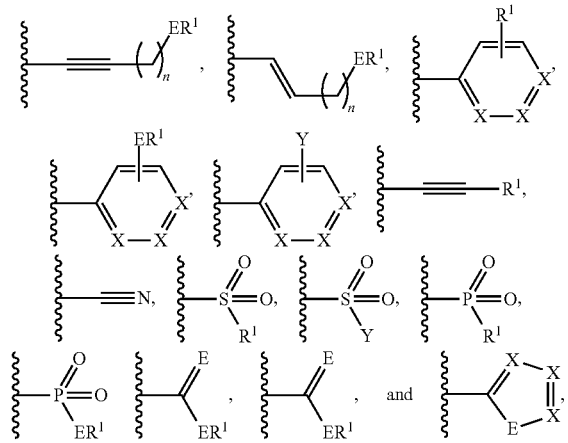

where E is selected from the group consisting of oxygen atom, sulfur atom, —N(R¹)—, and —N(OR¹)—. X is —N—, or —C(R¹)—. Y is selected from the group consisting of —R¹, -ER¹, —X(R¹)₂, and -halogen.

In an embodiment, the compound has the following general formula:

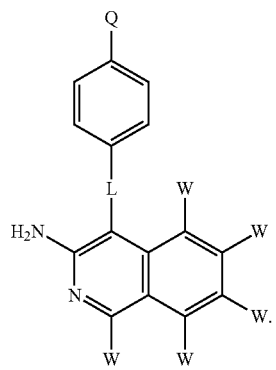

W is selected from the group consisting of —R¹, —OR¹, —N(R¹)₂, —NO₂, -halogen,

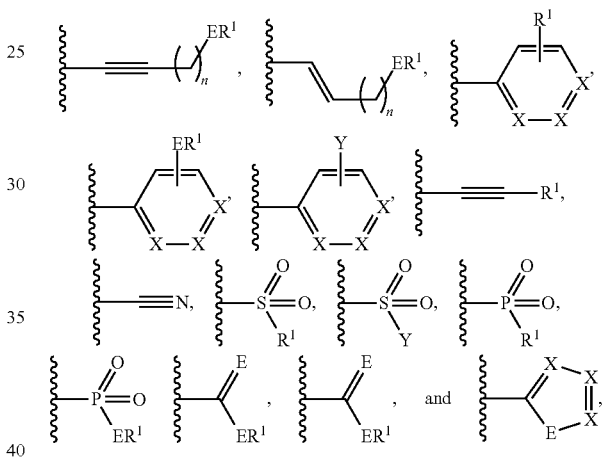

where E is selected from the group consisting of oxygen atom, sulfur atom, —N(R¹)—, and —N(OR¹)—. X is —N—, or —C(R¹)—. Y is selected from the group consisting of —R¹, -ER¹, —X(R¹)₂, and -halogen, where n is 0-6. R¹ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

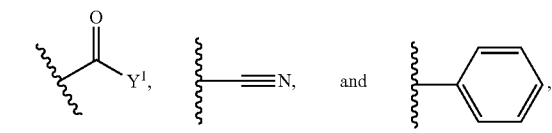

where $Y^1$ is selected from the group consisting of —OR¹, —NR¹, —SR¹, and —R¹. L is selected from the group consisting of direct bond, —O—, —NH—, —O—(CH$_2$)$_m$—O—, —NH—(CH$_2$)$_m$—NH—,

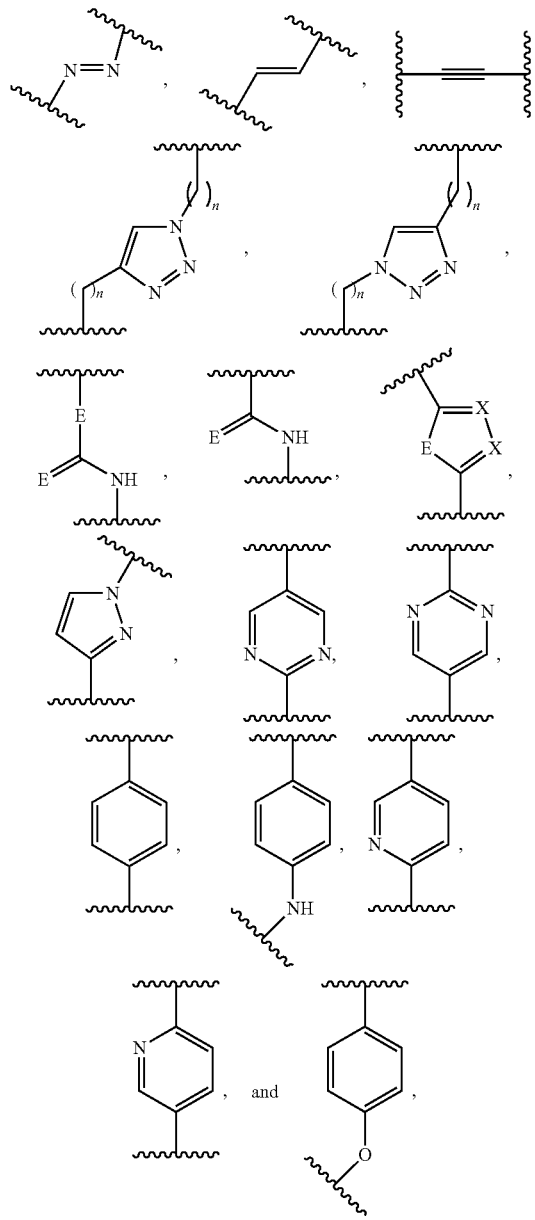

where m is 2-6. Q is selected from the group consisting of —OH, —SH, —NR$^1$,

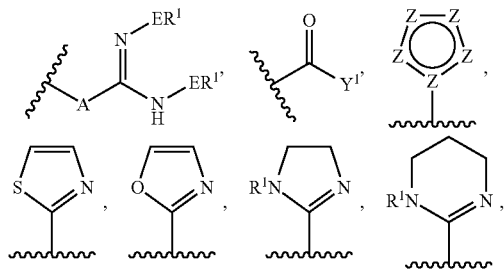

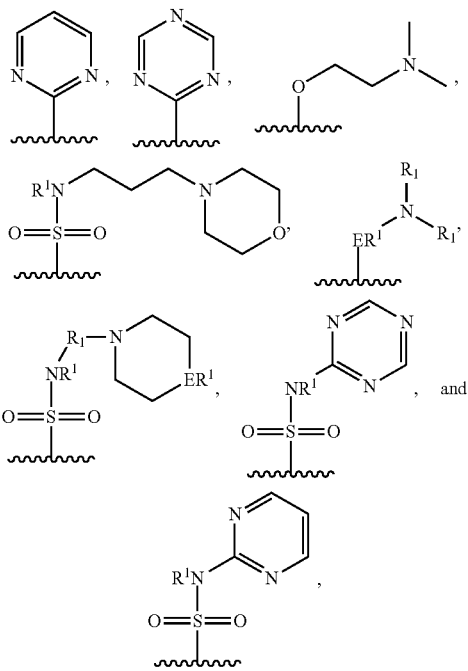

where A is selected from the group consisting of direct covalent bond, —SO$_2$—NH—, —NH—. Z is selected from the group consisting of —S—, —O—, -ER$^1$—, —CH, —N—, —NH—, —N$^+$(R$^1$)—, and —N(R$^1$)—.

In an embodiment, the compound has following general formula:

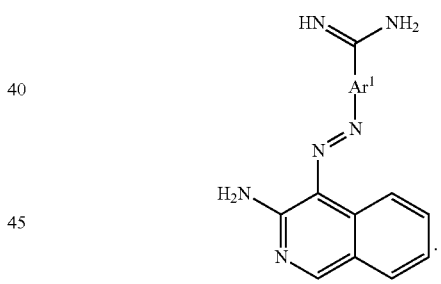

Ar$^1$ is selected from the group consisting of

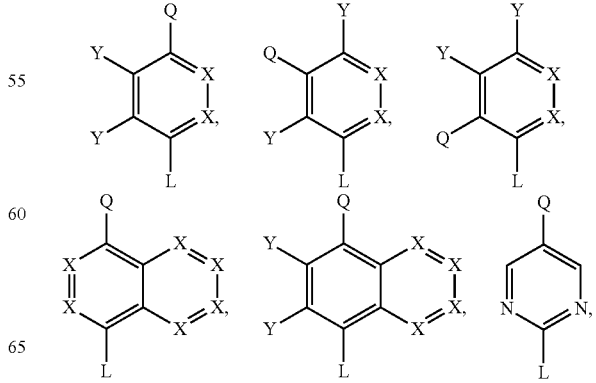

-continued

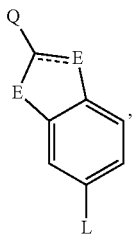 and 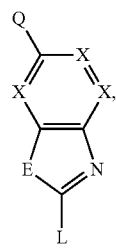

where E is selected from the group consisting of oxygen atom, sulfur atom, —N(R$^1$)—, and —N(OR$^1$)—. X is —N—, or —C(R$^1$)—. Y is selected from the group consisting of —R$^1$, -ER$^1$, —X(R$^1$)$_2$, and -halogen, where R$^1$ is selected from the group consisting of H, substituted or unsubstituted C$_1$-C$_{14}$ alkyl, substituted or unsubstituted C$_1$-C$_{14}$ heteroalkyl, where 1-7 of the chain atoms are independently O, N, S, P, or B, substituted or unsubstituted C$_1$-C$_{14}$ alkenyl, substituted or unsubstituted C$_1$-C$_{14}$ heteroalkenyl, where 1-7 of the chain atoms are independently O, N, S, P, or B, substituted or unsubstituted C$_1$-C$_{14}$ alkynyl, substituted or unsubstituted C$_1$-C$_{14}$ heteroalkynyl, where 1-7 of the chain atoms are independently O, N, S, P, or B, substituted or unsubstituted C$_5$-C$_{14}$ aryl, halo, heteroaryl having 5-14 ring atoms, where 1-8 of the ring atoms are independently O, N, S, P, or B,

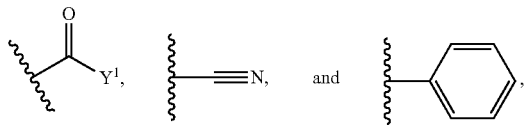

where Y$^1$ is selected from the group consisting of —OR$^1$, —NR$^1$, —SR$^1$, and —R$^1$.

In an embodiment, the compound has the following general formula: Q-Ar$^1$-L-Ar$^2$. Ar$^1$ is selected from the group consisting of

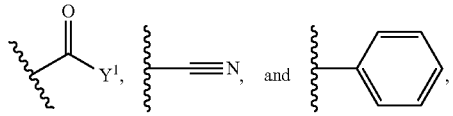

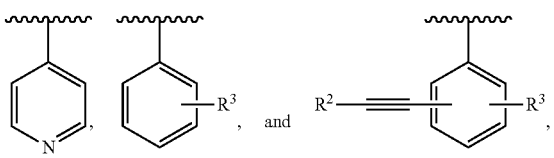

where X is —N—, or —C(R$^1$)—. Y is selected from the group consisting of —R$^1$, -ER$^1$, —X(R$^1$)$_2$, and -halogen. R$^1$ is selected from the group consisting of H, substituted or unsubstituted C$_1$-C$_{14}$ alkyl, substituted or unsubstituted C$_1$-C$_{14}$ heteroalkyl, where 1-7 of the chain atoms are independently O, N, S, P, or B, substituted or unsubstituted C$_1$-C$_{14}$ alkenyl, substituted or unsubstituted C$_1$-C$_{14}$ heteroalkenyl, where 1-7 of the chain atoms are independently O, N, S, P, or B, substituted or unsubstituted C$_1$-C$_{14}$ alkynyl, substituted or unsubstituted C$_1$-C$_{14}$ heteroalkynyl, where 1-7 of the chain atoms are independently O, N, S, P, or B, substituted or unsubstituted C$_5$-C$_{14}$ aryl, halo, heteroaryl having 5-14 ring atoms, where 1-8 of the ring atoms are independently O, N, S, P, or B,

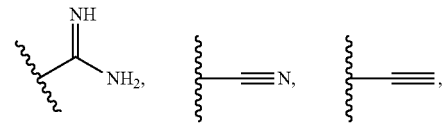

where Y$^1$ is selected from the group consisting of —OR$^1$, —NR$^1$, —SR$^1$, and —R$^1$. Ar$^2$ is selected from the group consisting of

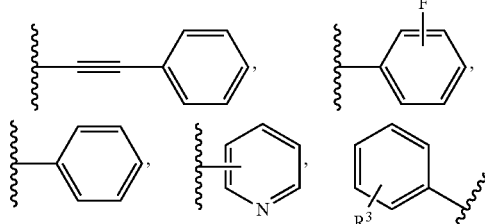

where R$^2$ is selected from the group consisting of H, R$^1$

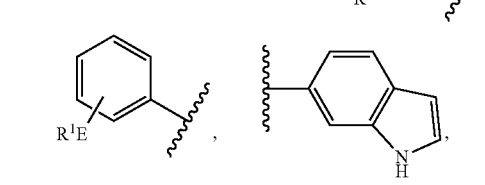

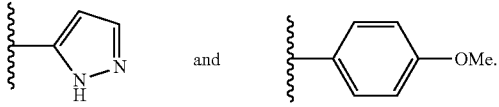

R$^3$ is selected from the group consisting —R$^1$, -halogen, -ER$^1$,

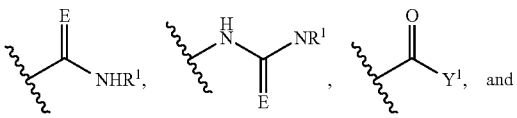

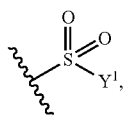

where E is selected from the group consisting of oxygen atom, sulfur atom, —N(R$^1$)—, and —N(OR$^1$)—. L is

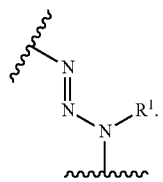

Q is

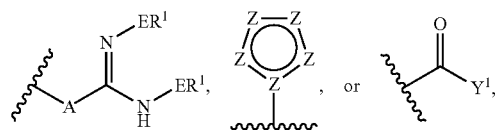

where A is selected from the group consisting of a direct covalent bond, —SO$_2$—NH—, and —NH—. Z is selected from the group consisting of —S—, —O—, -ER$^1$—, —CH, —N—, —NH—, N$^+$(R$^1$)—, and —N(R$^1$)—.

In an embodiment, the compound has the following general formula:

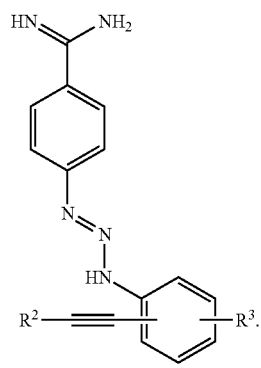

R$^2$ is selected from the group consisting of H, R$^1$

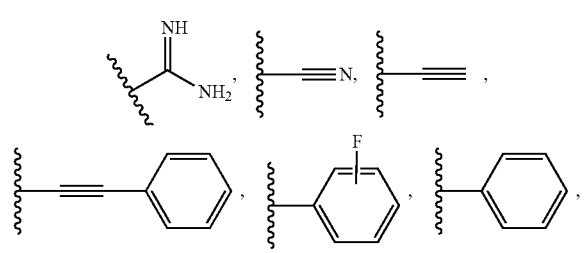

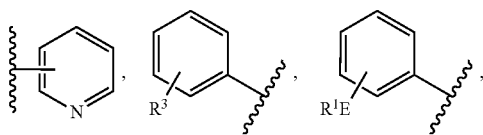

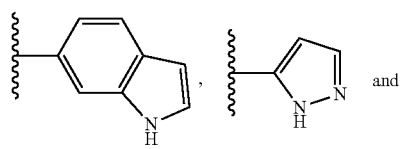

R$^3$ is selected from the group consisting —R$^1$, -halogen, -ER$^1$,

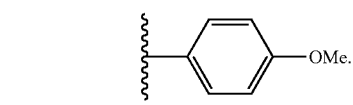

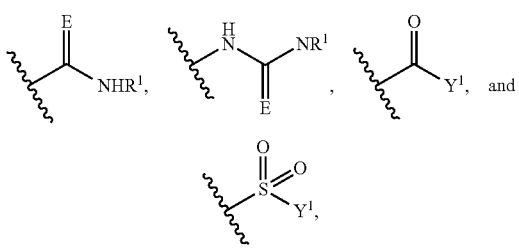

where R$^1$ is selected from the group consisting of H, substituted or unsubstituted C$_1$-C$_{14}$ alkyl, substituted or unsubstituted C$_1$-C$_{14}$ heteroalkyl, where 1-7 of the chain atoms are independently O, N, S, P, or B, substituted or unsubstituted C$_1$-C$_{14}$ alkenyl, substituted or unsubstituted C$_1$-C$_{14}$ heteroalkenyl, where 1-7 of the chain atoms are independently O, N, S, P, or B, substituted or unsubstituted C$_1$-C$_{14}$ alkynyl, substituted or unsubstituted C$_1$-C$_{14}$ heteroalkynyl, where 1-7 of the chain atoms are independently O, N, S, P, or B, substituted or unsubstituted C$_5$-C$_{14}$ aryl, halo, heteroaryl having 5-14 ring atoms, where 1-8 of the ring atoms are independently O, N, S, P, or B,

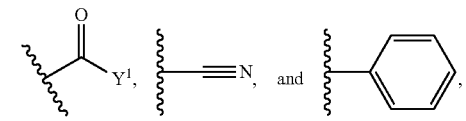

where Y$^1$ is selected from the group consisting of —OR$^1$, —NR$^1$, —SR$^1$, and —R$^1$; E is selected from the group consisting of oxygen atom, sulfur atom, —N(R$^1$)—, and —N(OR$^1$)—.

In an embodiment, the compound has the following general formula:

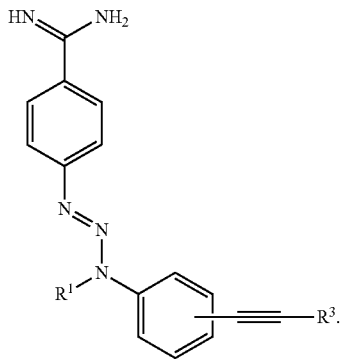

$R^1$ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

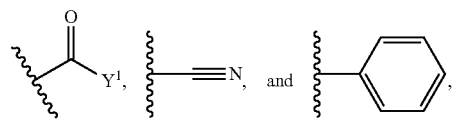

where $Y^1$ is selected from the group consisting of —$OR^1$, —$NR^1$, —$SR^1$, and —$R^1$. E is selected from the group consisting of oxygen atom, sulfur atom, —N($R^1$)—, and —N($OR^1$)—. $R^3$ is selected from the group consisting —$R^1$, -halogen, -$ER^1$,

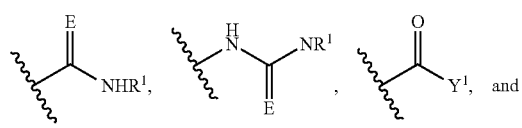

In an embodiment, the compound has the following general formula:

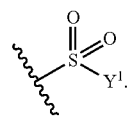

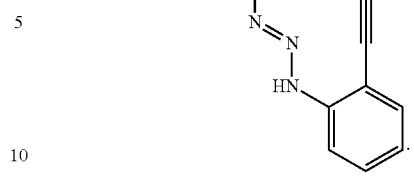

$Ar^1$ is selected from the group consisting of

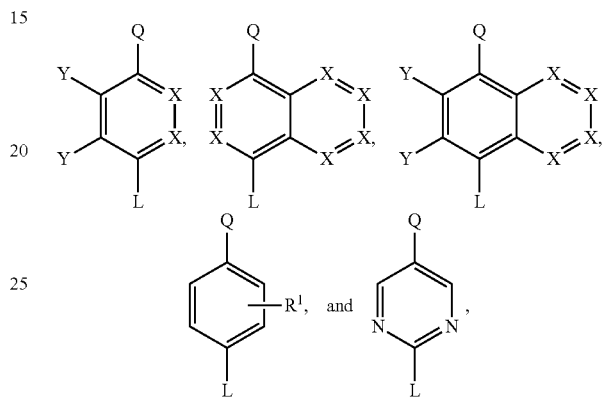

where X is —N—, or —C($R^1$)—. Y is selected from the group consisting of —$R^1$—, -$ER^1$, —X($R^1$)$_2$, and -halogen. $R^1$ is selected from the group consisting of H, substituted or unsubstituted $C_1$-$C_{14}$ alkyl, substituted or unsubstituted $C_1$-$C_{14}$ heteroalkyl, where 1-7 of the chain atoms are independently O, N, S, P, or B, substituted or unsubstituted $C_1$-$C_{14}$ alkenyl, substituted or unsubstituted $C_1$-$C_{14}$ heteroalkenyl, where 1-7 of the chain atoms are independently O, N, S, P, or B, substituted or unsubstituted $C_1$-$C_{14}$ alkynyl, substituted or unsubstituted $C_1$-$C_{14}$ heteroalkynyl, where 1-7 of the chain atoms are independently O, N, S, P, or B, substituted or unsubstituted $C_5$-$C_{14}$ aryl, halo, heteroaryl having 5-14 ring atoms, where 1-8 of the ring atoms are independently O, N, S, P, or B,

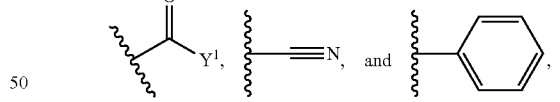

where $Y^1$ is selected from the group consisting of —$OR^1$, —$NR^1$, —$SR^1$, and —$R^1$. Q is

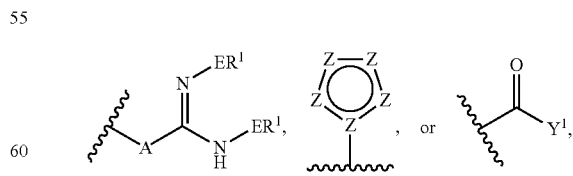

where A is selected from the group consisting of a direct covalent bond, —$SO_2$—NH—, and —NH—. Z is selected from the group consisting of —S—, —O—, -$ER^1$—, —CH, —N—, —NH—, —$N^+(R^1)$—, and —N($R^1$)—. $R^2$ is selected from the group consisting of H, $R^1$

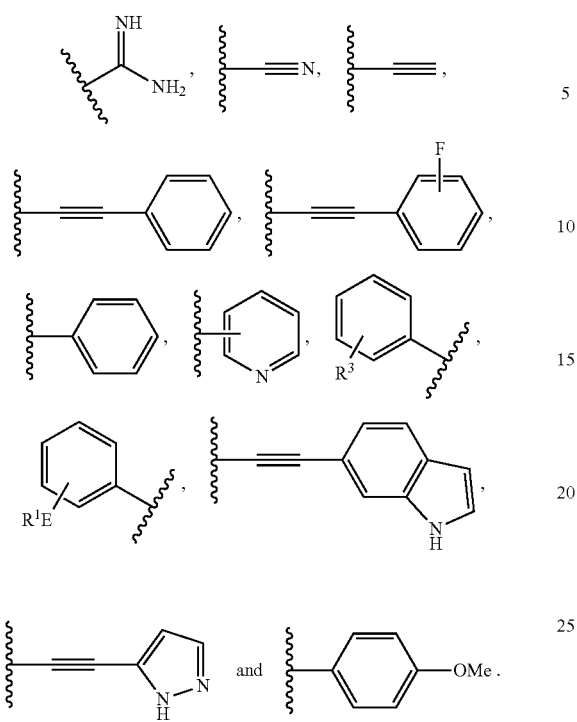
In an embodiment, the compound is selected from the group consisting of the following compounds:
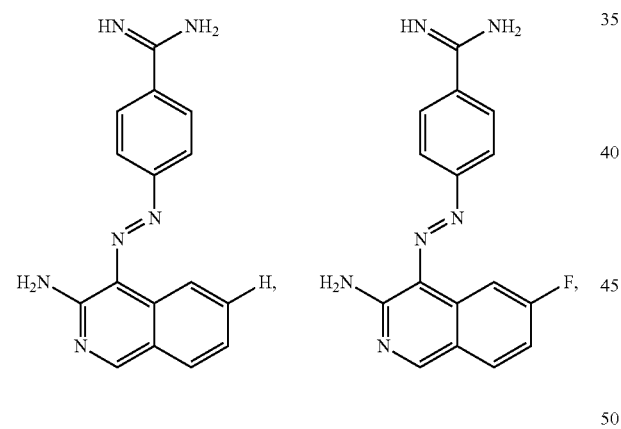
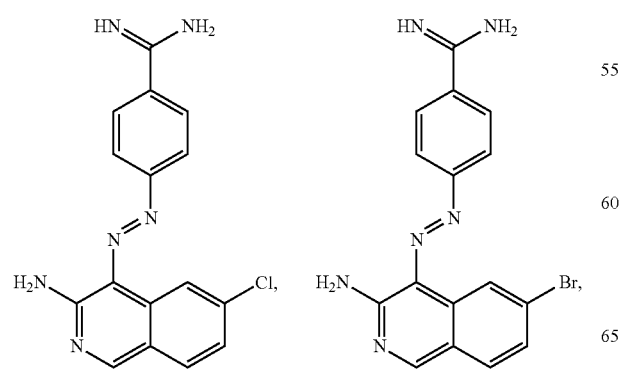
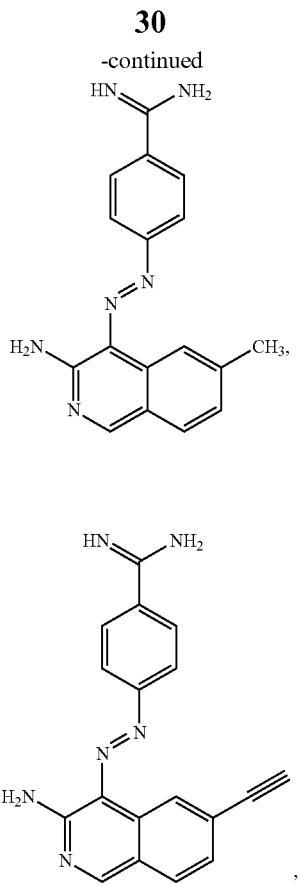
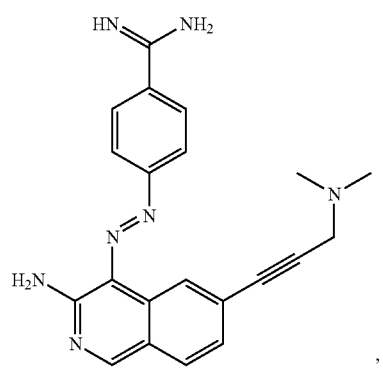
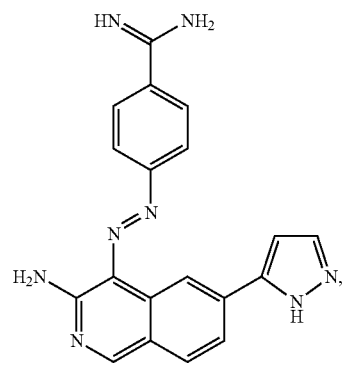

-continued
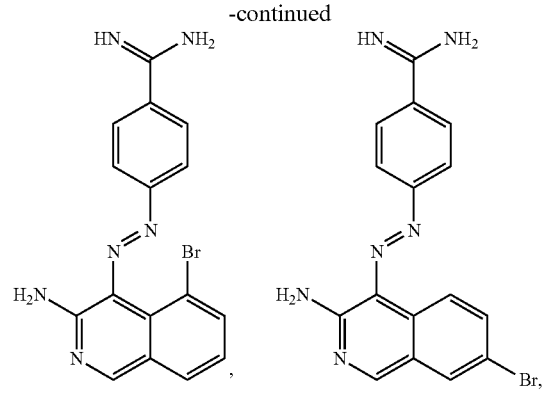
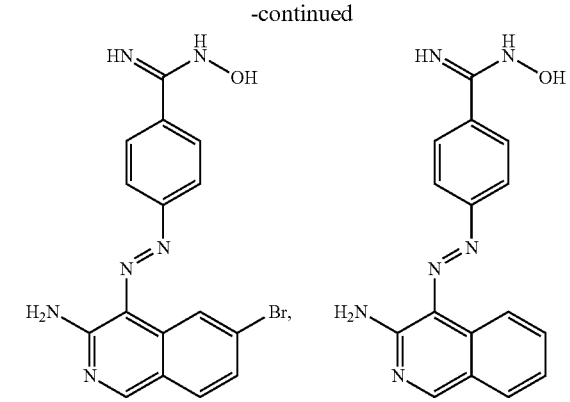
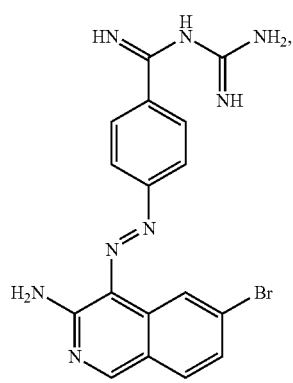
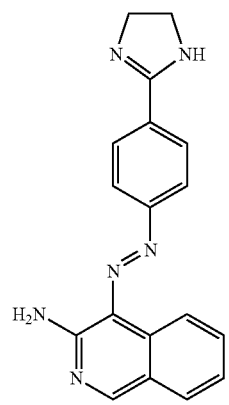
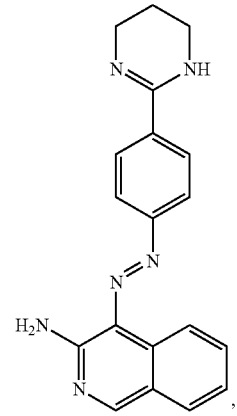
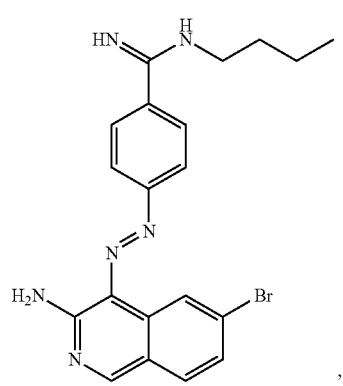
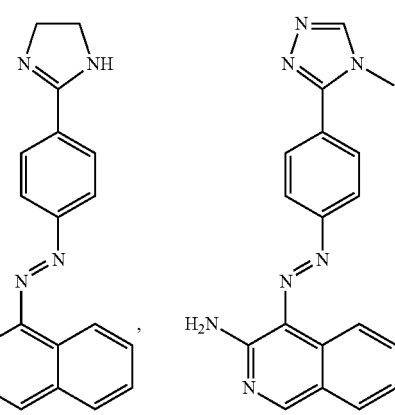
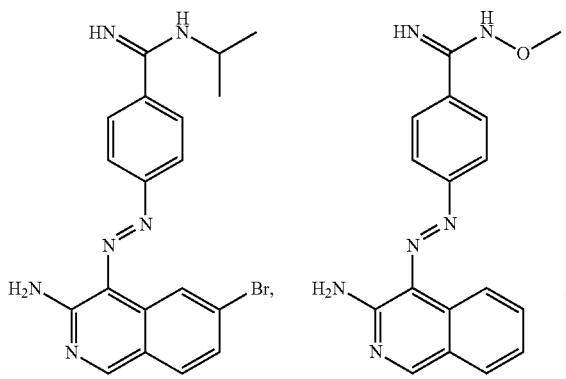
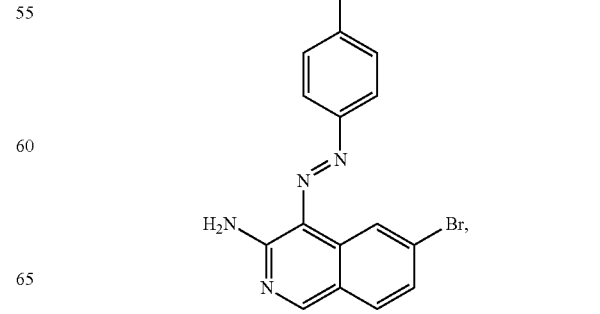

33
-continued
34
-continued
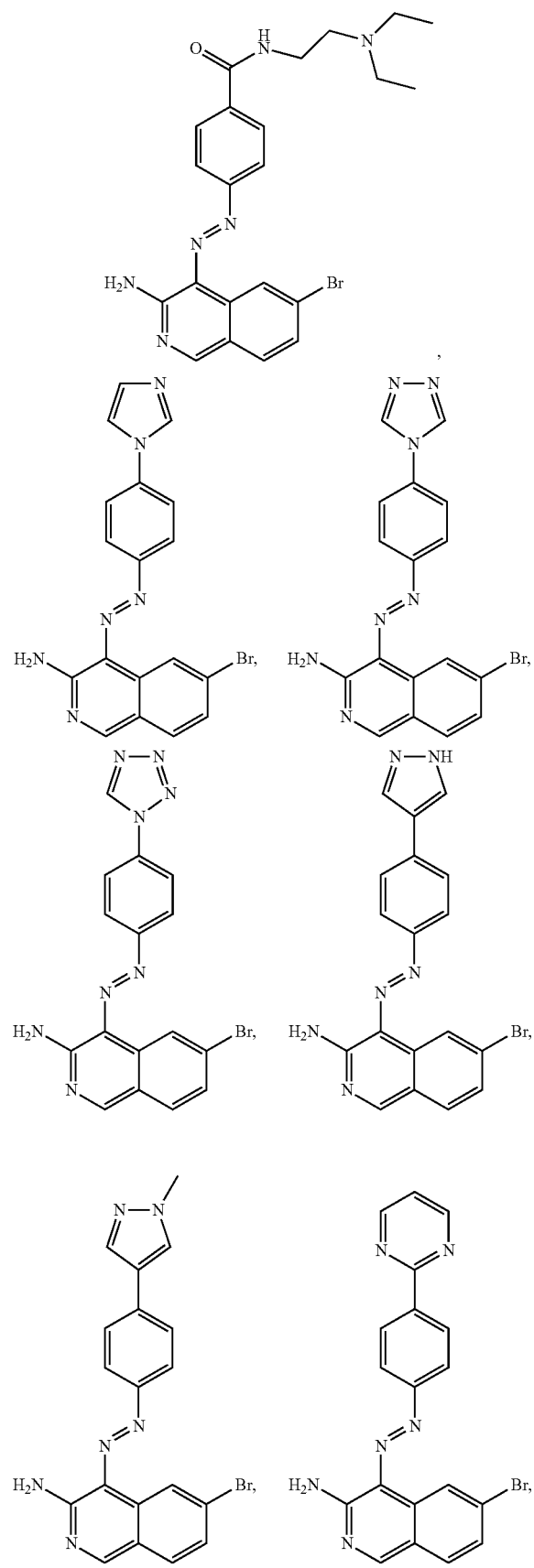
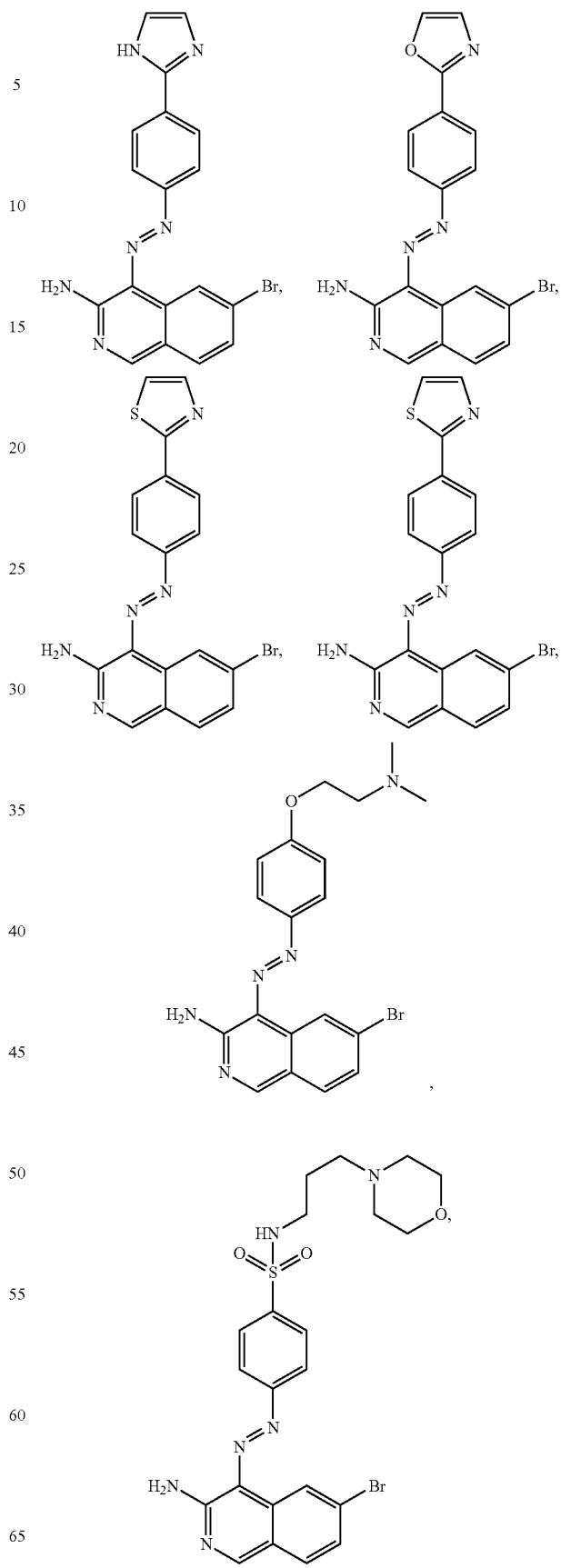

35
-continued

36
-continued

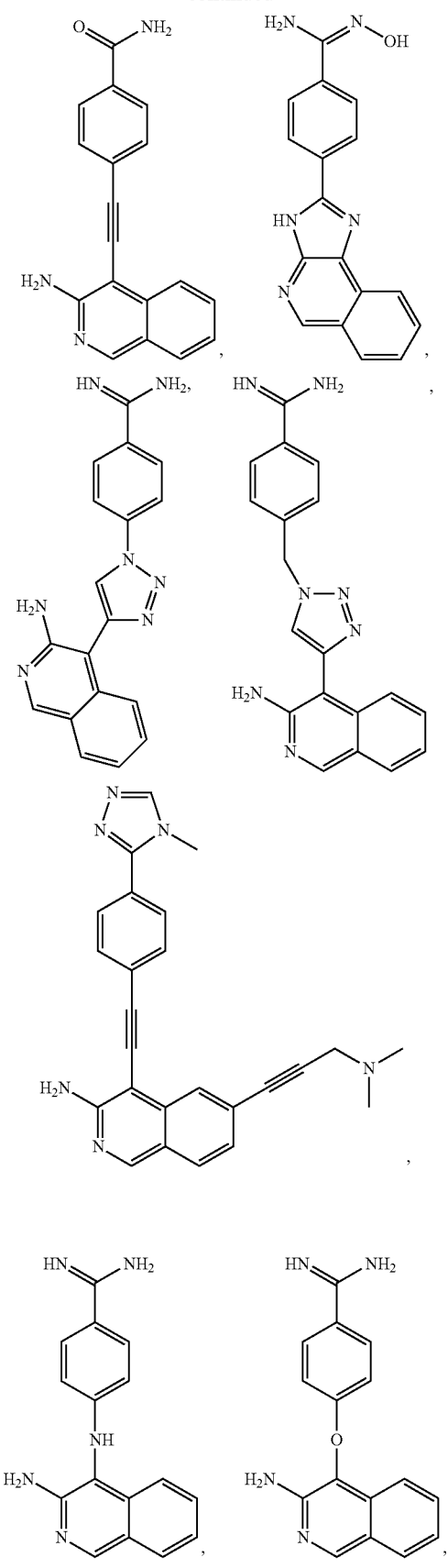
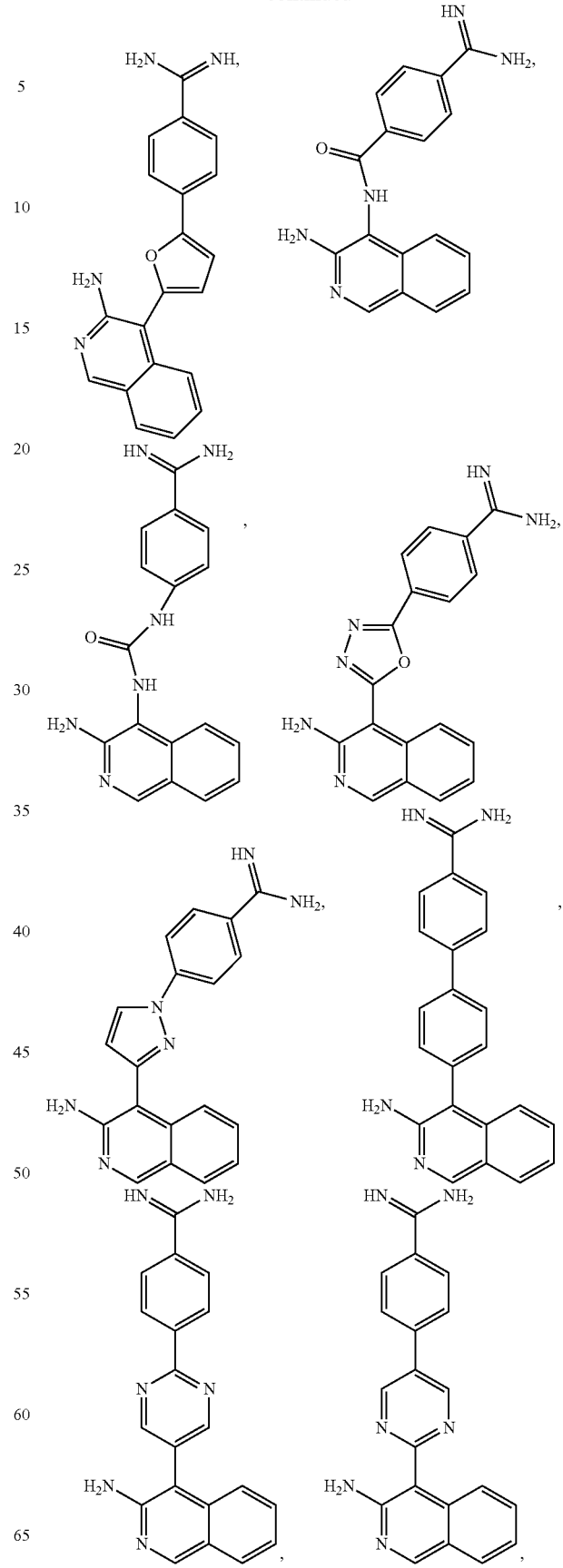

-continued
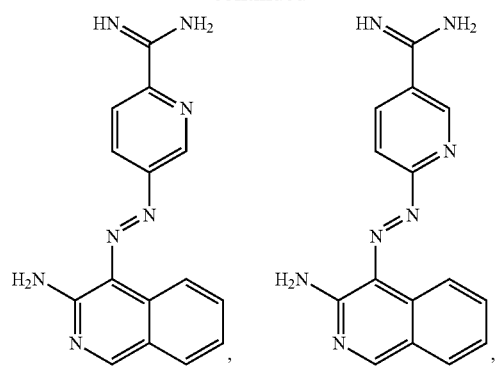
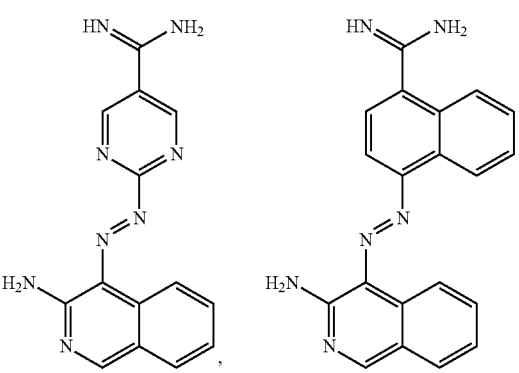
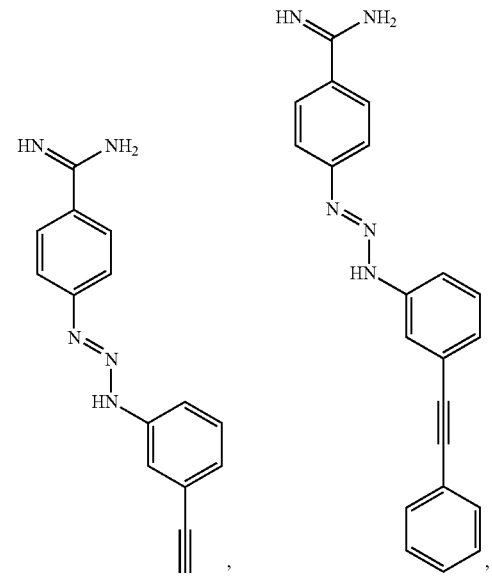
-continued
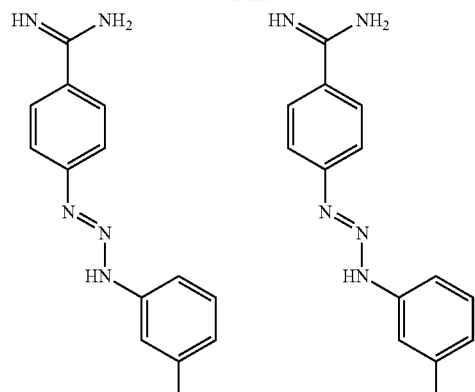

-continued
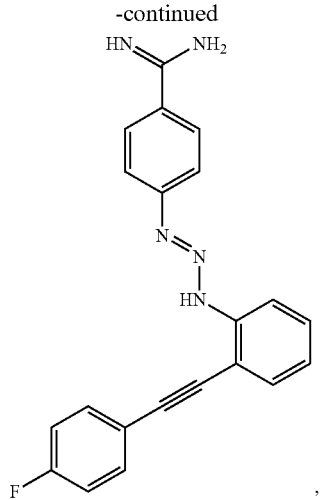
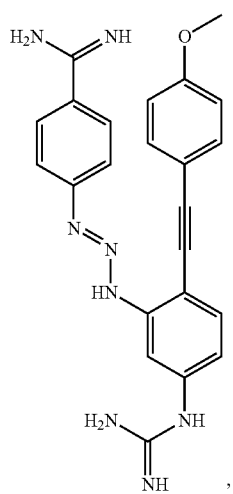
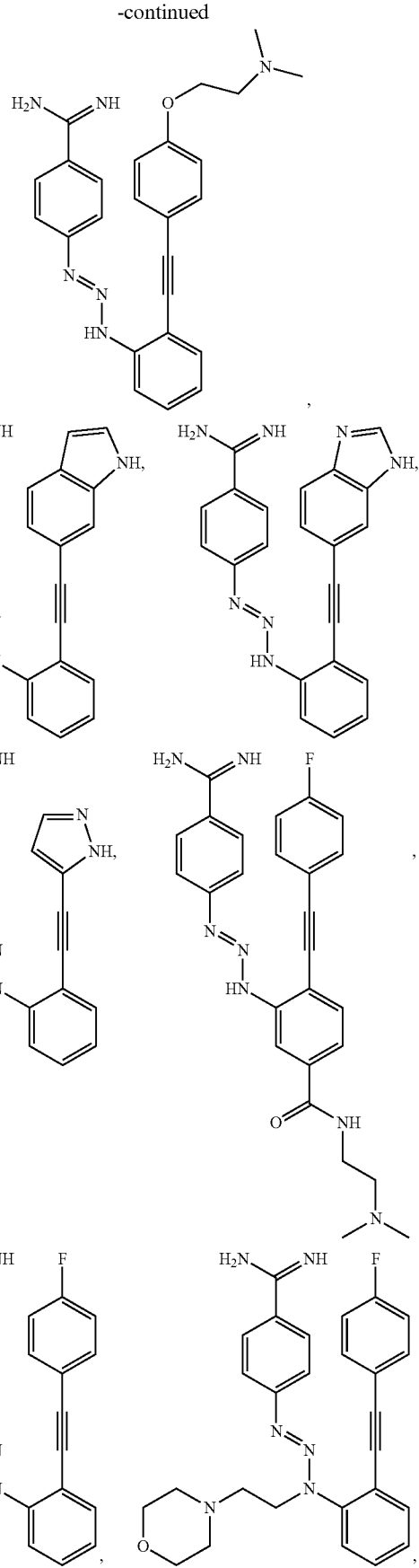

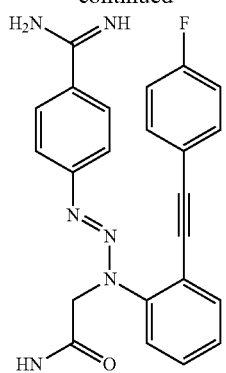
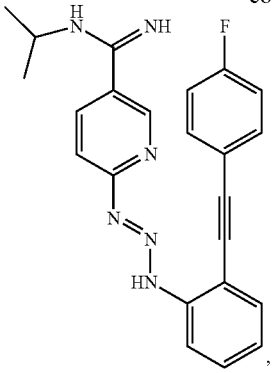
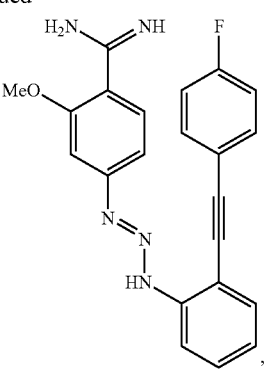
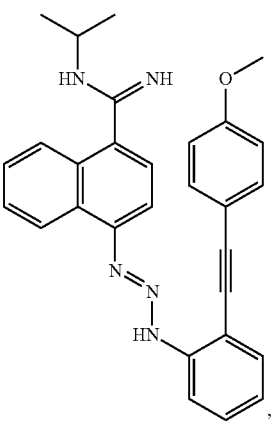
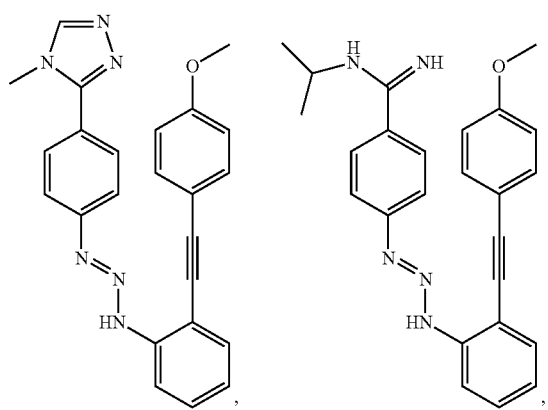
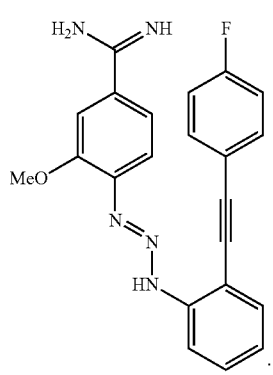
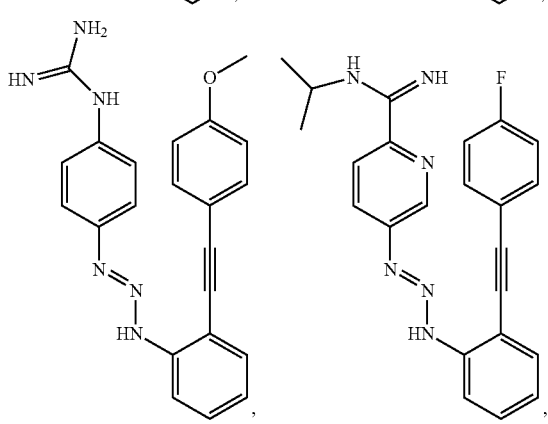

A compound of the present disclosure may be conjugated to a targeting ligand or a ligand that improves cell permeability. Acceptable ligands of the present disclosure include, but are not limited to, folate, biotin, amino acids, and peptides. In an embodiment, $R^1$ is conjugated to a targeting ligand or a ligand that improves cell permeability. Ligands can be connected to compounds of the present disclosure via labile linking moieties such as disulfide bonds, or groups that can be metabolized in vivo to release the active drug. Alternatively, ligands can be directly bonded to compounds of the present disclosure, for example, via a direct covalent bond between the compound and the ligand (e.g. with a primary amine of the compound and the carboxylic acid of biotin). The following examples serve to illustrate this point, and are not meant to be limiting in any way.

Scheme 1 Examples of targeting ligands.
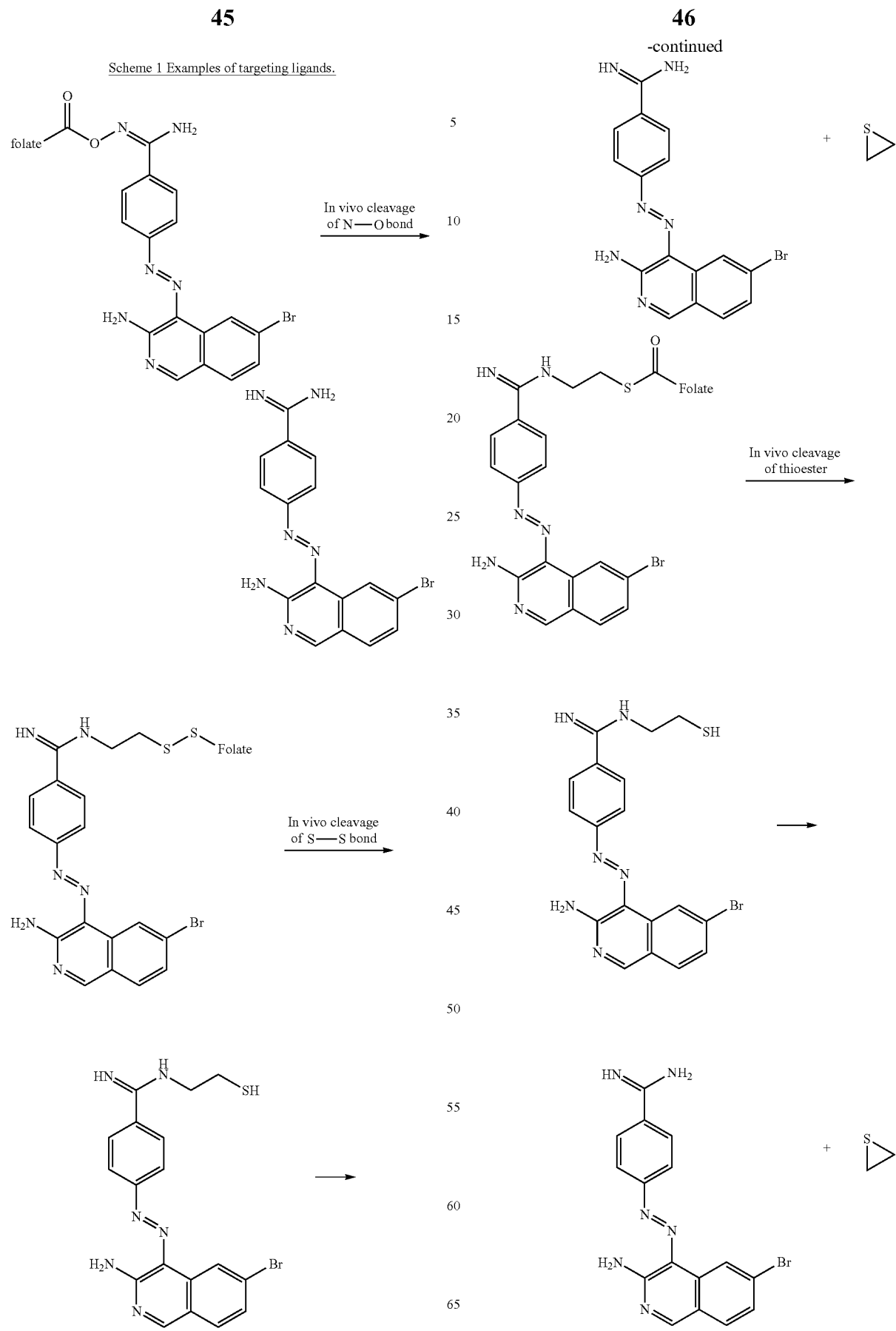

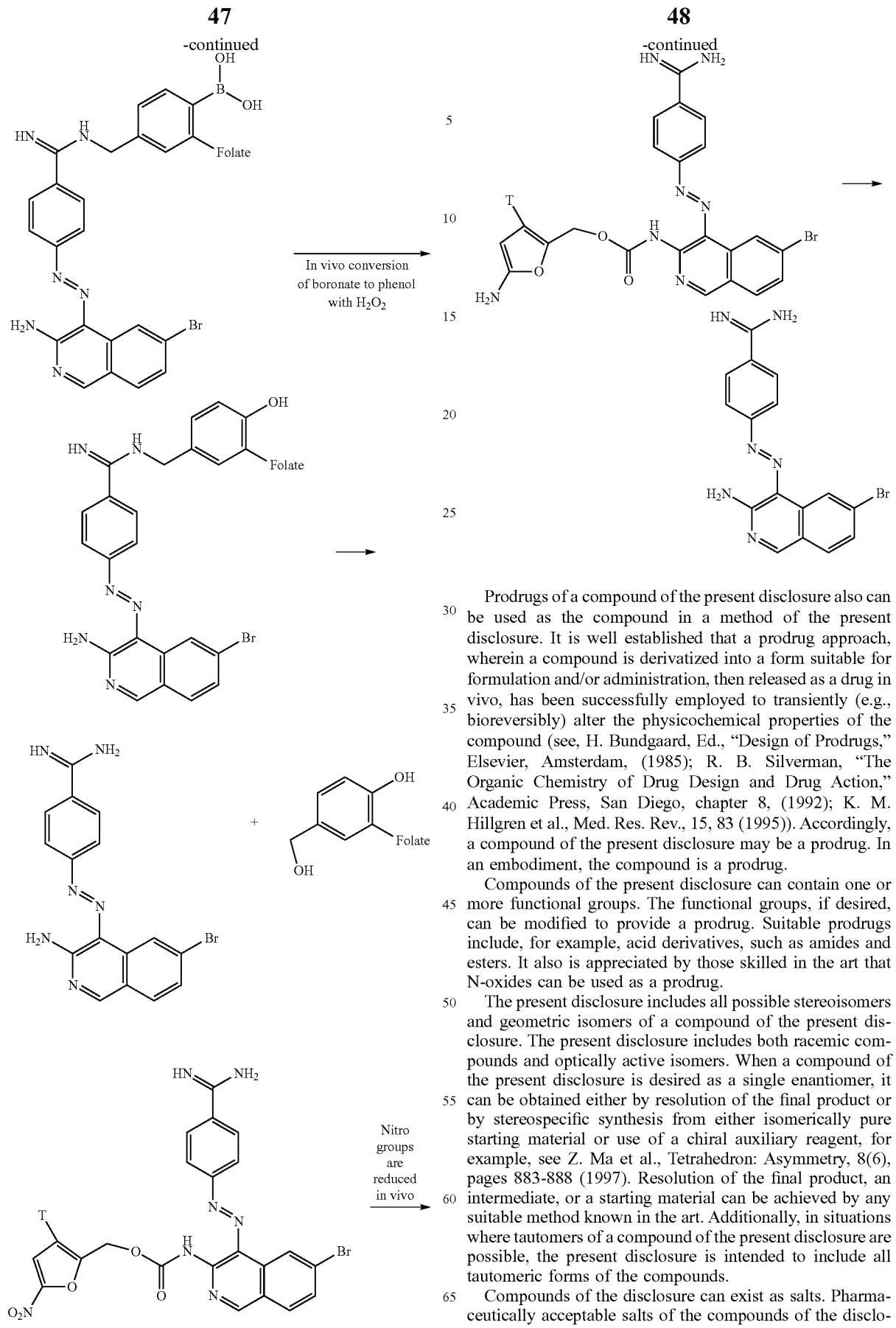

Prodrugs of a compound of the present disclosure also can be used as the compound in a method of the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)). Accordingly, a compound of the present disclosure may be a prodrug. In an embodiment, the compound is a prodrug.

Compounds of the present disclosure can contain one or more functional groups. The functional groups, if desired, can be modified to provide a prodrug. Suitable prodrugs include, for example, acid derivatives, such as amides and esters. It also is appreciated by those skilled in the art that N-oxides can be used as a prodrug.

The present disclosure includes all possible stereoisomers and geometric isomers of a compound of the present disclosure. The present disclosure includes both racemic compounds and optically active isomers. When a compound of the present disclosure is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of a compound of the present disclosure are possible, the present disclosure is intended to include all tautomeric forms of the compounds.

Compounds of the disclosure can exist as salts. Pharmaceutically acceptable salts of the compounds of the disclosure generally are preferred in the methods of the disclosure.

As used herein, the term "pharmaceutically acceptable salts" refers to salts or zwitterionic forms of a compound of the present disclosure. Salts of compounds having the structure can be prepared during the final isolation and purification of the compounds or separately by reacting the compound with an acid having a suitable cation. The pharmaceutically acceptable salts of a compound of the present disclosure are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include a compound of the present disclosure as well as pharmaceutically acceptable salts, hydrates, or prodrugs thereof.

In embodiments, the compounds of the disclosure may be protonated at a physiological pH. The disclosure further comprises compounds that mimic a protonated state as a consequence of a modification, including but not necessarily limited to the addition of an alkyl group.

In an aspect, the present disclosure provides a composition comprising at least one compound of the disclosure. The compositions include, for example, pharmaceutical preparations.

Compositions comprising a compound of the disclosure and a pharmaceutical agent can be prepared at a patient's bedside, or by a pharmaceutical manufacture. In the latter case, the compositions can be provided in any suitable container, such as a sealed sterile vial or ampoule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle (as encapsulated and/or surface modified), micellular delivery vehicle, inclusion compound, microsphere or liposome formulations, a variety of which are known in the art and are commercially available. Further, each composition described herein can comprise one or more pharmaceutical agents. The compositions described herein can include one or more standard pharmaceutically acceptable carriers. Some examples of pharmaceutically acceptable carriers can be found in: Remington: The Science and Practice of Pharmacy (2005) 21st Edition, Philadelphia, Pa. Lippincott Williams & Wilkins.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The dose of the composition comprising a compound of the disclosure and a pharmaceutical agent generally depends upon the needs of the individual to whom the composition of the disclosure is to be administered. These factors include, for example, the weight, age, sex, medical history, and nature and stage of the disease for which a therapeutic or prophylactic effect is desired. The compositions can be used in conjunction with any other conventional treatment modality designed to improve the disorder for which a desired therapeutic or prophylactic effect is intended, non-limiting examples of which include surgical interventions and radiation therapies. The compositions can be administered once, or over a series of administrations at various intervals determined using ordinary skill in the art, and given the benefit of the present disclosure.

Compositions of the disclosure can comprise more than one pharmaceutical agent. For example, a first composition comprising a compound of the disclosure and a first pharmaceutical agent can be separately prepared from a composition which comprises the same compound of the disclosure and a second pharmaceutical agent, and such preparations can be mixed to provide a two-pronged (or more) approach to achieving the desired prophylaxis or therapy in an individual. Further, compositions of the disclosure can be prepared using mixed preparations of any of the compounds disclosed herein.

The compounds of the present disclosure can be therapeutically administered as the neat chemical, but it is preferred to administer a compound of the present disclosure as a pharmaceutical composition or formulation. Thus, the present disclosure provides a pharmaceutical composition comprising a compound of the present disclosure together with a pharmaceutically acceptable diluent or carrier therefor. Also provided is a process of preparing a pharmaceutical composition comprising admixing a compound of the present disclosure with a pharmaceutically acceptable diluent or carrier therefor.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In one embodiment, the pharmaceutically-acceptable formulation is such that it provides sustained delivery of a compound of the present disclosure to an individual for at least 12 hours, 24 hours, 36 hours, 48 hours, one week, two weeks, three weeks, or four weeks after the pharmaceutically-acceptable formulation is administered to the individual.

In certain embodiments, these pharmaceutical compositions are suitable for oral administration to an individual. In other embodiments, as described in detail below, the pharmaceutical compositions of the present disclosure may be specially formulated for administration in solid or liquid form, including those adapted for the following: oral administration, for example, drenches (aqueous or non-aqueous solutions or suspensions), tablets, boluses, powders, granules, and pastes.

The compositions may conveniently be presented in unit dosage form and may be prepared by any methods well known in the art of pharmacy. The amount of active ingredient which can be combined with a carrier material to produce a single dosage form will vary depending upon the individual being treated, the particular mode of administration. The amount of active ingredient which can be combined with a carrier material to produce a single dosage form will generally be that amount of a compound of the present disclosure which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Compositions of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded Tablets may be made by molding in a suitable machine a mixture of the powdered active ingredient moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of a compound of the present disclosure include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to a compound of the disclosure, the composition may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When a compound of the present disclosure are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

In an aspect, the present disclosure provides methods of administering compounds or compositions comprising compounds of the present disclosure.

In certain embodiments, the methods of the disclosure include administering to an individual a therapeutically effective amount of a compound of the present disclosure in combination with another pharmaceutically active ingredient. Pharmaceutically active ingredients that may be used can be found in Harrison's Principles of Internal Medicine, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. A compound of the present disclosure and the pharmaceutically active ingredient may be administered to the individual in the same pharmaceutical composition or in different pharmaceutical compositions (at the same time or at different times).

Methods delineated herein include those wherein the individual is identified as in need of a particular stated treatment. Identifying an individual in need of such treatment can be in the judgment of an individual or a health care professional and can be subjective (e.g. opinion) or objective (e.g. measurable by a test or diagnostic method). In other methods, the individual is prescreened or identified as in need of such treatment by assessment for a relevant marker or indicator of suitability for such treatment.

When administered in combination with other therapeutics, a present compound may be administered at relatively lower dosages. In addition, the use of targeting agents may allow the necessary dosage to be relatively low. Certain compounds may be administered at relatively high dosages due to factors including, but not limited to, low toxicity and high clearance.

For human use, a compound of the present disclosure can be administered alone, but generally is administered in admixture with a pharmaceutical carrier selected with regard to the intended route of administration and standard pharmaceutical practice. Pharmaceutical compositions for use in accordance with the present disclosure can be formulated in a conventional manner using one or more physiologically acceptable carrier comprising excipients and auxiliaries that facilitate processing of a compound of the present disclosure into pharmaceutical preparations.

In certain embodiments, a compound of this disclosure comprises a human liver microsome stability property as further described herein. Such a stability profile can be determined using any suitable technique. In embodiments, the profile comprises a measurement of NADPH-dependent T1/2/min, and/or NADPH-independent T1/2/min. In embodiments, compounds of this disclosure exhibit single digit micromolar IC50 values, such as IC50 values determined in vitro using cancer cells.

In certain embodiments, the individual to whom one or a combination of compounds of this disclosure is administered has been diagnosed with, is suspected of having, or is at risk for developing a condition that is positively correlated with the presence of polynucleotides that comprise a G-quadruplex structure. In embodiments, the condition comprises a cancer, including but not necessarily limited to a solid or liquid cancer. Solid tumors, metastatic cancers, metastatic foci, a blood cancers are included. Also included are infectious agents wherein the genetic material of the infectious agent, and/or a combination of the genetic material of the infectious agent and the host genetic material, comprises a G-quadruplex structure. In embodiments the infectious agents are selected from viruses, and pathogenic microorganisms. In embodiments the viruses are retroviruses, including but not necessarily limited to HIV. In embodiments, the infectious agent is a member of the genus *Trypanosoma*, and includes but is not necessarily limited to *Trypanosoma brucei* and *Trypanosoma cruzi*. In embodiments, the individual in need of a compound of the invention is a non-human mammal, and thus the disclosure encompasses veterinary approaches.

In embodiments the disclosure includes forming a complex between a compound of this disclosure and polynucleotides comprising a G-quadruplex structure. In embodiments, the disclosure comprises testing a sample from an individual to determine if a G-quadruplex structure is present in the sample, and subsequently administering a compound of this disclosure to the individual. In embodiments, the disclosure comprises selective binding of G-quadruplexes using compounds of this disclosure. In embodiments the disclosure comprises inhibiting formation of G-quadruplexes. Interactions between compounds of this disclosure and G-quadruplexes can be determined using a wide variety of techniques known to those skilled in the art, some of which are described below.

In embodiments, compounds of the disclosure specifically or selectively inhibit phosphorylation by a kinase, and thus inhibit the activity of one or more kinases, including but not necessarily limited phosphorylation of serine, threonine, tyrosine, or histidine residues. Thus, in embodiments, a composition of the disclosure inhibits kinase activity in an individual. In an embodiment, the kinase is fms-related tyrosine kinase 3 (FLT-3). In embodiments, it is therefore expected the disclosure is suitable for approaches to treating disorders in which kinases are known to participate, including but not necessarily limited to a wide variety of cancers, as well as other disorders, such as diabetes, Alzheimer's disease, neurological pain, inflammation, pulmonary fibrosis, rheumatoid arthritis, diseases which require anticoagulants, polycystic kidney disease, and conditions that wherein modulation of the immune system by affecting kinase activity would be of benefit.

In embodiments, compounds of the disclosure specifically or selectively inhibit the activity of a non-kinase enzyme, such as the enzyme poly ADP ribose polymerase (PARP). Thus, in embodiments, a composition of the disclosure inhibits PARP in an individual. In embodiments, administration of a compound of this disclosure inhibits a kinase and another distinct enzyme, which can be a non-kinase enzyme, such as PARP, in an individual. In embodiments, the disclosure includes compositions comprising as an active ingredient any one or any combination of compounds disclosed herein, and methods of using such compositions. In embodiments, the only active ingredient in the compositions can comprise only one, or fewer than 10 of the compounds of this disclosure. In embodiments, a single compound is used concurrently as a G-quadruplex ligand, a kinase inhibitor and a PARP inhibitor. In embodiments, a compound of this disclosure inhibits the expression of c-MYC oncoprotein. In certain embodiments, the activity of telomerase in the individual is inhibited. In embodiments, telomerase activity is inhibited.

In embodiments, the individual to whom a compound of this disclosure is administered is diagnosed with, suspected of having or is at risk for developing a type of cancer that includes but is not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell cancers of any kind, including but not limited to lung carcinoma, pancrease, prostate, and kidney, bladder carcinoma, epithelial carcinoma, astrocytoma, medulloblastoma, glioblastoma, primitive neuroectodermal tumor, choroid plexus carcinoma, choroid plexus papilloma, craniopharyngioma, ependymoma, pinealoma, hemangioblastoma, acoustic neuroma, oliodendroglioma, meningioma, melanoma, neuroblastoma, retinoblastoma, thymoma, Waldenstrom's macroglobulinemia, and heavy chain disease.

In embodiments, the individual has, or is suspected of having, or is at risk for developing a cancer selected from ovarian, prostate, triple negative breast cancer, and leukemia, including but not limited to Acute myeloid leukemia (AML), Acute lymphoblastic leukemia (ALL), and glioblastoma.

In certain embodiments, a composition of this disclosure is used to inhibit metastasis in an individual, and thus inhibits the migration of cancer cells, and/or the formation of metastatic foci.

The following examples are presented to illustrate the present disclosure. They are not intended to be limiting in any manner.

EXAMPLE 1

This example provides syntheses of DMZ based derivatives, and evidence that the DMZ scaffold binds to G-quadruplexes.

Diminazene or berenil, a classic duplex minor groove binder, binds to G-quadruplexes with low nanomolar dissociation constants and the amidine groups are also critical for G-quadruplex binding.

Materials and Methods. General. 4-Aminobenzamidine dihydrochloride, aniline and diminazene aceturate (DMZ or Berenil) were purchased from Aldrich. All triazenes were stored at 4° C. and in dark since significant decomposition of triazenes was observed if stored at room temperature and in presence of light. Sequences of DNA used in this study are shown in Table 1. Purified oligonucleotides 22-mer c-kit1, 18-mer VEGF, 23-mer bcl-2 2345, 15-mer TBA and 20-mer 8 bp AT were purchased from IDT and analyzed for purity before use. Purified WT 27-mer bcl-2, WT 24-mer c-myc, WT 22-mer human telomere hTel were obtained from Midland oligos (Midland, Tex.).

UV measurements for titration studies were done using JASCO V-630. Fluorescence measurements for the displacement assay were done using Varian Cary Eclipse. NMR spectra for synthesized compounds were recorded with Bruker AV-400 and/or Bruker DRX-400. $^1$H-NMR chemical shifts are reported as ($\delta$) in ppm and are calibrated according to residual solvent peaks or indicated external standards. $^1$H NMR coupling constants (Jvalues) are reported in Hertz (Hz). $^{13}$C-NMR chemical shifts are reported as ppm relative to residual solvent peak. NMR measurement for binding study was done using Bruker Avance III HD 800 spectrometer equipped with Cryo-Probe. High-resolution mass spectra (HRMS) were recorded with JEOL AccuTOF-CS (ESI positive, needle voltage 1800~2400 eV).

Synthesis of Triazene-1 and Triazene-2. Triazene-1: To a cooled (0° C.) and stirred suspension of 4-aminobenzamidine dihydrochloride (1.0 g, 4.80 mmol) in water (6 mL) and concentrated hydrochloric acid (1 mL), a solution of sodium nitrite (0.36 g, 5.28 mmol) in water (1 mL) was added dropwise and the mixture was stirred for 20 minutes. To the resulting diazonium solution, a solution of aniline (0.43 mL, 4.80 mmol) in MeOH (1 mL) was added followed by addition of saturated aqueous sodium acetate (6 mL). After being stirred at 0° C. for 1 h, the resultant yellow solid was filtered off, washed with brine, dried and crystallized with MeOH/acetone (1:2, 20 mL) to afford analytically pure product (1.2 g, 84%) as an acetate salt. $^1$H NMR (DMSO-$d_6$, 400 MHz) $\delta$ 7.87-7.83 (m, 2H), 7.57-7.47 (m, 4H), 7.47-7.42 (m, 2H), 7.31-7.26 (m, 1H), 1.72 (s, 3H). $^{13}$C NMR (DMSO-$d_6$, 100 MHz,) $\delta$ 177.1, 165.8, 148.9, 148.4, 130.2, 130.1, 127.4, 123.4, 120.5, 116.1, 25.8. HRMS (ESI$^+$) m/z calcd. for $C_{13}H_{14}N_5$ [M+H]$^+$ 240.1249. found 240.1248.

Triazene-2: Following the procedure described above for the Triazene-1, diazonium solution of aniline (0.5 mL, 5.47 mmol) was treated with aniline (0.5 mL, 5.47 mmol) to afford Triazene-2 (1.1 g, 85%), as a yellow solid. $^1$H NMR (CDCl$_3$, 400 MHz) $\delta$ 7.47-7.39 (m, 8H), 7.20 (tt, J=6.9, 1.5 Hz, 2H). $^{13}$C NMR (DMSO-$d_6$, 100 MHz,) $\delta$ 150.7, 142.6, 130.1, 127.7, 123.1, 121.6, 114.9. HRMS (ESI$^+$) m/z calcd. for $C_{12}H_{12}N_3$ [M+H]$^+$ 198.1031. found 198.1031.

UV titration studies of DNA with the triazene ligands, DMZ and Triazene-1. The molar extinction coefficients at 260 nm for 22-mer c-kit1, 18-mer VEGF, 23-mer bcl-2 2345, 15-mer TBA and 20-mer 8 bp AT are as follows 226,700 M$^{-1}$ cm$^{-1}$, 169, 800 M$^{-1}$ cm$^{-1}$, 227,300 M$^{-1}$ cm$^{-1}$, 143,300 M$^{-1}$ cm$^{-1}$ and 205,500 M$^{-1}$ cm$^{-1}$, respectively. The concentration of ligands used in this study was 10 µM and the DNA concentrations were 0, 0.25, 1.5, 3, 5, 6, 7, 8, 9, 10, 20, 30, 40, 50, 100, and 150 µM. The buffer contained 250 mM KCl, 50 mM Tris-HCl (at pH 7.5). The following quadruplex DNA were tested: c-kit1, VEGF, bcl-2 2345, and TBA. Duplex DNA (8 bp AT) was also tested. The sample was first heated up to 95° C. for 5 min without the ligand and then cooled down to room temperature in 15 min. The ligand was then added and the mixture was incubated at 4° C. for ~12 h before recording the data. In case of Triazene-1 and Triazene-2, the sample mixture contained 1% DMSO.

NMR measurements for DNA binding of triazene ligands. The procedure was followed as described previously. The ligand concentration was 150 µM, and that of the DNA (c-kit1 or 8 bp AT) was 300 µM. The buffer used was 10 mM potassium phosphate (pH 7.5) containing 137 mM NaCl, 1 mM EDTA, and also contained 10% $D_2O$. The sample was initially heated up to 95° C. for 5 min without the ligand and then cooled down to room temperature in 15 min. Subsequently, the sample was incubated at 4° C. for ~12 h without the ligand (for G-quadruplex formation). Then, the ligand was added and incubated for 2 h before the NMR measurement (25° C.).

(Note: Because of the high concentrations being used for the NMR, incubating the DNA/ligand for longer periods caused precipitation, probably due to G-quadruplex polymer formation, which is catalyzed by the ligand).

Isothermal titration calorimetry. ITC experiments were performed using a VP-ITC calorimeter (GE-Healthcare). A typical ITC experiment involved as many as addition of 28 (10 µL) injections of as high as 1 mM ligand solutions into ~1.5 mL of a dilute DNA solution (10 µM). Corrected titration curves were achieved by subtracting the blank titration data from the ITC-data for the ligand-DNA titrations. Corrected ITC titrations were fit with a nonlinear regression algorithm again using the CHASM ITC data analysis program developed in our laboratory.

DNA stock solutions were prepared by reconstituting the lyophilized oligonucleotide into 20 mM Tris buffer with a salt concentration of 100 mM KCl and a pH of 7.2. Approximately 2 mL of the oligonucleotide was dialyzed (1000 Mw cutoff membrane) against three changes of buffer solution (1 L, 24 h each) at 4° C. The concentrations of stock DNA solutions were verified using UV-Vis. G-Quadruplex DNAs were annealed by quickly heating to sample to 100° C., holding at 100° C. for ten minutes then slowly cooling to 5° C. over three hours period. Molar extinction coefficient of the DNAs were determined using a nearest-neighbor method for single stranded DNA. The extinction coefficients at 260 nm for the WT 27-mer bcl-2, WT 24-mer c-myc, WT 22-mer human telomere hTel sequences are 267,200 $M^{-1}cm^{-1}$, 248,100 $M^{-1}cm^{-1}$, and 228,500 $M^{-1}cm^{-1}$ respectively. The extinction coefficient at 260 nm for the 7 base pair hairpin with $A_2T_2$ (7 bp HP·AT) and the 7 base pair hairpin without $A_2T_2$ (7 bp HP) are 165,200 $M^{-1}$ $cm^{-1}$ and 159,200 $M^{-1}$ $cm^{-1}$ respectively. Cell culture grade water purchased from Corning was used for all experiments.

Circular Dichroism (CD). CD titration experiments were performed with an Olis DSM-20 spectropolarimeter (Bogart, Ga.). All measurements were done at 25° C. using a 1 cm quartz cuvette and covering a spectral range of 220-420 nm. All DNA samples were prepared such that they had a nominal absorbance of less than 1.0 at 260 nm. Stock solutions of the ligand were added in small amount to reach a molar ratio of 1:1, 3:1, 6:1, and 10:1 of ligand per equivalence of DNA.

Electrospray Ionization Mass Spectrometry. ESI-MS experiments were carried out on a Bruker MicrOTOFQ mass spectrometer. Data acquisition was set to operate in negative ion mode. All experiments were performed in 50 mM ammonium acetate buffer containing 20% HPLC grade methanol and adjusted with 1 N KOH solution to reach pH of 7.0. The WT hTel 22-mer G-quadruplex sample was prepared at a concentration of approximately 10 µM in the ammonium acetate buffer and was exhaustedly dialyzed. Stock solutions of DMZ and Triazene-1 were prepared in the final dialysate buffer at concentration as high as 300 µM. The ESI-MS samples were prepared by mixing the DNA and ligand stock solutions to yield a mixture containing excess of each ligand per equivalence of DNA. The MS capillary voltage was set to +3500 V, dry $N_2$ gas flow was adjusted to 0.5 L/min at 110° C., and the G-quadruplex/ligand samples were directly infused into the MS by using a kD Scientific syringe pump set to a flow rate of 200 µL/hour. Data processing was performed by using Bruker Daltonics Data Analysis program.

Recently, there has been considerable interest in repurposing drugs for new therapeutic indications. Along this line, others have been interested in repurposing DNA duplex minor groove binders for targeting G-quadruplexes. Compounds that bind minor grooves of DNA duplexes have a track record of clinical efficacy for many indications including animal trypanosomosis and babesiosis. Because there are numerous toxicological data for these drugs, using them as starting points for the development of G-quadruplex-selective ligands appears to be a reasonable proposition. Curiously, although several duplex minor groove binders have been tested for G-quadruplex binding, DMZ a prototypical AT-rich minor groove binder, which is used clinically to treat animal trypanosomiasis has not been thoroughly investigated for G-quadruplex binding. Only a single report that demonstrated that DMZ aggregates the dinucleotide, c-di-GMP, into an ill-defined supramolecular aggregate via an uncharacterized mechanism exist.

TABLE 1

Sequences of DNA and their abbreviations used in the study.

| Abbreviation | Sequence (5' to 3') |
| --- | --- |
| 7bp HP* | GCAGTCCTCTCGGACTGC (SEQ ID NO: 1) |
| 7bp HP·AT* | GCAATTCTCTCGAATTGC (SEQ ID NO: 2) |
| 8bp AT* | CGAATTTCAAAAGAAATTCG (SEQ ID NO: 3) |
| TBA | GGTTGGTGTGGTTGG (SEQ ID NO: 4) |
| VEGF | GGGCGGGCCGGGGCGGG (SEQ ID NO: 5) |
| hTel | AGGGTTAGGGTTAGGGTTAGGG (SEQ ID NO: 6) |
| c-kit1 | AGGGAGGGCGCTGGGAGGAGGG (SEQ ID NO: 7) |
| c-myc | TGGGGAGGGTGGGGAGGGTGGGGA (SEQ ID NO: 8) |

TABLE 1-continued

Sequences of DNA and their abbreviations used in the study.

| Abbreviation | Sequence (5' to 3') |
|---|---|
| bcl-2 2345 | GGGCGCGGGAGGAATTGGGCGGG (SEQ ID NO: 9) |
| bcl-2 | CGGGCGCGGGAGGAAGGGGGCGGGAGC (SEQ ID NO: 10) |

*Stem-loop DNA. The bases colored as green form the stem part. Bases that are underlined are the $A_2T_2$ sequence, which widely known as the binding site for minor groove binders.

Figure 13:
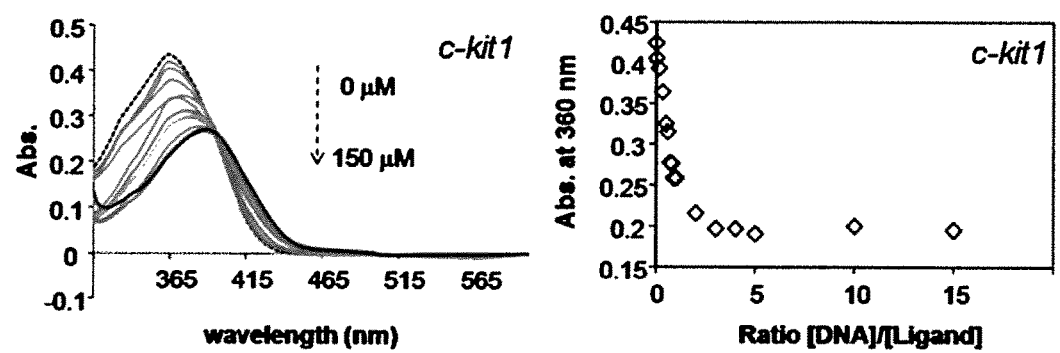
FIG. 13. UV-titration studies showing binding of DMZ with DNA. (Left) Absorption spectra of DMZ (10 µM) upon titration with c-kit1. The concentrations of DNA are 0, 0.25, 1.5, 3, 5, 6, 7, 8, 9, 10, 20, 30, 40, 50, 100, 150 µM. In the graph, 10 µM and 150 µM DNA concentrations are specifically emphasized as cyan and red line respectively. [KCl]= 250 mM, Buffer=50 mM Tris-HCl (pH 7.5). UV was measured at 20° C. (Right) Plot of absorbance at 360 nm against concentration ratio of DNA and Ligand (DMZ).
Figure 23:
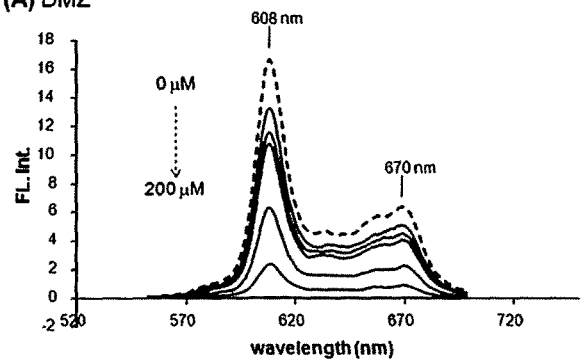
FIG. 23. Displacement of G4 ligand, NMM (A and B), by triazene ligands. (Left) Displacement of NMM (1 µM) upon titration of triazene ligands (A) DMZ, (B) Triazene-1 on c-kit1 (10 µM). The concentration of ligand is 0, 5, 10, 20, 50, 100, 200 µM. In the Figure, 200 µM ligand concentration is emphasized with red line. Buffer=50 mM Tris-HCl (pH 7.5), [KCl]=50 mM. Fluorescence was measured with excitation wavelength=400 nm for NMM, emission wavelength=550-700 nm. (Right) Fluorescence emission intensity at 608 nm (◇) and 670 nm (□) against ligand (A) DMZ, (B) Triazene-1 concentrations. The concentrations of ligand are 0, 5, 10, 20, 50, 100, 200 µM.
Figure 23:
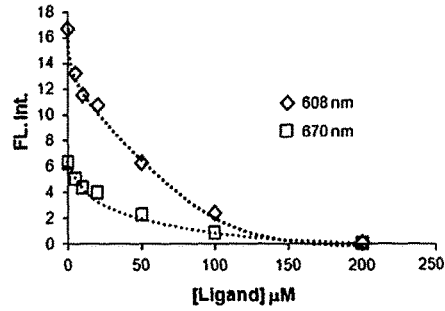
Figure 23:
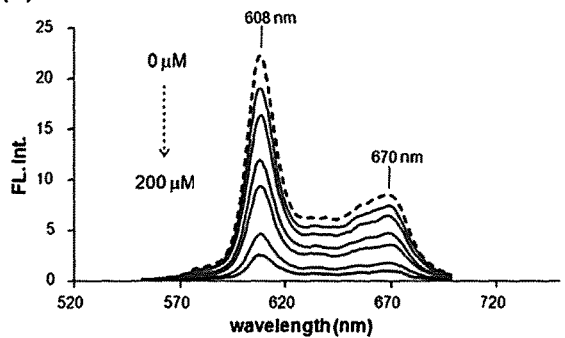
Figure 23:
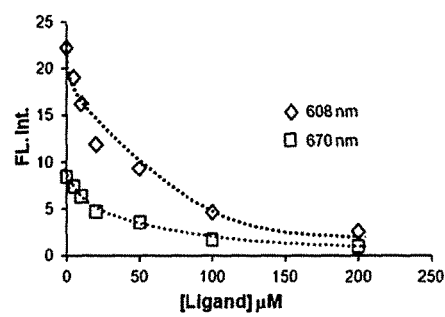
Figure 24:
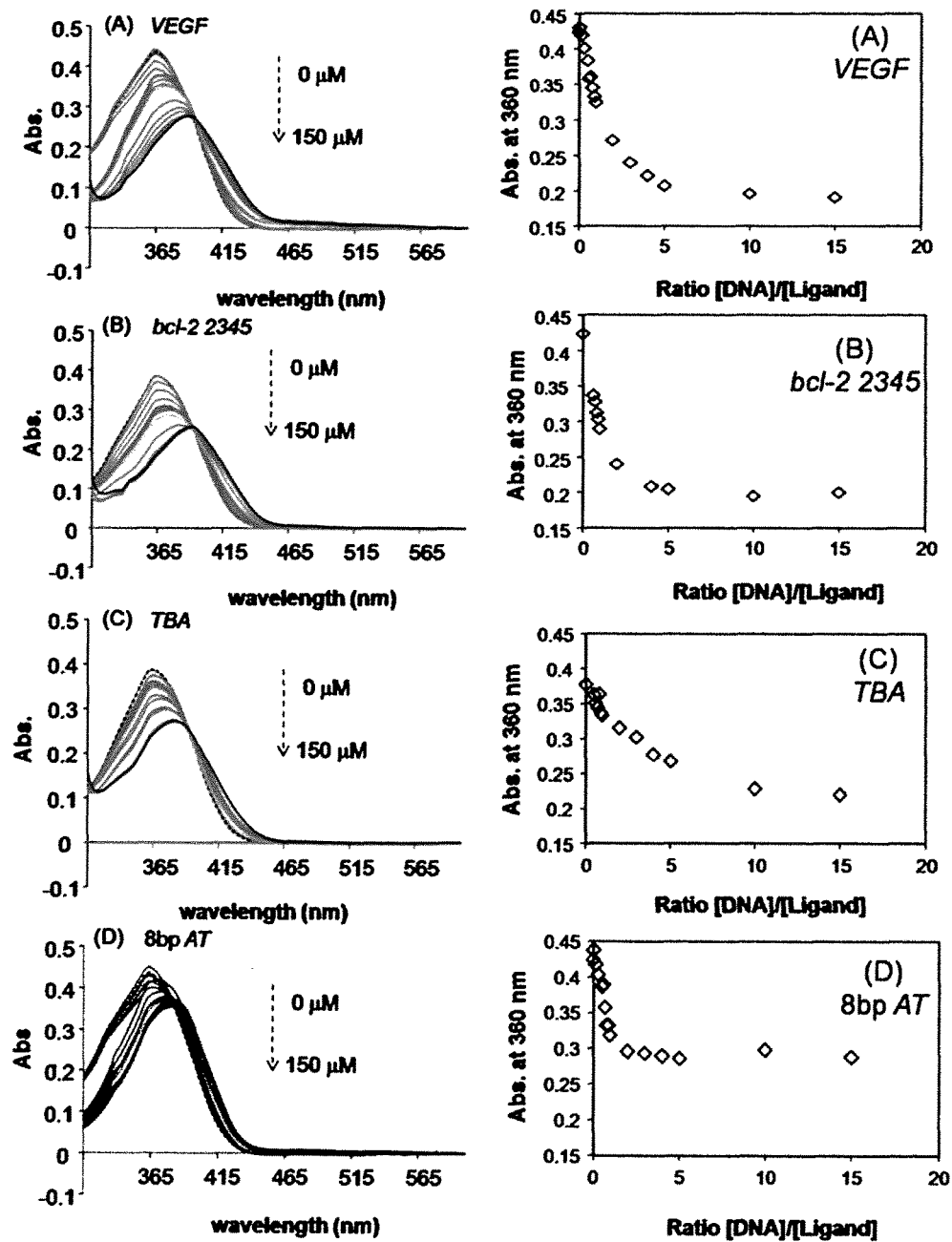
FIG. 24. UV-titration studies showing binding of DMZ with DNA. (Left) Absorption spectra of DMZ (10 µM) upon titration with (A) VEGF, (B) bcl-2 2345, (C) TBA, (D) 8 bp AT. The concentrations of DNA are 0, 0.25, 1.5, 3, 5, 6, 7, 8, 9, 10, 20, 30, 40, 50, 100, 150 µM. In the graph, 10 µM and 150 µM DNA concentrations are specifically emphasized as cyan and red line respectively. [KCl]=250 mM, Buffer=50 mM Tris-HCl (pH 7.5). UV was measured at 20° C. (Right) Plot of absorbance at 360 nm against concentration ratio of DNA and Ligand (DMZ). Ligand concentration is 10 µM, DNA=(A) VEGF, (B) bcl-2 2345, (C) TBA and (D) 8 bp AT. The concentrations of DNA are 0, 0.25, 1.5, 3, 5, 6, 7, 8, 9, 10, 20, 30, 40, 50, 100, 150 µM.

UV spectroscopy studies of DMZ binding to G quadruplexes and duplex DNA. initiated our study by testing if DMZ or analogs could compete with a known G-quadruplex ligand, such as the fluorogenic NMM, in binding to c-kit1 (FIG. 23). Having obtained preliminary results that DMZ could indeed compete with NMM for c-kit1 binding, we proceeded to perform a series of experiments to confirm if the binding of DMZ to DNA G-quadruplexes was real. This started with interaction studies of DMZ with various G-quadruplex DNAs (c-kit1, VEGF, bcl-2 2345 and TBA; see Table 1 for their sequences) by conventional UV-visible absorption titration method using AT-rich duplex DNA, 8 bp AT, as positive control. The absorption spectra of DMZ (10 µM) with different concentrations of G-quadruplex DNA (0-150 µM) is shown in FIGS. 13 and 24. Interestingly, with gradual increase in concentrations of DNA, DMZ showed a remarkable bathochromic shift (red shift) and a hypochromic effect on the Soret band with all of the tested G-quadruplex DNA (FIGS. 13 and 24). These observed effects in the UV-titration curves provide a direct evidence of interactions between the DMZ and DNA nucleobases.

Importance of amidine moiety in DMZ binding to duplex DNA and G-quadruplexes. Analysis of the crystal structure of DMZ/duplex DNA complex (FIG. 14) revealed that both amidine groups in DMZ make important and extensive contacts with the minor groove residues. Therefore we reasoned that the modification of one or both of the amidine groups could give an analog that would be incapable of binding to DNA minor groove. However it was unclear if the deletion of the amidine group would also reduce binding to G-quadruplexes.

Figure 14:
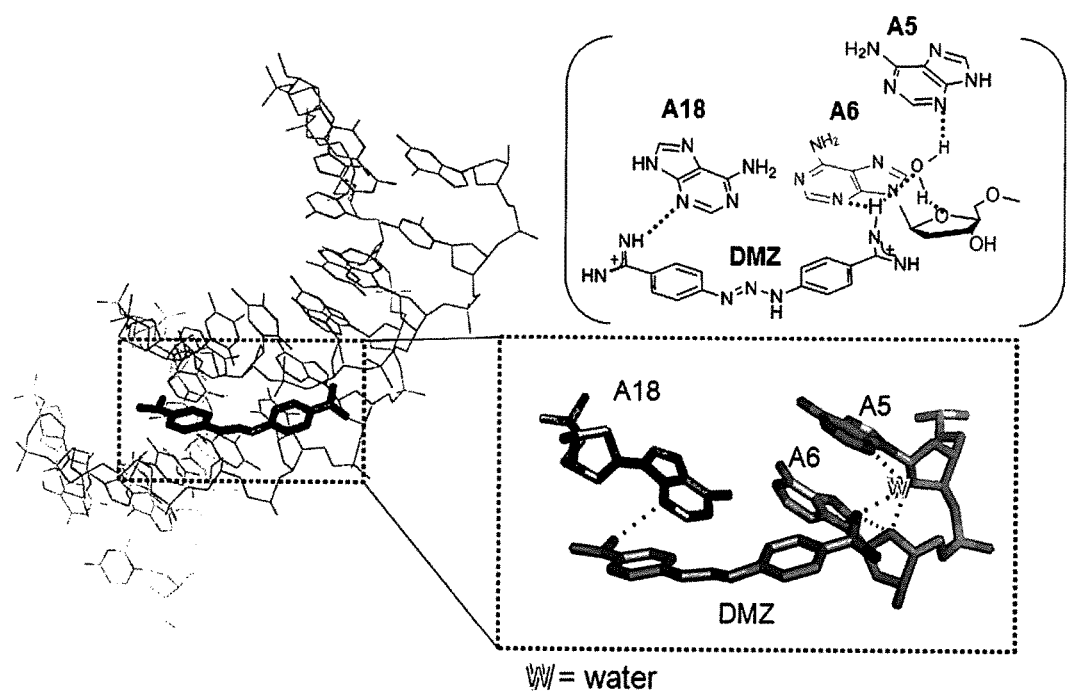
FIG. 14. DMZ interactions with duplex DNA (AT-rich). The amidine groups of DMZ make important hydrogen-bonding interactions with both DNA residues and water molecules in the minor groove of DNA (structure is from PDB#2DBE).
Figure 27:
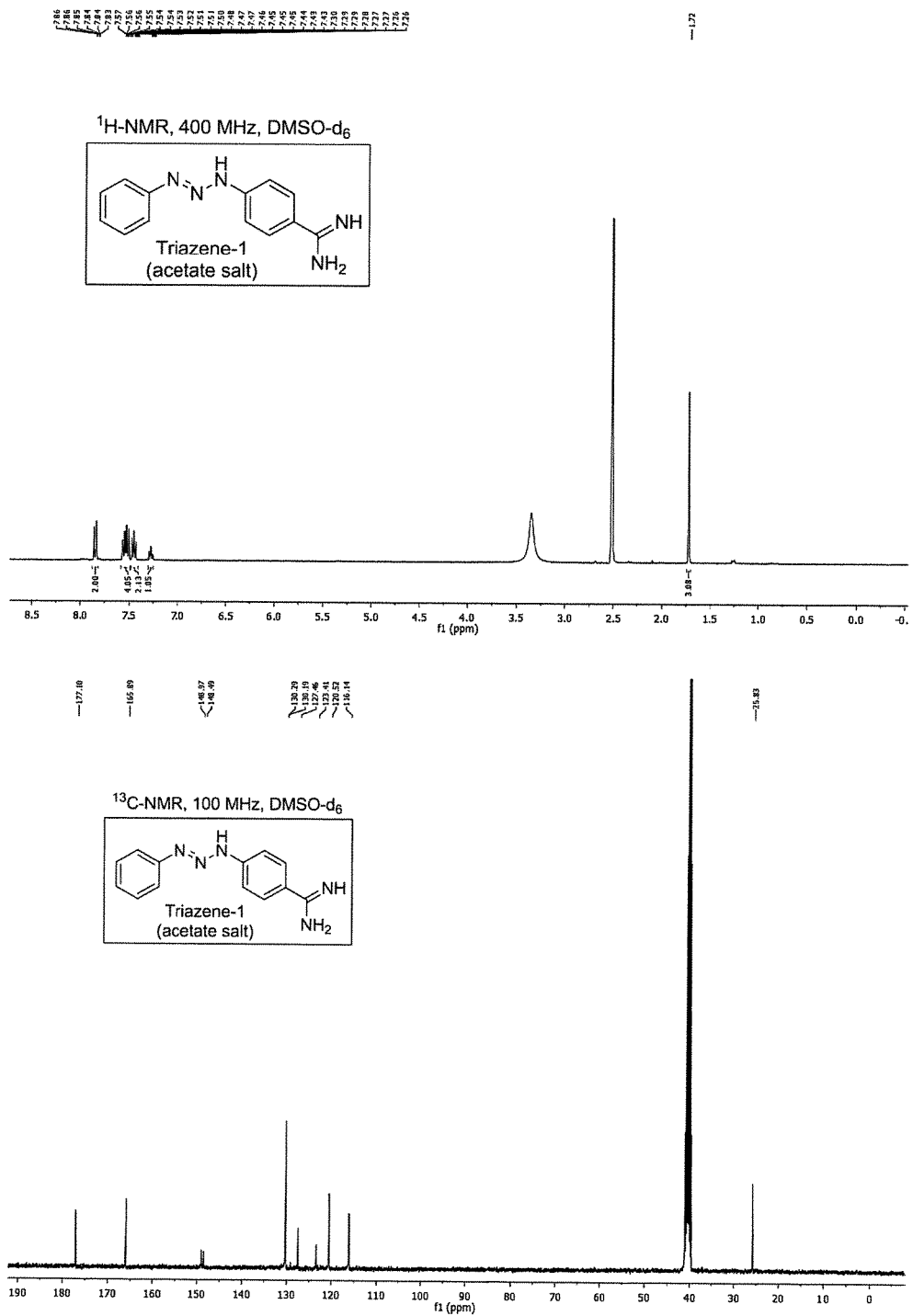
FIG. 27. NMR of Triazene 1.
Figure 28:
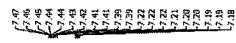
FIG. 28. NMR of Triazene 2.
Figure 28:
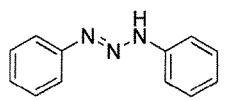
Figure 28:
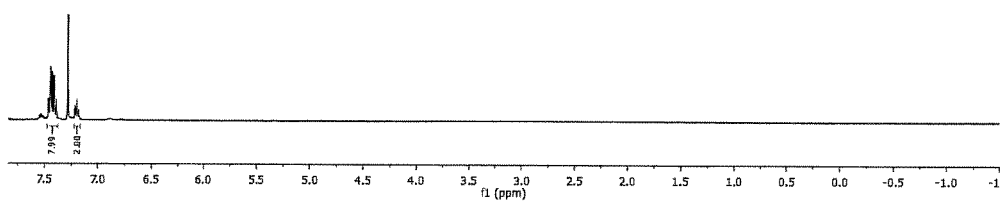
Figure 28:
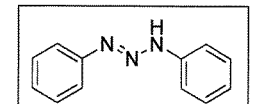
Figure 28:
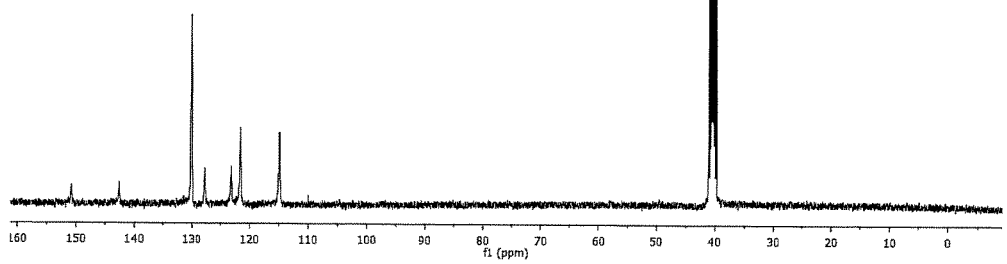
Figure 29:
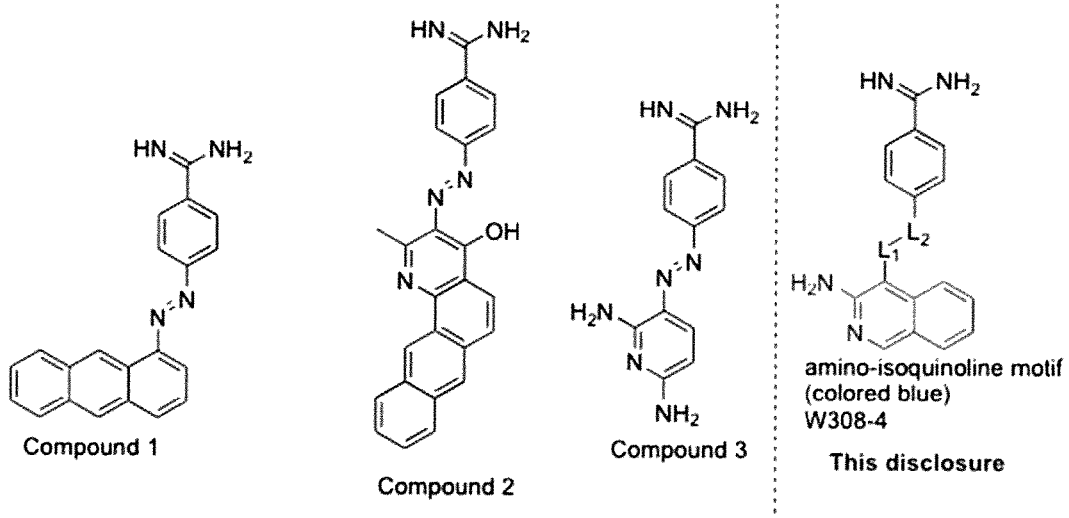
FIG. 29. Azo compounds with expanded pi-surface reported in US patent 4619, 994 and azolamidine-inspired compounds (this disclosure).
Figure 30:
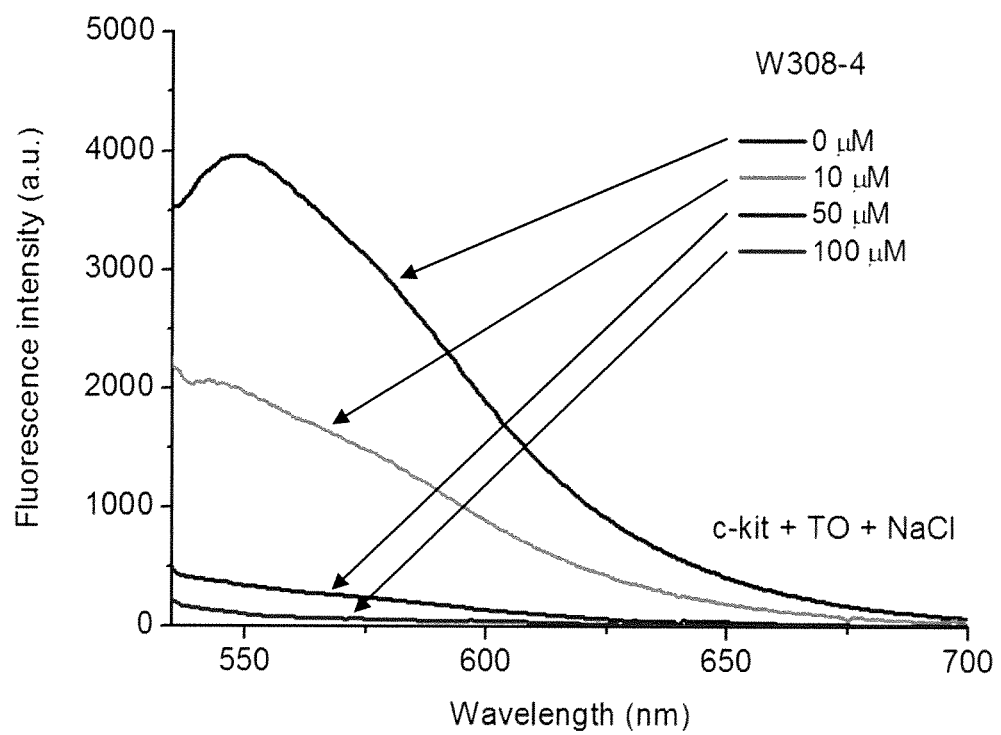
FIG. 30. Conditions: Thiazole Orange (5 µM), c-kit DNA (10 µM), NaCl (50 mM), buffer (50 mM, Tris-HCl, pH 7.5), W308-4 (0, 10, 50, 100 µM) with incubation time of 12 h. Ex. 507 nm, em. 517-700 nm.
Figure 31:
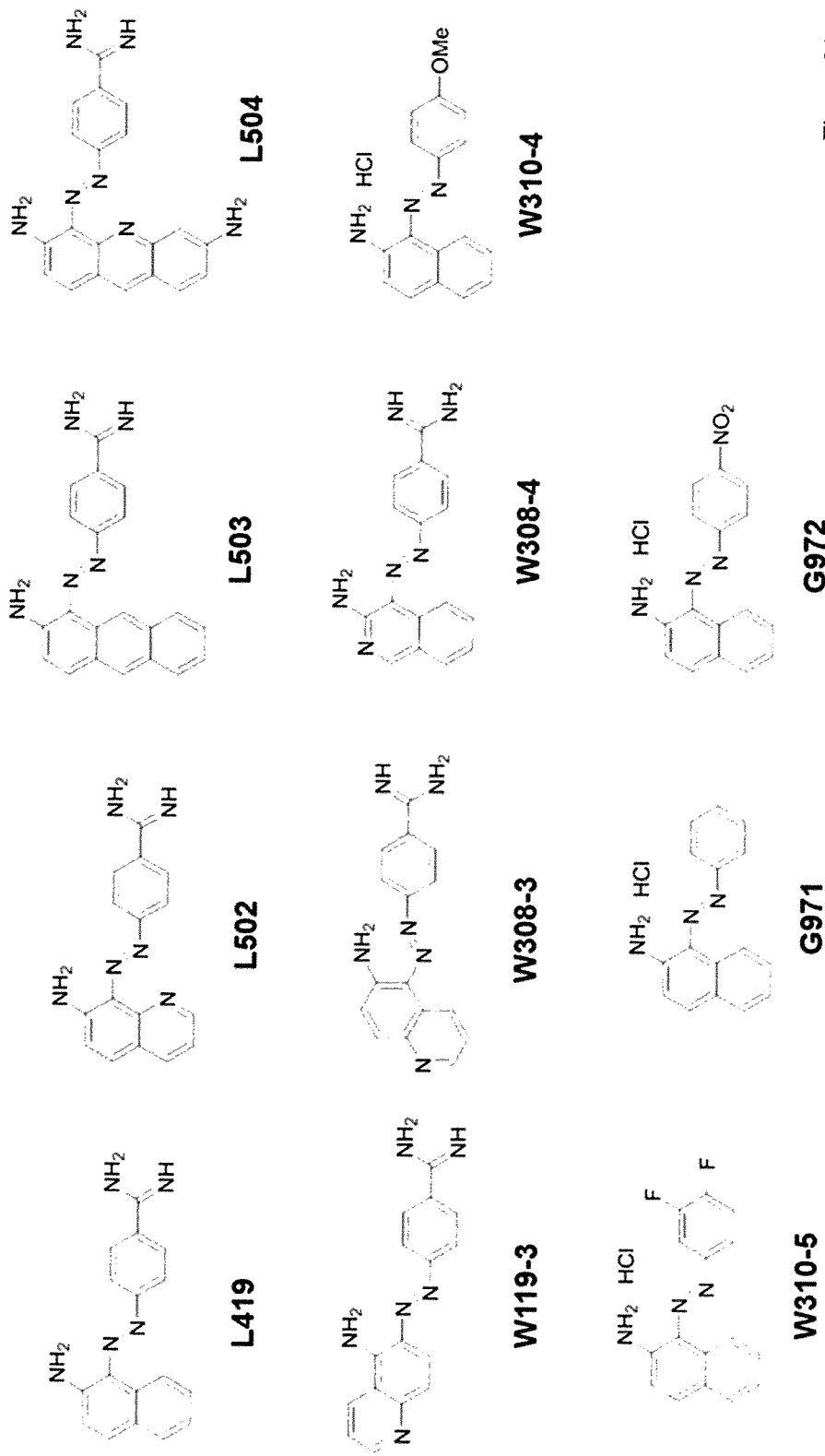
FIG. 31. Amino azo amidines screened against cancer cell lines. Compound L503 is reported in U.S. Pat. No. 4,619, 994 and is used as a control compound.

We synthesized two DMZ analogs (Triazene-1, which has one of the amidine groups in DMZ deleted and Triazene-2, which does not contain any amidine group, see FIG. 14) and tested their affinities for duplex and G-quadruplex DNA. The synthesis of Triazene-1 and Triazene-2, following precedent, is outlined in Scheme 2. First, the diazonium salts of p-aminobenzamidine and aniline were generated by treating with sodium nitrite followed by their coupling with aniline to give Triazene-1 and Triazene-2 in good yields. Both the synthesized triazenes were characterized by mass and NMR spectroscopy (FIGS. 27 and 28).

Scheme 2 Synthesis of triazene ligands.

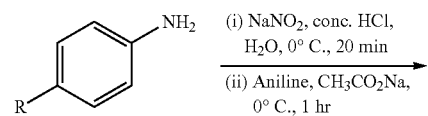

(i) NaNO₂, conc. HCl, H₂O, 0° C., 20 min
(ii) Aniline, CH₃CO₂Na, 0° C., 1 hr

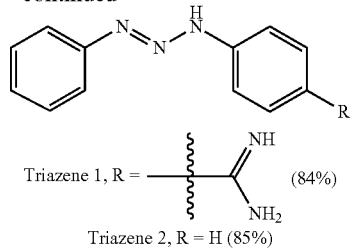

Triazene 1, R = –C(NH)NH₂ (84%)
Triazene 2, R = H (85%)

Figure 15:
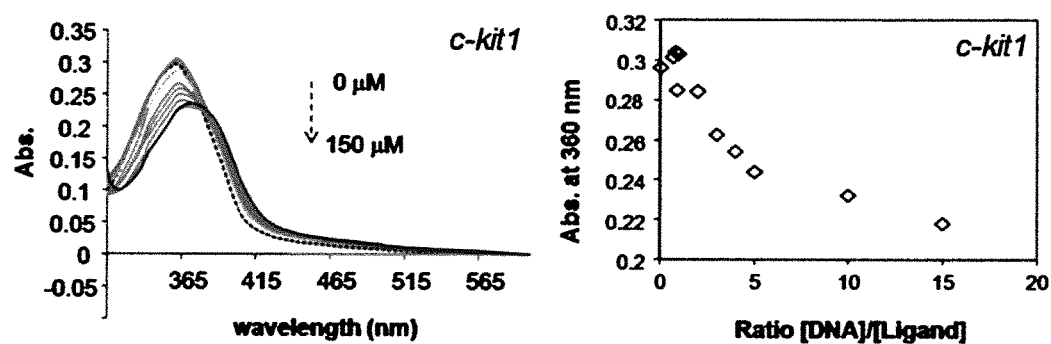
FIG. 15. UV-titration studies of binding of Triazene-1 with DNA. (Left) Absorption spectra of Triazene-1 (10 µM) upon titration with c-kit1. The concentrations of DNA are 0, 0.25, 1.5, 3, 5, 6, 7, 8, 9, 10, 20, 30, 40, 50, 100, 150 µM. In the graph, 10 µM and 150 µM DNA concentration is specifically emphasized as cyan and red line. [KCl]=250 mM, Buffer=50 mM Tris-HCl (pH 7.5). UV was measured at 20° C. (Right) Plot of absorbance at 360 nm against concentration ratio of DNA and Ligand (Triazene-1).
Figure 25:
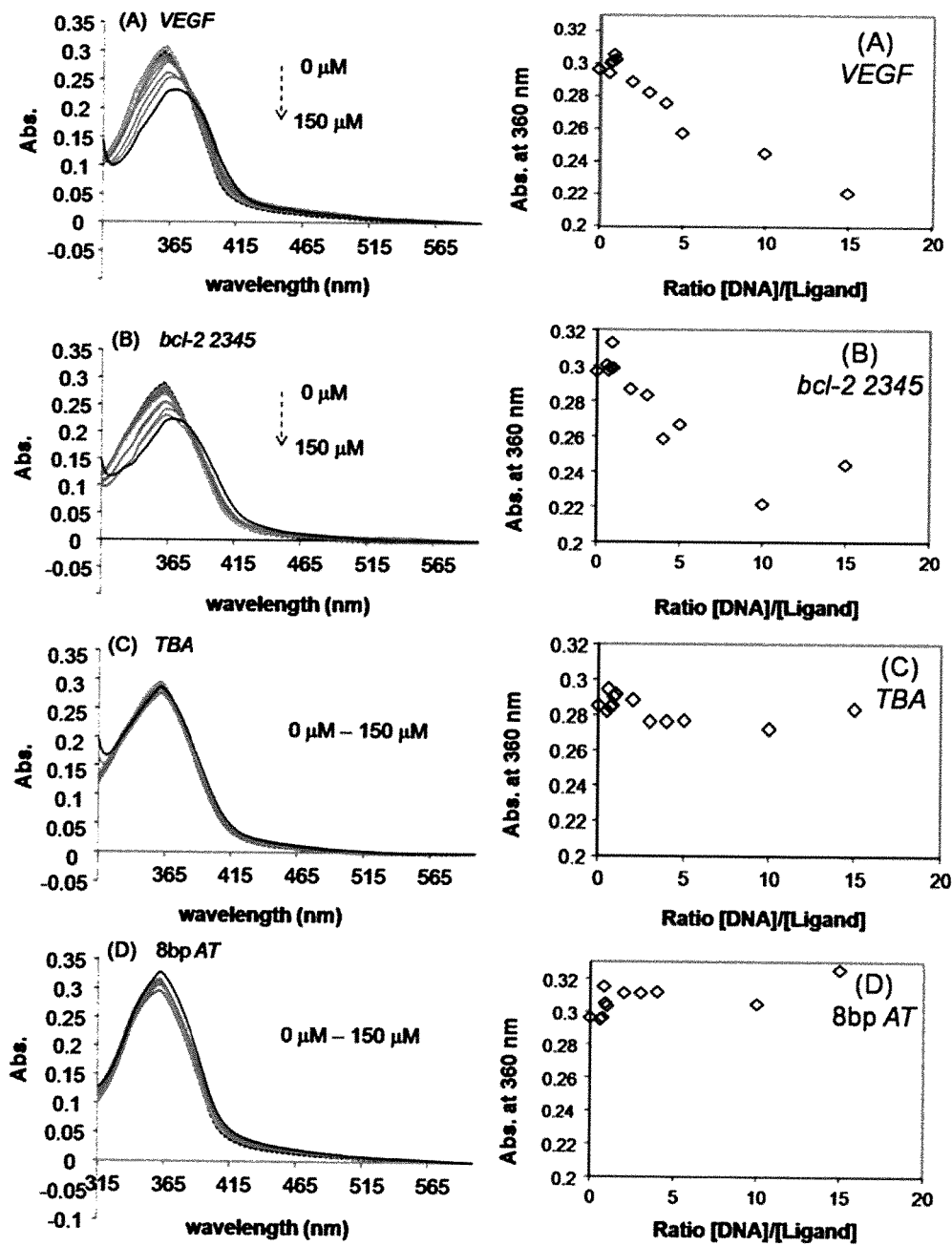
FIG. 25. UV-titration studies of binding of Triazene-1 with DNA. (Left) Absorption spectra of Triazene-1 (10 µM) upon titration with (A) VEGF, (B) bcl-2 2345, (C) TBA, (D) 8 bp AT. The concentrations of DNA are 0, 0.25, 1.5, 3, 5, 6, 7, 8, 9, 10, 20, 30, 40, 50, 100, 150 µM. In the graph, 10 µM and 150 µM DNA concentration is specifically emphasized as cyan and red line. [KCl]=250 mM, Buffer=50 mM Tris-HCl (pH 7.5). UV was measured at 20° C. (Right) Plot of absorbance at 360 nm against concentration ratio of DNA and Ligand (Triazene-1). Ligand concentration is 10 µM, DNA=(A) VEGF, (B) bcl-2 2345, (C) TBA, (D) 8 bp AT. The concentration of DNA is 0, 0.25, 1.5, 3, 5, 6, 7, 8, 9, 10, 20, 30, 40, 50, 100, 150 µM.

UV spectroscopy studies of Triazene-1 binding to G quadruplexes and duplex DNA. With the two new triazene compounds in hand, we next studied their interactions with both duplex and quadruplex DNA, qualitatively, by utilizing UV-visible titration experiments. Triazene-2, exhibited self-aggregation (data not shown here) and was not considered for this experiment. The absorbance maxima of Triazene-1 (10 µM) displayed a red shift with increasing concentrations of various G-quadruplex DNA (FIGS. 15 and 25), implying binding. In contrast, no such shift was observed when Triazene-1 was incubated with duplex DNA (FIG. 25), suggesting no robust interactions between the compound and the nucleic acid. Visual inspection of the UV titration experiments (compare FIGS. 13, 24 and 15, 25) revealed that DMZ had a higher affinity to the G-quadruplexes than the analog that had one amidine group removed, triazene-1. The degree of nucleic acid binding selectivity between DMZ and triazene-1 was quantified using ITC experiments, vide infra.

Figure 16:
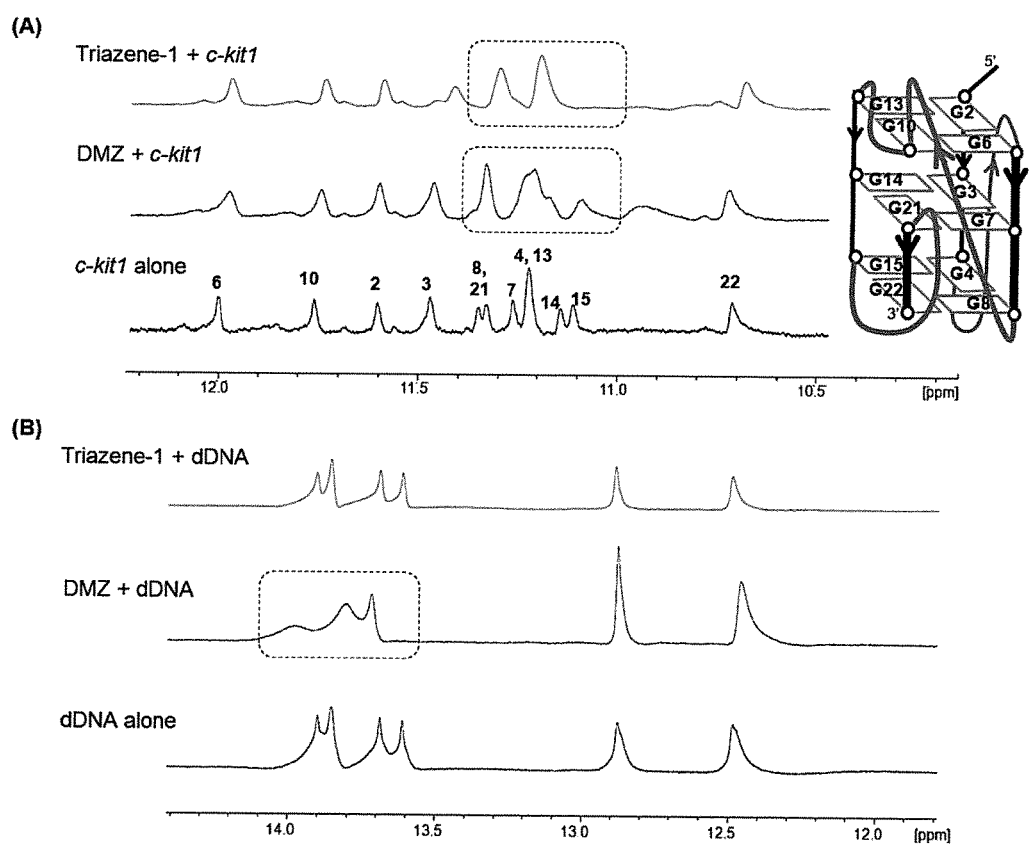

NMR analysis of binding of DMZ and Triazene-1 to DNA. To provide direct evidence for the binding of DMZ and Triazene-1 to c-kit1 (G-quadruplex) and duplex DNA, we performed ¹H-NMR titration experiments. Xu and co-workers used NMR to investigate the binding of a cyanine dye to c-kit1 so we decided to start with c-kit1, based on this precedent. In general, the guanine imino protons resonate between 10.0 to 12.5 ppm in a quadruplex matrix and this represents guanine NH . . . O hydrogen bonds in the Hoogsteen alignments of G-quartets. Upon binding of small molecules, the chemical environment around these imino protons changes, resulting in changes in their NMR chemical shifts. FIG. 16 shows the NMR spectra of the guanine imino protons of c-kit1 in presence of the ligands, DMZ and Triazene-1 in 90% H₂O/D₂O. The chemical shifts for the guanine imino protons in the spectrum of c-kit1 alone (FIG. 16A), [ligand]:[c-kit1]=0:1) was assigned based on the earlier work. The NMR titration spectra of DMZ and Triazene-1 with c-kit1 show considerable decrease in the peak intensities and line-broadening in the imino proton spectra (FIG. 16A). These results demonstrate direct binding of DMZ and Triazene-1 to c-kit1 (NMR resonances between 11.1 and 11.4 ppm are different between the case with no ligand added and when DMZ or triazene are added), consistent with our UV-visible titration experiments (FIGS. 13, 24 and 15, 25). When DMZ or Triazene-1 was added to c-kit1, the chemical shifts associated with the imino protons of G6, G10 and G2 did not change thereby excluding the possibility of end-stacking with the 5'-terminal tetrad of the quadruplex. Other NMR titration experiments with other G-quadruplexes, such as VEGF and bcl-2 2345 did not give stable baselines (data not shown), probably due to aggregation of the ligand/DNA complex. Despite this technical difficulty, the c-kit1 NMR titration experiment provides good evidence that DMZ does indeed bind to G-quadruplexes.

To study the interaction of the ligands with duplex DNA, NMR experiments in which 8 bp-AT was incubated with triazene ligands (DMZ and Triazene-1) were performed as described for c-kit1 above. In the case of duplex DNA (8 bp AT), only DMZ (but not Triazene-1) showed considerable changes in the imino region of spectrum of duplex DNA (see FIG. 16B). This is consistent with the UV titration data, which showed that Triazene-1 did not bind to AT-rich duplex DNA (see FIGS. 15 and 25).

NMR titration experiments have demonstrated that both DMZ and Triazene-1 bind to the c-kit1 G-quadruplex. However, a definitive identification of the DMZ and Triazene-1 binding sites was not possible with the current NMR data (FIG. 16A).

Initial screening experiments employing UV and NMR titration methods, provided qualitative evidence that DMZ and Triazene-1 bind to both duplex and G-quadruplex DNA. However, neither method is sensitive enough for the accurate determination sub-micromolar binding constants. By employing ITC, we were able to determine the energetics for the interactions of DMZ and Triazene-1 with several commonly studied G-quadruplex constructs hTel, c-myc, bcl-2. We also used ITC to study the interactions between DMZ and Triazene-1 and two hairpin duplex DNA constructs, one having an $A_2T_2$ binding site, 7 bp HP·AT, and one without the $A_2T_2$ site, 7 bp HP. The sequences for the DNA targets were shown in Table 1.

Figure 17:
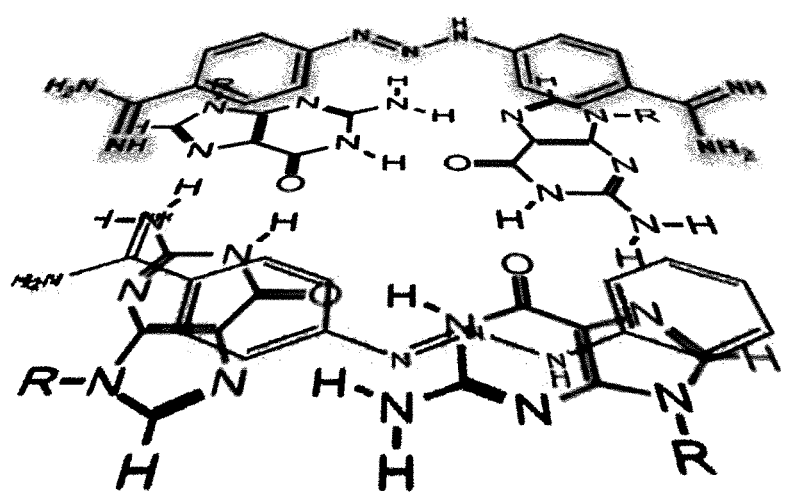
FIG. 17. Chemical structures of Diminazene aceturate (DMZ) and compound Triazene-1 in comparison to a chemical representation of a G-quartet.
Figure 18:
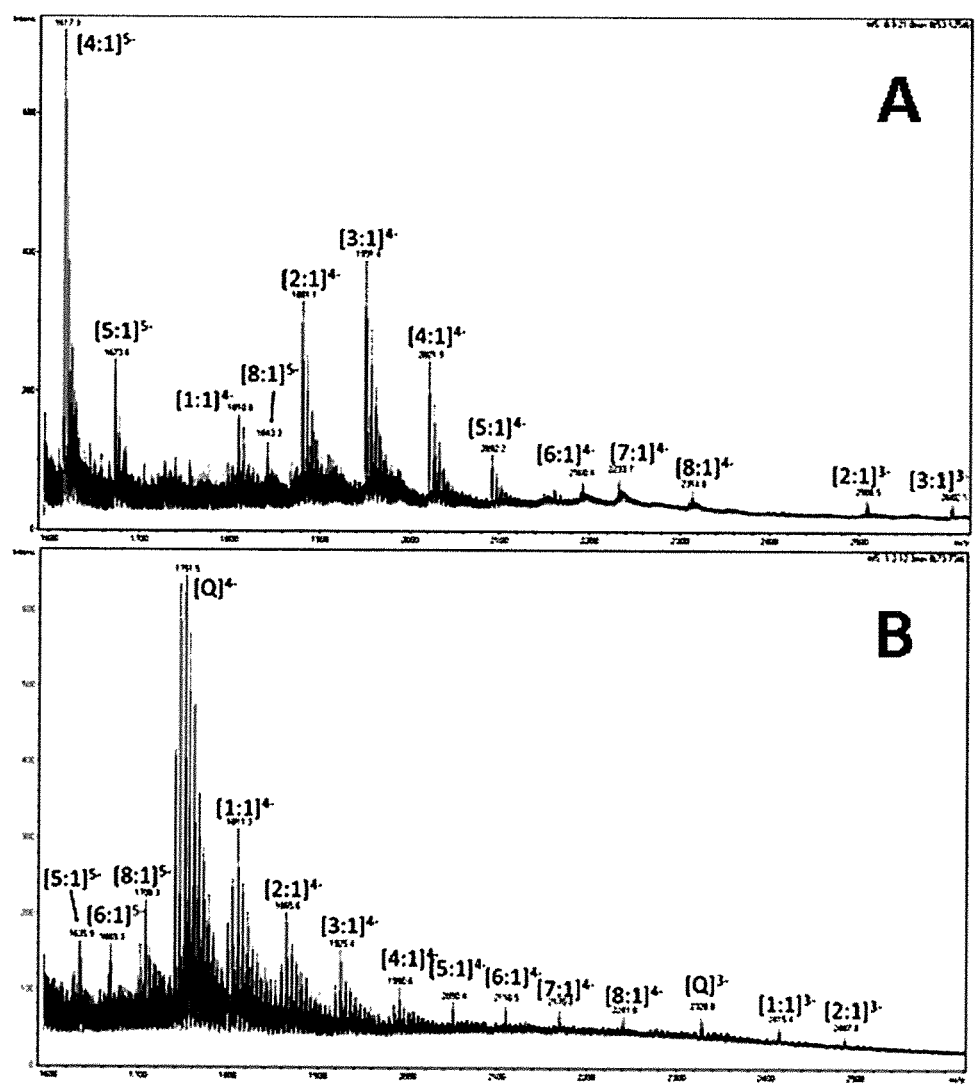
FIG. 18. ESI mass spectrum for hTel22 solution containing excess amount of DMZ (panel A) and ESI mass spectrum for hTel22 solution containing excess amount of Triazene-1 (panel B)

We have previously reported on the saturation stoichiometry and thermodynamic properties for the binding of several porphyrins and porphyrin derivatives to several oncogene promoter sequence G-quadruplex. In order to determine correct binding thermodynamic properties of any new G-quadruplex interactive ligands, it is important to know the saturation stoichiometry of the ligands. From the structural point of view, it can be seen in FIG. 17 that the surface area of any of the two compounds in this study (DMZ and Triazene-1) is about half of the surface area of the G-quartet. Therefore, we predicted that at saturation, the stoichiometry of both of these compounds would be approximately twice the saturation stoichiometry previously reported for TMPyP4 and G-quadruplex (having a 4:1 molar ratio of TMPyP4/G4-DNA). In FIG. 18, the ESI mass spectra for solutions containing hTel22 DNA sample in excess amount of DMZ (panel A) and excess amount of Triazene-1 (panel B) are shown. Three important features can be observed from panel A: first, there is no observable m/z peaks for free DNA; second, there are multiple m/z peaks indicating stoichiometry larger than 4:1; and third, DMZ and hTel22 complex exhibits saturation stoichiometry of 8:1 evidenced from m/z peaks at 1843.3 and 2314.0. Similarly, the ESI mass spectrum shown in FIG. 18 panel B for the solution containing hTel22 in excess amount of Triazene-1 also suggested a saturation stoichiometry of 8:1. However, the notable difference between panel A and B is that panel B clearly shows the presence of free/uncomplexed DNA evidenced by m/z peaks at 1751.5 and 2328. The presence of free DNA even in excess amount of Triazene-1 ligand suggests a low binding affinity for the binding of Triazene-1 to hTel22.

Figure 19:
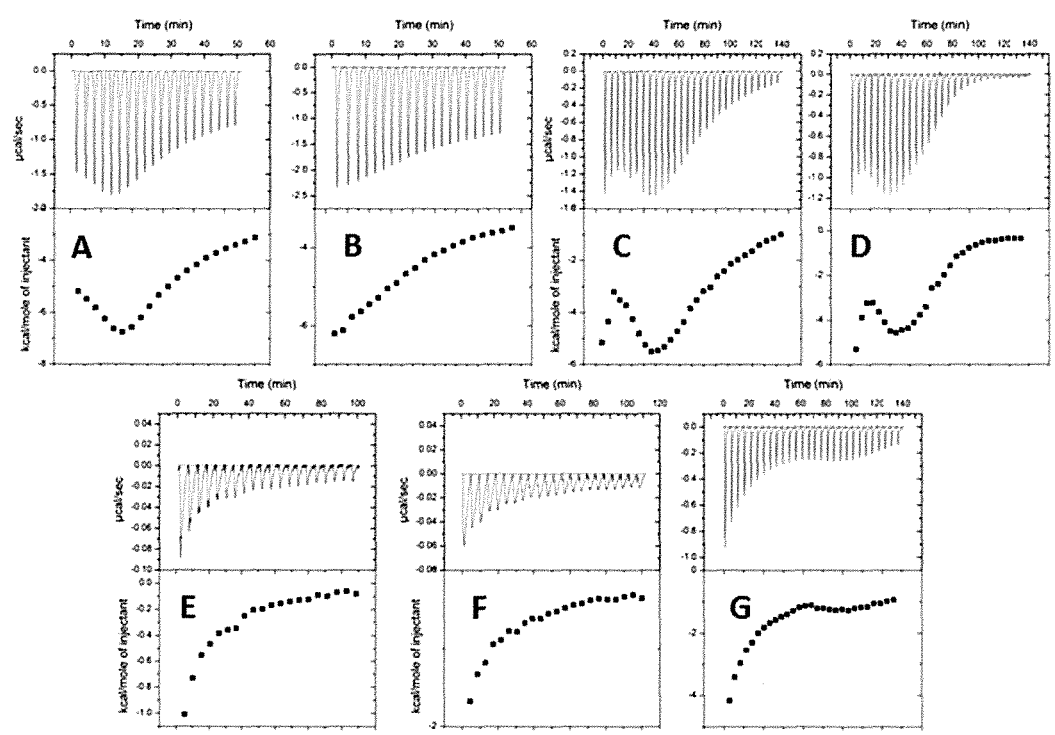
FIG. 19. Heat data obtained from ITC titration experiments for the interactions between DMZ and A) 7 bp HP·AT, B) 7 bp HP, C) 27mer bcl-2, D) 24mer c-myc, E) Tris buffer, F) 22mer hTelNa$^+$, and G) 22mer hTel K$^+$.

The ITC heat data for the titrations of DMZ to five different DNA sequences (two DNA hairpins and three G-quadruplex DNAs) is shown in FIG. 19. Upon visual inspection, it can be seen that DMZ binding to 7 bp HP·AT exhibits two overlapping binding sites (see panel A). The phenomenon of two overlapping sites observed for a single $A_2T_2$ site has been recently reported in the literature for minor groove binders. As expected, the interactions of DMZ and the 7 bp HP sequence lacking the $A_2T_2$ site exhibits only one binding event (see panel B). Interestingly, from initial inspection of the binding thermograms, the interactions between DMZ and 27mer bcl-2 and 24mer c-myc could be described by at least three different processes. Finally, the interactions of DMZ to the $Na^+$ form and the $K^+$ form of hTel22 G-quadruplexes are presented in the thermograms shown in panels F and G. By comparison with the blank titration experiment achieved by diluting the DMZ ligand solution into Tris buffer (compare panel E and F, FIG. 19), it seems that the interactions between DMZ with the $Na^+$ form of hTel22 G-quadruplex is calorimetrically silent under this experimental condition. On the contrary, the $K^+$ form of hTel22 G-quadruplex seems to interact with DMZ (compare panel E with G, FIG. 19). The interaction between DMZ and $K^+$ form hTel22 G-quadruplex must be described by at least two or three overlapping processes. The thermodynamic values obtained from fitting the ITC heat data shown in FIG. 19 panels A through G are listed in Table 2.

TABLE 2

Thermodynamic data obtained from ITC experiments for the interactions between DMZ compound and several different types of DNA.

| Sequences | $K_1$ ($M^{-1}$) | $\Delta H_1$ (kcal/mol) | $K_2$ ($M^{-1}$) | $\Delta H_2$ (kcal/mol) | $K_3$ ($M^{-1}$) | $\Delta H_3$ (kcal/mol) |
|---|---|---|---|---|---|---|
| 7bp HP · AT | $9.8 \times 10^5$ | −2.2 | $4.5 \times 10^4$ | −8.7 | — | — |
| 7bp HP | — | — | $1.8 \times 10^4$ | −5.3 | — | — |
| 27mer bcl-2 | $8.8 \times 10^8$ | −4.5 | $1.9 \times 10^6$ | −2.2 | $6.4 \times 10^4$ | −7.3 |
| 24mer c-myc | $7.6 \times 10^8$ | −5.5 | $1.9 \times 10^7$ | −2.5 | $2.8 \times 10^5$ | −4.7 |
| 22mer hTel $Na^+$ | nd | Nd | nd | nd | nd | nd |
| 22mer hTel $K^+$ | — | — | — | — | $5.5 \times 10^4$ | −3.8 | nd = not determined

Our ITC data reveals that DMZ binds to some G-quadruplex DNAs (for example 27mer bcl-2 and c-myc) with dissociation constants as low as ~1 nM, and this is a stronger affinity than that exhibited by guanidine phthalocyanines, considered to be one of the tightest binders of G-quadruplexes. Also the ligand TMPyP4, a classic G-tetrad-motif ligand, binds to G-quadruplexes weaker ($K_a \approx 5 \times 10^6$ $M^{-1}$) than DMZ does. Of note is the observation that even the second binding constant, $K_{a2}$ of $1.9 \times 10^7 M^{-1}$, for DMZ binding to c-Myc is an order of magnitude higher than the binding affinity ($K_1 \approx 1 \times 10^6$ $M^{-1}$) obtained from fitting our ITC thermograms for the interactions between DMZ and the 7 bp HP·AT. Our Ka value for DMZ binding to 7 bp HP·AT is very similar to the binding affinity ($K_{avg} \approx 1 \times 10^6$ $M^{-1}$) measured by NMR experiments previously reported by Jenkins et al. also for DMZ interactions with several types of B-DNAs containing the AT rich sequence. Interestingly, Jenkins et al. also mentioned of the two overlapping events exhibited by the interactions of DMZ with AT rich sequences. The phenomenon of two overlapping sites observed for AT rich sequence has been well documented and several possible mechanisms have been suggested, including: 1) two binding orientations of the minor groove binder to the DNA minor groove or 2) entrapment of one or several molecules between the minor groove binder and the floor of the DNA.

Figure 20:
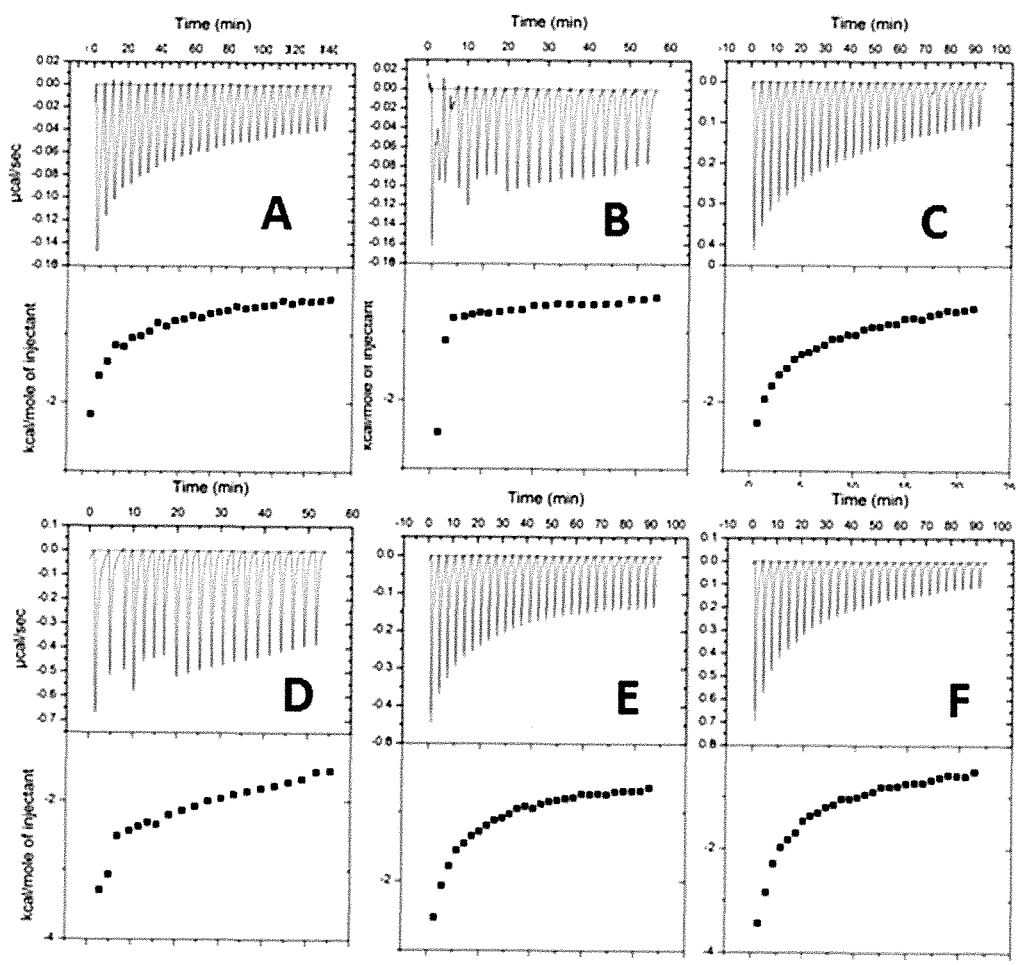
FIG. 20. Heat data obtained from ITC titration experiments for the interactions between Triazene-1 and A) with Tris buffer, B) 22mer hTelNa$^+$, C) 22mer hTel K$^+$, D) 7 bp HP·AT, E) 27mer bcl-2, and F) 24mer c-myc.

The ITC heat data for the titrations of Triazene-1 to four different DNA sequences (a DNA hairpin and three G-quadruplex DNAs) is shown in FIG. 20. Again, from visual inspection, on the basis of injection heat, it seems that the titration of Triazene-1 into $Na^+$ form of hTel22 is calorimetrically silent under this experimental conditions but not the $K^+$ form of hTel22. However, a notable difference between the heat data from DMZ titration experiments and the Triazene-1 titration experiments for the DNA samples is that Triazene-1 exhibited single binding events for the $K^+$ forms of hTel22, bcl-2, and c-myc G-quadruplexes. Also the binding affinities for these three G-quadruplexes are similar for Triazene-1, in contrast to what was observed for DMZ. Triazene-1 binds to all of the tested G-quadruplexes significantly less (4-5 orders of magnitude less, compare Tables 2 and 3). The same diminution in binding affinity is also seen with the interactions of Triazene-1 with 7 bp HP·AT (~30 times reduction in binding affinity). Furthermore, the second binding event observed in the DMZ binding to 7 bp HP·AT is now eliminated in binding of Triazene-1 to 7 bp HP·AT. Clearly, the removal of the diamidine group from the parent DMZ compound to create the Triazene-1 ligand resulted in the loss of $A_2T_2$ recognition in the minor groove of the DNA. This was expected as the presence of diamidine group has been observed in almost all minor groove binders such as distamycin, netropsin, DAPI and pentamidine. It however remains to be answered why the loss of $A_2T_2$ recognition in the minor groove as exhibited by Triazene-1 also resulted in much lower binding affinities for the interactions of Triazene-1 to different G-quadruplex.

TABLE 3

Thermodynamic data obtained from ITC experiments for the interactions between Triazene-1 compound and several different types of DNA.

| Sequences | $K_1$ ($M^{-1}$) | $\Delta H_1$ (kcal/mol) |
|---|---|---|
| 7bp HP·AT | $2.9 \times 10^4$ | −1.9 |
| 7bp HP | nd | nd |
| 27mer bcl-2 | $3.5 \times 10^3$ | −1.8 |
| 24mer c-myc | $3.6 \times 10^4$ | −1.1 |
| 22mer hTel $Na^+$ | nd | nd |
| 22mer hTel $K^+$ | $2.1 \times 10^3$ | −2.7 |

Figure 21:
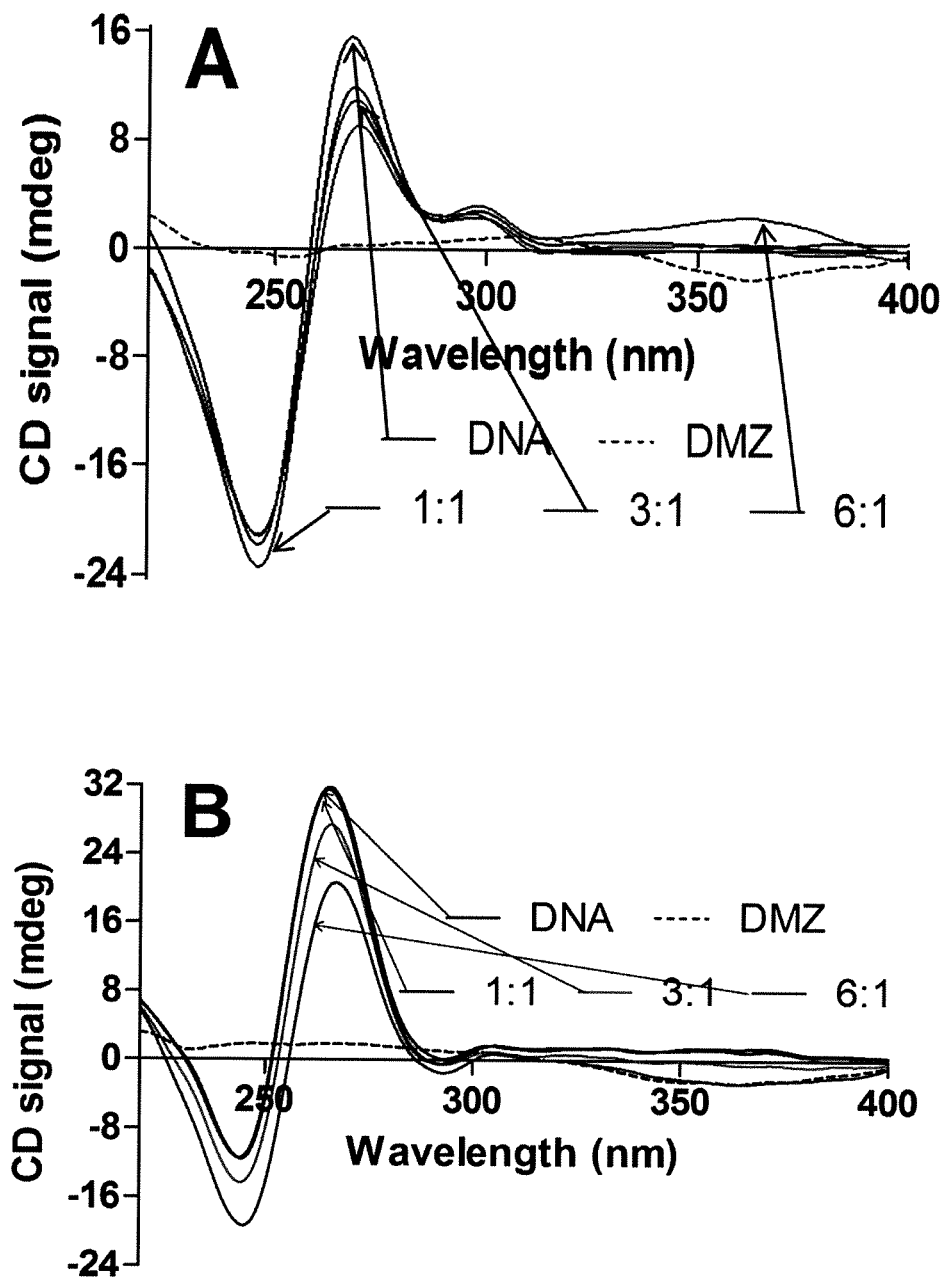
FIG. 21. CD spectra obtained from titration experiments for the additions of DMZ into a 27mer WT bcl-2 (4.5 µM, panel A) and into 24mer WT c-myc (3.9 µM, panel B).
Figure 22:
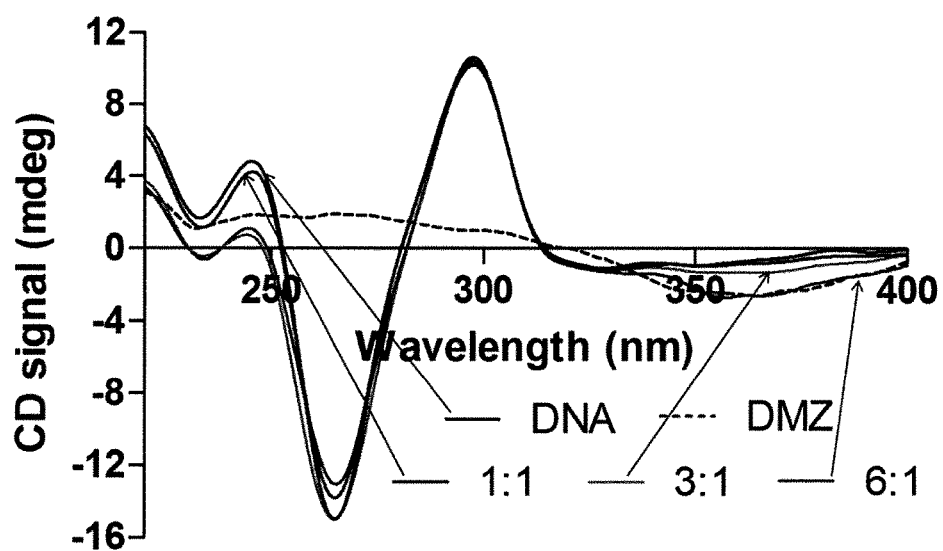
FIG. 22. CD spectra obtained from titration experiment for the additions of DMZ into a hTel22 (5.1 µM).
Figure 26:
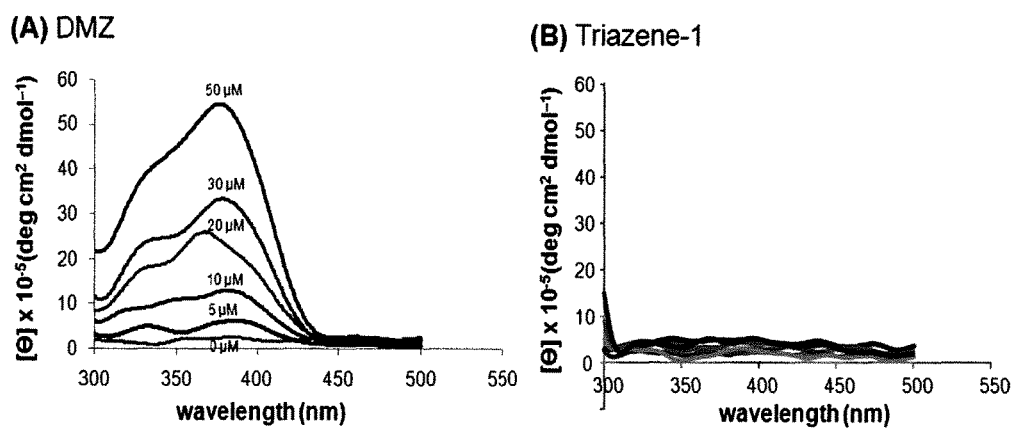
FIG. 26. CD titration studies. Increasing concentrations of duplex DNA were added to (A) DMZ (40 µM), (B) Triazene-1 (40 µM). The concentrations of added duplex DNA were 0, 5, 10, 15, 20, 25, 30, 50 µM. Buffer=50 mM Tris-HCl (pH 7.5), [KCl]=250 mM. CD measurement was done at 20° C.

DMZ binding to G quadruplexes studied by circular dichroism (CD). To determine the structural effects of the interactions between the DMZ and G-quadruplex DNAs, we performed a series of CD titration experiments between DMZ and different sequences of G-quadruplex. Shown in FIGS. 21 and 22 are the CD spectra for the titrations of DMZ into three different G-quadruplexes, bcl-2, c-myc, and hTel22. These CD titrations were performed in $K^+$ Tris buffer. Under the experimental buffer conditions ($K^+$ salt), the CD spectra for free or uncomplexed WT bcl-2, WT c-myc, and hTel22 G-quadruplexes exhibited characteristic CD features that similar to those that have been previously reported in the literature. However, upon complexation with DMZ, the CD signals for both 27mer WT bcl-2 and 24mer WT c-myc dramatically decreased as more DMZ was added. A plausible explanation for this is that the π-π stacking interactions in both 27mer WT bcl-2 and 24mer WT c-myc G-quadruplexes weakens upon DMZ binding. This cannot be explained by an end-stacking, which would instead probably increase the π-π stacking interactions and so suggests that DMZ initially either binds to a G-quadruplex groove or intercalates into adjacent G-tetrads, leading to lengthening of the G-quadruplex and partial interruption of the π-π stacks. DMZ does not have extended π-surfaces, such as is the case of TmPyP to interact extensively with the G-tetrad in end-stacking mode so groove binding or intercalation could also help explain the surprisingly tight affinity of DMZ for G-quadruplexes. For DMZ binding to hTel22 however, the additions of the DMZ had very little effect on the structure of hTel22, see FIG. 22. In contrast to the binding of DMZ to duplex DNA, which exhibits induced CD in DMZ but not Triazene-1 (FIG. 26), there was no appreciation induced CD in the region that DMZ absorbs when bound to the different G-quadruplexes. Typically a lack of induced CD is suggestive of intercalative mode of binding and not groove binding.

Displacement assays with the G-quadruplex binder, NMM. In these assays, the triazene ligand was used at various concentrations: 0, 5, 10, 20, 50, 100, and 200 μM; and the DNA concentration was kept at 10 μM, whereas the concentration of NMM was 1 μM. The experiments were performed in 50 mM Tris-HCl buffer (pH 7.5) in the presence of 50 mM KCl. The excitation wavelength used for NMM was 400 nm and the emission was monitored between 550 and 700 nm (slit width=5 nm, scan speed=600 nm/min, averaging time=0.1 sec, data interval=1 nm, PMT detector voltage=600 V, measurement temperature=20° C.). The sample was initially heated to 95° C. and kept at this temperature for 5 min without ligand or NMM and then cooled down to room temperature for 15 min. Subsequently, the triazene ligand was added to the DNA and incubated for ~12 h.

CD experiments for binding of ligands with duplex DNA (AT-rich). CD titration experiments, monitoring in the wavelength region corresponding to the bound ligand, were performed with different concentrations of 8 bp AT (0-50 μM) added to a fixed concentration of either DMZ or Triazene-1 (40 μM). No induced CD was observed for Triazene-1 but a large positive induced CD was observed upon incubating 8 bp AT (0-50 μM) with DMZ (compare FIGS. 23A and 23B). The resulting large positive signal in the CD spectrum of DMZ, upon addition of AT-rich duplex DNA, suggests a groove-binding mode of DMZ with duplex DNA, consistent with literature. The lack of induced CD of Triazene-1 suggests that Triazene-1 does not bind to the minor groove of AT-rich DNA.

This finding that DMZ could also bind to DNA G-quadruplexes is exciting for the following reasons: a) DMZ does not readily form i-aggregates and hence it is not as prone to non-specific binding to other biomolecules as other aromatic-containing G-quadruplex ligands; b) the amidine groups on DMZ facilitates solubilization in water (an important factor for drugs); c) Unlike other structurally complex minor groove binders such as netropsin, DMZ has a simple structure and could be readily diversified and synthesized cheaply on a large scale and d) the amidine group, which is protonated at physiological pH, would facilitate drug permeation across lipid membranes that are externally decorated with anionic phosphates.

Data presented in this disclosure also indicate that some of the toxic effects or even the clinical benefits of DMZ could be due to its binding to G-quadruplexes. Without intending to be bound by any particular theory, it is ironic that a ligand such as DMZ, which has long been considered as AT-rich specific minor groove binder does in fact strongly bind to G-quadruplexes.

EXAMPLE 2

This example provides syntheses of alkyne-substituted DMZ analogs, their G-quadruplex binding activity, and their anticancer properties.

Alkyne-substituted diminazene as G-quadruplex binders with anticancer activities.

Using a panel of biophysical tools, including NMR, FRET melting assay and FRET competition assay, we discovered that monoamidine analogues of DMZ bearing alkyne substitutes selectively bind to G-quadruplexes. The lead DMZ analogs were shown to be able to target c-MYC G-quadruplex in vitro by using PCR stop assay (see FIG. 1 for DMZ analogs). Additionally Western analysis showed that one of the alkyne DMZ analogs could inhibit the expression of c-MYC oncoprotein in vivo. Interestingly alkyne DMZ analogs were also able to inhibit telomerase expression in MDA-MB-231 cells. Alkyne DMZ analogs display suitable anticancer activities (single digit micromolar $IC_{50}$) against ovarian (OVCAR-3), prostate (PC-3) and triple negative breast (MDA-MB-231) cancer cell lines and represent interesting new leads to develop anticancer agents.

Experimental. General information. Diminazene aceturate (DMZ), 4-aminobenzamidine dihydrochloride, most of aromatic amines were purchased from Sigma-Aldrich and used without further purification. DMZ1 (also referred to herein as triazene-1) was obtained following published procedure. 3-(Phenylethynyl)aniline and 3-(pyridin-2-yl-ethynyl)aniline were purchased from EnamineStore Ltd. c-kit1 22-mer (5'-AGG GAG GGC GCT GGG AGG GAG G-3') (SEQ ID NO:7), F21T 21-mer (5'-FAM-GGG TTA GGG TTA GGG TTA GGG-TAMRA-3') (SEQ ID NO:11), c-kit2 26-mer (5'-FAM-CCC GGG CGG GCG CGA GGG AGG GGA GG-TAMRA-3') (SEQ ID NO:12), k-RAS21R 21-mer (5'-FAM-AGG GCG GTG TGG GAA GAG GGA-TAMRA-3') (SEQ ID NO:13), c-MYC 22-mer (5'-FAM-TGA GGG TGG GTA GGG TGG GTA A-TAMRA-3') (SEQ ID NO:14), duplex 26-mer (5'-FAM-TAT AGC TAT ATT TTT TTA TAG CTA TA-TAMRA-3') (SEQ ID NO:15) and double-stranded competitor 26ds DNA (5'-CAA TCG GAT CGA ATT CGA TCC GAT TG-3') (SEQ ID NO:16) were purchased from IDT, where FAM is 6-carboxyfluorescein and TAMRA is 6-carboxytetramethylrhodamine. The concentrations of DNA stock solutions were determined by measuring the absorbance at 260 nm using the extinction coefficient values published in the literature. Nuclear magnetic resonance (NMR) spectra were recorded on Bruker DRX-400 MHz instrument ($^1$H, 400 MHz; $^{13}$C, 100 MHz) or Bruker DRX-500 MHz instrument ($^1$H, 500 MHz; $^{13}$C, 125 MHz). Data for $^1$H NMR and $^{13}$C spectra were recorded as follows: chemical shift (δ, ppm), multiplicity (s, singlet; d, doublet; t, triplet; q, quartet; m, multiplet), integration, coupling constant (Hz). High-resolution mass spectra (HRMS) have been obtained by a TOF instrument with ESI positive mode as the ionization method.

Synthesis of the DMZ Analogues. Synthesis of Alkyne-Substituted Aromatic Amines Via Sonogashira Coupling

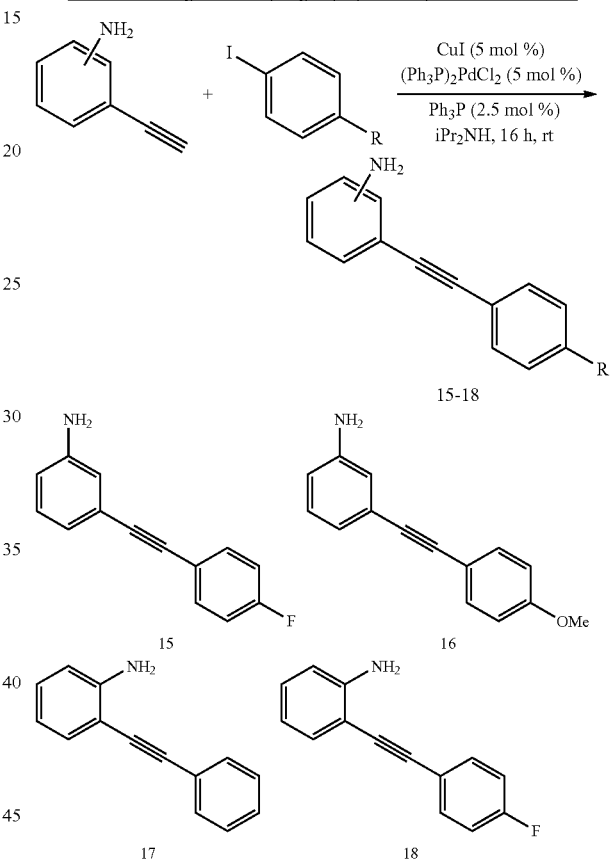

The syntheses of alkyne-substituted aromatic amines (15-18) followed the general Scheme 3. A 50 ml Schlenk flask was charged with aryl iodide (2 mmol, 1.0 eq.), bis-(triphenylphosphine) palladium dichloride (70 mg, 0.05 eq.), cuprous iodide (10 mg, 0.05 eq.), triphenylphosphine (13 mg, 0.025 eq.), and a stir bar and sealed with rubber septum. The flask was evacuated and refilled three times with Argon. Ethynylaniline (1.1 eq.) was added to 10 mL of distilled dry iPr$_2$NH and degassed together in a separated round bottom flask for 15 minutes and then transferred to the Schlenk flask through cannula. The mixture was stirred for 16 hours at room temperature (65° C. in the case of aryl bromide). After completion of the reaction, the mixture was diluted with ethyl acetate (50 mL) and the slurry was filtered through a pad of Celite in a sintered glass funnel (medium frit). The tan solids were additionally washed with ethyl acetate until the filtrate was nearly colorless. The filtrate was washed with H$_2$O and brine and dried over magnesium sulfate. The combined organic fraction filtrates were concentrated in vacuum, yielding a black solid. The residue was further purified by flash column chromatography on silica gel using ethyl acetate/hexane mixture as eluent.

General Procedure for the Synthesis of DMZ Analogues.

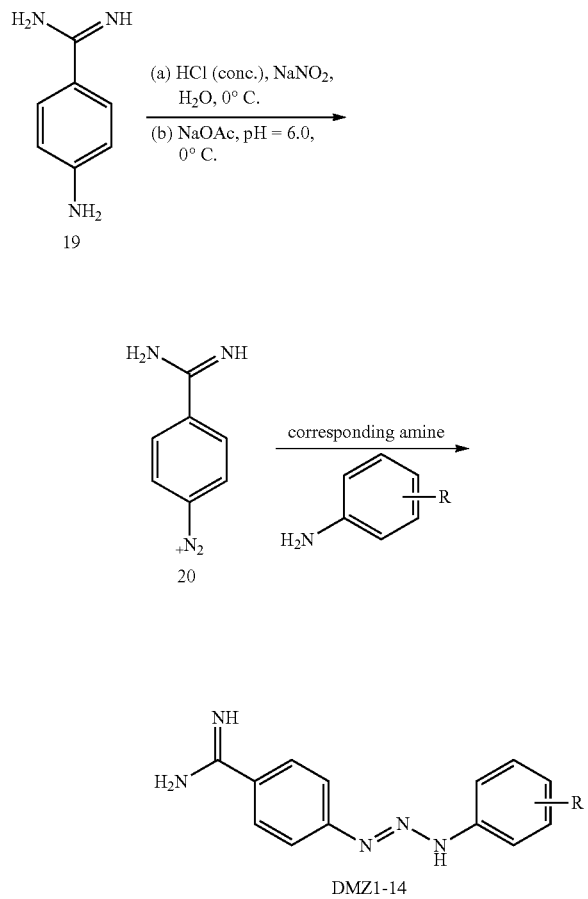

Scheme 4 Facile synthesis of DMZ analogues via diazonium intermediates.

The synthesis of DMZ analogues followed previously reported procedure, see Scheme 4. 4-Aminobenzamidine dihydrochloride (212 mg, 1.0 mmol) was added to a stirred solution of 12 N HCl (0.27 mL) and water (1.5 mL) in a 10 mL flask at 0° C. and stirring was continued for 15 min. To the mixture was added (dropwise) cold (~0° C.) NaNO$_2$ solution (76 mg in 0.27 mL water, 1.1 eq.) and stirring was continued for 15 min before cold (~0° C.) NaOAc solution (328 mg in 1.5 mL water, 4.0 eq.) was added dropwise over 15 min to adjust the pH to 6.0. Cold (–0° C.) aromatic amine solution (1.0 mmol in 1.0 mL methanol) was added dropwise to the above solution and stirring was continued for another 1-12 hours at 0° C. After the reaction was completed, the solvent was removed under reduced pressure. Water (100 mL) was added to the residue and the aqueous mixture was washed with dichloromethane (2×15 mL). The aqueous layer was then basified with 2.5% NaOH solution to make the pH>10.0. The desired compound was then extracted from the aqueous layer with ethyl acetate (2×100 mL). The organic layer was washed with brine and dried with sodium sulfate. Finally, the solvent was removed under reduced pressure and the final product was obtained with purity >95%.

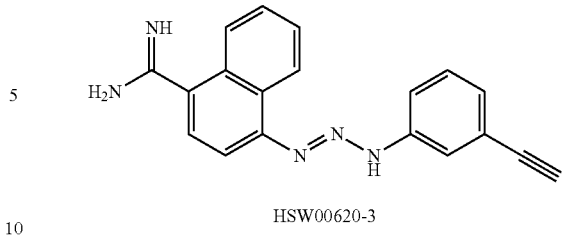

HSW00620-3

Following the procedure described above, HSW00620-3 was obtained as yellow solid. $^1$H NMR (500 MHz, MeOD) δ=8.67-8.61 (m, 1H), 8.20 (d, J=8.2, 1H), 7.72 (d, J=7.8, 1H), 7.68-7.64 (m, 1H), 7.64-7.56 (m, 2H), 7.53 (s, 1H), 7.45 (d, J=8.2, 1H), 7.37-7.33 (m, 1H), 7.20 (d, J=7.6, 1H). $^{13}$C NMR (125 MHz, MeOD) δ 169.04, 147.57, 145.01, 132.23, 130.72, 130.56, 129.96, 129.52, 128.53, 128.43, 127.39, 127.21, 127.12, 125.96, 124.97, 124.75, 120.12, 117.44, 112.51, 83.91, 78.45. HRMS (ESI+) [M+H] calcd for C$_{19}$H$_{16}$N$_5$ 314.1406. found 314.1409.

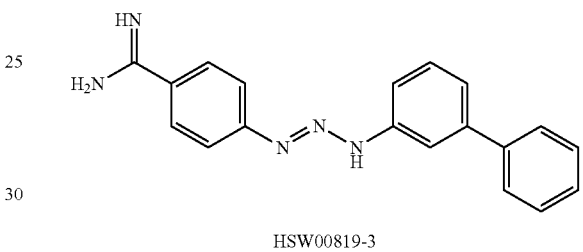

HSW00819-3

Following the procedure scribed in [00153], HSW00819-3 was obtained as yellow solid. $^1$H NMR (500 MHz, MeOD) δ=7.79-7.76 (m, 3H), 7.71-7.66 (m, 2H), 7.45 (d, J=8.0, 3H), 7.42-7.34 (m, 3H), 6.77 (d, J=2.2, 1H), 6.71 (dd, J=8.9, 2.3, 1H). $^{13}$C NMR (125 MHz, MeOD) δ 168.00, 157.51, 154.84, 147.74, 142.89, 141.56, 132.29, 130.41, 129.71, 128.91, 128.69, 128.53, 124.07, 118.88, 116.20, 115.62. HRMS (ESI+) [M+H] calcd for C$_{19}$H$_{18}$N$_5$ 316.1562. found 316.1579.

Cell lines and culturing. The following human cell lines were purchased from ATCC (ATCC, Manassas, Va.): prostate cancer cells (PC-3), triple negative breast cancer cells (MDA-MB-231), ovarian cancer cells (OVCAR-3), normal bone marrow (NBM) and normal fibroblast cells (MCRSA). MDA-MB-231 cells were grown at 37° C. with 5% CO$_2$ atmosphere with DMEM (Life technologies, Carlsbad, Calif.) supplemented with heat-inactivated 10% (V/V) fetal bovine serum. OVCAR-3 and PC-3 cells were grown at 37° C. with 5% CO$_2$ atmosphere with RPMI (Life technologies, Carlsbad, Calif.) supplemented with heat-inactivated 10% (V/V) fetal bovine serum. Cell lines were grown and maintained according to ATCC recommendations.

IC$_{50}$ determination. Cell lines were seeded into 96-well plates the afternoon prior to treatment. Cell seeding number was determined by growing cells in log phase growth during drug treatment. Approximately 18 hours later, compounds were semi-serially diluted in dimethyl sulfoxide (DMSO) and then growth medium, and added to cells. Plates were incubated for 72 hours prior to addition of WST-1 (Promega, Madison Wis.). Plates were read after 4 additional hours of incubation at 37° C. using a Bio-Tek Synergy HT plate reader (Bio-Tek, Winooski, Vt.). Data was analyzed, graphed and IC50s generated using GraphPad Prism Software (Graphpad, La Jolla, Calif.).

Fluorescence resonance energy transfer (FRET) assay to determine $T_m$ in absence and presence of ligands. Dual-labelled DNA was diluted from stock (50 µM) to 400 nM in 60 mM potassium cacodylate buffer (pH 7.2) and then annealed by heating at 85° C. for 10 min followed by cooling to room temperature in the heating block. Compounds were diluted from stock (20 mM in DMSO) to 2 µM in 60 mM cacodylate buffer (pH 7.2). 25 µL annealed DNA was added to 96-well plate followed by 25 µL diluted compounds. The sequences of labelled oligonucleotides were as follows: F21T 21-mer (5'-FAM-GGG TTA GGG TTA GGG TTA GGG-TAMRA-3') (SEQ ID NO:11), c-kit2 26-mer (5'-FAM-CCC GGG CGG GCG CGA GGG AGG GGA GG-TAMRA-3') (SEQ ID NO:12), k-RAS21R 21-mer (5'-FAM-AGG GCG GTG TGG GAA GAG GGA-TAMRA-3') (SEQ ID NO:13), c-MYC 22-mer (5'-FAM-TGA GGG TGG GTA GGG TGG GTA A-TAMRA-3') (SEQ ID NO:14) and duplex 26-mer (5'-FAM-TAT AGC TAT ATT TTT TTA TAG CTA TA-TAMRA-3') (SEQ ID NO:15). Measurements were made in triplicate by using a LightCycler 480 System RT-PCR machine (Roche) and average values were reported. Fluorescence readings were made with excitation at 450-495 nm and detection at 515-545 nm, taken at intervals of 1.2° C./min in the range 25° C. to 95° C.

FRET DNA melting in competition with duplex DNA. FRET competition assay was performed by adding 2 µM, 20 µM and 100 µM double-stranded competitor 26ds DNA (5'-CAA TCG GAT CGA ATT CGA TCC GAT TG-3') (SEQ ID NO:16) in the presence of 0.2 µM c-MYC G-quadruplex and 1 µM DMZ analogs. Both c-MYC G-quadruplex and 26ds DNA were diluted in 60 mM potassium cacodylate buffer (pH 7.2) and then annealed by heating at 85° C. for 10 min followed by cooling to room temperature in the heating block. Experiments were performed in triplicate.

NMR of DNA/DNA analogue complexes. NMR of spectra (c-kit1 or 8 bp AT) in absence or presence of ligands were obtained following precedent. The sample solution containing c-kit1 (300 µM), $D_2O$ (10%, v/v), NaCl (137 mM), EDTA (1 mM) and potassium phosphate buffer (10 mM, pH 7.5) was heated up to 95° C. for 5 min, then cooled down to room temperature, and subsequently incubated for another 12 hours at 4° C. The DMZ analogue (150 µM) was then added and incubated for 2 hours at 4° C. The $^1H$ NMR spectra were recorded at 25° C., using NaOAc as an internal standard (NaOAc was in a sealed capillary tube that was inserted in the NMR tube). The $^1H$ NMR spectra was recorded on Bruker Avance III HD 800 MHz spectrometer with a CPQCI cryoprobe.

PCR Stop Assay. This assay was performed by modifying a previously published protocol. Sequences of the tested oligomers, Pu27, Pu27-13,14 and the corresponding complementary oligomer Pu27rev were presented in Table 4.

TABLE 4

Sequences of Oligomers used in the PCR Stop Assay.

| Name of Oligomers | Sequence | Description |
|---|---|---|
| Pu27 | 5'-TGGGGAGGGTGGGGAGGGTGGGGAAGG-3' (SEQ ID NO: 17) | Partial sequence of promoter of oncogene c-MYC. |
| Pu27-13,14 | 5'-TGGGGAGGGTGGAAAGGGTGGGGAAGG-3' (SEQ ID NO: 18) | A mutated Pu27 whose guanines at $13^{th}$ and $14^{th}$ positions were changed to adenosines. This non-G-quadruplex forming DNA was used as a control template. |
| Pu27rev | 5'-ATCGATCGCTTCTCGTCCTTCCCCA-3' (SEQ ID NO: 19) | Complementary sequence of Pu27 |

To the PCR reaction mixture (25 µL), 1×PCR buffer (New England Biolabs), 5 µM Pu27 and Pu27rev oligomers, various concentrations of ligands (DMZ, TMPyP4, DMZ1, DMZ9 and DMZ13) were added and incubated at 4° C. for 6 h. After that, 1 mM dNTPs, 5 units of Taq DNA polymerase (New England Biolabs) were added and PCR reactions were performed in a thermocycler, with the following conditions: 94° C. for 3 min, followed by 20 repeated cycles each having 94° C. for 30 s, 58° C. for 30 s, and 72° C. for 30 s. After PCR, amplified products were analyzed on 12% polyacrylamide gel with 1×TBE and SYBR Gold stained. This assay was also performed under the same conditions with Pu27-13,14 and Pu27rev.

Telomerase Activity Assay. MDA-MB-231 cells were routinely cultured in DMEM with 10% FBS and 1% L-glutamine. The evening prior to treatment, actively growing MDA-MB-231 cells were sub-cultured and seeded into T-25 flasks at $2 \times 10^5$ cells/flask. The following morning, cells were treated with either vehicle, DMZ9, DMZ13, or TMPyP4 at 0.5×, 1×, or 2×$IC_{50}$. At 48 and 72 hours after treatment, cells were harvested, washed with PBS, and pelleted. Cell pellets were resuspended in 200 µl CHAPS lysis buffer with 200 units/mL RNase inhibitor, mixed by pipetting, and incubated on ice for 30 minutes. Lysates were then centrifuged at 12,000×g for 20 minutes at 4° C., and supernatants were collected, snap frozen, and stored at −80° C. until analysis. Telomerase activity was assayed using a fluorescence-based TRAPeze XL telomerase detection kit (Intergen, Purchase, N.Y.). According to manufacturer, lysates (1000 cell-equivalents) were mixed with TRAPeze XL reaction mix containing Amplifuor primers and incubated at 30° C. for 30 min to allow the elongation of "TS" primer by telomerase. Amplified telomerase products were quantitated with a fluorescence plate reader. Telomerase activity (in TPG units) was calculated by comparing the ratio of telomerase products to an internal standard for each lysate, as described by the manufacturer. Each unit of TPG (Total Product Generated) corresponds to the number of TS primers extended with at least 3 telomeric repeats by telomerase in the extract in a 30 minute incubation at 30° C.

Figure 3:
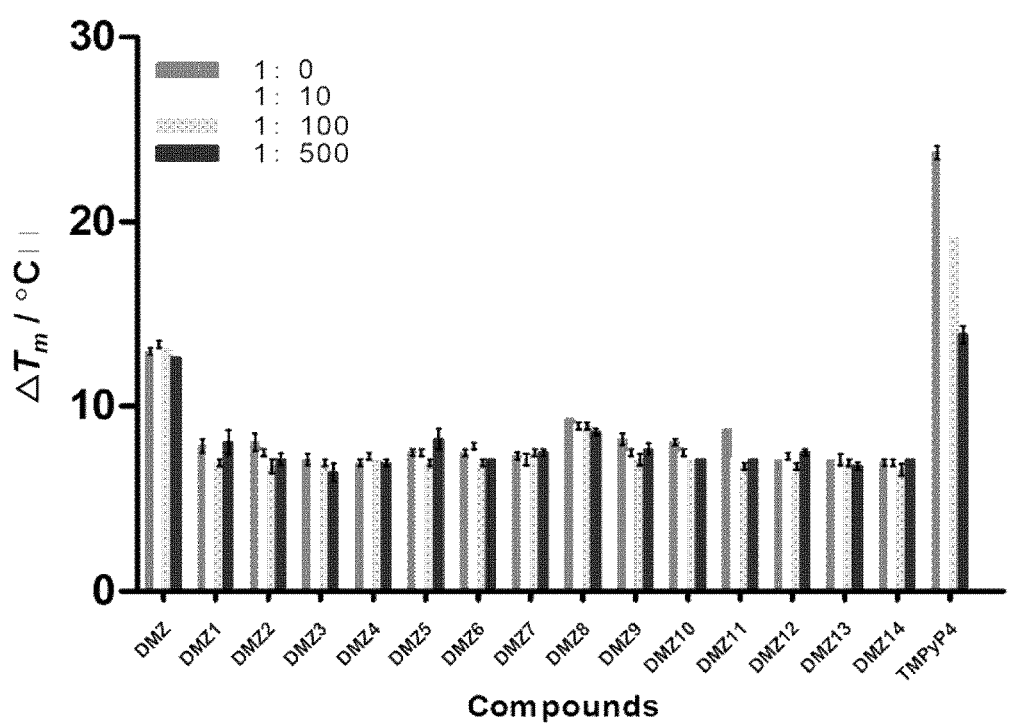
FIG. 3. FRET-melting competition results at 1 µM DMZ analogs in the presence of dual-labeled c-MYC (0.2 µM) and unlabeled ds-DNA (0 µM, 2 µM, 20 µM and 100 µM). $\Delta T_m$ is calculated by melting temperature in the presence and absence of DMZ analogues. 0.2 µM TMPyP4 was added to get meaningful melting temperature.

Results and discussion. Alkyne-substituted DMZ analogues as G-quadruplex binders. To improve alkyne DMZ analogues for use as anticancer agents, we sought to verify that like the parent DMZ, these compounds also bind to G-quadruplexes. Also, we asked if the compounds were selective for G-quadruplexes over DNA duplexes. Others have used FRET melting of fluorophore-labeled G-quadruplexes to determine the binding of ligands to G-quadruplexes and also selectivity between G-quadruplexes and duplexes, so we decided to adopt this protocol. Thus, we investigated the change in melting temperature ($T_m$) by fluorescence resonance energy transfer (FRET) assay (Table 5 and FIG. 3). We chose dual-labeled F21T, c-MYC, c-kit2 and k-RAS21R because c-MYC G-quadruplex affects the c-MYC transcriptional activity, while c-kit and k-RAS G-quadruplexes control the expression of oncogenic c-kit and KRAS proteins and F21T is a good model for telomere. Double-stranded DNA (26ds) can form a duplex structure at human chromosome ends and so the fluorophore-labeled 26ds was used to determine if the ligands could also bind to duplexes. The FRET-labeled oligonucleotides used in this study have also been used by others and shown to be well-behaved in determining the potency of G-quadruplex ligands.

Removing one of the amidine groups from DMZ to afford compound DMZ1 improved the G-quadruplex-duplex selectivity ($\Delta T_m < 1°$ C. for double-stranded DNA). Interestingly, adding an alkyne group to compound DMZ1 increased ability to stabilize G-quadruplex structures but not double-stranded DNA (for example compare entries ii and ix in Table 5). To provide additional evidence that compound DMZ1 and alkyne analogues have superior G-quadruplex over duplex DNA selectivity than the parent DMZ, we determined the melting temperature of c-MYC in the presence of ligands and increasing concentrations of non-fluorescent double-stranded DNA (with same sequence as 26ds, except for the removal of labeled groups), see FIG. 3. When compound DMZ1 or alkyne derivatives were used as ligands, adding up to 500 equivalence of double-stranded DNA did not affect the $T_m$ of c-MYC. This is in agreement with the FRET melting data in Table 5.

TABLE 5

Change in melting temperatures of G-quadruplex and duplex DNA in the presence of various DMZ analogues.[a]

| Entry | Compound | $\Delta T_m$ (° C.)[b] | | | | |
|---|---|---|---|---|---|---|
| | | F21T | c-MYC | c-kit2 | k-RAS21R | duplex |
| i | DMZ | 10.05 ± 0.52 | 12.97 ± 0.26 | 11.70 ± 0.26 | 18.27 ± 0.52 | 6.40 ± 0.00 |
| ii | DMZ1 | 4.20 ± 0.00 | 7.87 ± 0.53 | 6.40 ± 0.26 | 5.47 ± 0.93 | NE[d] |
| iii | DMZ2 | 4.20 ± 0.00 | 8.06 ± 0.68 | 5.30 ± 0.26 | 7.49 ± 0.00 | NE |
| iv | DMZ3 | 4.57 ± 0.26 | 7.13 ± 0.45 | 5.30 ± 0.26 | 5.66 ± 0.51 | NE |
| v | DMZ4 | 4.57 ± 0.26 | 6.94 ± 0.26 | 6.22 ± 0.26 | 2.00 ± 0.45 | NE |
| vi | DMZ5 | 4.39 ± 0.26 | 7.51 ± 0.26 | 5.48 ± 0.45 | 6.39 ± 0.89 | NE |
| vii | DMZ6 | 4.57 ± 0.26 | 7.49 ± 0.26 | 5.48 ± 0.45 | 4.20 ± 0.90 | NE |
| viii | DMZ7 | 4.20 ± 0.00 | 7.33 ± 0.26 | 6.40 ± 0.26 | 2.56 ± 0.00 | NE |
| ix | DMZ8 | 4.75 ± 0.00 | 9.32 ± 0.00 | 8.04 ± 0.26 | 14.62 ± 0.45 | NE |
| x | DMZ9 | 4.20 ± 0.00 | 8.22 ± 0.45 | 5.67 ± 0.26 | 6.58 ± 1.29 | NE |
| xi | DMZ10 | 4.39 ± 0.26 | 8.06 ± 0.26 | 5.48 ± 0.00 | 1.65 ± 0.26 | NE |
| xii | DMZ11 | 4.20 ± 0.00 | 8.77 ± 0.00 | 7.68 ± 0.00 | 2.19 ± 0.26 | NE |
| xiii | DMZ12 | 4.20 ± 0.00 | 7.15 ± 0.00 | 5.12 ± 0.26 | 2.19 ± 0.26 | NE |
| xiv | DMZ13 | 4.20 ± 0.00 | 7.15 ± 0.00 | 5.12 ± 0.26 | 2.01 ± 0.00 | NE |
| xv | DMZ14 | 4.20 ± 0.00 | 6.97 ± 0.26 | 6.58 ± 0.78 | 2.19 ± 0.26 | NE |
| xvi | TMPyP4[c] | 4.01 ± 0.26 | 23.75 ± 0.52 | 3.46 ± 1.03 | 34.71 ± 0.93 | 1.14 ± 0.52 |

[a]G-quadruplex DNA: F21T (5'-FAM-GGG TTA GGG TTA GGG TTA GGG-TAMRA-3') (SEQ ID NO: 11), c-kit2 (5'-FAM-CCC GGG CGG GCG CGA GGG AGG GGA GG-TAMRA-3') (SEQ ID NO: 12), k-RAS21R (5'-FAM-AGG GCG GTG TGG GAA GAG GGA-TAMRA-3') (SEQ ID NO: 13), c-MYC (5'-FAM-TGA GGG TGG GTA GGG TGG GTA A-TAMRA-3') (SEQ ID NO: 14). Duplex DNA: duplex (5'-FAM-TAT AGC TAT ATT TTT TTA TAG CTA TA-TAMRA-3') (SEQ ID NO: 15). Conditions: dual-labeled DNA (0.2 µM), DMZ analogues (1 µM), potassium cacodylate buffer (60 mM, pH 7.2).
[b]$\Delta T_m$ is calculated by melting temperature in the presence and absence of DMZ analogues.
[c]For TMPyP4, 0.2 µM dual-labeled DNA and TMPyP4 were applied to get meaningful melting temperatures.
[d]NE means not effective binding ($\Delta T_m < 1°$ C.).

TMPyP4, a prototypical G-quadruplex ligand was the most stabilizing ligand (note that a lower concentration of TMPyP4 was used in the FRET melting assay, compared to the amidine ligands). Of the tested triazenes, DMZ, which has two amidine groups, was the best stabilizer of the tested G-quadruplexes but showed low selectivity between G-quadruplexes and duplex DNA. For example, DMZ could stabilize K-RAS21R ($\Delta T_m = 18.3°$ C.) but could also stabilize double-stranded DNA ($\Delta T_m = 6.4°$ C.), see Table 5, entry i.

Viability Assay. We initially synthesized 8 DMZ analogues (compounds DMZ1-DMZ6, and DMZ11) bearing different substituents (cyano, amidine, alkyne and aryl groups) and initially evaluated them against three human cancer cell lines, ovarian cancer cell (OVCAR-3), prostate cancer cell (PC-3) and triple negative breast cancer cell (MDA-MB-231), two human normal cell lines, normal bone marrow (NBM) and normal fibroblast cell (MCRSA) for cytotoxicity, using WST-1 assay. This initial cytotoxicity assay revealed that only the alkyne derivatives (DMZ3, DMZ5 and DMZ11) were active (see Table 6, entries iv, vi and xii), albeit not very potent. Interestingly DMZ, which potently binds to G-quadruplexes, and the monoamidine analogue DMZ1 were also not effective at inhibiting cancer proliferation. Encouraged by the initial positive results with the alkynes analogues we sought to optimize the anticancer potency and made further alkyne analogues by appending various aromatic moieties to the alkyne to give compounds DMZ7-DMZ10 and DMZ12-DMZ14 (see FIG. 1). We initially rationalized that by adding aromatic appendages to the initial alkyne compounds, stacking interactions between the G-quadruplex tetrad and the compounds would increase. Pleasingly the new alkyne analogues (DMZ7-DMZ10 and DMZ12-DMZ14) displayed improved anticancer properties (see Table 6). Of note, the $IC_{50}$ values of some of the DMZ analogs (DMZ7, DMZ9, DMZ10, DMZ12 and DMZ13) are similar to or better than those of cisplatin against the three tested cancer cell lines (compare entries ix, xi, xii, xiv, xv with xviii in Table 6). These analogs also had superior $IC_{50}$ than TMPyP4, which has been extensively studied as a G-quadruplex ligand. Cisplatin is an anticancer drug that is still used in the clinic to treat various cancers so the $IC_{50}$ values that we have obtained for some of the alkyne DMZ derivatives are encouraging and calls for further development of alkyne DMZ analogues as anticancer agents.

DMZ analogues are not derived from their amine metabolism products, we also tested the anticancer properties of 4-aminobenzamidine and amino alkyne 15 but none of these were active.

NMR analysis of the interaction between c-kit1 and DMZ analogues. Having demonstrated that G-quadruplex-interactive DMZ analogs, bearing alkyne moieties, have anticancer properties we performed further experiments to confirm that these molecules do indeed bind to G-quadruplexes and do so selectively. The aforementioned experiments (the FRET melting) that investigated the interactions of alkyne analogues of DMZ with G-quadruplexes are all indirect. NMR has been demonstrated to be a direct tool to study the interaction between DNA and ligands. Recently we reported NMR titration study of DMZ and triazene-1 with c-kit1 (a well-behaved G-quadruplex with distinct NMR peaks). The NMR peaks of c-kit1 have already been assigned so we rationalized that it was prudent to use c-kit1 to investigate the binding of some of our DMZ ligands to G-quadruplexes. We investigated DMZ analogues bearing alkyne moiety at the -ortho position (compound DMZ13) and meta position (compound DMZ9) as these compounds had shown the most promising anticancer activities (see Table 6). When both compounds DMZ9 and 13 were incubated with c-kit1, there were changes in peak positions and shapes of c-kit1 NMR spectra. Such behavior could arise from ligand-induced

TABLE 6

Anticancer activity of DMZ analogues with different cancer cell lines.

| | | Anticancer activities for different cancer cell lines ($IC_{50} \pm SD, \mu M$)[a] | | | | |
|---|---|---|---|---|---|---|
| Entry | Compound | OVCAR-3 | PC-3 | MDA-MB-231 | NBM | MCR5A |
| i | DMZ | >25 | NE | NE | —[c] | — |
| ii | DMZ1 | NE | NE | NE | — | — |
| iii | DMZ2 | NE | NE | NE | — | — |
| iv | DMZ3 | 11.8 ± 1.7 | 22.5 ± 8.8 | 30.2 ± 1.8 | — | — |
| v | DMZ4 | NE | NE | NE | — | — |
| vi | DMZ5 | 16.8 ± 3.1 | 18.0 ± 5.7 | 20.5 ± 4.2 | — | — |
| vii | DMZ6 | NE | NE | NE | — | — |
| viii | DMZ7 | 6.5 ± 2.1 | 5.8 ± 0.2 | 9.5 ± 1.3 | — | — |
| ix | DMZ8 | 10.7 ± 1.5 | 10.4 ± 1.4 | 14.4 ± 0.9 | — | — |
| x | DMZ9 | 5.0 ± 0.1 | 5.3 ± 1.6 | 5.5 ± 0.1 | 5.6 | 8.3 ± 4.0 |
| xi | DMZ10 | 5.2 ± 0.4 | 5.0 ± 0.9 | 5.5 | — | — |
| xii | DMZ11 | >25 | >50 | 23.2 | — | — |
| xiii | DMZ12 | 8.1 ± 0.5 | 5.3 ± 0.2 | 5.1 ± 0.4 | — | — |
| xiv | DMZ13 | 9.5 ± 2.2 | 7.4 ± 0.2 | 6.2 ± 1.0 | NE | NE |
| xv | DMZ14 | NE | NE | NE | — | — |
| xvi[b] | Cisplatin | 4.1 ± 1.8 | 10.5 ± 1.3 | 11.7 ± 1.0 | — | — |
| xvii | 15 | NE | NE | NE | — | — |
| xviii | 4-aminobenzamidine | NE | NE | NE | — | — |
| xix | TMPyP4 | 14.6 ± 5.7 | 14.0 ± 5.4 | 14.3 ± 4.0 | 16.8 | 15.2 ± 6.6 |

Figure 4:
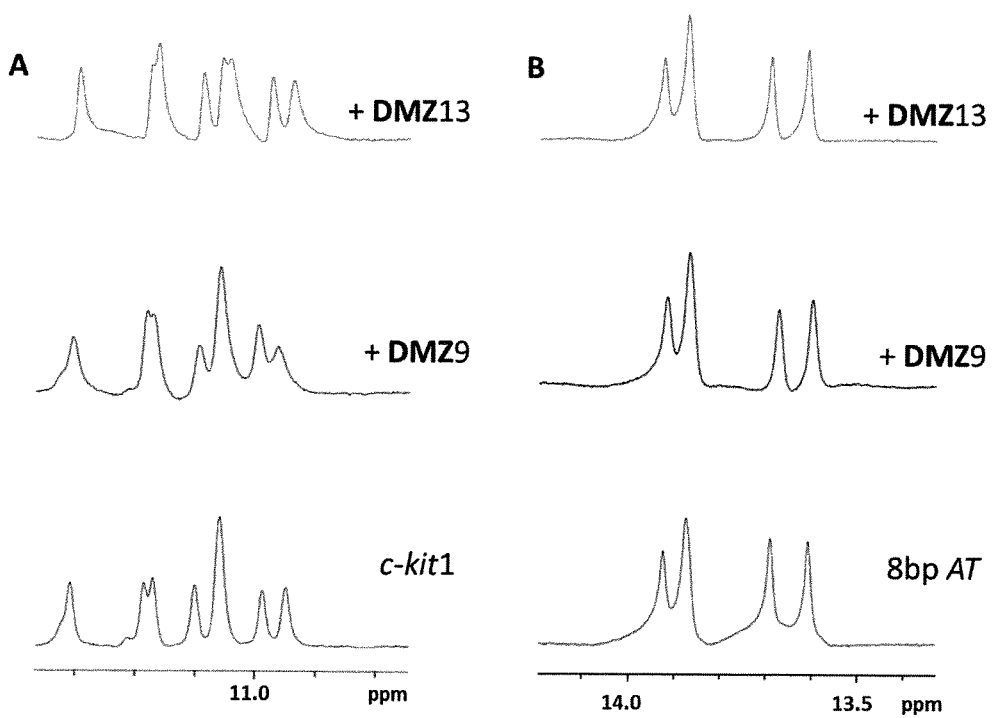
FIG. 4. $^1$H NMR imino region of c-kit1 (A, 11.4-10.8 ppm) or 8 bp AT (B, 14.0 to 13.5 ppm) with alkyne-substituted DMZ analogues (DMZ9 and 13). Conditions: DMZ analogue 9 and 13 (150 µM), c-kit1 or 8 bp AT (300 µM), D$_2$O (10%, V/V), NaCl (137 mM), EDTA (1 mM), K-phosphate buffer (10 mM, pH 7.5). The DMZ analogue was added to sample solution for 2 h in advance at 4° C. The NMR spectra were recorded on an 800 MHz instrument at 25° C. with acetate salt in an internal standard capillary tube.

[a]Human cancer cell lines: ovarian cancer cell (OVCAR-3), prostate cancer cell (PC-3) and breast cancer cell (MDA-MB-231). NE means not effective. Cell viability was the same or greater than 75% of the DMSO control at 20 μM compound concentration. Therefore, accurate $IC_{50}$ for these compounds were not determined.
[b]Cisplatin as a control compound.
[c]Not determined To gain some insights into potential toxicities of these DMZ analogs, we proceeded to evaluate analogs DMZ9, DMZ13 and TMPyP4 against two human normal cell lines (NBM and MCR5A) (see entries x, xiv and xix in Table 6). For analogs DMZ9 and TMPyP4, the $IC_{50}$ values against NBM and MCR5A cells are similar to the three tested cancer cells (hence these compounds might have low therapeutic window). However, and pleasingly, analog DMZ13 killed the three tested cancer cells with single digit IC50 but was not effective against NBM and MCR5A cells. To rule out the possibility that the anti-proliferative properties of the alkyne G-quadruplex multimerization or disruption of the G-tetrad upon ligand binding. (FIG. 4). These two analogs (compound DMZ9 and DMZ13) were also titrated with duplex DNA (8 bp AT duplex DNA) in order to confirm the earlier observation (see FIG. 3; competition FRET melting) that alkyne DMZ analogs do not bind to duplex DNA. Upon incubation of compounds DMZ9 and DMZ13 with duplex DNA, no change was observed in the spectrum of the duplex DNA. This is consistent with the competition FRET data (see FIG. 3), which indicated that alkyne-substituted DMZ compounds, such as DMZ9 and DMZ13 have excellent selectivity to G-quadruplex over duplex.

The pharmacology of G-quadruplex ligands is due to the inhibition of several oncogenes but prominent amongst these oncogenes is c-MYC, which is over-expressed in several cancers (including TNBC). We therefore performed two types of experiments, PCR stop assay (in-vitro) and Western analysis of c-MYC expression (in-vivo) in the presence and absence of some of our DMZ analogs to determine if the pharmacology of the analogs is at least derived from c-MYC inhibition.

The pharmacology of G-quadruplex ligands is due to the inhibition of several oncogenes but prominent amongst these oncogenes is c-MYC, which is over-expressed in several cancers (including TNBC). We therefore performed two types of experiments, PCR stop assay (in-vitro) and Western analysis of c-MYC expression (in-vivo) in the presence and absence of some of our DMZ analogs to determine if the pharmacology of the analogs is at least derived from c-MYC inhibition.

PCR stop assay. PCR stop assay, using templates that contain G-quadruplex sequences, has been used by several investigators to demonstrate the binding of ligands to G-quadruplexes. We investigated the effects of analogs DMZ9, DMZ13, DMZ, DMZ1 and TMPyP4 on c-MYC G-quadruplex stabilization via the PCR stop assay. Pu27 and Pu27-13,14 were used as templates. Pu27 is contained in the nuclear hypersensitivity element $III_1$ (NHE $III_1$), which controls 80-90% transcription level of c-MYC$^{x1}$. Pu27-13, 14 is a mutated Pu27 strand, which is a non-G-quadruplex DNA template.

Figure 5:
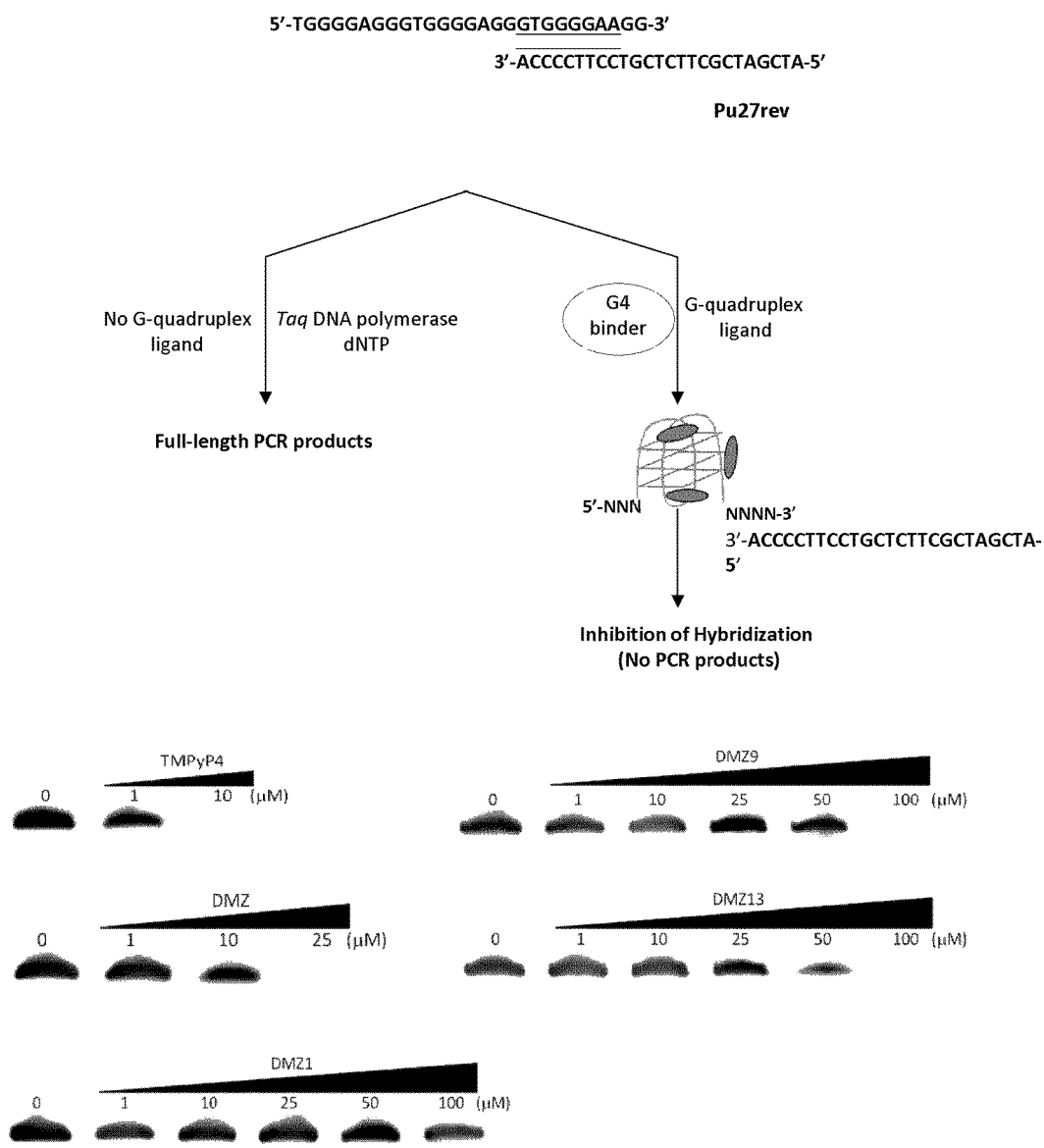
FIG. 5. Effects of DMZ analogs (DMZ1, DMZ 9, DMZ13), DMZ and TMPyP4 on the PCR stop assay with c-MYC Pu27 and mutated c-MYC template Pu27-13,14. Compounds were added to the reaction mixture containing 1×PCR buffer (New England Biolabs), 5 µM Pu27 or Pu27-13.14, 5 µM Pu27rev, 1 mM dNTPs and 5 units of Taq polymerase (New England Biolabs) separately. No compound added was treated as control.
Figure 5:
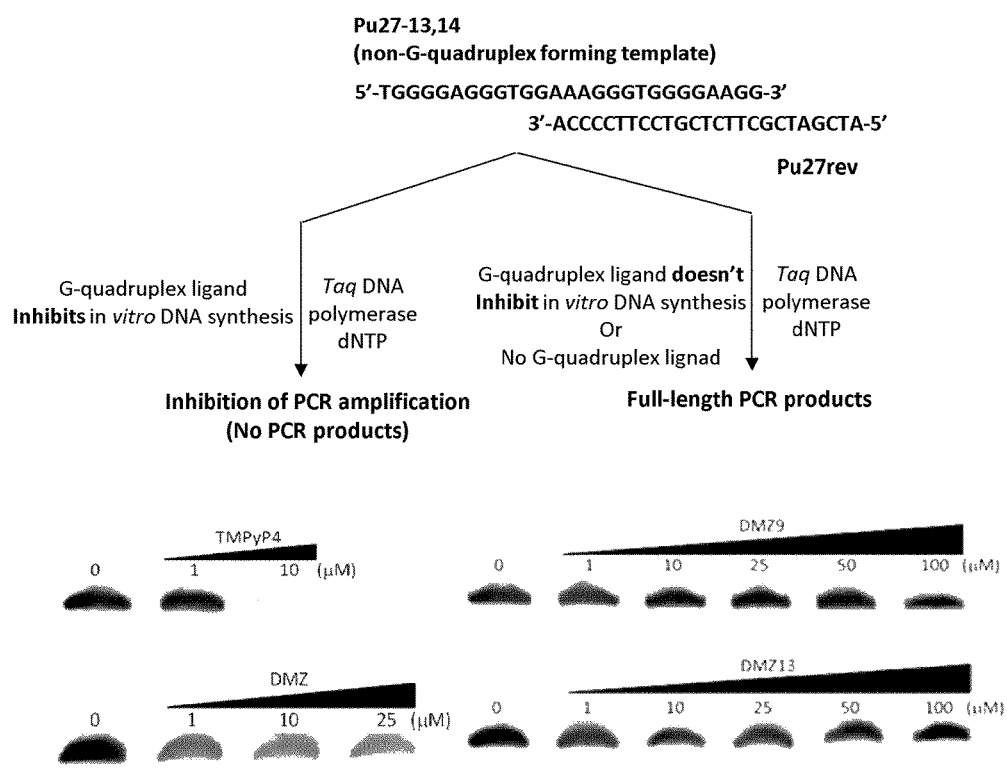

In the PCR reaction system, 5 µM of Pu27, 5 µM of Pu27rev and various concentrations of DMZ1, DMZ9, DMZ13 (1 µM, 10 µM, 25 µM, 50 µM and 100 µM), DMZ (1 µM, 10 µM and 25 µM) and TMPyP4 (1 µM and 10 µM) were added. The polymerization/extension of oligomers Pu27 and Pu27rev was completely inhibited in the presence of 100 µM DMZ9 and DMZ13 (see FIG. 5). Also, DMZ and TMPyP4 showed inhibition at 25 µM and 10 µM, respectively. To eliminate the possibility that the inhibition of DNA extension was caused by the direct inhibition of the polymerase enzyme by the ligands, a non-G-quadruplex DNA template Pu27-13,14 (see FIG. 5) was extended in the presence of various concentrations of DMZ9, DMZ13, DMZ and TMPyP4. For this control reaction, amplified PCR product was observed in the presence of 100 µM DMZ9, DMZ13 and 25 µM DMZ. However, no PCR product was observed in the presence of 10 µM TMPyP4. Based on these results, we conclude that the DMZ analogs inhibit the extension of a template containing c-MYC sequences via the stabilization of a G-quadruplex structure in the template and not via direct polymerase inhibition, as observed with the TMPyP4 case.

Figure 7:
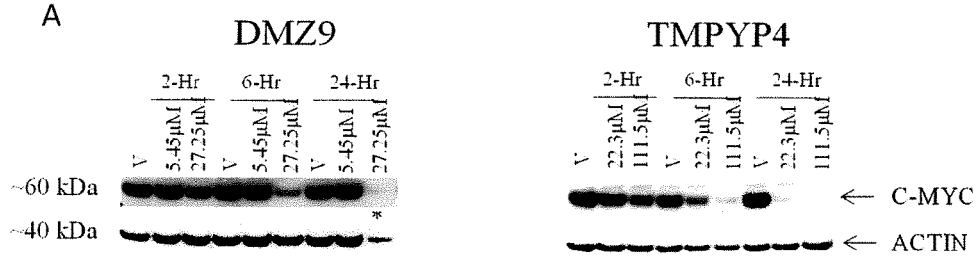
FIG. 7. Western Blot analysis of c-MYC protein expression in MDA-MB-231 after treated with TMPyP4 and DMZ9. A, MDA-MB-231 cells were treated with DMSO vehicle, DMZ9 (5.45 µM and 27.25 µM), TMPyP4 (22.3 µM and 111.5 µM) for 2 h, 6 h and 24 h. Total protein was extracted and analyzed by Western Blot with 1:1,000 C-MYC (Cell Signaling) and 1:10,000 HRP-linked anti-rabbit IgG (Cell Signaling). *Observed high level of cytotoxicity and low protein levels. B and C, the graphs show the relative density as compared with the DMSO vehicle. Scanned images were analyzed using image J software.
Figure 7:
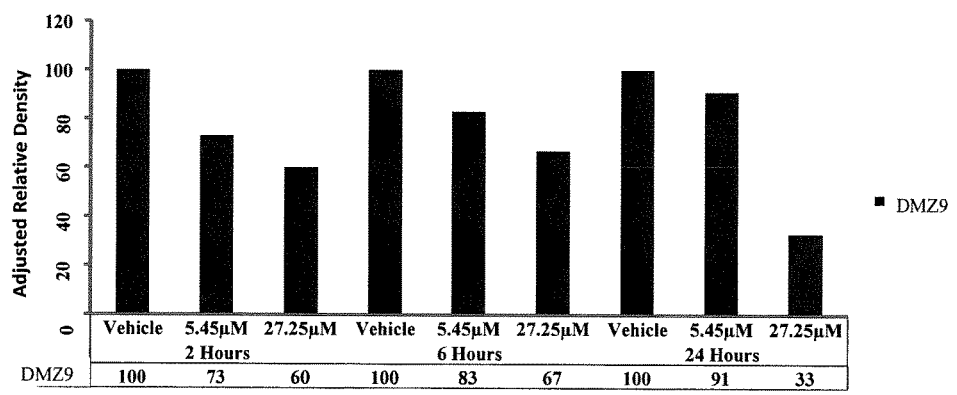
Figure 7:
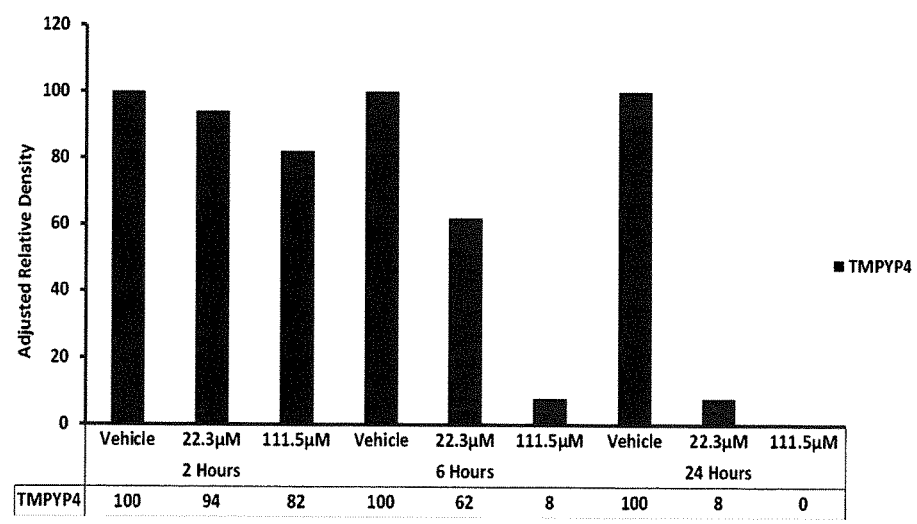
Figure 8:
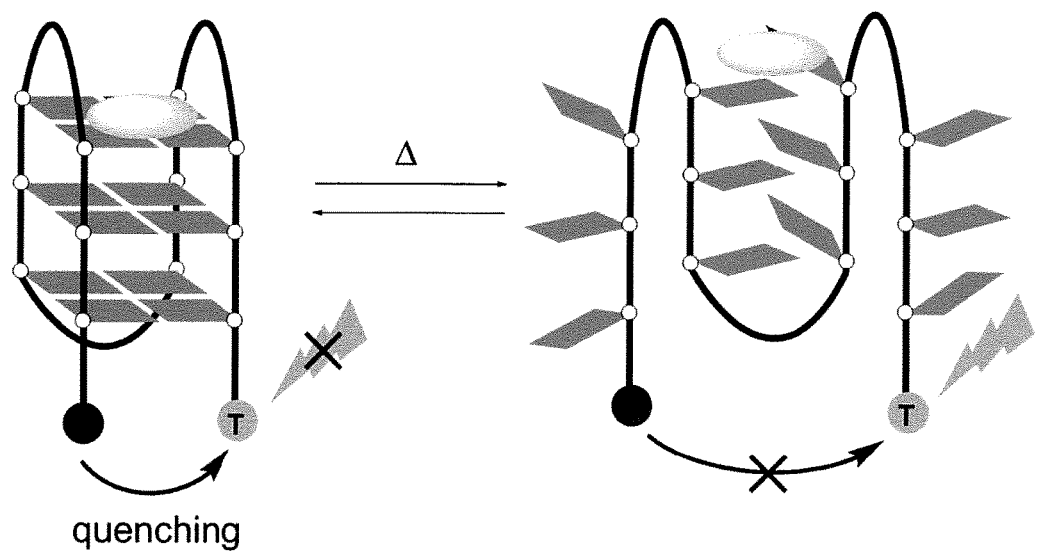
FIG. 8. Model of FRET-based melting temperature experiment. At higher temperature fluorophore and quencher are separated. Ligand stabilizes structure, leading to higher melting temperature.
Figure 9:
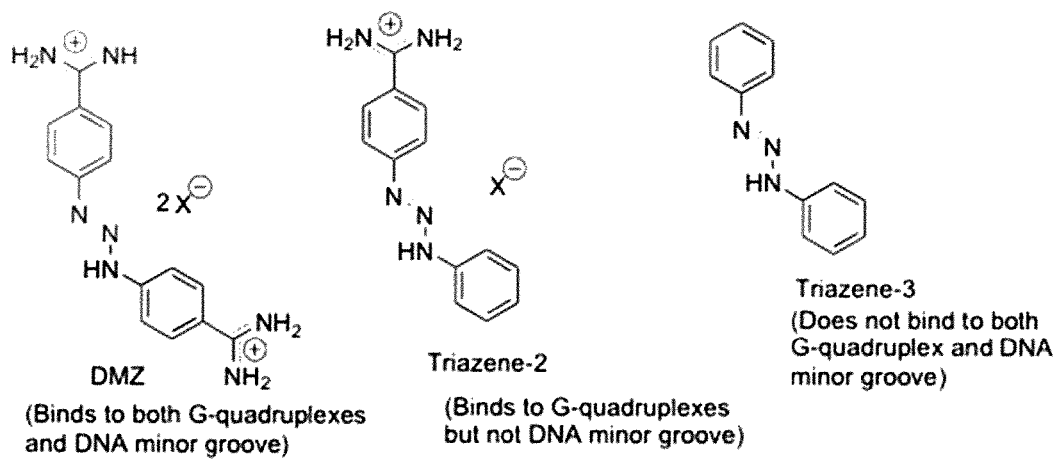
FIG. 9. DMZ-like molecules that bind to G-quadruplexes. X=an anion.
Figure 10:
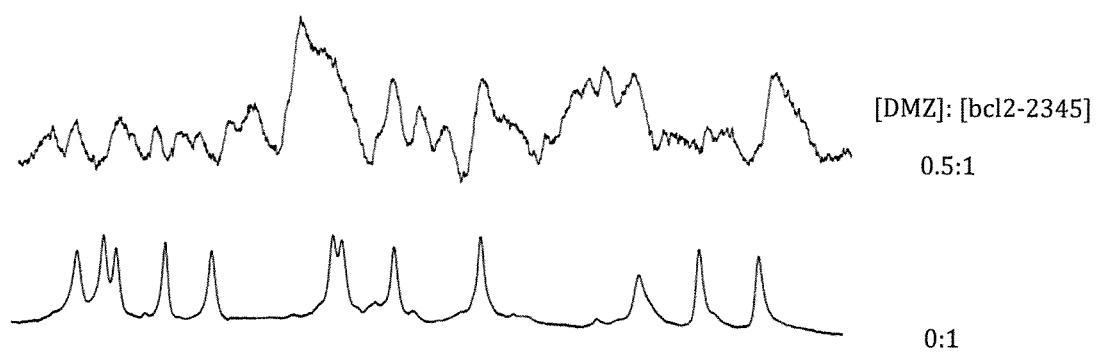
FIG. 10. NMR of DNA G-quadruplex (bcl2-2345) in the presence and absence of DMZ. 0.5:1 [DMZ]: 150 µM as final concentration, [blc2-2345]: 300 µM. 1:1 [DMZ]: 300 µM as final concentration, [blc2-2345]: 300 µM.
Figure 11:
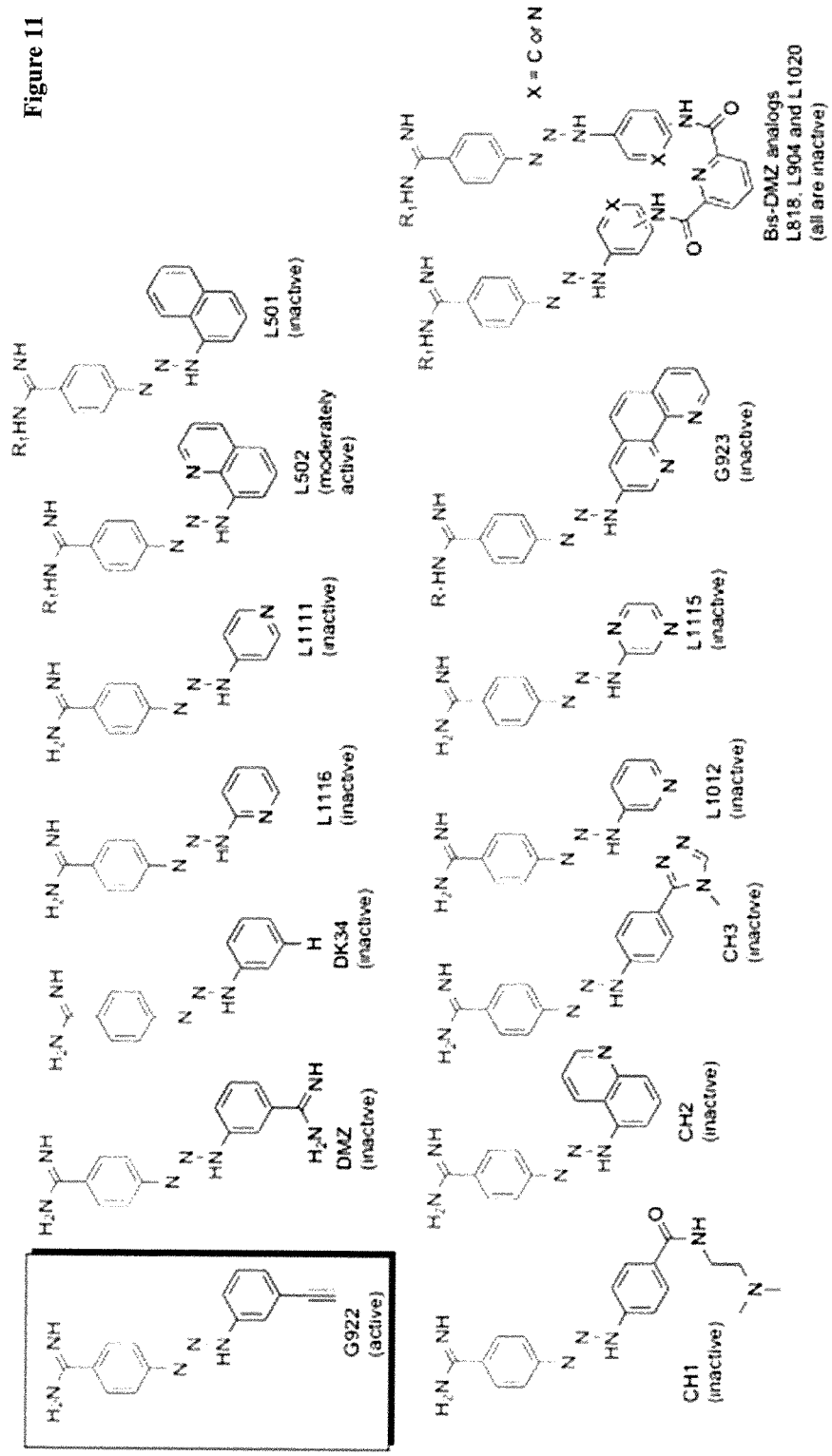
FIG. 11. Out of 16 amidinyl 1,2,3-triazenes that were screed for anticancer properties, only one (G922, with alkynyl substitution) displayed significant cancer cell killing for all three cell lines (breast, prostate and ovarian), see FIG. 4.
Figure 12:
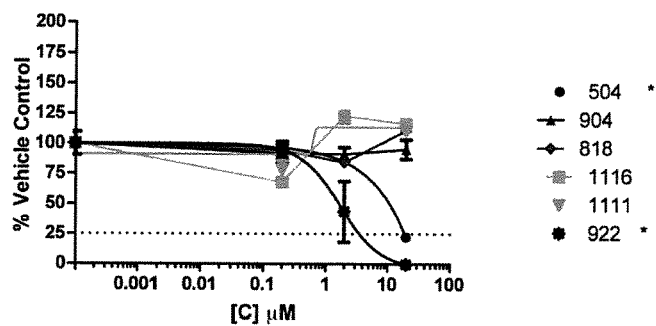
FIG. 12. WST-1 cell proliferation assays of various aryl groups.
Figure 12:
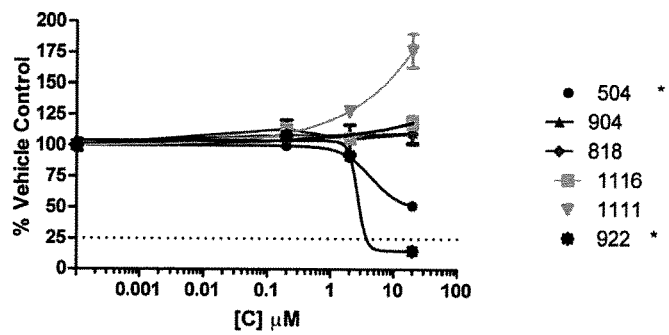
Figure 12:
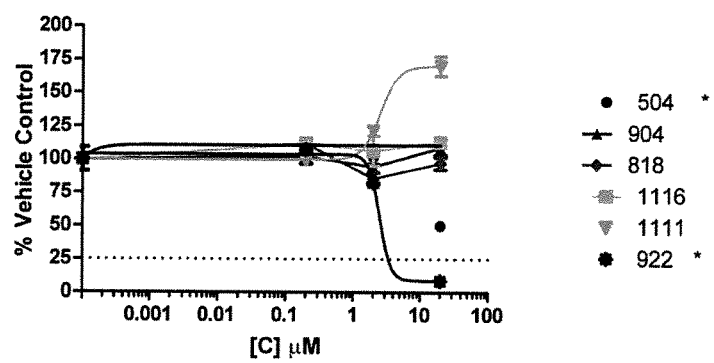

Western Blot Analysis of c-MYC Protein Expression. C-MYC protein levels in MDA-MB-231 cells were evaluated by performing Western Blot. MDA-MB-231 breast cancer cells were treated with 22.3 or 111.5 µM TMPyP4 and 5.45 or 27.25 µM DMZ9 for 2, 6 or 24 hours. The results are shown in FIG. 7. TMPyP4 has previously been shown to down regulate c-MYC protein expression level so TMPyP4 was included in this experiment as a positive control. The results show that DMZ9 caused a decrease in the c-MYC protein expression.

Figure 6:
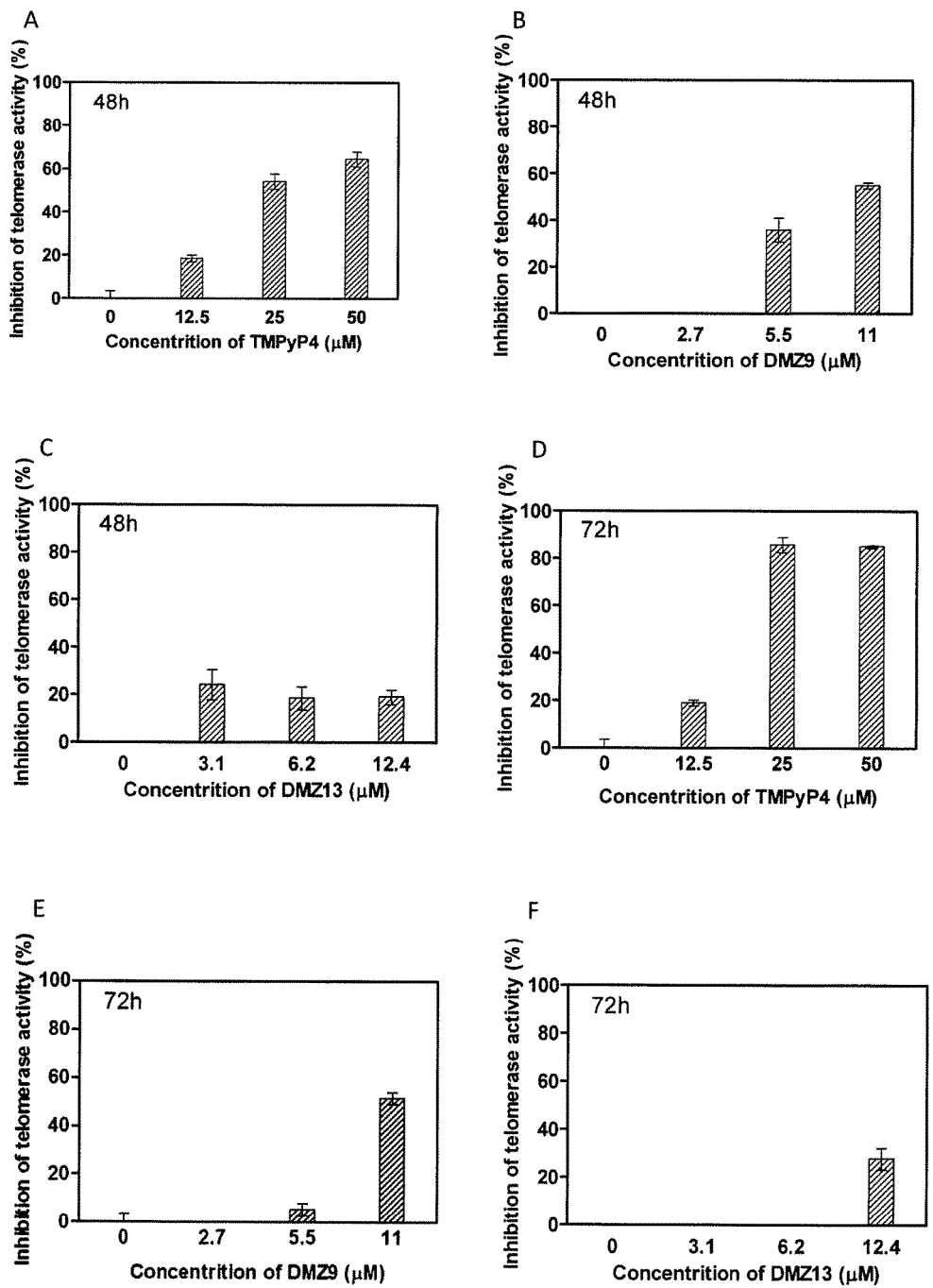
FIG. 6. Telomerase activity in lysates of TMPyP4-, DMZ9- or DMZ13-treated MDA-MB-231 cells for 48 h (upper panel) and 72 h (lower panel). Telomerase activity was determined using the TRAPeze XL Telomerase Detection Kit (Intergen). Lysate (1000 cell-equivalents) was mixed with TRAPeze XL reaction mix containing Amplifuor primers, and incubated for 30 min at 30° C. Telomerase products were quantitated using a Fluorescence plate reader. A, percentage inhibition of Telomerase activity in TMPyP4 treated MDA-MB-231 cells relative to untreated control is shown. B, percentage inhibition of telomerase activity in 916-1-treated MDA-MB-231 cells relative to untreated control is shown. C, percentage inhibition of telomerase activity in 1104-2-treated MDA-MB-231 cells relative to untreated control is shown.

Inhibition of Telomerase Activity in Breast Cancer Cells. Some G-quadruplex interactive ligands have been shown to achieve cancer cell killing via the inhibition of telomerase expression and/or inhibition of telomere extension. We therefore investigated if the anticancer activities of some of our analogs are derived (at least partially) from telomerase or telomere extension inhibition. We evaluated the effect of compounds DMZ9, DMZ13 and TMPyP4 at various concentrations ($0.5 \times IC_{50}$, $1 \times IC_{50}$, $2 \times IC_{50}$) on telomerase activity in human breast cancer cell line (MDA-MB-231) using TRAPeze XL Telomerase Detection Kit (Intergen). Cells were treated with compounds for 48 h and 72 h respectively. Inhibition of telomerase was evaluated by comparing the telomerase activity in untreated cells. The results showed that telomerase activity in MDA-MB-231 could be inhibited by up to 50% after treating the cell lines with 11 µM DMZ9 for 48 h or 72 h (see FIGS. 6B and 6E). DMZ13 at 12.4 µM could inhibit about 20% of telomerase activity in MDA-MB-231 after treating the cells for 48 h with compound and it could inhibit about 30% after treating MDA-MB-231 with compound for 72 h. The inhibition of telomerase expression could occur via several pathways. It has been proposed that this inhibition may be caused by the stabilization of G-quadruplex in the core promoter of hTERT (catalytic domain of telomerase). Also, hTERT is activated by c-MYC protein. Our Western blot data shows that analog DMZ9 could inhibit c-MYC protein level of MDA-MB-231 cells (see FIG. 7), hence the effect of the DMZ analogs on telomerase level could be an indirect one.

It will be apparent from the foregoing that, given the benefit of the present disclosure, DMZ analogues are easy to synthesize and monoamidine analogues that bear alkyne moieties are selective G-quadruplex binders with good anticancer properties. Aspects of this Example include the determination that G-quadruplex binding or selectivity are not sole determinants of anticancer efficacy. For example compound DMZ11 could increase the melting temperatures of several G-quadruplexes by up to 8° C., yet it was not an effective anticancer agent. Other factors, such as cell permeation or metabolism or sub-cellular localization could all come into play to modulate the efficacy of a particular agent. The synthetic tractability of the DMZ analogues makes it easy to make diverse libraries to screen. G-quadruplexes are emerging as important structural elements that regulate other disease states and it is therefore feasible that the molecules of this disclosure could find utility in diverse areas, such as anti-HIV therapy.

EXAMPLE 3

This example provides the syntheses of azo containing DMZ based analogs, their G-quadruplex binding activity, their kinase inhibition activity, their PARP inhibition activity, and their anticancer properties.

Azolamidine-inspired antitumor agents bind to G-quadruplexes and are potent anticancer agents.

Materials and Methods. General Synthesis Overview.

General procedure I: Aromatic amine (1.0 mmol) was added to a stirred solution of 12 N HCl (0.27 mL) and water (1.5 mL) in a 10 mL flask at 0° C. for 15 min. The resultant stirring mixture was treated dropwise with a cooled $NaNO_2$ solution (76 mg in 0.27 mL water) for 15 min followed by the addition of a cooled NaOAc solution (328 mg in 1.5 mL water) to adjust the pH=6.0 for 15 min. Then a chilled isoquinoline or indole solution (1.0 mmol in 1.0 mL methanol) was added dropwise to the above solution for stirring another 1 hour at 0° C. After the reaction was finished, the solvent was removed under reduced pressure. The residue was treated with a large amount of water (100 mL) and followed by the extract of dichloromethane (2×15 mL). The aqueous layer was treated with 2.5% NaOH solution to make the pH>10.0 followed by the extraction of large amount of ethyl acetate (2×100 mL). Then, the organic layer was washed with brine and dried by sodium sulfate. Finally, the solvent was removed under reduced pressure and the product was obtained.

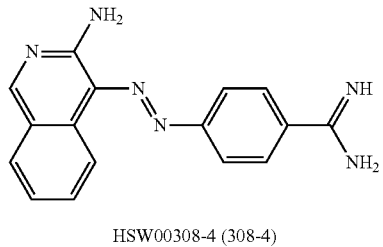 [SMILES: N=C(N)c1ccc(/N=N/c2c(N)ncc3ccccc23)cc1]

HSW00308-4 (308-4)

Following the described general procedure I, brown solid was obtained. $^1$H NMR (400 MHz, MeOD) δ=8.86 (s, 1H), 8.68 (dd, J=8.5, 0.6, 1H), 7.97-7.90 (m, 2H), 7.89-7.82 (m, 3H), 7.69 (ddd, J=8.4, 6.9, 1.3, 1H), 7.36 (ddd, J=8.0, 6.9, 1.0, 1H). $^{13}$C NMR (100 MHz, MeOD) δ 167.34, 158.63, 156.28, 147.86, 139.27, 137.27, 133.48, 131.96, 129.72, 129.08, 125.11, 125.04, 123.05, 121.89, 121.85. HRMS (ESI+) [M+H] calcd for $C_{16}H_{15}N_6$ 291.1358. found 291.1339.

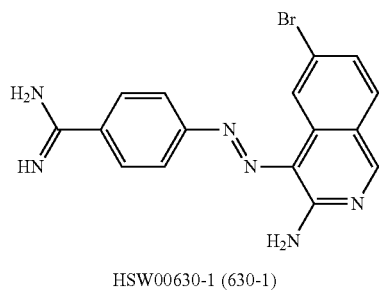 [SMILES: N=C(N)c1ccc(/N=N/c2c(N)ncc3ccc(Br)cc23)cc1]

HSW00630-1 (630-1)

Following the described general procedure I, red solid was obtained. $^1$H NMR (400 MHz, DMSO) δ=9.87 (s, 1H), 9.06 (s, 1H), 8.78 (d, J=1.8, 1H), 8.01-7.91 (m, 5H), 7.53 (dd, J=8.5, 1.9, 1H). $^{13}$C NMR (100 MHz, DMSO) δ 162.27, 157.85, 153.71, 147.41, 137.99, 136.37, 131.07, 127.92, 126.82, 126.63, 122.26, 121.50, 121.44, 118.22. HRMS (ESI+) [M+H] calcd for $C_{16}K_4N_6Br$ 369.0463 found 369.0477.

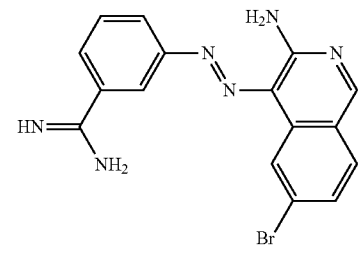

HSW00801-2 (801-2)

Following the described general procedure I, red solid was obtained. $^1$H NMR (400 MHz, MeOD) δ=8.90-8.83 (m, 2H), 8.26 (t, J=1.7, 1H), 8.03 (ddd, J=8.0, 1.9, 1.1, 1H), 7.82-7.76 (m, 2H), 7.63 (t, J=7.8, 1H), 7.46 (dd, J=8.6, 1.9, 1H). HRMS (ESI+) [M+H] calcd for $C_{16}H_{14}BrN_6$ 369.0463. found 369.0475.

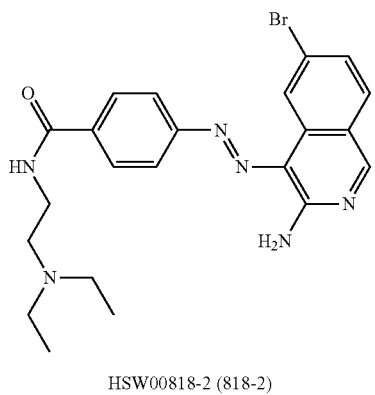 [SMILES: CCN(CC)CCNC(=O)c1ccc(/N=N/c2c(N)ncc3ccc(Br)cc23)cc1]

HSW00818-2 (818-2)

Following the described general procedure I, orange solid was obtained. $^1$H NMR (400 MHz, DMSO) δ=9.91 (s, 1H), 9.08 (s, 1H), 8.81 (s, 1H), 8.51 (s, 2H), 8.02 (q, J=8.7, 4H), 7.96 (d, J=8.5, 1H), 7.56 (dd, J=8.5, 1.6, 1H), 2.64-2.52 (m, 8H), 0.99 (t, J=7.1, 6H). $^{13}$C NMR (100 MHz, MeOD) δ 169.60, 158.75, 156.65, 148.59, 140.24, 136.08, 132.82, 131.71, 129.88, 129.72, 129.65, 128.72, 128.38, 128.34, 124.22, 123.37, 123.06, 120.61, 52.67, 52.64, 48.36, 48.34, 38.55, 38.42, 11.77, 11.74. HRMS (ESI+) [M+H] calcd for $C_{22}H_{26}N_6BrO$ 469.1351. found 469.1382.

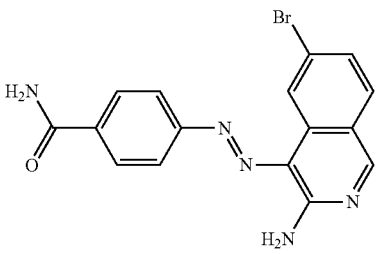

HSW00819-1 (819-1)

Following the described general procedure I, orange solid was obtained. $^1$H NMR (400 MHz, DMSO) δ=9.91 (s, 1H), 9.08 (s, 1H), 8.80 (d, J=1.8, 1H), 8.56 (s, 1H), 8.09 (s, 1H), 8.07-8.00 (m, 4H), 7.96 (d, J=8.5, 1H), 7.55 (dd, J=8.5, 1.9, 1H), 7.47 (s, 1H). $^{13}$C NMR (100 MHz, DMSO) δ 167.33, 158.07, 154.34, 147.44, 137.93, 134.49, 131.04, 128.76, 126.83, 126.64, 122.22, 121.50, 121.41, 118.28. HRMS (ESI+) [M+H] calcd for $C_{16}H_{13}BrN_5O$ 370.0303. found 370.0272.

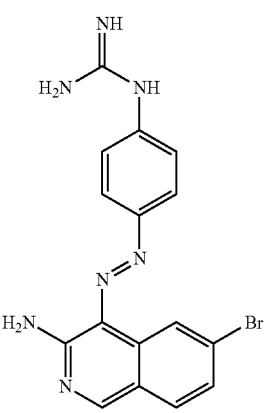

HSW00821-3 (821-3)

Following the described general procedure I, orange solid was obtained. $^1$H NMR (500 MHz, MeOD) δ=8.93 (s, 1H), 8.88 (s, 1H), 8.06-8.02 (m, 2H), 7.85 (d, J=8.6, 1H), 7.50 (dd, J=8.5, 1.8, 1H), 7.47 (d, J=8.6, 2H). $^{13}$C NMR (125 MHz, MeOD) δ 158.33, 153.52, 140.15, 137.63, 131.68, 128.58, 128.39, 127.06, 124.60, 124.26, 123.43, 120.51, 111.10, 105.79. HRMS (ESI+) [M+H] calcd for $C_{16}H_{15}N_7Br$ 384.0572. found 384.0588.

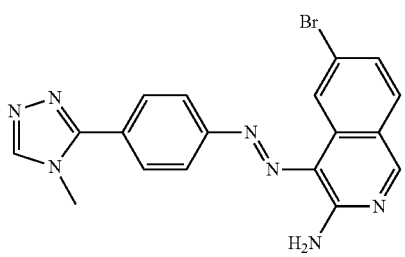

HSW00909-1 (909-1)

Following the described general procedure I, red solid was obtained. $^1$H NMR (400 MHz, CDCl$_3$) δ=8.93 (d, J=1.5, 1H), 8.88 (s, 1H), 8.26 (s, 1H), 8.04 (d, J=8.6, 2H), 7.89 (d, J=8.6, 2H), 7.71 (d, J=8.5, 1H), 7.49 (dd, J=8.6, 1.8, 1H), 3.87 (s, 3H). $^{13}$C NMR (100 MHz, CDCl$_3$) δ 157.11, 154.06, 146.83, 145.78, 139.05, 130.07, 129.78, 127.81, 127.76, 127.56, 123.85, 122.81, 122.42, 120.18, 32.73. HRMS (ESI+) [M+H] calcd for $C_{18}H_{15}N_7Br$ 408.0572. found 408.0565.

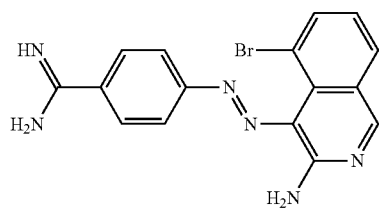

HSW00919-1 (919-1)

Following the described general procedure I, orange solid was obtained. $^1$H NMR (400 MHz, MeOD) δ=8.94 (s, 1H), 8.15-8.10 (m, 3H), 7.95 (dd, J=7.9, 1.2, 1H), 7.91-7.86 (m, 2H), 7.23 (t, J=7.7, 1H). $^{13}$C NMR (100 MHz, MeOD) δ 167.60, 160.19, 156.59, 148.33, 141.31, 135.33, 134.42, 131.05, 129.41, 127.12, 125.44, 123.77, 121.23, 115.57. HRMS (ESI+) [M+H] calcd for $C_{16}H_{14}BrN_6$ 369.0463. found 369.0485.

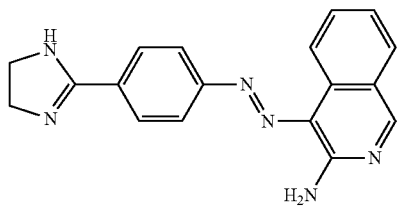

HSW00925-1 (925-1)

Following the described general procedure I, orange solid was obtained. $^1$H NMR (600 MHz, MeOD) δ=8.94 (s, 1H), 8.77 (d, J=8.4, 1H), 8.01 (d, J=8.6, 2H), 7.94 (dd, J=18.9, 8.3, 3H), 7.75 (t, J=7.7, 1H), 7.42 (t, J=7.4, 1H), 3.83 (s, 4H). $^{13}$C NMR (151 MHz, MeOD) δ 167.19, 158.91, 156.67, 148.01, 139.35, 133.62, 131.23, 129.81, 129.73, 125.23, 125.16, 123.10, 122.02, 121.94, 49.72. HRMS (ESI+) [M+H] calcd for $C_{18}H_{17}N_6$ 317.1515. found 317.1537.

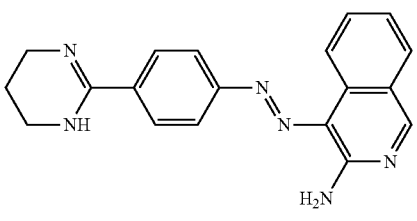

HSW00925-2 (925-2)

Following the described general procedure I, orange solid was obtained. $^1$H NMR (500 MHz, MeOD) δ=8.94 (s, 1H), 8.77 (d, J=8.5, 1H), 8.01 (d, J=7.2, 2H), 7.93 (d, J=8.0, 1H), 7.84-7.79 (m, 2H), 7.75 (t, J=7.7, 1H), 7.42 (t, J=7.5, 1H), 3.52 (t, J=5.3, 4H), 1.99-1.91 (m, 2H). $^{13}$C NMR (125 MHz, MeOD) δ 159.00, 158.80, 156.43, 147.99, 139.35, 133.58, 129.80, 129.12, 125.21, 125.17, 123.12, 121.98, 121.92, 42.52, 21.22. HRMS (ESI+) [M+H] calcd for $C_{19}H_{19}N_6$ 331.1671. found 331.1661.

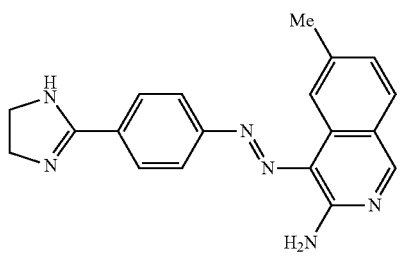

HSW001009-2 (1009-2)

Following the described general procedure I, red solid was obtained. $^1$H NMR (500 MHz, MeOD) δ=8.86 (s, 1H), 8.55 (s, 1H), 8.01 (d, J=8.8, 2H), 7.97 (d, J=8.7, 2H), 7.82 (d, J=8.2, 1H), 7.27 (d, J=8.3, 1H), 3.86 (s, 4H), 2.58 (s, 3H). HRMS (ESI+) [M+H] calcd for $C_{19}H_{19}N_6$ 331.1671. found 331.1649.

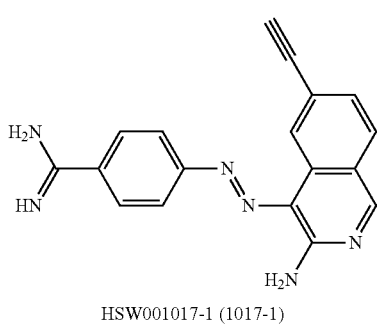 [SMILES: C#Cc1ccc2cnc(N)c(/N=N/c3ccc(C(=N)N)cc3)c2c1]

HSW001017-1 (1017-1)

Following the described general procedure I, red solid was obtained. $^1$H NMR (500 MHz, MeOD) δ=8.91 (s, 1H), 8.78 (s, 1H), 8.01 (d, J=8.6, 2H), 7.94-7.90 (m, 2H), 7.87 (d, J=8.3, 1H), 7.39 (dd, J=8.3, 1.4, 1H). $^{13}$C NMR (125 MHz, MeOD) δ 167.63, 158.80, 157.04, 148.55, 138.77, 134.73, 130.07, 129.64, 127.81, 127.62, 125.76, 124.17, 123.30, 121.14, 84.35, 80.94. HRMS (ESI+) [M+H] calcd for $C_{18}H_{15}N_6$ 315.1358. found 315.1353.

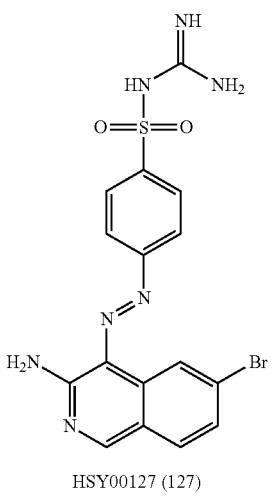 [SMILES: N=C(N)NS(=O)(=O)c1ccc(/N=N/c2c(N)ncc3ccc(Br)cc23)cc1]

HSY00127 (127)

Following the described general procedure I, red solid was obtained. 1H NMR (400 MHz, DMSO-d6) δ 9.91 (s, 1H), 9.05 (s, 1H), 8.75 (s, 1H), 8.60 (s, 1H), 8.03 (d, J=8.4 Hz, 2H), 7.92 (d, J=8.4 Hz, 3H), 7.60-7.47 (m, 1H), 6.80 (s, 4H). 13C NMR (101 MHz, DMSO) δ 158.29, 158.19, 154.03, 147.48, 144.43, 137.91, 131.03, 126.94, 126.91, 126.70, 122.19, 121.88, 121.40, 118.35.

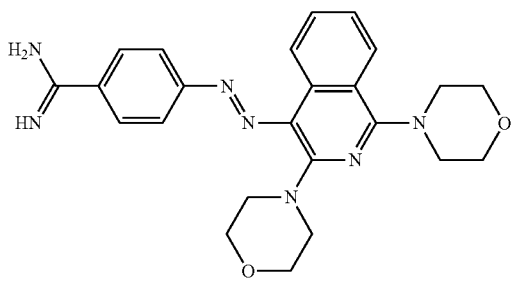

HSW001009-3 (1009-3)

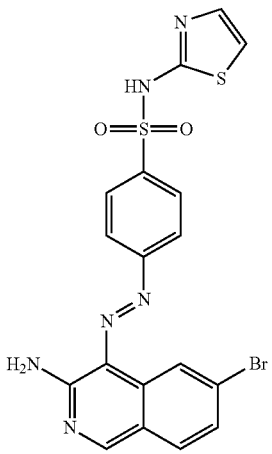

HSY00135 (135)

Following the described general procedure I, red solid was obtained. $^1$H NMR (400 MHz, CDCl$_3$) δ=9.23 (d, J=8.5, 1H), 7.79 (d, J=8.6 Hz, 2H), 7.75 (d, J=7.9, 1H), 7.69 (d, J=8.5, 2H), 7.62 (t, J=7.8, 1H), 7.29 (d, J=8.0, 1H), 4.01-3.95 (m, 4H), 3.86 (dd, J=9.0, 4.4, 8H), 3.77-3.71 (m, 4H). $^{13}$C NMR (100 MHz, CDCl$_3$) δ 165.78, 160.62, 156.77, 153.97, 134.67, 131.93, 126.99, 125.96, 125.49, 123.26, 121.30, 120.24, 116.09, 68.11, 67.40, 66.84, 50.65, 50.09, 46.49. HRMS (ESI+) [M+H] calcd for $C_{24}H_{28}N_7O_2$ 446.2304. found 446.2294.

Following the described general procedure I, red solid was obtained. 1H NMR (400 MHz, DMSO-d6) δ 12.84 (s, 1H), 9.94 (s, 1H), 9.06 (s, 1H), 8.74 (s, 1H), 8.65 (s, 1H), 8.07 (d, J=8.6 Hz, 2H), 7.96 (d, J=8.6 Hz, 2H), 7.92 (d, J=8.6 Hz, 1H), 7.53 (dd, J=8.5, 1.8 Hz, 1H), 7.29 (d, J=4.6 Hz, 1H), 6.87 (d, J=4.6 Hz, 1H). 13C NMR (101 MHz, DMSO) δ 168.95, 158.51, 154.54, 147.50, 141.98, 137.88, 131.04, 127.15, 126.96, 126.75, 124.55, 122.16, 122.08, 121.40, 118.44, 108.41.

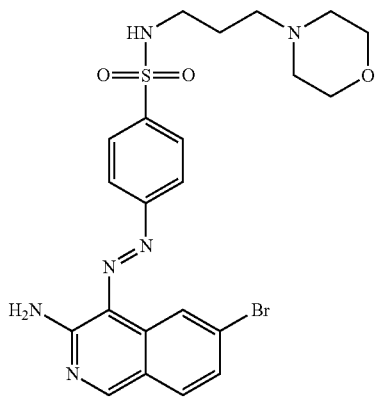

HSY00136 (136)

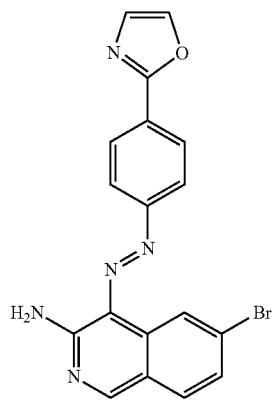

HSY00162 (162)

Following the described general procedure I, red solid was obtained. 1H NMR (400 MHz, DMSO-d6) δ 9.96 (s, 1H), 9.07 (s, 1H), 8.79-8.74 (m, 1H), 8.69 (s, 1H), 8.12 (d, J=8.5 Hz, 2H), 8.01 (s, 1H) 7.86 (m, 3H), 7.72 (t, J=5.1 Hz, 1H), 7.59-7.47 (m, 1H), 3.49 (s, 4H), 2.84 (q, J=6.3 Hz, 2H), 2.32-2.14 (m, 6H), 1.59-1.48 (m, 2H). 13C NMR (101 MHz, DMSO) δ 158.66, 154.77, 147.55, 140.15, 137.91, 131.08, 127.92, 127.01, 126.80, 122.29, 122.19, 121.44, 118.51, 66.10, 55.22, 53.17, 40.81, 25.82.

Following the described general procedure I, red solid was obtained. 1H NMR (400 MHz, DMSO-d6) δ 9.93 (s, 1H), 9.07 (s, 1H), 8.80 (d, J=1.8 Hz, 1H), 8.57 (s, 1H), 8.28 (s, 1H), 8.20-8.06 (m, 4H), 7.95 (d, J=8.6 Hz, 1H), 7.54 (dd, J=8.4, 1.9 Hz, 1H), 7.45 (s, 1H).

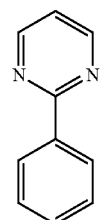
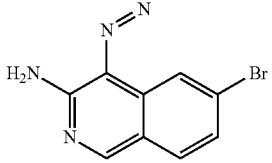

HSY00164 (164)

Following the described general procedure I, red solid was obtained. 1H NMR (400 MHz, DMSO-d6) δ 9.95 (s, 1H), 9.08 (s, 1H), 8.95 (d, J=4.8 Hz, 2H), 8.83 (s, 1H), 8.58 (d, J=8.4 Hz, 3H), 8.11 (d, J=8.3 Hz, 2H), 7.96 (d, J=8.5 Hz, 1H), 7.55 (d, J=8.5 Hz, 1H), 7.49 (d, J=5.6 Hz, 1H).

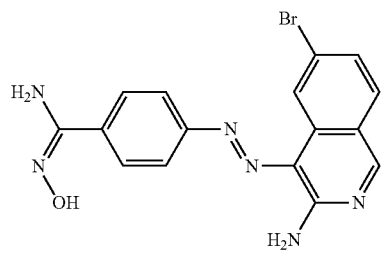

HSY00155 (155)

HSW00818-3 (818-3)

Following the described general procedure I, red solid was obtained. 1H NMR (400 MHz, DMSO-d6) δ 9.84 (s, 1H), 9.24 (s, 2H), 9.08 (s, 1H), 8.82 (s, 1H), 8.54 (s, 1H), 8.16 (d, J=8.6 Hz, 2H), 7.96 (d, J=8.5 Hz, 1H), 7.91 (d, J=8.7 Hz, 2H), 7.55 (d, J=7.1 Hz, 1H).

Following the described general procedure I, red solid was obtained. ¹H NMR (500 MHz, DMSO) δ=9.82 (d, J=15.8, 2H), 9.05 (d, J=16.2, 1H), 8.79 (d, J=15.5, 1H), 8.43

(s, 1H), 8.02-7.90 (m, 3H), 7.90-7.80 (m, 2H), 7.54 (d, J=8.6, 1H), 5.91 (d, J=14.2, 2H). $^{13}$C NMR (125 MHz, DMSO) δ 157.47, 152.91, 150.35, 147.36, 137.90, 134.11, 130.97, 126.67, 126.51, 126.34, 122.24, 121.58, 121.40, 118.13. HRMS (ESI+) [M+H] calcd for $C_{16}H_{14}BrN_6O$ 385.0412. found 385.0439.

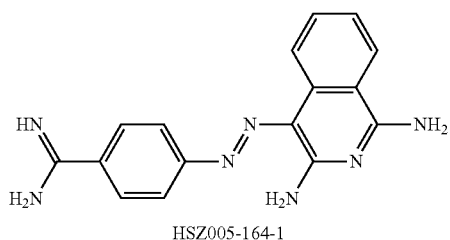 [SMILES: N=C(N)c1ccc(/N=N/c2c(N)nc(N)c3ccccc23)cc1]

HSZ005-164-1

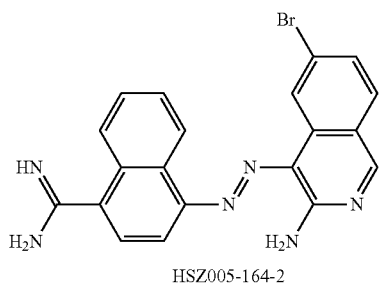 [SMILES: N=C(N)c1ccc(/N=N/c2c(N)ncc3ccc(Br)cc23)c2ccccc12]

HSZ005-164-2

Following the described general procedure I, red solid was obtained. LRMS (ESI+) [M+H] calcd for $C_{20}H_{16}BrN_6$ 419.06. found 418.99.

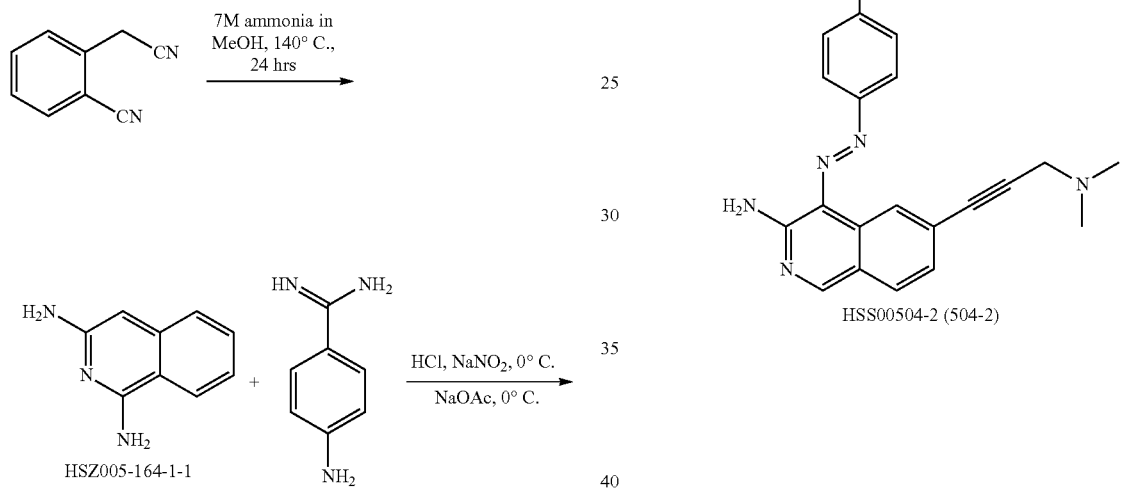

Scheme 5 Synthesis of HSZ005-164-1.

2-(cyanomethyl)benzonitrile (400 mg, 2.8 mmol, 1 eq) was mixed with 7M ammonia in methanol (8 mL, 20 eq) and heated at 140° C. for 24 hrs to obtain HSZ005-164-1-1. Then following the described general procedure I, red solid was obtained. LRMS (ESI+) [M+H] calcd for $C_{16}H_{16}N_7$ 306.10. found 369.08.

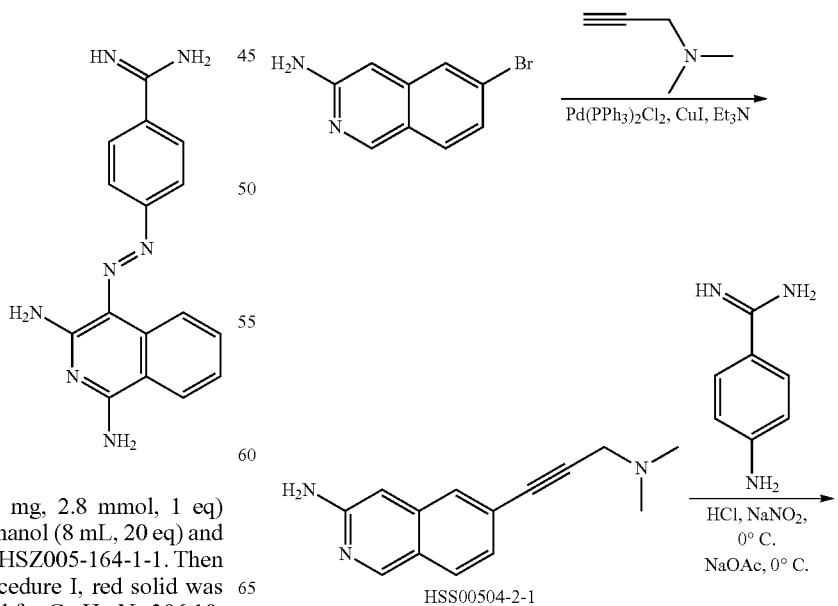

Scheme 6 Synthisis of HSS00504-2.

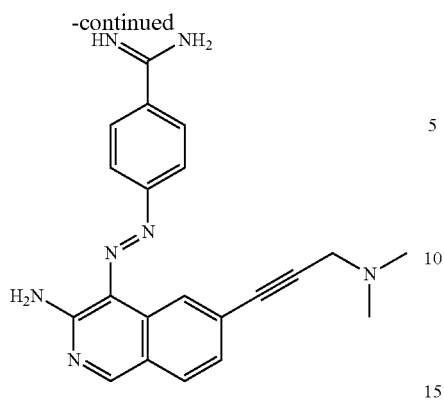

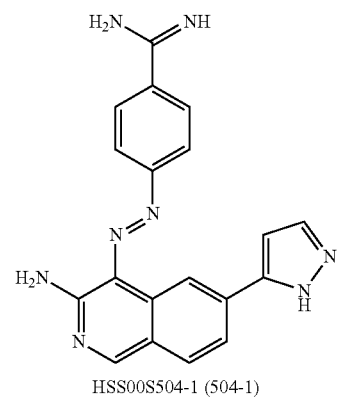 [SMILES: N=C(N)c1ccc(/N=N/c2c(N)ncc3ccc(-c4ccn[nH]4)cc23)cc1]

HSS00S504-1 (504-1)

HSS00504-2-1. A 50 ml Schlenk flask was charged with 6-bromoisoquinolin-3-amine (111.5 mg, 0.5 mmol, 1.0 equiv), Bis-(triphenylphosphine)palladium dichloride ((Ph$_3$P)$_2$PdCl$_2$; 17.5 mg, 0.025 mmol, 5 mol %), cuprous iodide (CuI; 5.0 mg, 0.025 mmol, 5 mol %), and N,N-dimethylprop-2-yn-1-amine (125 mg, 1.5 mmol, 3 equiv) and a stir bar and sealed by rubber septum. The flask was evacuated-refilled three times with Ar. 3 ml Et$_3$N was degassed in a separated round bottom flask for 15 minutes then transferred to the Schlenk flask through cannula. The mixture was stirred for 12 hours at 70° C. temperature. After reaction, the reaction mixture was diluted with ethyl acetate (10 mL) and the slurry filtered through a pad of Celite in a sintered glass funnel (medium frit). The tan solids were washed additionally with ethyl acetate until the filtrate was nearly colorless. The filtrate was washed with H$_2$O and brine followed by dried over magnesium sulfate. The combined organic fraction filtrates were concentrated in vacuo to yield a black solid. The residue was further purified by flash column chromatography on silica gel where 5% methanol/dichloromethane was used as mobile phase. Crystalline bright yellow solid was afforded after removing the solvent by rotary evaporation. $^1$H NMR (400 MHz, DMSO) δ 8.80 (s, 1H), 7.76 (d, J=8.4 Hz, 1H), 7.63 (s, 1H), 7.09 (d, J=8.4 Hz, 1H), 6.58 (s, 1H), 6.04 (s, 2H), 3.51 (s, 2H), 2.27 (s, 6H). $^{13}$C NMR (101 MHz, DMSO) δ 157.86, 152.19, 138.93, 129.01, 128.22, 124.77, 124.68, 122.09, 97.44, 87.62, 86.20, 48.59, 44.61. HRMS (ESI+) [M+H] calcd for C$_{21}$H$_{22}$N$_7^+$ 266.1339 found 266.1332.

HSS00504-2. Following the described general procedure I, red solid was obtained. $^1$H NMR (600 MHz, DMSO) δ 9.61 (s, 2H), 9.43 (s, 2H), 9.06 (d, J=6.5 Hz, 2H), 8.19 (d, J=8.3 Hz, 2H), 8.08-8.00 (m, 3H), 7.90 (d, J=8.3 Hz, 1H), 7.85 (s, 1H), 6.97 (d, J=2.0 Hz, 1H). $^{13}$C NMR (126 MHz, MeOD) δ 165.31, 158.78, 158.54, 158.29, 158.03, 157.78, 156.25, 147.58, 137.22, 129.57, 127.62, 122.39, 121.81, 120.16, 118.16, 115.80, 115.45, 103.28.

Scheme 7 Synthesis of HSS00S504-1.

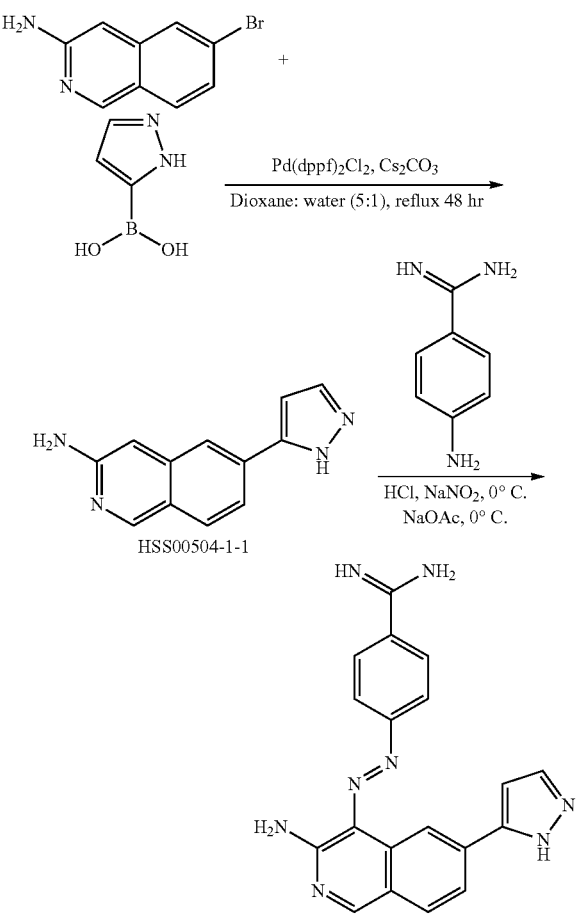

HSS00504-1-1. To a stirred suspension of 6-bromoisoquinolin-3-amine (111.5 mg, 0.5 mmol, 1.0 equiv), (1H-pyrazol-5-yl)boronic acid (85 mg, 0.75 mmol, 1.5 equiv) and Cs$_2$CO$_3$ (325.8 mg, 3 mmol) in dioxane (10 ml) and H$_2$O (2 ml) was added a catalytic amount (73 mg 0.1 mmol) of Pd(dppf)$_2$Cl$_2$, under nitrogen. The resulting mixture was refluxed for 24 hours. TLC (EtOAc/Hexane 1:2) indicated the reaction was complete. The reaction mixture was cooled to room temperature and filtered. The filtrate was concentrated in vacuo to give a residue which was dissolved in dichloromethane (30 ml). After washing with water (30 ml×3) and brine (30 ml), the dichloromethane layer was dried over anhydrous Na$_2$SO$_4$ and concentrated in vacuo to give the crude product which was purified by column chromatography (silica gel, methanol:DCM 1:0.05) to afford pure compound as an off white solid. $^1$H NMR (400 MHz, DMSO) δ 13.01 (s, 1H), 8.77 (s, 1H), 7.91 (s, 1H), 7.81 (d, J=7.9 Hz, 2H), 7.67 (s, 1H), 6.86 (s, 1H), 6.64 (s, 1H), 5.97 (s, 2H). $^{13}$C NMR (101 MHz, DMSO) δ 157.55, 151.86, 150.68, 139.67, 135.90, 130.88, 128.93, 122.63, 120.69, 120.37, 103.43, 98.16. LRMS (ESI+) [M+H] calcd for C$_{12}$H$_{11}$N$_4$$^+$ 211.0978 found 211.0643.

HSS00504-1. Following the described general procedure I, red solid was obtained. $^1$H NMR (400 MHz, MeOD) δ 8.72 (s, 1H), 8.47 (s, 1H), 7.83 (s, 4H), 7.68 (s, 1H), 7.20 (s, 1H), 3.49 (s, 2H), 2.36 (s, 6H). $^{13}$C NMR (101 MHz, MeOD) δ 166.39, 160.61, 157.65, 156.01, 147.29, 137.50, 132.05, 128.82, 128.60, 126.83, 126.48, 123.84, 122.71, 122.15, 119.95, 86.96, 85.92, 43.48. HRMS (ESI+) [M+H] calcd for C$_{24}$H$_{22}$N$_7$$^+$ 372.1931 found 372.1930.

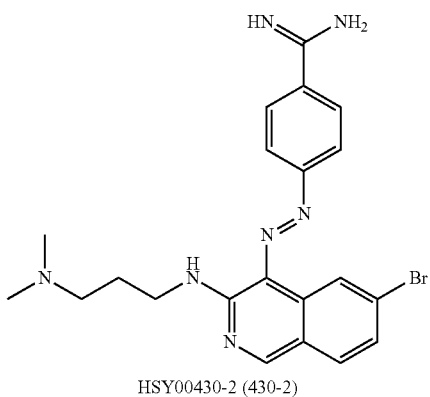 [SMILES: CN(C)CCCNc1ncc2ccc(Br)cc2c1/N=N/c1ccc(C(=N)N)cc1]

HSY00430-2 (430-2)

Scheme 8 Synthesis of HSY00430-2.

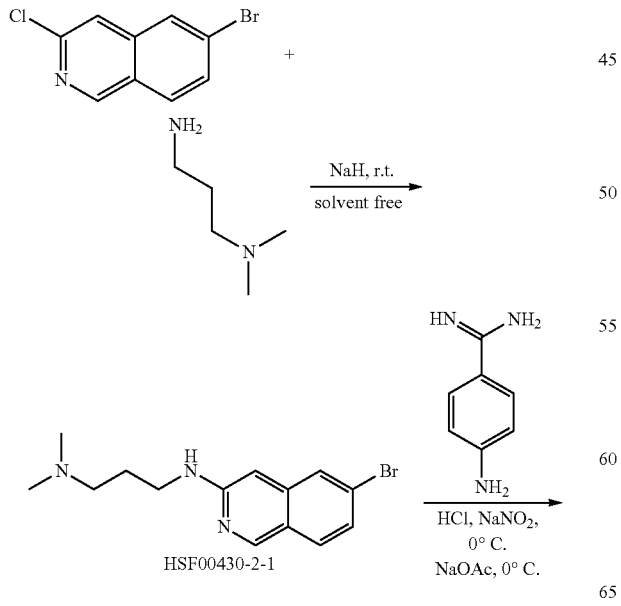

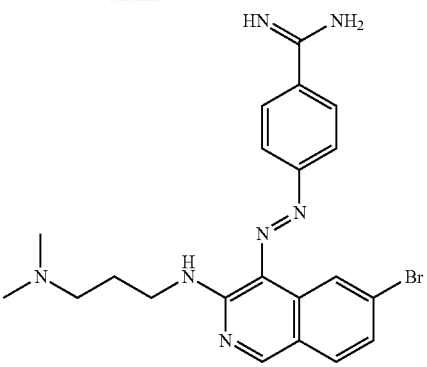

HSF00430-2-1. A dry 5 mL round bottom flask was charged with 0.4 mL of the starting amine, and NaH (24 mg, 1 mmol) under argon. The suspended mixture was stirred at r.t. under argon for 20 min until no more bubbles evolve. Then 6-bromo-3-chloroisoquiniline (100 mg, 0.45 mmol) was added and the reaction was stirred at r.t. under argon until TLC indicated complete consumption of 6-bromo-3-chloroisoquiniline. The reaction was then quenched by saturated aq. NaHCO$_3$ solution and extracted by EtOAc. The product was purified on column chromatography and a yellowish-green solid was obtained (68 mg). $^1$H NMR (400 MHz, CDCl$_3$) δ 8.75 (s, 1H), 7.66 (d, J=1.5 Hz, 1H), 7.55 (d, J=8.7 Hz, 1H), 7.21 (dd, J=8.6, 1.5 Hz, 1H), 6.35 (s, 1H), 5.40 (br, 1H), 3.31 (t, J=6.7 Hz, 2H), 2.46 (t, J=6.8 Hz, 2H), 2.27 (s, 6H), 1.85 (q, J=6.7 Hz, 2H); $^{13}$C NMR (101 MHz, CDCl$_3$) δ 156.38, 151.95, 140.20, 129.54, 126.83, 125.70, 125.41, 121.69, 94.37, 57.98, 45.54, 41.82, 26.68.

HSF00430-2. Following the described general procedure I, red solid was obtained. $^1$H NMR (400 MHz, DMSO-d6) δ 11.17 (t, J=5.7 Hz, 1H), 9.13 (s, 1H), 8.76 (d, J=1.7 Hz, 1H), 8.00-7.92 (m, 5H), 7.54 (dd, J=8.5, 1.9 Hz, 1H), 3.79 (q, J=6.7 Hz, 2H), 2.33 (t, J=6.9 Hz, 2H), 2.14 (s, 6H), 1.81 (p, J=6.9 Hz, 2H). $^{13}$C NMR (101 MHz, DMSO) δ 162.75, 157.93, 153.85, 146.63, 137.94, 134.30, 130.97, 128.18, 127.01, 126.82, 126.58, 122.08, 121.25, 120.78, 118.54, 56.84, 48.59, 45.30, 39.52, 27.07.

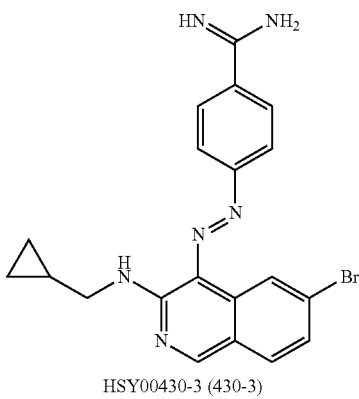 [SMILES: N=C(N)c1ccc(/N=N/c2c(NCC3CC3)ncc3ccc(Br)cc23)cc1]

HSY00430-3 (430-3)

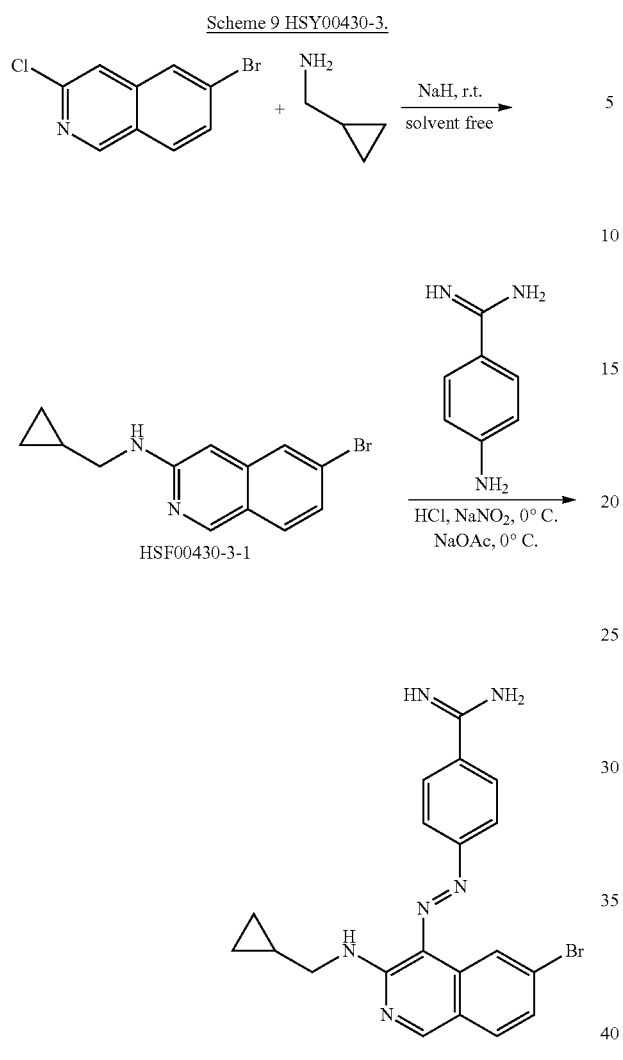

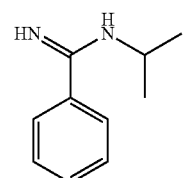

HSY00430-5 (430-5)

Scheme 10 Synthesis of HSY00430-5.

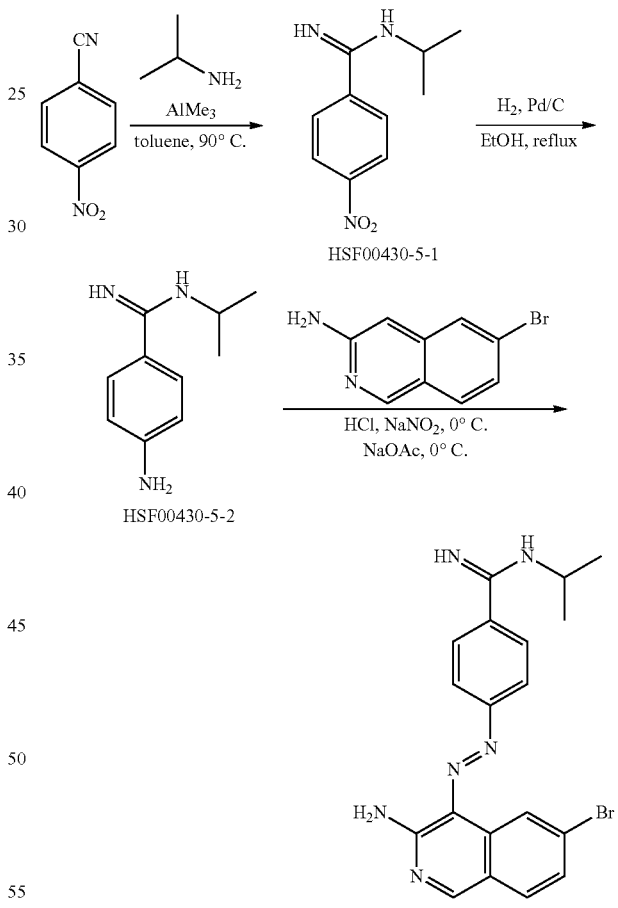

HSF00430-3-1. A dry 5 mL round bottom flask was charged with 0.4 mL of the starting amine, and NaH (24 mg, 1 mmol) under argon. The suspended mixture was stirred at r.t. under argon for 20 min until no more bubbles evolve. Then 6-bromo-3-chloroisoquiniline (100 mg, 0.45 mmol) was added and the reaction was stirred at r.t. under argon until TLC indicated complete consumption of 6-bromo-3-chloroisoquiniline. The reaction was then quenched by saturated aq. NaHCO$_3$ solution and extracted by EtOAc. The product was purified on column chromatography and a yellowish-green solid was obtained. $^1$H NMR (400 MHz, CDCl$_3$) δ 8.76 (s, 1H), 7.68 (s, 1H), 7.57 (d, J=8.7 Hz, 1H), 7.23 (d, J=8.7 Hz, 1H), 6.35 (s, 1H), 4.99 (br, 1H), 3.10 (d, J=6.9 Hz, 2H), 1.15 (m, 1H), 0.59 (m, 2H), 0.30 (m, 2H); $^{13}$C NMR (101 MHz, CDCl$_3$) δ 156.00, 151.63, 140.29, 129.60, 126.90, 125.95, 125.70, 121.70, 94.57, 47.99, 10.73, 3.66.

HSF00430-3. Following the described general procedure I, red solid was obtained. 1H NMR (400 MHz, DMSO-d6) δ 11.41 (s, 1H), 9.11 (br, 1H), 8.71 (s, 1H), 8.04 (q, J=8.4 Hz, 4H), 7.92 (d, J=8.5 Hz, 1H), 7.53 (d, J=8.4 Hz, 1H), 1.22 (m, 1H), 0.55 (d, J=7.3 Hz, 2H), 0.37 (d, J=4.2 Hz, 2H). 13C NMR (101 MHz, DMSO) δ 164.95, 159.06, 155.58, 146.64, 138.03, 131.23, 129.57, 127.81, 127.24, 127.00, 122.16, 121.69, 121.02, 118.85, 44.99, 11.04, 3.44.

HSF00430-5-1. A 100 mL round bottom flask was charged with 30 mL anhydrous toluene and the starting amine (27.0 mmol) under argon, followed by slow addition of AlMe$_3$ (13.5 mL, 2M in toluene). The resulting solution was stirred at r.t. over 30 minutes before the addition of 4-nitrobenzonitrile (2 g, 13.5 mmol). The reaction was raised to 80° C. and stirred overnight. After TLC indicated finish of the reaction, 10 mL sat. aq. ammonium tartrate solution was added to quench excess AlMe$_3$, and 6N NaOH solution was added to adjust pH to 12. Then the reaction was extracted with EtOAc and the product was purified on alumina column (5% MeOH in DCM). A brown solid was obtained (1.7 g). ¹H NMR (400 MHz, CDCl₃) δ 8.21 (d, J=8.8 Hz, 2H), 7.73 (d, J=8.7 Hz, 2H), 5.33 (br, 2H), 3.94 (m, J=6.4 Hz, 1H), 1.26 (d, J=6.4 Hz, 6H); ¹³C NMR (101 MHz, CDCl₃) δ 160.26, 148.68, 144.09, 127.49, 123.93, 43.84, 22.76.

HSF00430-5-2. A 25 mL round bottom flask was charged with the N-alkyl-4-nitrobenzimidamide (HSF00430-5-1, 300 mg), palladium on carbon powder (10 wt. % loading, 80 mg) and ammonium formate (500 mg). The air in the flask was exchanged with argon, then 3 mL anhydrous ethanol was added. The reaction was refluxed under argon overnight. After the reaction was finished, Pd/C and ammonium formate was removed by filtration. The filtrate was evaporated to afford the crude product, which was recrystallized in acetonitrile to give the pure product. A 25 mL round bottom flask was charged with the N-alkyl-4-nitrobenzimidamide (300 mg), palladium on carbon powder (10 wt. % loading, 80 mg) and ammonium formate (500 mg). The air in the flask was exchanged with argon, then 3 mL anhydrous ethanol was added. The reaction was refluxed under argon overnight. After the reaction was finished, Pd/C and ammonium formate was removed by filtration. The filtrate was evaporated to afford the crude product, which was recrystallized in acetonitrile to give the pure product. 1H NMR (400 MHz, MeOD) δ 7.37 (d, J=8.6 Hz, 2H), 6.68 (d, J=8.6 Hz, 2H), 3.90 (sep, J=6.4 Hz, 1H), 1.23 (d, J=6.4 Hz, 6H). ¹³C NMR (101 MHz, MeOD) δ 165.07, 151.64, 128.84, 126.58, 115.27, 44.35, 22.78.

HSF00430-5. Following the described general procedure I, red solid was obtained. ¹H NMR (400 MHz, DMSO-d6) δ 9.84 (br, 1H), 9.03 (s, 1H), 8.74 (s, 1H), 8.45 (br, 1H), 7.91 (m, 5H), 7.50 (d, J=8.5 Hz, 1H), 3.81 (m, 6.2 Hz, 1H), 1.15 (d, J=6.3 Hz, 6H); ¹³C NMR (101 MHz, DMSO) δ 157.53, 153.23, 147.31, 138.18, 137.91, 130.92, 127.67, 126.64, 126.46, 122.20, 121.35, 121.31, 118.09, 44.08, 23.08.

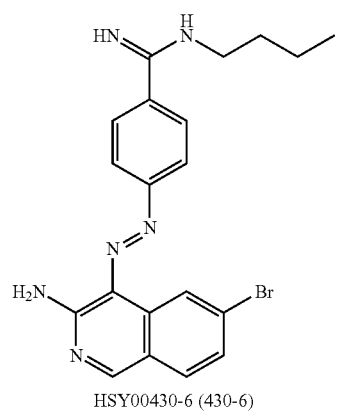 [SMILES: CCCCNC(=N)c1ccc(/N=N/c2c(N)ncc3ccc(Br)cc23)cc1]

HSY00430-6 (430-6)

Scheme 11 Synthesis of HSY00430-6.

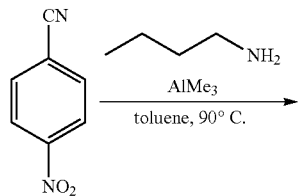

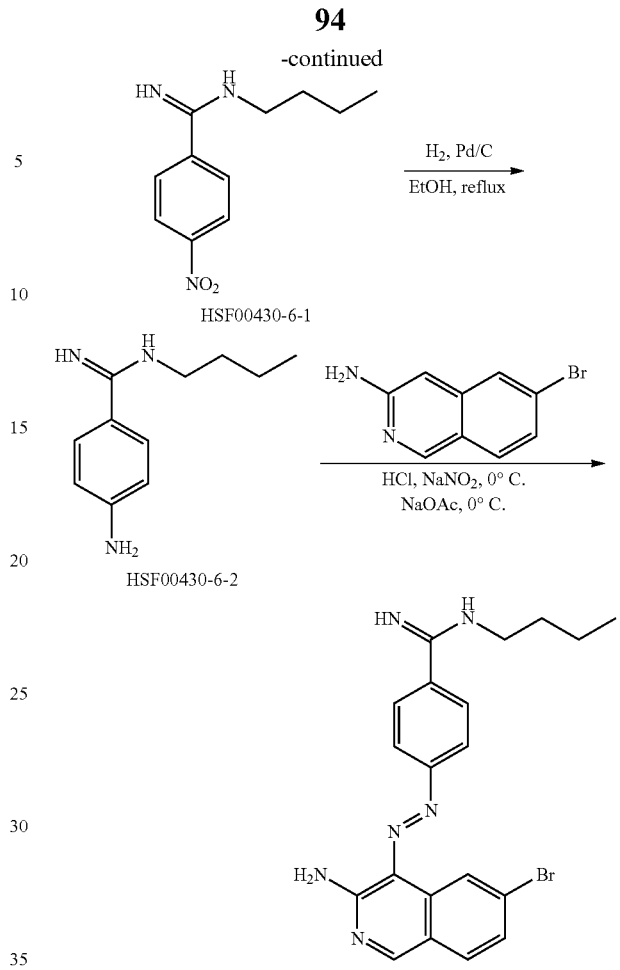

HSF00430-6-1. A 100 mL round bottom flask was charged with 30 mL anhydrous toluene and the starting amine (27.0 mmol) under argon, followed by slow addition of AlMe₃ (13.5 mL, 2M in toluene). The resulting solution was stirred at r.t. over 30 minutes before the addition of 4-nitrobenzonitrile (2 g, 13.5 mmol). The reaction was raised to 80° C. and stirred overnight. After TLC indicated finish of the reaction, 10 mL sat. aq. ammonium tartrate solution was added to quench excess AlMe₃, and 6N NaOH solution was added to adjust pH to 12. Then the reaction was extracted with EtOAc and the product was purified on alumina column (5% MeOH in DCM). A brown solid was obtained ¹H NMR (400 MHz, CDCl₃) δ 8.04 (d, J=8.8 Hz, 2H), 7.65 (d, J=8.8 Hz, 2H), 5.49 (br, 2H), 3.13 (t, J=7.2 Hz, 2H), 1.53 (quin, J=7.4 Hz, 2H), 1.31 (sex, J=7.4 Hz, 2H), 0.83 (t, J=7.4 Hz, 3H). ¹³C NMR (101 MHz, CDCl₃) δ 160.04, 148.27, 143.46, 127.38, 123.42, 42.86, 31.29, 20.27, 13.68.

HSF00430-6-2. A 25 mL round bottom flask was charged with the N-alkyl-4-nitrobenzimidamide (HSF00430-6-1, 300 mg), palladium on carbon powder (10 wt. % loading, 80 mg) and ammonium formate (500 mg). The air in the flask was exchanged with argon, then 3 mL anhydrous ethanol was added. The reaction was refluxed under argon overnight. After the reaction was finished, Pd/C and ammonium formate was removed by filtration. The filtrate was evaporated to afford the crude product, which was recrystallized in acetonitrile to give the pure product. A 25 mL round bottom flask was charged with the N-alkyl-4-nitrobenzimidamide (300 mg), palladium on carbon powder (10 wt. % loading, 80 mg) and ammonium formate (500 mg). The air in the flask was exchanged with argon, then 3 mL anhydrous ethanol was added. The reaction was refluxed under argon overnight. After the reaction was finished, Pd/C and ammonium formate was removed by filtration. The filtrate was evaporated to afford the crude product, which was recrystallized in acetonitrile to give the pure product. $^1$H NMR (400 MHz, Methanol-d4) δ 7.90 (d, J=8.2 Hz, 2H), 7.62 (d, J=8.6, 2H), 3.48 (t, J=7.3, 2H), 1.76 (p, J=7.4 Hz, 2H), 1.50 (h, J=7.4 Hz, 2H), 1.02 (t, J=7.3 Hz, 3H).

HSF00430-6. Following the described general procedure I, red solid was obtained. $^1$H NMR (400 MHz, DMSO-d6) δ 9.85 (br, 1H), 9.06 (s, 1H), 8.79 (s, 1H), 8.47 (br, 1H), 7.95 (m, 5H), 7.50 (dd, J=8.4, 0.8 Hz, 2H), 6.61 (br, 2H), 3.14 (t, J=6.8 Hz, 3H), 1.60 (m, 2H), 1.43 (m, 2H), 0.94 (t, J=7.3 Hz, 3H); $^{13}$C NMR (101 MHz, DMSO) δ 157.57, 153.22, 147.33, 137.83, 130.97, 127.58, 126.68, 126.50, 122.22, 121.34, 118.10, 44.79, 32.29, 20.27, 14.00.

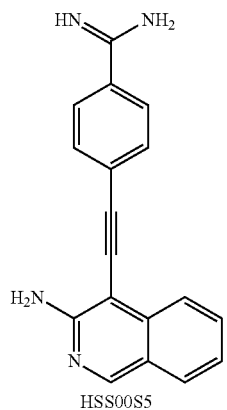

HSS00S5

Scheme 12 Synthesis of HSS00S5.

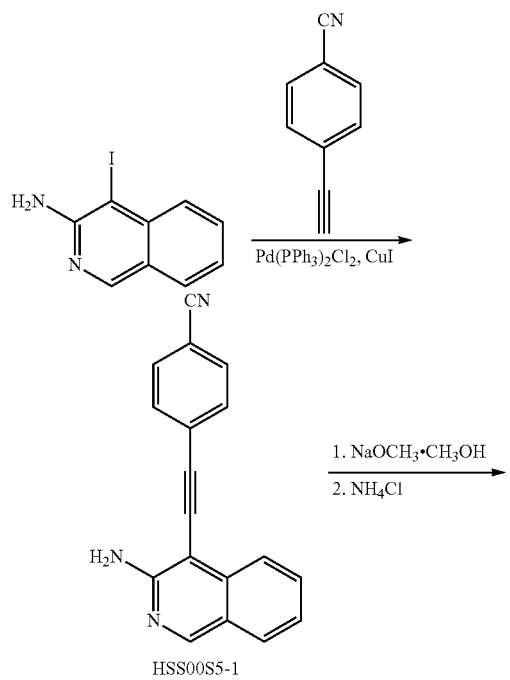

HSS00S5-1

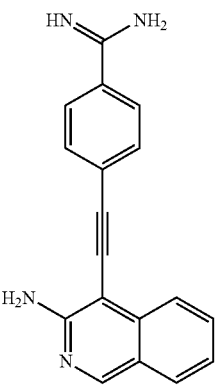

HSS005-1. A 50 ml Schlenk flask was charged with 4-iodoisoquinolin-3-amine (270 mg 1 mmol, 1.0 equiv), Bis-(triphenylphosphine)palladium dichloride ((Ph$_3$P)$_3$ PdCl$_2$; 35 mg, 0.05 mmol, 5 mol %), cuprous iodide (CuI; 9.5 mg, 0.05 mmol, 5 mol %), triphenylphosphine (PPh$_3$; 6.6 mg, 0.025 mmol, 2.5 mol %), 4-ethynylbenzonitrile (152 mg, 10 mmol, 1.2 equiv) and a stir bar and sealed by rubber septum. The flask was evacuated-refilled three times with Ar. 7 ml iPr$_2$NH was degassed in a separated round bottom flask for 15 minutes then transferred to the Schlenk flask through cannula. The mixture was stirred for 12 hours at room temperature followed by 4 hours stirring at 45° C. After reaction, the reaction mixture was diluted with ethyl acetate (20 mL) and the slurry filtered through a pad of Celite in a sintered glass funnel (medium frit). The tan solids were washed additionally with ethyl acetate until the filtrate was nearly colorless. The filtrate was washed with H$_2$O and brine followed by dried over magnesium sulfate. The combined organic fraction filtrates were concentrated in vacuo to yield a black solid. The residue was further purified by flash column chromatography on silica gel where 30% ethyl acetate/hexane was used as mobile phase. Crystalline bright yellow solid was afforded after removing the solvent by rotary evaporation to obtain HSS00S5-1. $^1$H NMR (400 MHz, CDCl$_3$) δ 8.87 (s, 1H), 7.99 (d, J=8.4 Hz, 1H), 7.82 (d, J=8.2 Hz, 1H), 7.68 (s, 4H), 7.66-7.62 (m, 1H), 7.33 (t, J=7.5 Hz, 1H), 5.22 (s, 2H). $^{13}$C NMR (100 MHz, CDCl$_3$) δ 156.56, 152.85, 137.83, 133.00, 132.17, 131.72, 128.49, 128.07, 123.71, 123.11, 118.49, 111.44, 98.44, 91.55, 88.12, 77.20, LRMS (ESI+) [M+H] calcd for C$_{18}$H$_{12}$N$_3$ 270.1026. found 270.0648.

HSS00S5. A 50 ml round-bottom flask was equipped with a magnetic stirrer was charged with 4-((3-aminoisoquinolin-4-yl)ethynyl)benzonitrile (HSS00S5-1, 67.3 mg, 0.25 mmol) and MeOH (anhydrous, 10 mL). Sodium methoxide (54.0 mg, 1 mmol) was dissolved in methanol (10 mL) was added and the mixture was refluxed for 24 h. Solid ammonium chloride (53.5 mg, 1 mmol) was added and the mixture was stirred for an additional 24 hour at reflux condition. Methanol was removed completely at reduced pressure at a rotovap. The crude product was extracted by ethyl acetate 20 ml×3 from water 25 ml. Combined organic fraction was dried over Na₂SO₄, filtered off and filtrate was concentrated at a rotovap. The product was purified through preparative flash column chromatography where silica was stationary phase and 5-10% MeOH:DCM was mobile phase. Pure orange powder product (HSS00S5) was obtained after removing the solvent in a rotovap at reduced pressure. 1H NMR (400 MHz, MeOD) δ 8.82 (s, 1H), 8.01 (d, J=8.5 Hz, 1H), 7.91-7.85 (m, 5H), 7.73-7.62 (m, 1H), 7.32 (t, J=7.5 Hz, 1H). 13C NMR (101 MHz, MeOD) δ 167.83, 158.58, 153.82, 139.50, 133.17, 132.89, 130.80, 129.81, 129.25, 128.55, 124.57, 124.06, 123.85, 99.65, 92.08, 88.62.

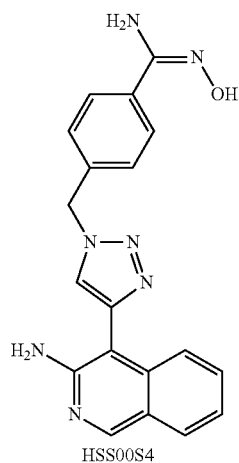

HSS00S4

Scheme 13 Synthesis of HSS00S4.

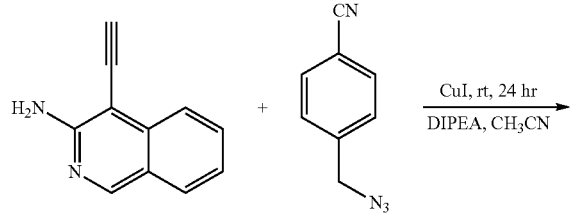

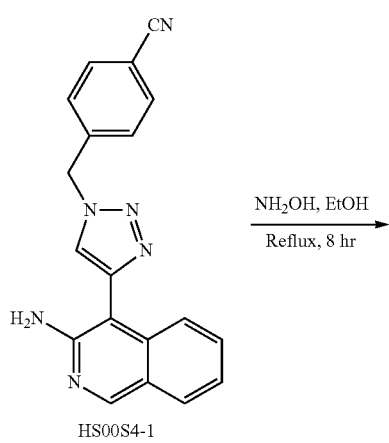

HS00S4-1

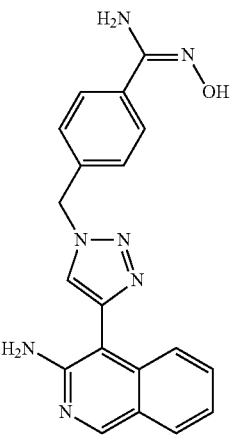

HS00S4-1. To a solution of 4-ethynylisoquinolin-3-amine (75 mg, 0.44 mmol) and 4-(azidomethyl)benzonitrile (1.33 ml, 0.66 mmol (0.5 M solution in dimethyl ether) in acetonitrile (5 ml) was added 5 ml DIPEA, a catalytic amount of CuI (10 mol %). Then the reaction was stirred at room temperature for 24 hr until completion (TLC monitored). After completion of the reaction, solvent was removed at reduced pressure. The residue was dissolved in ethyl acetate and washed by brine. The combined organic layers were dried (Na₂SO₄) and filtered. After concentration under reduced pressure, the residue was purified by flash chromatography on silica gel where 50% EA:HEX were used as mobile phase. Evaporation of the solvent yielded greenish powder pure product (HS00S4-1). ¹H NMR (500 MHz, DMSO) δ 13.23 (bs, 2H), 9.19 (s, 1H), 8.95 (s, 1H), 8.31-8.11 (m, 4H), 7.91 (d, J=7.9 Hz, 1H), 7.63 (d, J=8.3 Hz, 1H), 7.52 (t, J=7.0 Hz, 1H), 7.25 (t, J=7.0 Hz, 1H), 6.14 (s, 2H).

HSS00S4. To a stirred solution of 4-((4-(3-aminoisoquinolin-4-yl)-1H-1,2,3-triazol-1-yl)methyl)benzonitrile (HS00S4-1, 40 mg, 0.12 mmol, 1 equivalent) in ethanol (20 mL), 50% aqueous hydroxylamine solution (1.2 mL) was added and refluxed for 16 h. The completion of the reaction was confirmed by TLC, and ethanol was removed by rotary evaporation. The crude product was dissolved in ethyl acetate (50 mL) and washed one time with water (15 mL). The organic layer was separated and dried over anhydrous Na₂SO₄. After filtration and removal of the organic solvent by rotary evaporation, light green color Pure crystalline product was afforded. ¹H NMR (500 MHz, DMSO) δ 9.67 (s, 1H), 8.90 (s, 1H), 8.58 (s, 1H), 7.90 (d, J=8.1 Hz, 1H), 7.70 (d, J=8.4 Hz, 2H), 7.61 (d, J=8.6 Hz, 1H), 7.52 (dd, J=7.8, 6.3 Hz, 1H), 7.42 (d, J=8.3 Hz, 2H), 7.24 (t, J=7.0 Hz, 1H), 6.16 (s, 2H), 5.83 (s, 2H), 5.74 (s, 2H).

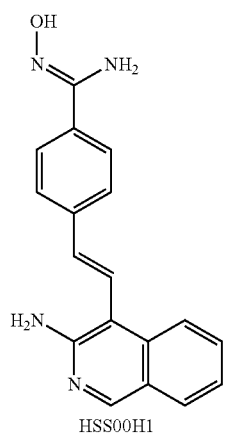

HSS00H1

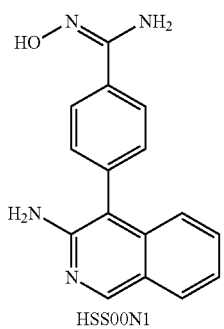

HSS00N1

Scheme 15 Synthesis of HSS00N1.

Scheme 14 Synthesis of HSS00H1.

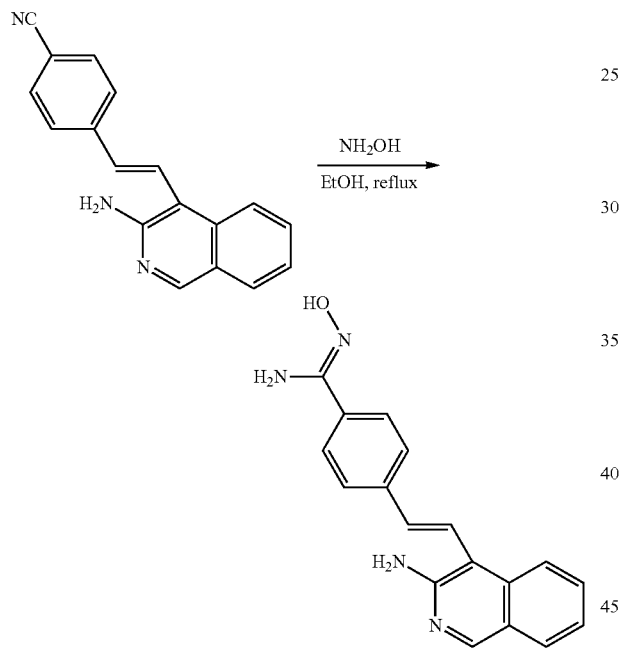

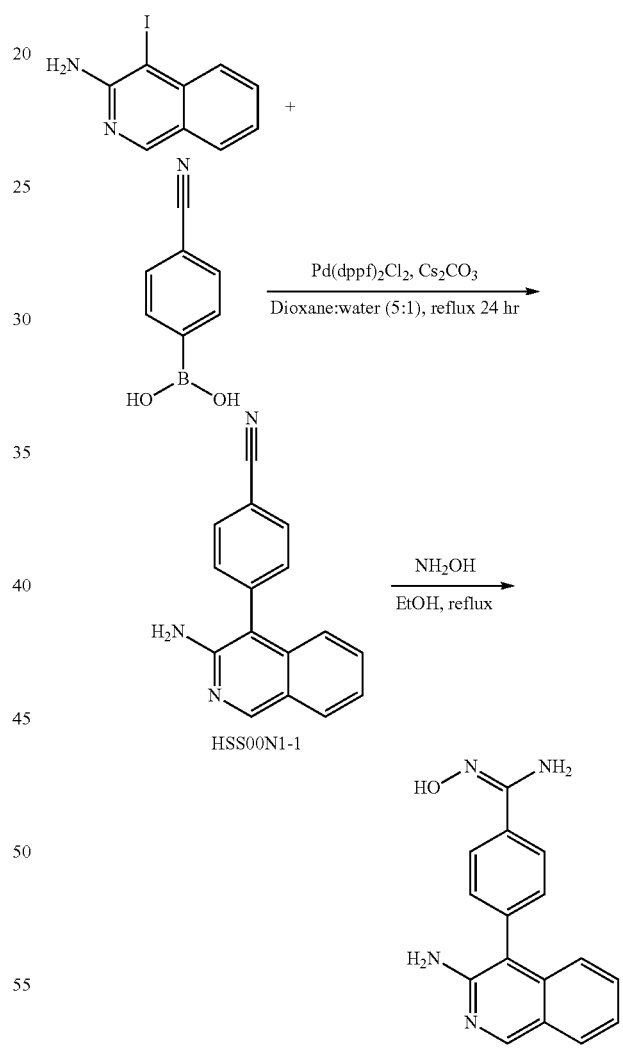

HSS00H1. To a stirred solution of (E)-4-(2-(3-aminoisoquinolin-4-yl)vinyl)benzonitrile (27 mg, 0.1 mmol, 1 equivalent) in ethanol (15 mL), 50% aqueous hydroxylamine solution (0.5 mL) was added and refluxed for 8 h. The completion of the reaction was confirmed by TLC, and ethanol was removed by rotary evaporation. The crude product was dissolved in ethyl acetate (50 mL) and washed one time with water (20 mL). The organic layer was separated and dried over anhydrous $Na_2SO_4$. After filtration and removal of the organic solvent by rotary evaporation, the crude product was further purified by recrystallization. $^1$H NMR (600 MHz, DMSO) δ 9.61 (s, 1H), 8.86 (s, 1H), 7.85 (d, J=8.0 Hz, 1H), 7.49-7.34 (m, 4H), 7.16 (t, J=7.3 Hz, 1H), 7.07 (d, J=8.4 Hz, 2H), 6.93 (d, J=12.1 Hz, 1H), 6.62 (d, J=12.1 Hz, 1H), 5.71 (d, J=9.5 Hz, 4H). $^{13}$C NMR (126 MHz, DMSO) δ 152.48, 151.19, 150.23, 137.15, 134.87, 132.94, 132.11, 130.31, 128.33, 127.91, 124.98, 123.64, 122.44, 122.18, 121.81, 104.33. LRMS (ESI+) [M+H] calcd for $C_{18}H_{17}N_4O^+$ 305.1397 found 305.2728.

HSS00N1-1. To a stirred suspension of 4-iodoisoquinolin-3-amine (180 mg, 0.67 mmol), (4-cyanophenyl)boronic acid (146.94 mg, 1 mmol) and $Cs_2CO_3$ (325.8 mg, 3 mmol) in dioxane (10 ml) and $H_2O$ (2 ml) was added a catalytic amount (73 mg 0.1 mmol) of $Pd(dppf)_2Cl_2$, under nitrogen. The resulting mixture was refluxed for 24 hours. TLC (EtOAc/Hexane 1:2) indicated the reaction was complete. The reaction mixture was cooled to room temperature and filtered. The filtrate was concentrated in vacuo to give a residue which was dissolved in dichloromethane (30 ml). After washing with water (30 ml×3) and brine (30 ml), the dichloromethane layer was dried over anhydrous $Na_2SO_4$ and concentrated in vacuo to give the crude product which was purified by column chromatography (silica gel, EtOAc/hexane 1:2) to title afford compound (135 mg, 82%) as an off white solid. $^1$H NMR (600 MHz, DMSO) δ 8.94 (s, 1H), 8.05-7.98 (m, 2H), 7.90 (d, J=8.0 Hz, 1H), 7.57-7.53 (m, 2H), 7.47-7.39 (m, 1H), 7.22 (ddd, J=7.9, 6.7, 1.0 Hz, 1H), 7.04 (dd, J=8.6, 0.8 Hz, 1H), 5.54 (s, 2H).

HSS00N1. To a stirred solution of 4-(3-aminoisoquinolin-4-yl)benzonitrile (HSS00N1-2, 177 mg, 0.72 mmol, 1 equivalent) in ethanol (15 mL), 50% aqueous hydroxylamine solution (3 mL) was added and refluxed for 16 h. The completion of the reaction was confirmed by TLC, and ethanol was removed by rotary evaporation. The crude product was dissolved in ethyl acetate (50 mL) and washed one time with water (20 mL). The organic layer was separated and dried over anhydrous $Na_2SO_4$. After filtration and removal of the organic solvent by rotary evaporation, the crude product was further purified by column chromatography on silica gel by 50% EA:Hex solvent system. $^1$H NMR (400 MHz, DMSO) δ 9.74 (s, 1H), 8.90 (s, 1H), 7.88 (d, J=7.9 Hz, 3H), 7.41 (t, J=7.6 Hz, 1H), 7.34 (d, J=7.9 Hz, 2H), 7.20 (t, J=7.4 Hz, 1H), 7.11 (d, J=8.6 Hz, 1H), 5.90 (s, 2H), 5.33 (s, 2H). $^{13}$C NMR (101 MHz, DMSO) δ 152.72, 151.20, 150.59, 136.51, 136.21, 132.53, 130.44, 130.34, 127.99, 126.28, 122.65, 121.90, 121.84, 108.71. LRMS (ESI+) [M+H] calcd for $C_{16}H_{15}N_4O^+$ 279.1240 found 279.2446.

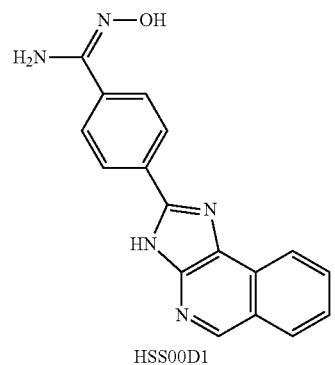 [SMILES: N/C(=N/O)c1ccc(-c2nc3c(ncc4ccccc43)[nH]2)cc1 ; "HSS00D1"]

HSS00D1

Scheme 16 Synthesis of HSS00D1.

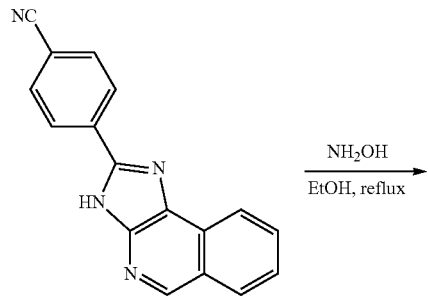

NH$_2$OH
EtOH, reflux

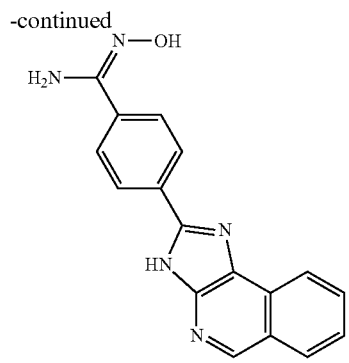

HSS00D1. To a stirred solution of 4-(3H-imidazo[4,5-c]isoquinolin-2-yl)benzonitrile (27 mg, 0.1 mmol, 1 equivalent) in ethanol (15 mL), 50% aqueous hydroxylamine solution (0.5 mL) was added and refluxed for 8 h. The completion of the reaction was confirmed by TLC, and ethanol was removed by rotary evaporation. The crude product was dissolved in ethyl acetate (50 mL) and washed one time with water (20 mL). The organic layer was separated and dried over anhydrous $Na_2SO_4$. After filtration and removal of the organic solvent by rotary evaporation, the crude product was further purified by recrystallization. $^1$H NMR (600 MHz, DMSO) δ 9.81 (s, 1H), 9.08 (s, 1H), 8.47 (d, J=8.3 Hz, 1H), 8.27 (d, J=8.3 Hz, 2H), 8.24 (d, J=8.2 Hz, 1H), 7.88 (d, J=7.4 Hz, 3H), 7.64 (t, J=7.5 Hz, 1H), 5.93 (s, 2H). $^{13}$C NMR (101 MHz, DMSO) δ 150.32, 148.99, 147.67, 143.81, 134.41, 130.75, 130.31, 129.45, 128.90, 126.00, 125.86, 125.38, 125.11, 120.84, 120.60. LRMS (ESI+) [M+H] calcd for $C_{17}H_{14}N_5O^+$ 304.1193 found 304.0553.

IC50 determination: For the determination of IC50 for the azolamide class, the same protocol as described previously was followed.

G-quadruplex binding: A solution (89 μL) of c-kit1 (10 μM) and NaCl or KCl (50 mM) in Tris-HCl buffer (50 mM, pH 7.5) was initially heated to 95° C. and kept at this temperature for 5 min. The solution was then cooled at room temperature for 15 min. Subsequently, TO (10 μL) and azolamidine analogues (1 μL) were added to give a final concentrations of 5 μM and 10 μM respectively and the solution was incubated for 12 hours at 4° C. Fluorescence measurements were then performed on a Molecular devices SpectraMax M5e plate reader at 25° C. with λ(ex.)=507 nm and λ(em.)=517-700 nm. The experiments were done in triplicate.

Kinase activity: Phosphorylation by respective kinases using 10 μM ATP in the presence and absence of HSW00630-1 was followed. Activity with DMSO control was designated as 100% activity and percent inhibition in the presence of 10 μM HSW00630-1 was calculated using the percent activity of the kinase enzyme in the presence of HSW00630-1.

PARP inhibition: The effect of HSW00630-1 on PARP-1 enzyme activity was evaluated using a HT Universal Colorimetric PARP Assay Kit with Histone-Coated Strip Wells from Trevigen. The assay was performed according to the manufacturer's instructions. This kit is designed to measure the incorporation of biotinylated poly (ADP-ribose) onto histone proteins in a 96-well strip well format. 0.05 units of PARP-HSA were added to each well. Compounds were diluted in PARP buffer to obtain various concentrations of 3-aminobenzamide (0.1 μM, 1 μM, 5 μM, 10 μM, 100 μM and 1 mM) and 630-1 (10 nM, 100 nM, 1 μM, 5 μM, 20 μM, 50 μM and 100 μM). Each concentration was triplicated. Absorbance was read at 450 nM. Data was analyzed by using Prism.

Based in part on the discovery that aryl amidines are potent G-quadruplex binders we designed new compounds bearing aryl and amidine groups that have enhanced anticancer activities. We have discovered that the isoquinoline ring enhances anticancer activity. We have further discovered that in addition to G-quadruplex binding, the isoquinoline amidine compounds are also kinase inhibitors, as well as PARP inhibitors. We used PARP1 as an illustrative PARP inhibitor in the data presented in this disclosure. Although G-quadruplex ligands, kinase inhibitors and PARP inhibitors have been described before, this is the first time to our knowledge that a single compound targets all of these three important cancer targets. Without intending to be bound by theory, it is considered that that the higher potency of the isoquinoline ring is due to the multiple targeting.

We have discovered that G-quadruplexes are macromolecular targets for azo amidine compounds and that binding to G-quadruplexes account for some of the anti-tumor effects observed with these compounds.

Figure 32:
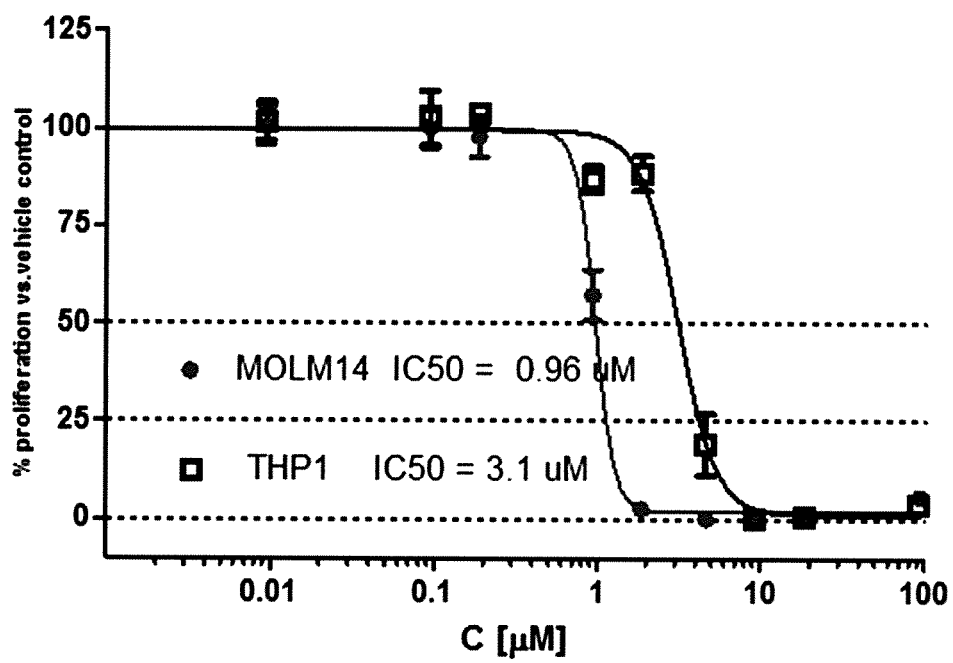
FIG. 32. WST-1 cell proliferation assay, cell lines treated with azolamidine (W308-4) in leukemia cell lines for 72 h.
Figure 33:
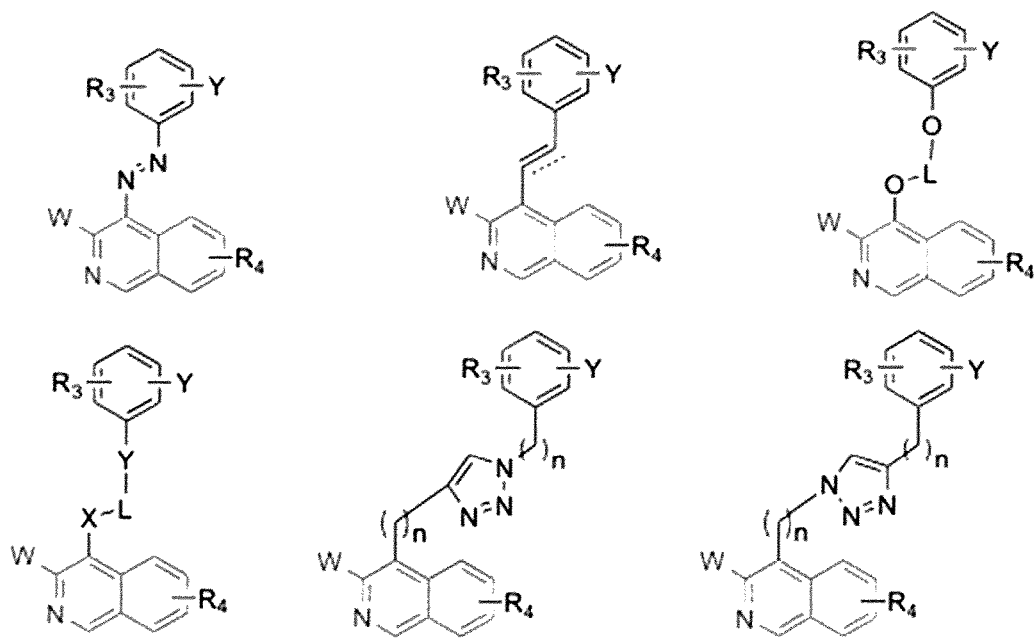
FIG. 33. Azolamidine-inspired anti-tumor agents with enhanced half-lives. Y=amidine or guanidine groups, $R^3$ and $R^4$=alkyl, aryl, heteroatom, heteroaryl, L=linker such as C=O, C=S, C=NR, aromatic moiety, alkyl linker, X and Y=O, N, S, or C, W=amine, alkyl, aryl, or heteroatom.
Figure 34:
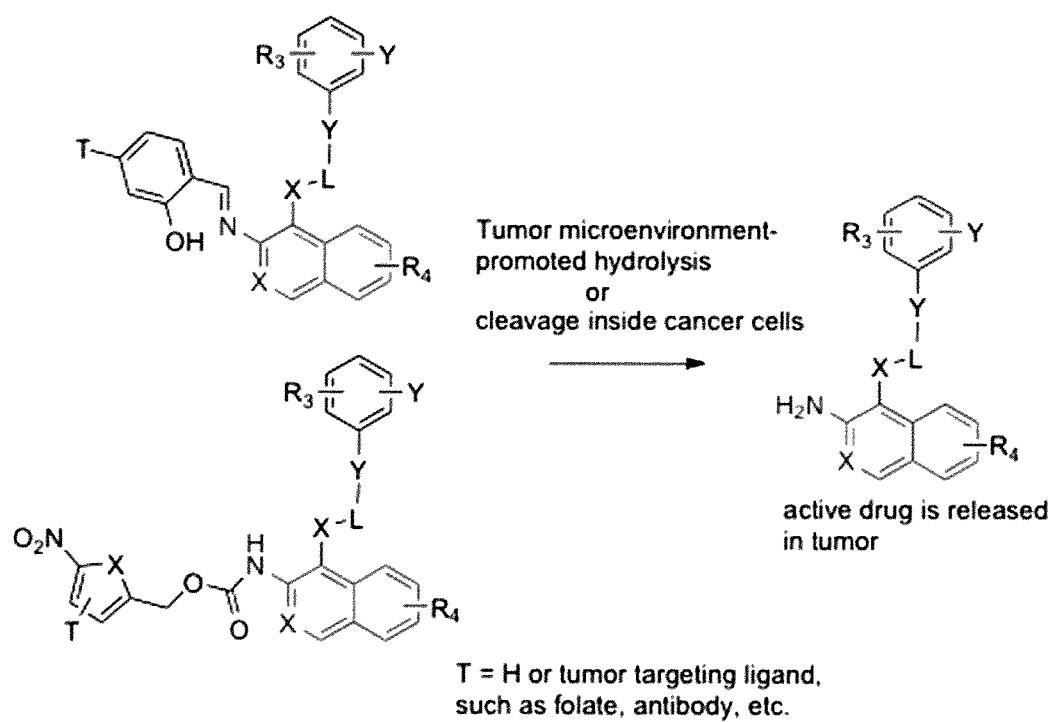
FIG. 34. Proposed mechanism of active drug release inside tumors.
Figure 35:
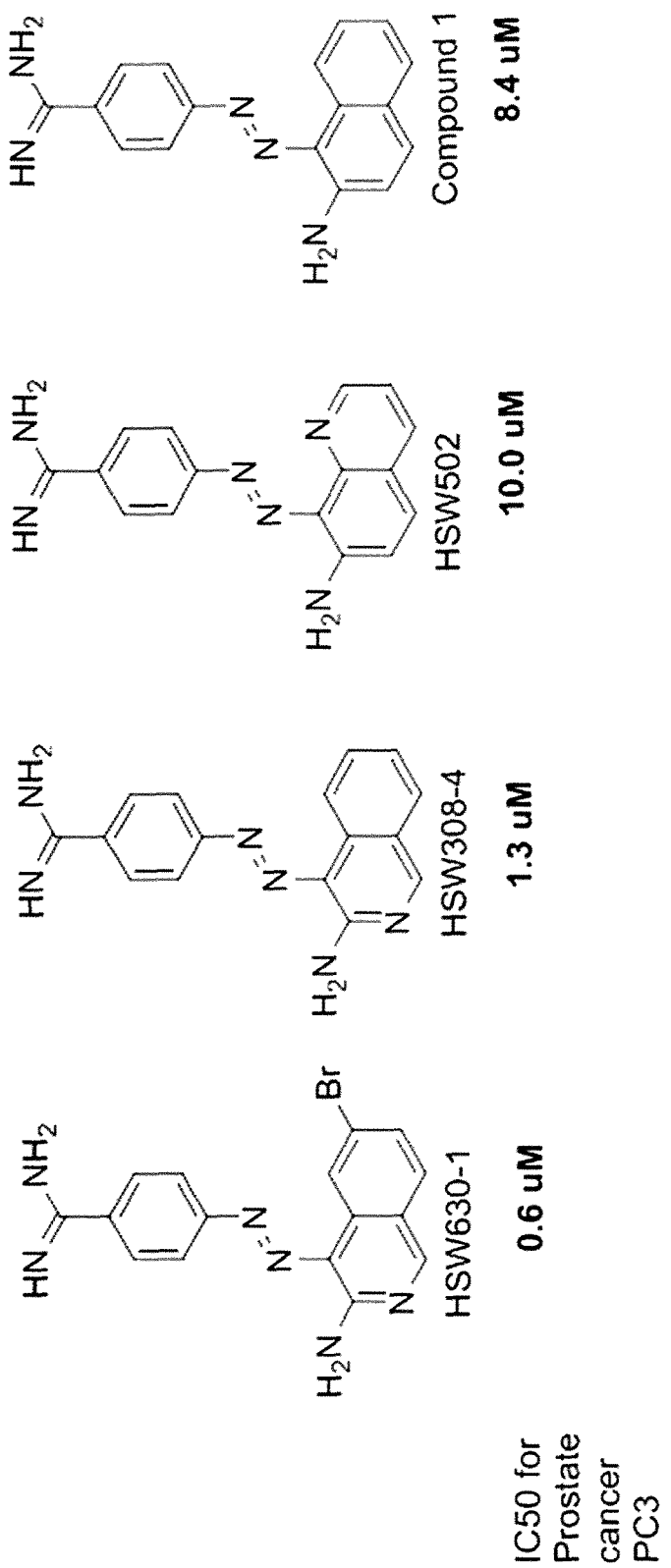
FIG. 35. IC50 for prostate cancer PC3.

We have also identified the isoquinoline azo amidine (W308-4, referred to as Azolamidine), a new compound, as the most potent anti-tumor azo amidine amongst the tested compounds (see FIG. 32). We disclose aminoisoquinoline and amidine moiety with a suitable linker as a potent anti-tumor agent.

The amidine group is important for anti-tumor activity (W310-4, W310-5, G971 and G972, which do not contain an amidine group are not active). However, not all azo amidines have good anti-tumor activity. L419, L503, L504, W310, L502, L504, W119-3, W308-3 and W308-4 all contain azo amidines but have very different bioactivities (with orders of magnitude differences in potencies, see Table 7). Interestingly, very small structural changes can dramatically affect drug potency. For example compounds L502, W308-3 and W308-4 are isomers (only the position of the ring nitrogen differs) yet the IC50 of these compounds for prostate cancer cell line are very different: L502 (10 µM); W308-3 (23.5 µM) and W304-4 (1.3 µM) potently inhibit the growth of several cancer cell lines (Table 7). The amidine group is important for anticancer activities because compounds W310-4, W310-5, G971 and G972 are not effective anticancer agents whereas the analogous compound, which contains amidine group (L419) kills several cancer cell lines with IC50 of ~8 µM.

Table 7:

TABLE 7

Inhibition of cancer cell lines.

IC$_{50}$ for killing triple negative breast cancer cell line (231)

419 (8.2 µM); 502 (5.8 µM); 503 (4.9 µM); 504 (33 µM); 308-4 (1.9 µM); 308-3 (14.8 µM)

TABLE 7-continued

Inhibition of cancer cell lines.

IC$_{50}$ for killing ovarian cancer cell line (OVCAR-3)

419 (8.1 µM); 502 (11.8 µM); 503 (6.2 µM); 504 (NE)*; 308-4 (4.2 µM); 308-3 (13.2 µM)

IC$_{50}$ for killing prostate cancer cell line (PC-3)

419 (8.3 µM); 502 (10 µM); 503 (4.5 µM); 504 (16.6 µM); 308-4 (1.3 µM); 308-3 (23.5 µM)

IC$_{50}$ for killing Leukemia cell line 308-4 (0.98 µM for MOLM14 and 2.6 µM for THP1)

*= not effective at 50 µM.

The incorporation of known DNA duplex intercalators into the azo amidine scaffold did not lead to improved anti-tumor activity. For example whereas the IC50 for the killing of breast cancer by compound 308-4 (azolamidine, containing isoquinoline moiety) is 1.9 µM, that for L504 (which contains acridine moiety, a duplex intercalator with anti-tumor activity) is over 50 µM.

One of the compounds, azolamidine (W308-4) has very good IC50s for all tested cancer cell lines and even inhibits leukemia cell line growth with sub micromolar IC50 (see Table 7). For comparison purposes, the IC50 of cisplatin (one of the most prescribed anticancer drugs) for various cancer cell lines are as follows: SH-SY5Y (2 µAA), PNT1 (5 µM), SW872 (5 µM), RD (6 µM), A375 (6 µM), Hep2 (7 µM), MCF-7/DX (7 µM), HT1080 (9 µM), HOS (10 µM), SAOS-2 (11 µM), PC3 (12 µM), HepG2 (12 µM), HeLa (13 µM), MCF-7 (15 µM), PANC-1 (15 µM), Caco-2 (17 µM), A431 (20 µM), U2-OS (20 µM), HT29 (22 µM), A549 (36 µM), CFPAC-1 (38 µM), Calu-3 (>50 µM) and CAPAN-1 (>50 µM).

Azolamidine (compound W308-4) and derivatives thereof have therefore emerged as an interesting anticancer agent and derivatives.

The introduction of a nitrogen atom into the naphthalene ring (to give 4-substituted 3-aminoisoquinoline) increases anticancer activity by up to 10 times. The IC50 values for HSW308-4 and HSW630-1 against prostate cancer cell line are 1.3 µM and 0.6 µM respectively. Interestingly HSW502, also an isoquinoline compound is only moderately active against cancer cells, with an IC50 against prostate cancer cell line PC-3 of 10 µM. Likewise compound 1, a known anticancer agent, has an IC50 of 8.4 µM against PC-3. These results show that the position of the ring nitrogen, together with the relative position of the exocyclic amine affects anticancer activity. Compounds HSW630-1, HSW308-4 and HSW502 are among the novel compounds presented in this disclosure.

TABLE 8

Anticancer activities.

| compounds | TNBC 231 | PC3 | U87 | Molm14 | MV4-11 | NBM |
|---|---|---|---|---|---|---|
| HSW308-4 | 1.85 µM | 1.30 µM | 1.32 µM | 0.98 µM | 0.92 µM | 8.7 µM |
| HSW630-1 | 0.48-0.92 µM | 0.59 µM | 0.56 µM | 0.14 µM | 0.15 µM | 5.1 µM |
| HSW909-1 | — | 0.89 µM | 1.18 µM | — | 0.49 µM | — |
| Cisplatin | 11.70 µM | 10.45 µM | — | — | — | — |

Figure 36:
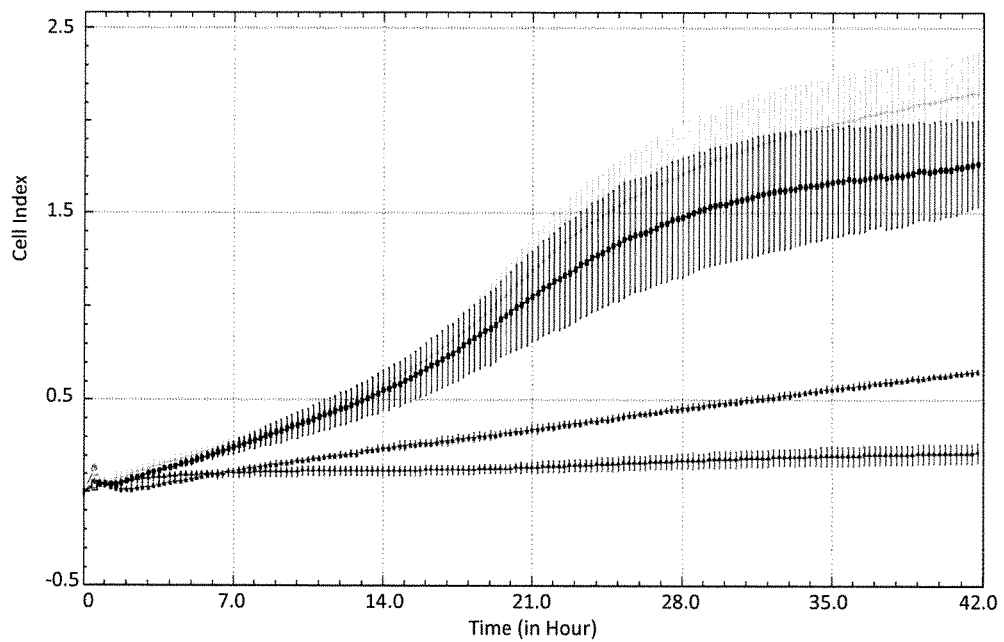
FIG. 36. 630-1 can inhibit migration of triple-negative. Red=negative control-no FCS in bottom well. Green=DMSO. Blue and pink=increasing concentration of 630-1.

TNBC 231 = triple negative breast cancer
PC3 = prostate cancer
U87 = Glioblastoma from human gliomas (brain cancer)
Molm4 = Acute lymphoblastic leukemia
MV4-11 = Acute monocytic leukemia
NBM = Normal bone marrow cells We have also determined that HSW630-1 prevents cancer cells from migrating (see FIG. 36). This indicates that 630-1 may be active against metastatic cancer.

630-1 is active against triple-negative breast cancer at sub micromolar concentrations. It is also active against acute leukemia with nanomolar IC50. Notably, 630-1 is active against brain cancer at sub-micromolar concentrations.

The ratio of IC50 of 630-1 against normal bone marrow cancer and leukemia=5.1/0.14=36. In other words, 630-1 is more selective towards cancer cells by 36 times.

Figure 37:
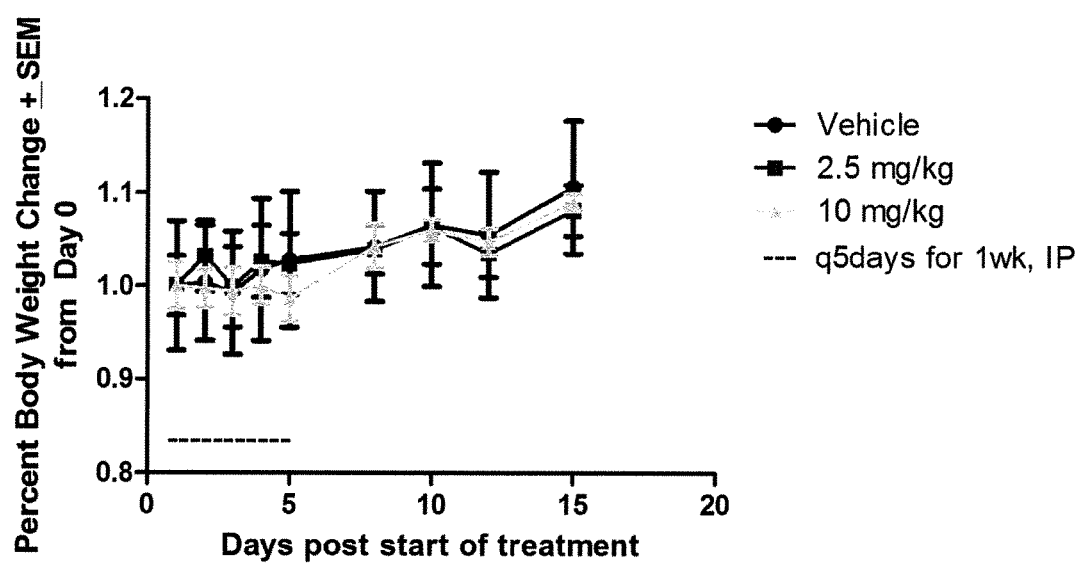
FIG. 37. Tolerability studies.
Figure 38:
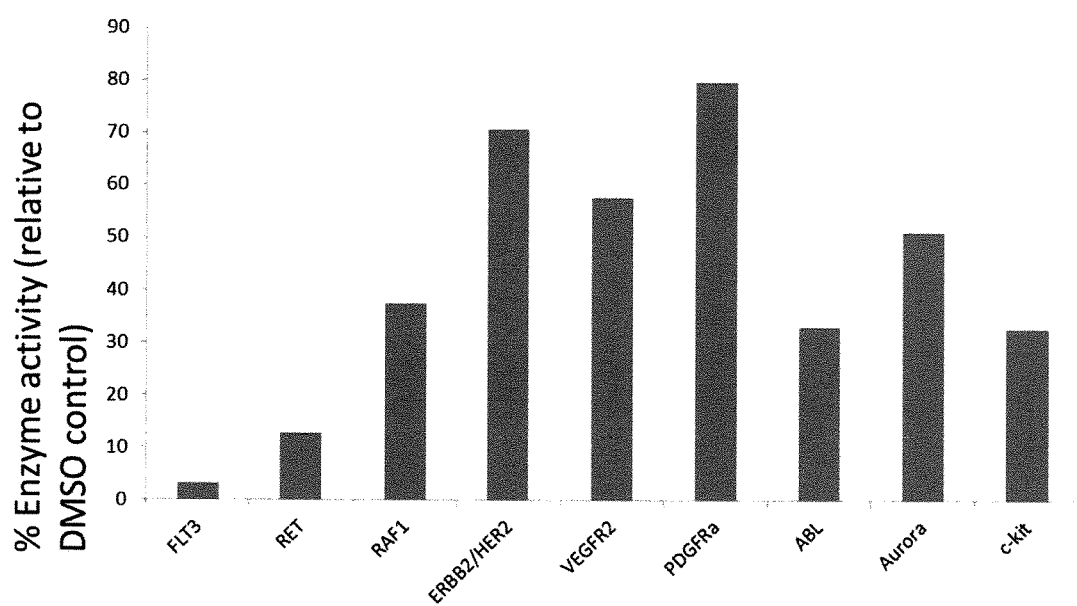
FIG. 38. Inhibition of kinase by 10 µM HSW630-1. HSW630-1 inhibits FLT-3 better than most tested kinases. FLT-3 is important for AML so there is a correlation between FLT-3 inhibition and potency against AML.
Figure 39:
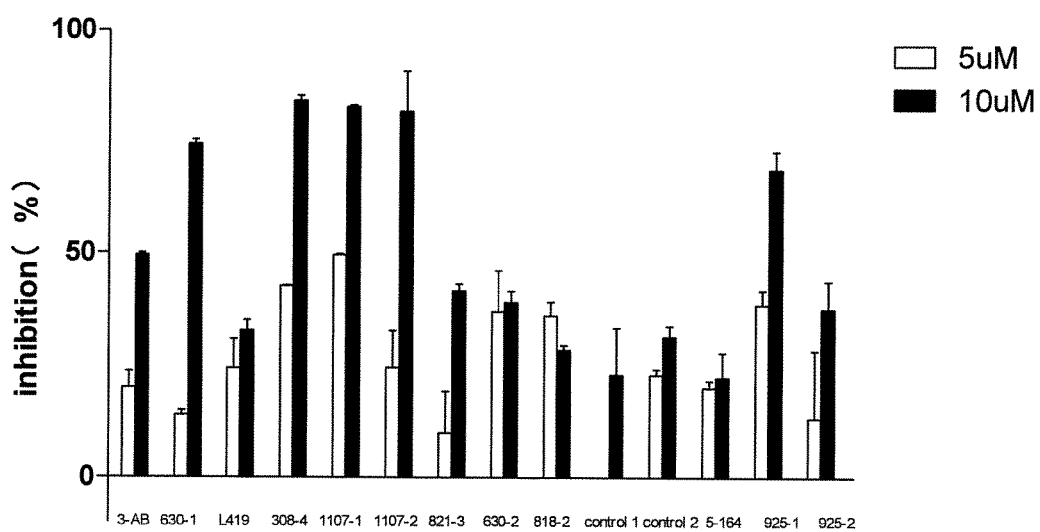
FIG. 39. PARP inhibition. Control 1: degradation product of 630-1: 4-aminobenzamidine. Control 2: bromoisoquinoline-3,4-diamine. Each concentration was duplicated. 3-AB=3-aminobenzamide-a known PARP inhibitor-positive control.

Tolerability studies using mice also suggest that 630-1 and 308-4 can be tolerated by mice at 10 mg/Kg (FIG. 37).

An established method to determine the pharmacokinetic clearance of a compound in humans is to measure the degradation of the compound in the presence of human liver microsomes. The following is the half-lives of the four compounds in human liver microsomes:

TABLE 9

Half-lives of compounds in human liver microsomes.

| Compound | NADPH-dependent T½/min | NADPH-independent T½/min |
| --- | --- | --- |
| HSW308-4 | 196 | >240 |
| HSW630-1 | 191 | 124 |

TABLE 9-continued

Half-lives of compounds in human liver microsomes.

| Compound | NADPH-dependent T½/min | NADPH-independent T½/min |
| --- | --- | --- |
| HSY430-5 | >240 | >240 |
| HSY430-6 | 154 | 143 |

Substitution of the isoquinoline ring affects metabolic stability (compare 308-4 with 630-1); b) substitution of the amidine affects metabolic stability (compare 630-1 with 430-5 and 430-6).

While the invention has been particularly shown and described with reference to specific embodiments (some of which are preferred embodiments), it should be understood by those having skill in the art that various changes in form and detail may be made therein without departing from the spirit and scope of the present invention as disclosed herein.

The invention claimed is:

1. A compound having the following formula:

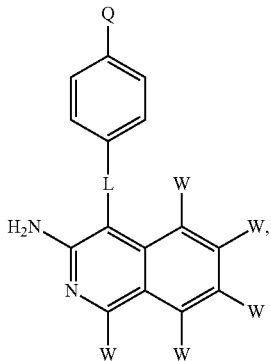

wherein

W is selected from the group consisting of —R$^1$, —OR$^1$, —N(R$^1$)$_2$, —NO$_2$, -halogen,

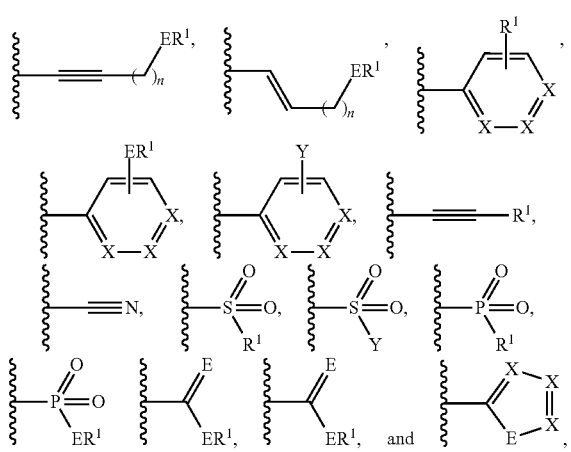

wherein

E is selected from the group consisting of oxygen atom, sulfur atom, —N(R$^1$)—, and —N(OR$^1$)—;

X is —N—, or —C(R$^1$)—;

Y is selected from the group consisting of —R$^1$, -ER$^1$, —X(R$^1$)$_2$, and -halogen;

n is 0-6; and

R$^1$ is selected from the group consisting of H, substituted or unsubstituted C$_1$-C$_{14}$ alkyl, substituted or unsubstituted C$_1$-C$_{14}$ heteroalkyl, wherein 1-7 of the chain atoms are independently O, N, S, P, or B, substituted or unsubstituted C$_1$-C$_{14}$ alkenyl, substituted or unsubstituted C$_1$-C$_{14}$ heteroalkenyl, wherein 1-7 of the chain atoms are independently O, N, S, P, or B, substituted or unsubstituted C$_1$-C$_{14}$ alkynyl, substituted or unsubstituted C$_1$-C$_{14}$ heteroalkynyl, wherein 1-7 of the chain atoms are independently O, N, S, P, or B, substituted or unsubstituted C$_5$-C$_{14}$ aryl, halo, heteroaryl having 5-14 ring atoms, wherein 1-8 of the ring atoms are independently O, N, S, P, or B,

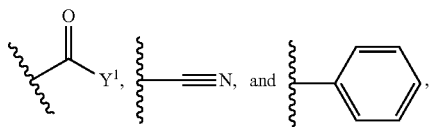

wherein

Y$^1$ is selected from the group consisting of —OR$^1$, —NR$^1$, —SR$^1$, and —R$^1$;

L is selected from the group consisting of direct bond, —O—, —NH—, —O—(CH$_2$)$_m$—O—, —NH—(CH$_2$)$_m$—NH—,

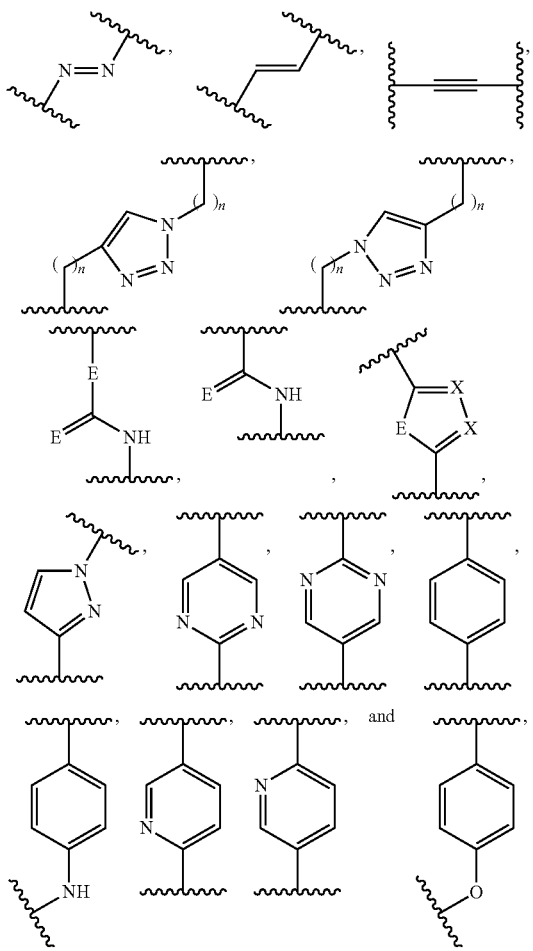

wherein m is 2-6;

Q is selected from the group consisting of —OH, —SH, —NR$^1$,

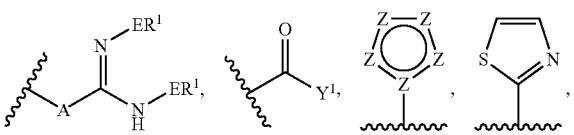

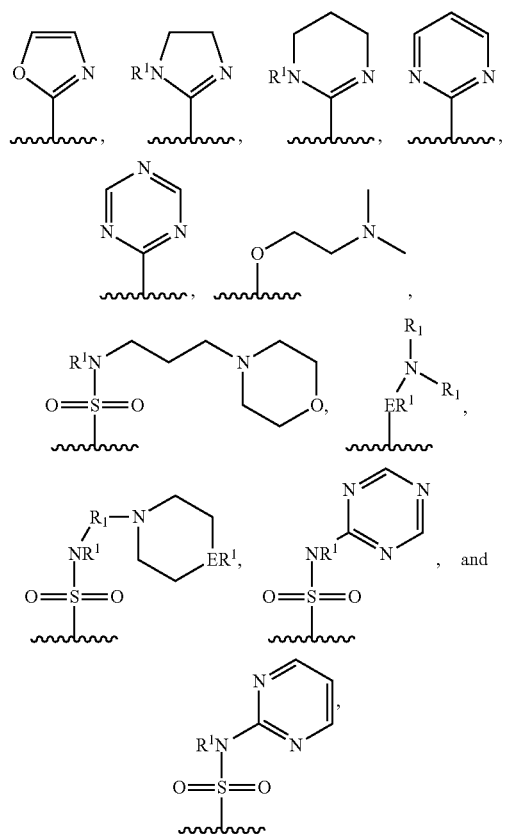

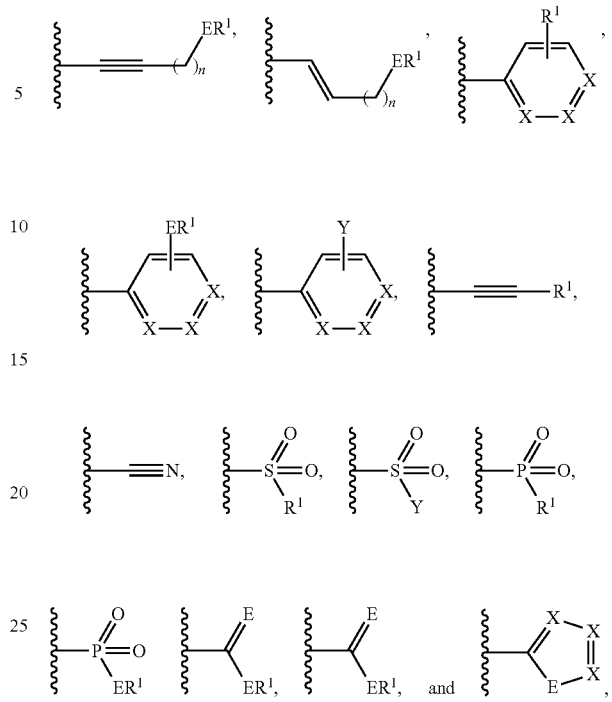

wherein

A is selected from the group consisting of direct covalent bond, —SO$_2$—NH—, —NH—; and Z is selected from the group consisting of —S—, —O—, -ER$^1$—, —CH, —N—, —NH—, —N$^+$(R$^1$)—, and —N(R$^1$)—.

2. The compound of claim 1, wherein the compound has the following formula:

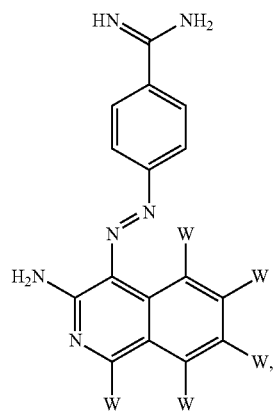

wherein

W is selected from the group consisting of —R$^1$, —OR$^1$, —N(R$^1$)$_2$, —NO$_2$, -halogen, wherein E is selected from the group consisting of oxygen atom, sulfur atom, —N(R$^1$)—, and —N(OR$^1$)—;

X is —N—, or —C(R$^1$)—;

Y is selected from the group consisting of —R$^1$, -ER$^1$, —X(R$^1$)$_2$, and -halogen; and R$^1$ is selected from the group consisting of H, substituted or unsubstituted C$_1$-C$_{14}$ alkyl, substituted or unsubstituted C$_1$-C$_{14}$ heteroalkyl, wherein 1-7 of the chain atoms are independently O, N, S, P, or B, substituted or unsubstituted C$_1$-C$_{14}$ alkenyl, substituted or unsubstituted C$_1$-C$_{14}$ heteroalkenyl, wherein 1-7 of the chain atoms are independently O, N, S, P, or B, substituted or unsubstituted C$_1$-C$_{14}$ alkynyl, substituted or unsubstituted C$_1$-C$_{14}$ heteroalkynyl, wherein 1-7 of the chain atoms are independently O, N, S, P, or B, substituted or unsubstituted C$_5$-C$_{14}$ aryl, halo, heteroaryl having 5-14 ring atoms, wherein 1-8 of the ring atoms are independently O, N, S, P, or B,

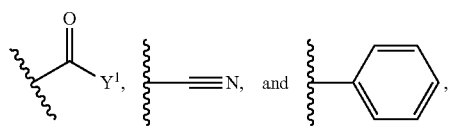

wherein n is 0-6; and

Y$^1$ is selected from the group consisting of —OR$^1$, —NR$^1$, —SR$^1$, and —R$^1$.

3. The compound of claim 1, wherein the compound is selected from the group consisting of:

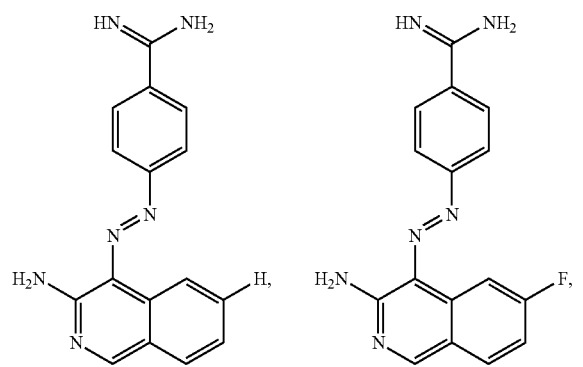
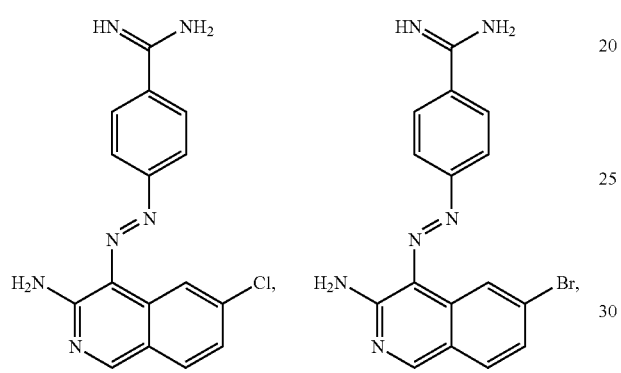
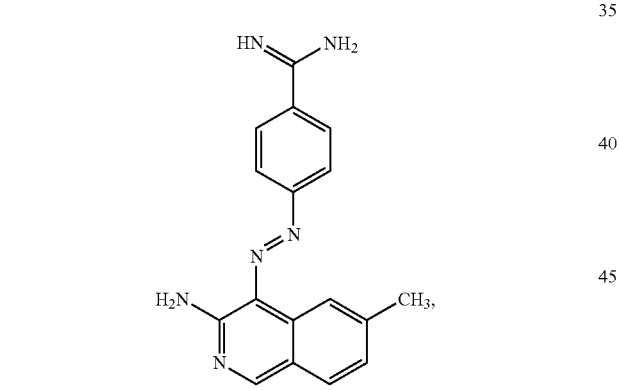
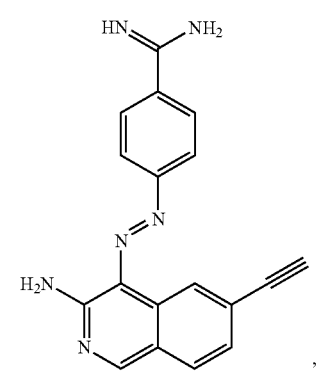
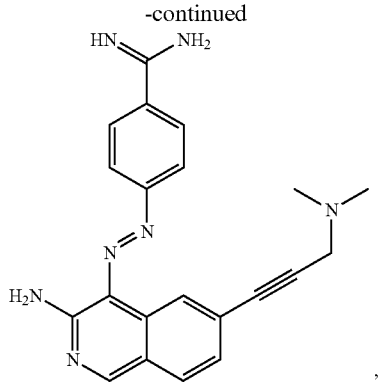
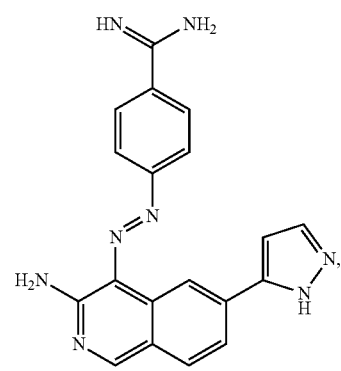
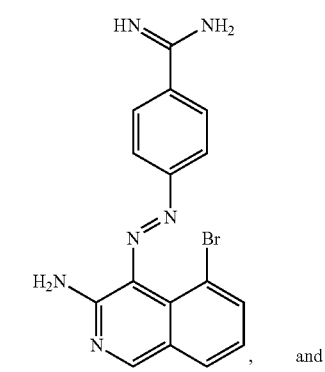
, and
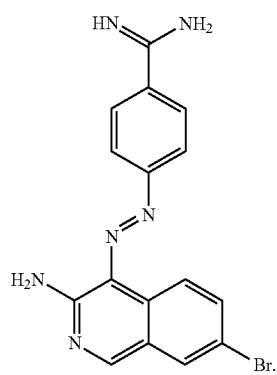
4. The compound of claim 1, wherein the compound has the following formula:

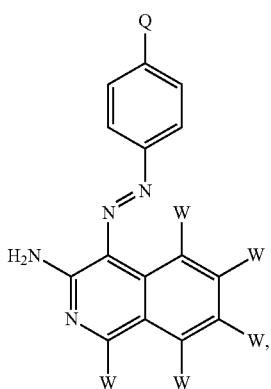

wherein
Q is selected from the group consisting of —OH, —SH, —NR¹,

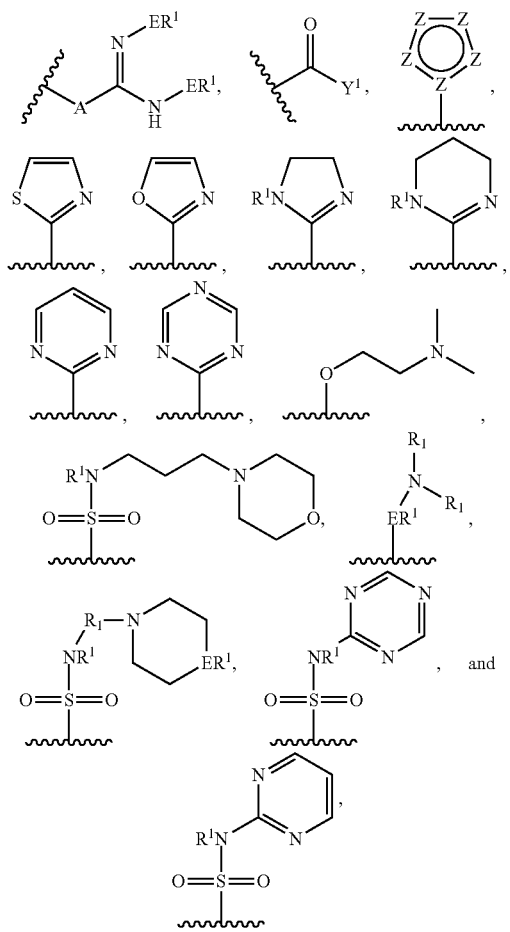

wherein
E is selected from the group consisting of oxygen atom, sulfur atom, —N(R¹)—, and —N(OR¹)—;
R¹ is selected from the group consisting of H, substituted or unsubstituted $C_1$-$C_{14}$ alkyl, substituted or unsubstituted $C_1$-$C_{14}$ heteroalkyl, wherein 1-7 of the chain atoms are independently O, N, S, P, or B, substituted or unsubstituted $C_1$-$C_{14}$ alkenyl, substituted or unsubstituted $C_1$-$C_{14}$ heteroalkenyl, wherein 1-7 of the chain atoms are independently O, N, S, P, or B, substituted or unsubstituted $C_1$-$C_{14}$ alkynyl, substituted or unsubstituted $C_1$-$C_{14}$ heteroalkynyl, wherein 1-7 of the chain atoms are independently O, N, S, P, or B, substituted or unsubstituted $C_5$-$C_{14}$ aryl, halo, heteroaryl having 5-14 ring atoms, wherein 1-8 of the ring atoms are independently O, N, S, P, or B,

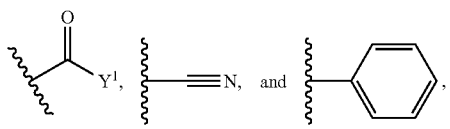

wherein
Y¹ is selected from the group consisting of —OR¹, —NR¹, —SR¹, and —R¹;
A is selected from the group consisting of direct covalent bond, —SO₂—NH—, —NH—; and
Z is selected from the group consisting of —S—, —O—, -ER¹—, —CH, —N—, —NH—, —N⁺(R¹)—, and —N(R¹)—;
W is selected from the group consisting of —N(R¹)₂, —NO₂, -halogen,

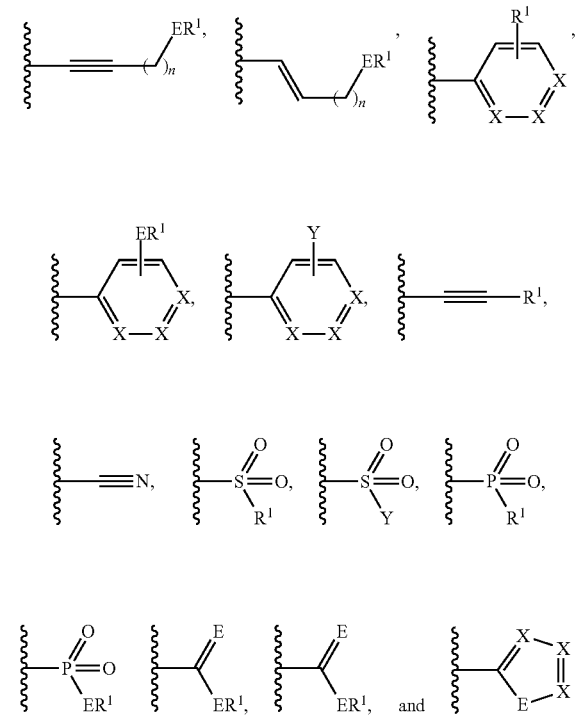

wherein
X is —N—, or —C(R¹)—; and
Y is selected from the group consisting of —R¹, -ER¹, —X(R¹)₂, and -halogen.

5. The compound of claim 1, wherein the compound is selected from the group consisting of:

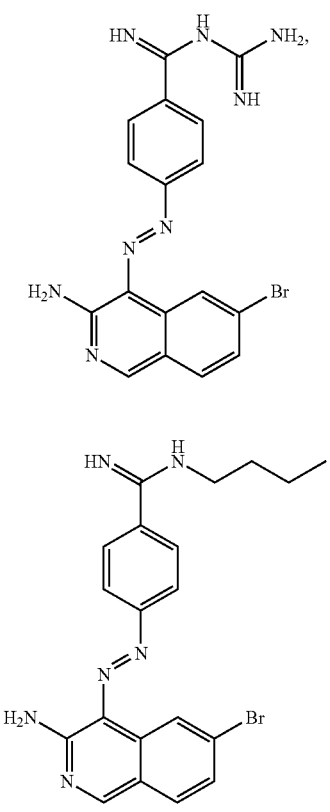
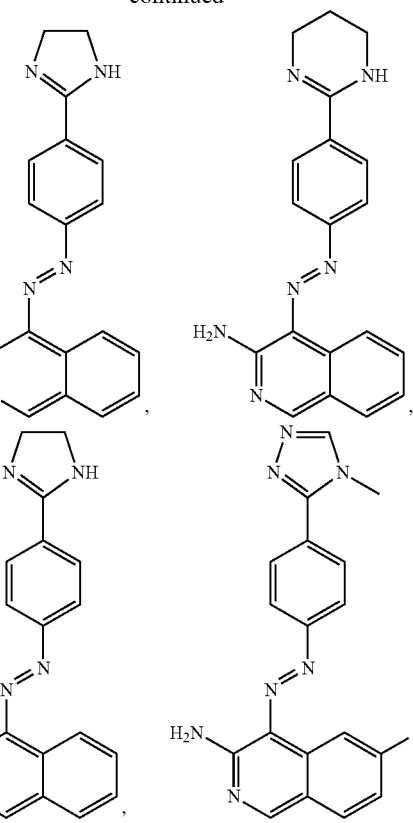
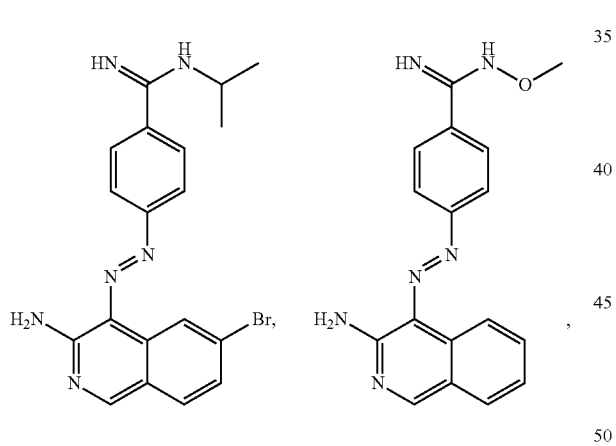
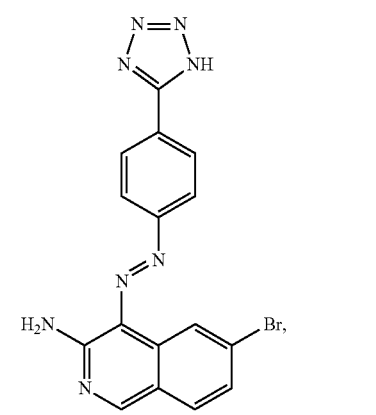
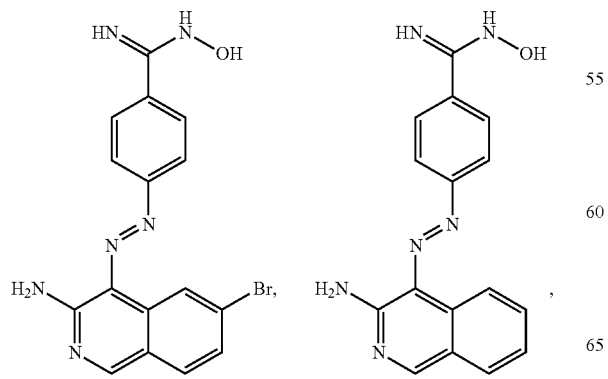
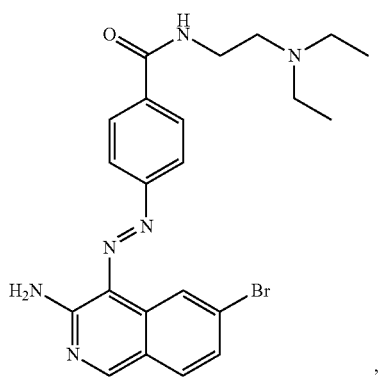

121
-continued
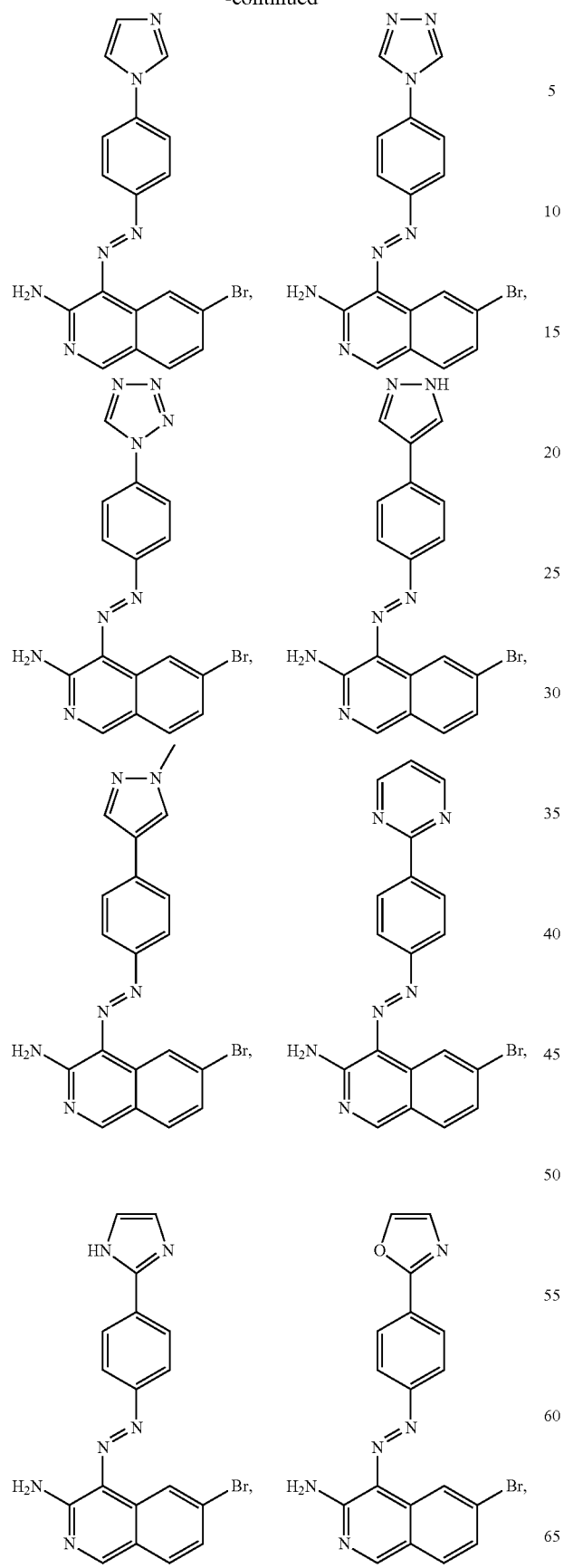
122
-continued
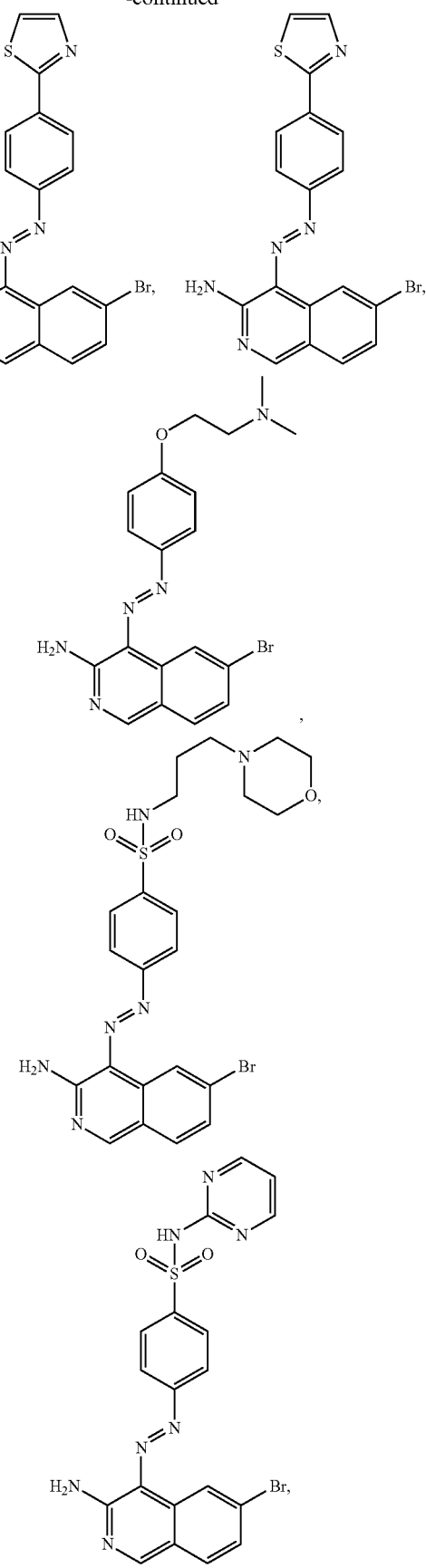

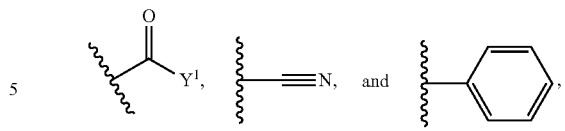

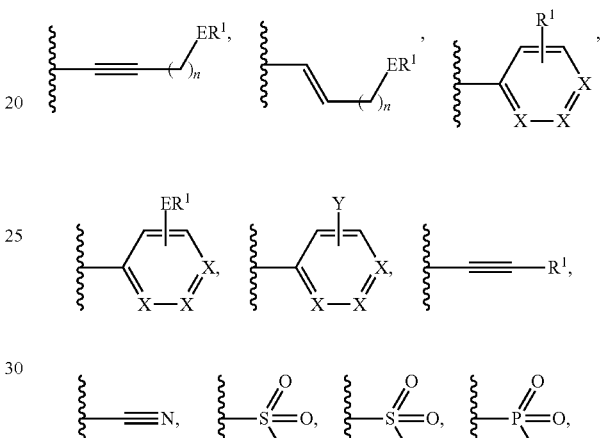

wherein $Y^1$ is selected from the group consisting of —$OR^1$, —$NR^1$, —$SR^1$, and —$R^1$;

W is selected from the group consisting of —$R^1$, —$OR^1$, —$N(R^1)_2$, —$NO_2$, -halogen, wherein E is selected from the group consisting of oxygen atom, sulfur atom, —$N(R^1)$—, and —$N(OR^1)$—;

X is —N—, or —$C(R^1)$—; and

Y is selected from the group consisting of —$R^1$, -$ER^1$, —$X(R^1)_2$, and -halogen.

7. The compound of claim 1, wherein the compound is selected from the group consisting of:

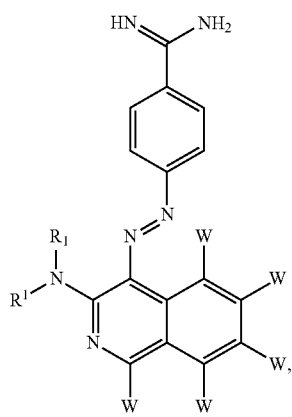

and

6. The compound of claim 1, wherein the compound has the following formula:

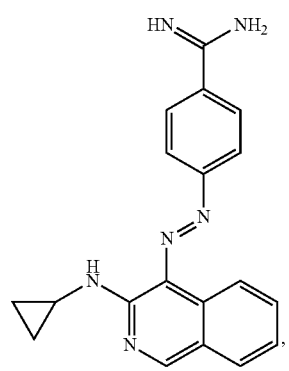

wherein $R^1$ is selected from the group consisting of H, substituted or unsubstituted $C_1$-$C_{14}$ alkyl, substituted or unsubstituted $C_1$-$C_{14}$ heteroalkyl, wherein 1-7 of the chain atoms are independently O, N, S, P, or B, substituted or unsubstituted $C_1$-$C_{14}$ alkenyl, substituted or unsubstituted $C_1$-$C_{14}$ heteroalkenyl, wherein 1-7 of the chain atoms are independently O, N, S, P, or B, substituted or unsubstituted $C_1$-$C_{14}$ alkynyl, substituted or unsubstituted $C_1$-$C_{14}$ heteroalkynyl, wherein 1-7 of the chain atoms are independently O, N, S, P, or B, substituted or unsubstituted $C_5$-$C_{14}$ aryl, halo, heteroaryl having 5-14 ring atoms, wherein 1-8 of the ring atoms are independently O, N, S, P, or B,

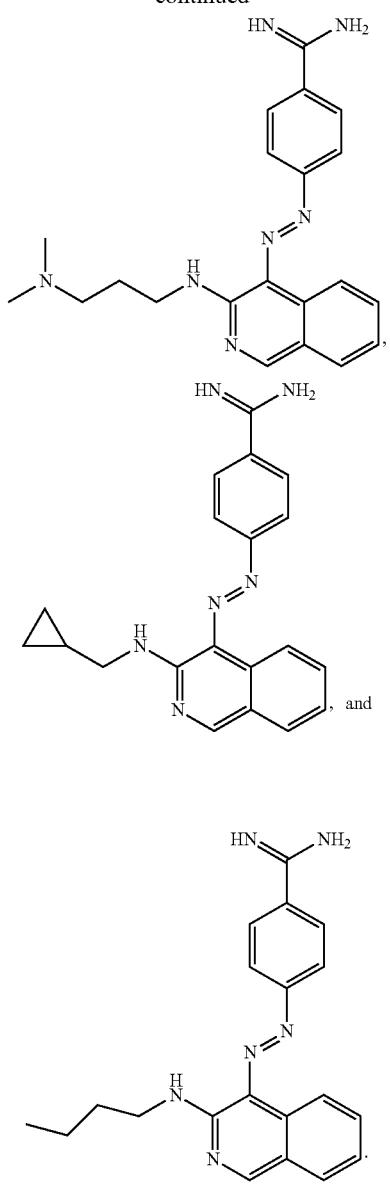
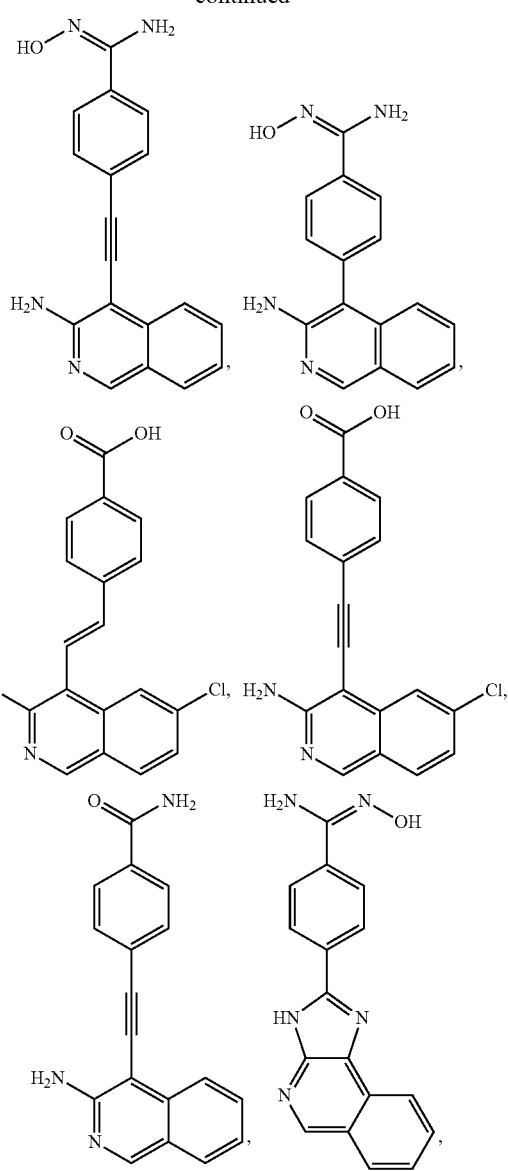
8. The compound of claim 1, wherein the compound is selected from the group consisting of:
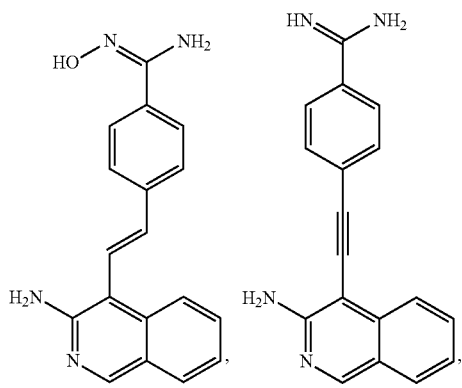
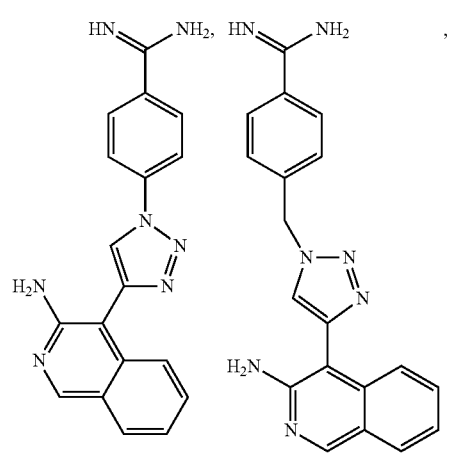

127
-continued
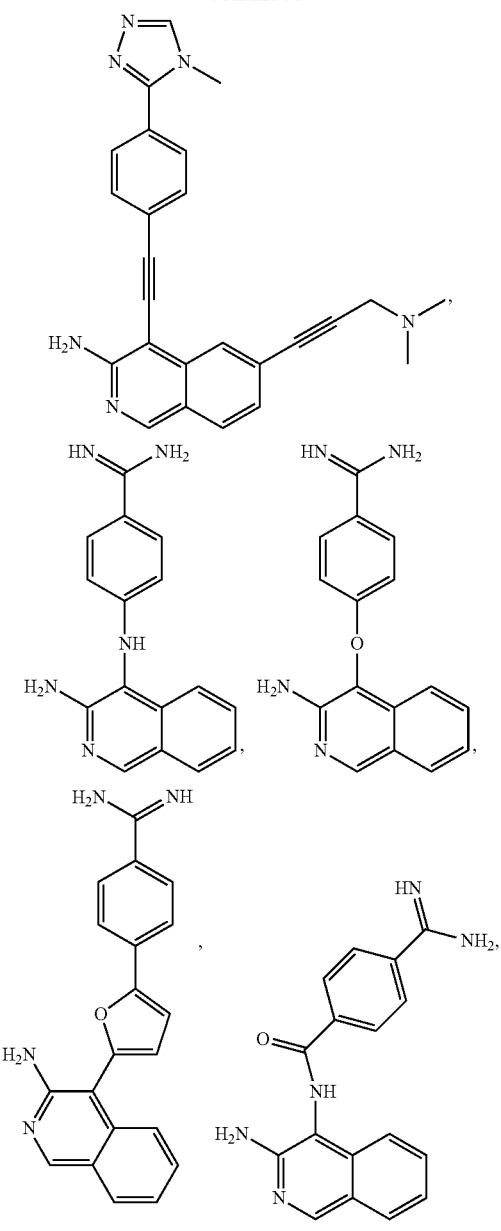
128
-continued
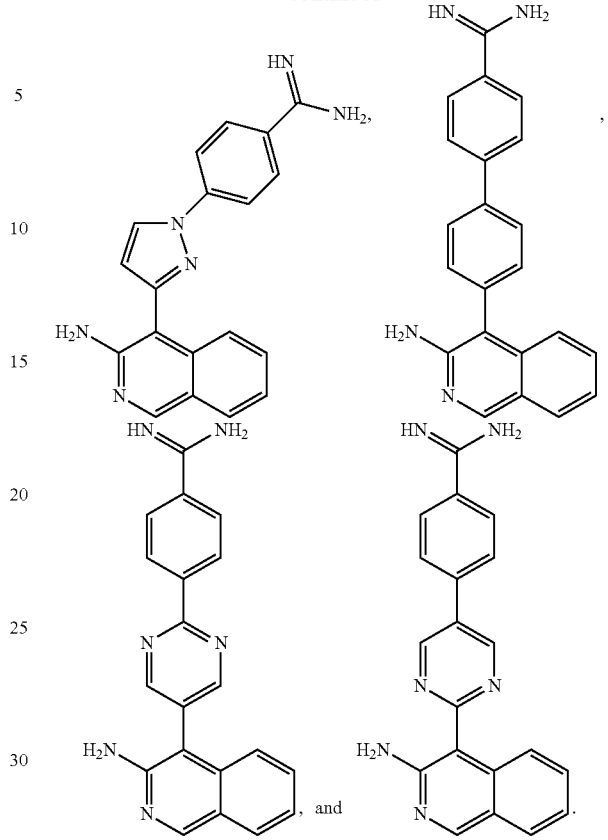
, and
9. The compound of claim 1, wherein the compound has following formula:
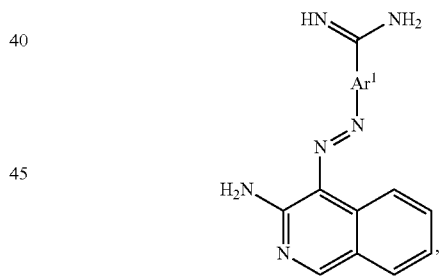
wherein
Ar$^1$ is selected from the group consisting of
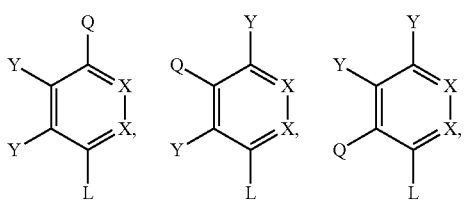
wherein
E is selected from the group consisting of oxygen atom, sulfur atom, —N(R$^1$)—, and —N(OR$^1$)—;

X is —C(R$^1$)—; and

Y is selected from the group consisting of —R$^1$, -ER$^1$, —X(R$^1$)$_2$, and -halogen, wherein R$^1$ is selected from the group consisting of H, substituted or unsubstituted C$_1$-C$_{14}$ alkyl, substituted or unsubstituted C$_1$-C$_{14}$ heteroalkyl, wherein 1-7 of the chain atoms are independently O, N, S, P, or B, substituted or unsubstituted C$_1$-C$_{14}$ alkenyl, substituted or unsubstituted C$_1$-C$_{14}$ heteroalkenyl, wherein 1-7 of the chain atoms are independently O, N, S, P, or B, substituted or unsubstituted C$_1$-C$_{14}$ alkynyl, substituted or unsubstituted C$_1$-C$_{14}$ heteroalkynyl, wherein 1-7 of the chain atoms are independently O, N, S, P, or B, substituted or unsubstituted C$_5$-C$_{14}$ aryl, halo, heteroaryl having 5-14 ring atoms, wherein 1-8 of the ring atoms are independently O, N, S, P, or B,

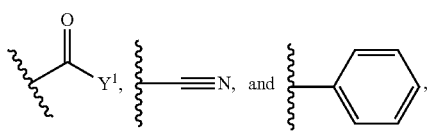

wherein

Y$^1$ is selected from the group consisting of —OR$^1$, —NR$^1$, —SR$^1$, and —R$^1$.

10. The compound of claim 1, wherein the compound is selected from the group consisting of:

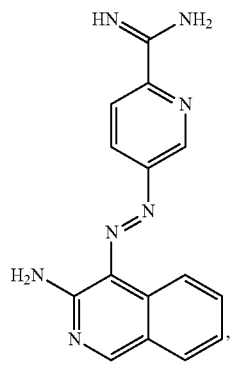

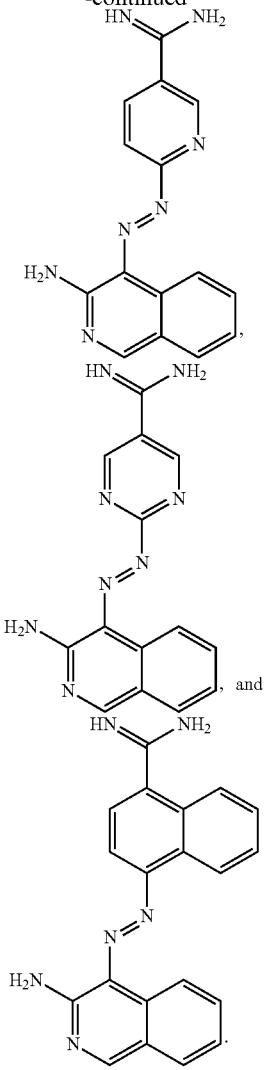

11. A method for inhibiting growth of cancer cells comprising introducing into the cancer cells a compound of claim 1, wherein the cancer cells are selected from ovarian, prostate and breast cancer cells.

* * * * *